US007329654B2

(12) United States Patent
Kanojia et al.

(10) Patent No.: US 7,329,654 B2
(45) Date of Patent: *Feb. 12, 2008

(54) HETEROATOM CONTAINING TETRACYCLIC DERIVATIVES AS SELECTIVE ESTROGEN RECEPTOR MODULATORS

(75) Inventors: Ramesh M. Kanojia, Raritan, NJ (US); Nareshkumar F. Jain, Raritan, NJ (US); Raymond Ng, Raritan, NJ (US); Zhihua Sui, Raritan, NJ (US); Jiayi Xu, Raritan, NJ (US)

(73) Assignee: Janssen Pharmaceutica N.V. (BE)

( * ) Notice: Subject to any disclaimer, the term of this patent is extended or adjusted under 35 U.S.C. 154(b) by 334 days.

This patent is subject to a terminal disclaimer.

(21) Appl. No.: 10/307,735

(22) Filed: Dec. 2, 2002

(65) Prior Publication Data

US 2003/0216463 A1 Nov. 20, 2003

Related U.S. Application Data

(60) Provisional application No. 60/341,957, filed on Dec. 19, 2001.

(51) Int. Cl.
*A61P 19/10* (2006.01)
*A61K 31/35* (2006.01)
*C07D 493/04* (2006.01)

(52) U.S. Cl. ............... 514/217.03; 514/63; 514/232.8; 514/321; 514/422; 514/431; 514/432; 514/450; 514/453; 540/596; 544/69; 544/148; 546/14; 546/197; 548/406; 548/526; 549/4; 549/12; 549/24; 549/25; 549/214; 549/268; 549/276

(58) Field of Classification Search ............... 514/63, 514/217.03, 232.8, 321, 422, 431, 432, 450, 514/453; 540/596; 544/69, 148; 546/14; 546/197; 548/406, 526; 549/4, 12, 24, 25, 549/214, 268, 276, 277, 354, 384
See application file for complete search history.

(56) References Cited

U.S. PATENT DOCUMENTS

| | | | |
|---|---|---|---|
| 5,395,842 A | 3/1995 | Labrie et al. | 514/456 |
| 5,686,465 A | 11/1997 | Labrie et al. | 514/320 |
| 5,840,735 A | 11/1998 | Labrie et al. | 514/320 |
| 6,060,503 A | 5/2000 | Labrie et al. | 514/428 |
| 6,133,458 A | 10/2000 | Bell et al. | 549/42 |
| 6,153,768 A | 11/2000 | Jo et al. | 549/406 |

FOREIGN PATENT DOCUMENTS

| | | |
|---|---|---|
| EP | 0470310 B1 | 2/1992 |
| GB | 1094806 | 12/1967 |
| IN | 173337 | 4/1994 |
| WO | WO 93/10741 A2 | 6/1993 |
| WO | WO 96/26201 A1 | 8/1996 |
| WO | WO 9709044 | 3/1997 |
| WO | WO 03053977 | 7/2003 |

OTHER PUBLICATIONS

Federov et al., Aryllead Triacetates in the Synthesis of Oxaphenanthrene Derivatives, Tetrahedron Letters, vol. 42, No. 34, Aug. 20, 2001, pp. 5875-5877.*
Miller et al., Targeting the Estrogen Receptor with SERMs, Annual Reports in Medicinal Chemistry, vol. 36, pp. 149-158, 2001.*
Albert, J.L. et al.: "Estrogen Regulation of Placental Alkaline Phosphatase Gene Expression in a Human Endometrial Adenocarcinoma Cell Line[1]"; Cancer Research 50, 1990, pp. 3306-3310.
Allan, G.F. et al.: "An Ultrahigh-Throughput Screening Assay for Estrogen Receptor Ligands"; Analytical Biochem. 275, 1999, pp. 243-247.
Baran-Marszak, M. et al.: "Nouvelle synthase de lla dehydrorotenone et d'autres rotenoides (*)"; No. 34., Manuscript date Jul. 21, 1970; pp. 191-198, 1971.
Cornia, M. et al.: "Oxygen Heterocycles by Oxidation of *ortho*-Alkylphenols. Oxidation of *ortho*-Propenylphenols."; Gassetta Chim. Italiana, 107, 1977, pp. 299-304.
Grese, T.A. et al.: "Structure-Activity Relationships of Selective Estrogen Receptor Modulators: Modifications to the 2-Arylbenzothiophene Core of Raloxifene"; J. Med. Chem. 1997, 40, pp. 146-167.
Grese,T.A. et al.: "Synthesis and Pharmacology of Conformationally Restricted Raloxifene Analogues: Highly Potent Selective Estrogen Receptor Modulators"; J. Med. Chem. 1998, 41, pp. 1272-1283.
Khan, K.Z. et al.: "Reaction of Dimethyl Sulphoxide & Acetic Anhydride with 3-Substituted 4-Hydroxycoumarins[B"]; Indian J. of Chem. vol. 24B, 1985, pp. 42-46.
Nicolaou, K.C. et al.: "Total Synthesis of Amphoteronolide B and Amphotericin B. 1. Strategy and Stereocontrolled Construction of Key Building Blocks"; J. Am. Chem. Soc. 1998, 110, pp. 4672-4685.
Saeed, A. et al.: "Structure-Activity Relationship of Antiestrogens. Studied on 2,3-Diaryl-1-benzopyrans"; J. Med. Chem. 1990, 33, pp. 3210-3216.
Sharma, A.P. et al.: "Structure-Activity Relationship of Antiestrogens. Effect of the Side Chain and Its Position on the Activity of 2,3-Diarly-2H-1-benzopyrans"; J. Med. Chem. 1990 33, 3216-3222.
Sharma, A.P. et al.: "Structure—Activity Relationship of Antiestrogens. Phenolic Analogues of 2,3-Diarly-2H-1-benzopyrans"; J. Med. Chem. 1990, 33, pp. 3222-3229.

(Continued)

*Primary Examiner*—Brenda Coleman

(57) ABSTRACT

The present invention is directed to novel heteroatom containing tetracyclic derivatives, pharmaceutical compositions containing them, their use in the treatment and/or prevention of disorders mediated by one or more estrogen receptors and processes for their preparation. The compounds of the invention are useful in the treatment and/or prevention of disorders associated with the depletion of estrogen such as hot flashes, vaginal dryness, osteopenia and osteoporosis; hormone sensitive cancers and hyperplasia of the breast, endometrium, cervix and prostate; endometriosis, uterine fibroids, osteoarthritis and as contraceptive agents, alone or in combination with a progestogen or progestogen antagonist.

26 Claims, No Drawings

OTHER PUBLICATIONS

Welshons, W.V. et al.: "Stimulation of breast cancer cells in vitro by the environmental estrogen enterolactone and the phytoestrogen equol"; Breast Cancer Research and Treatment 10: 1987, pp. 169-175.

PCT International Search Report dated Mar. 3, 2003 for International Application No. PCT/US02/38486.

PCT International Search Report for International Application PCT/US03/37419, dated Mar. 16, 2004.

Jordan, V. Craig: Antiestrogens and Selective Estrogen Receptor Modulators as Multifunctional Medicines. 1. Receptor Interactions; J. of Medicinal Chemistry, 2003, vol. 46, No. 6, pp. 883-908.

Jordan V. Craig: Antiestrogens and Selective Estrogen Receptor Modulators as Multifunctional Medicines. 2. Clinical Considerations and New Agents; J. of Medicinal Chemistry, 2003, vol. 46, No. 7, pp. 1081-1111.

Riggs, B. Lawrence, M.D. et al.: Selective Estrogen-Receptor Modulators—Mechanisms of Action and Application to Clinical Practice; New England J. Med. 348:7 (2003), pp. 618-629.

Riggs, B. Lawrence, M.D. et al: Selective Estrogen-Receptor Modulators—Mechanisms of Action and Application to Clinical Practice (Feb. 13, 2003; 348:618-29). Correction in Figure 2; New England J. Med. 348:12 (2003) p. 1192.

* cited by examiner

HETEROATOM CONTAINING TETRACYCLIC DERIVATIVES AS SELECTIVE ESTROGEN RECEPTOR MODULATORS

CROSS REFERENCE TO RELATED APPLICATION

This application claims the benefit of U.S. Provisional Application 60/341,957, filed on Dec. 19, 2001, which is incorporated by reference herein in its entirety.

FIELD OF THE INVENTION

The present invention is directed to novel heteroatom containing tetracyclic derivatives, pharmaceutical compositions containing them, their use in the treatment of disorders mediated by one or more estrogen receptors and processes for their preparation. The compounds of the invention are thus useful for the treatment and/or prevention of disorders associated with estrogen depletion (including, but not limited to hot flashes, vaginal dryness, osteopenia, osteoporosis, hyperlipidemia, loss of cognitive function, degenerative brain diseases, cardiovascular and cerebrovascular diseases); for the treatment of hormone sensitive cancers and hyperplasia (in tissues including breast, endometrium, and cervix in women and prostate in men); for the treatment and prevention of endometriosis, uterine fibroids, and osteoarthritis; and as contraceptive agents either alone or in combination with a progestogen or progestogen antagonist.

BACKGROUND OF THE INVENTION

Estrogens are a group of female hormones essential for the reproductive process and for the development of the uterus, breasts, and other physical changes associated with puberty. Estrogens have an effect on various tissues throughout a woman's body, not only those involved in the reproductive process, such as the uterus, breasts, and external genitalia, but also tissues in the central nervous system, bones, the liver, skin, and the urinary tract. The ovaries produce most of the estrogens in a woman's body.

Menopause is defined as the permanent cessation of menses due to loss of ovarian follicular function and the near complete termination of estrogen production. The midlife transition of menopause is characterized by a decrease in estrogen that provokes both short-term and long-term symptoms with the vasomotor, urogenital, cardiovascular, skeletal and centra nervous systems, such as hot flushes, urogenital atrophy, increased risk of cardiovascular disease, osteoporosis, cognitive and psychological impairment, including an increased risk of cognitive disorders and Alzheimer's disease (AD).

Seventy-five percent of all women experience some occurrence of vasomotor symptoms associated with the onset of menopause such as body sweating and hot flushes. These complaints may begin several years before menopause and in some women may continue for more than 10 years either relatively constant, or as instant attacks without a definable, provoking cause.

Urogenital symptoms associated with the onset of menopause involving the vagina include a sensation of dryness, burning, itching, pain during intercourse, superficial bleeding and discharge, along with atrophy and stenosis. Symptoms involving the urinary tract include a burning sensation during urination, frequent urgency, recurrent urinary tract infections, and urinary incontinence. These symptoms have been reported to occur in up to 50% of all women near the time of menopause and are more frequent a few years after menopause. If left untreated, the problems can become permanent.

Heart attack and stroke are major causes of morbidity and mortality among senior women. Female morbidity from these diseases increases rapidly after menopause. Women who undergo premature menopause are at greater coronary risk than menstruating women of similar age. The presence of serum estrogen has a positive effect on serum lipids. The hormone promotes vasodilation of blood vessels, and enhances the formation of new blood vessels. Thus the decrease in serum estrogen levels in postmenopausal women results in adverse cardiovascular effect. Additionally, it is theorized that differences in the ability of blood to coagulate may account for the observed difference in the occurrence of heart disease before and after menopause.

The skeleton is under a continuous process of bone degeneration and regeneration in a carefully regulated interaction among the bone cells. These cells are directly affected by estrogen. Estrogen deficiency results in a loss of bone structure, and decrease of bone strength. Rapid loss of bone mass during the year immediately following menopause leads to postmenopausal osteoporosis and increased risk of fracture.

Estrogen deficiency is also one of the causes for the degenerative changes in the central nervous system and may lead to Alzheimer's disease (AD) and decline of cognition. Recent evidence suggests an association between estrogen, menopause and cognition. More particularly, it has been reported that estrogen replacement therapy and the use of estrogen in women may prevent the development of AD and improve cognitive function.

Hormone replacement therapy (HRT)—more specifically estrogen replacement therapy (ERT)—is commonly prescribed to address the medical problems associated with menopause, and also to help hinder osteoporosis and primary cardiovascular complications (such as coronary artery disease) in both a preventive and therapeutical manner. As such, HRT is considered a medical therapy for prolonging the average life span of postmenopausal women and providing a better quality of life.

ERT effectively relieves the climacteric symptoms and urogenital symptoms and has shown some benefits in the prevention and treatment of heart disease in postmenopausal women. Clinical reports have shown that ERT lowered heart attack rates and mortality rates in populations that received ERT versus similar populations not on ERT. ERT initiated soon after menopause may also help maintain bone mass for several years. Controlled investigations have shown that treatment with ERT has a positive effect even in older women up to age of 75 years.

However, there are numerous undesirable effects associated with ERT that reduce patient compliance. Venous thromboembolism, gallbladder disease, resumption of menses, mastodynia, and a possible increased risk of developing uterine and/or breast cancer are the risks associated with ERT. Up to 30% of women who are prescribed ERT do not fill the prescription, and the discontinuation rate for ERT is between 38% and 70%, with safety concerns, and adverse effects (bloating and break-through bleeding) the most important reasons for discontinuation.

A new class of pharmacological agents known as Selective Estrogen Receptor Modulators or SERMs have been designed and developed as alternatives for HRT. Raloxifene, a nonsteroidal benzothiophere SERM is marketed in the US and Europe for the prevention and treatment of osteoporosis under the trademark of Evista®. Raloxifene has been shown to reduce bone loss and prevent fracture without adversely stimulating endometrial and mammary tissue, though raloxifene is somewhat less efficacious than ERT for protecting against bone loss. Raloxifene is unique and differs significantly from ERT in that it does not stimulate the endometrium and has the potential for preventing breast cancer. Raloxifene has also demonstrated beneficial estrogen agonist effects on cardiovascular risk factors, more specifically through a rapid and sustained decrease in total and low-density lipoprotein cholesterol levels in patients treated with raloxifene. In addition, raloxifene has been shown to reduce plasma concentration of homocysteine, an independent risk factor for atherosclerosis and thromboembolic disease.

However, raloxifene has been reported to exacerbate symptoms associated with menopause such as hot flushes and vaginal dryness, and does not improve cognitive function in senior patients. Patients taking raloxifene have reported higher rates of hot flashes compared with either placebo or ERT users and more leg cramps than placebo users, although women who took ERT had a higher incidence of vaginal bleeding and breast discomfort than raloxifene or placebo users.

As yet, neither raloxifene nor any of the other currently available SERM compounds has been shown to have the ability to provide all the benefits of currently available ERT such as controlling postmenopausal syndrome and preventing AD, without causing adverse side effects such as increasing risk of endometrial and breast cancer and bleeding. Thus there exists a need for compounds which are selective estrogen receptor modulators and which provide all of the benefits of ERT while also addressing the vasomotor, urogenital and cognitive disorders or conditions associated with the decrease in systemic estrogen associated with menopause.

SUMMARY OF THE INVENTION

The present invention is directed to a compound of formula (I)

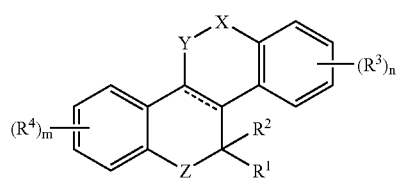

(I)

wherein
----represents a single or double bond,
X is selected from the group consisting of O and S and Y is selected from the group consisting of $CR^AR^B$, $CR_AR^B(CR^AR^B)_{1-2}$ (preferably $CR^AR^B(CR^AR^B)_{1-2}$ is selected from $-CR^AR^B(CH_2)_{1-2}$, $-CH_2CR^AR^BCH_2-$, $-CR^AR^B-CH(OH)-CR^AR^B-$ or $-CR^AR^B-CH_2-CR^AR^B-$), $CR^AR^B$ C(O), $CR^AR^BC(O)CR^AR^B$ (preferably $CH_2C(O)CH_2$), and C(O); alternatively Y is selected from the group consisting of O and S and X is selected from the group consisting of $CR^AR^B$ and C(O);
provided that when X is S, then Y is selected from the group consisting of $CR^AR^B$, $CR^AR^B(CR^AR^B)_{1-2}$ and $CH_2C(O)CH_2$; provided further that when Y is S, then X is selected from the group consisting of $CR^AR^B$;

wherein each $R^A$ and $R^B$ is independently selected from hydrogen, hydroxy, alkyl or alkoxy; provided that $R^A$ and $R^B$ are not each hydroxy;
Z is selected from the group consisting of O and S;
$R^1$ is selected from the group consisting of hydrogen, alkyl, alkenyl, cycloalkyl, aryl, —C(O)-aryl, aralkyl, heteroaryl and heteroaryl-alkyl; wherein the alkyl, cycloalkyl, aryl, aralkyl, heteroaryl or heteroaryl-alkyl group is optionally substituted with one or more substituents independently selected from halogen, hydroxy, alkyl, alkoxy, —SH, —S(alkyl), $SO_2$, $NO_2$, CN, $CO_2H$, $R^C$, —$OR^C$, —C(O)—$OR^C$, —C(O)O-(alkyl)-$NR^DR^E$, —C(O)NR-(alkyl)-$NR^D$ $R^E$, —C(O)-(heterocycloalkyl)-$NR^DR^E$, —C(O)-(heterocycloalkyl)-$R^F$, —$SO_2$—$NR^DR^E$, —$NR^DR^E$, $NR^D$—$SO_2$—$R^F$, -(alkyl)$_{0-4}$-C(O)$NR^DR^E$, (alkyl)$_{0-4}$-$NR^D$—C(O)—$R^F$, -(alkyl)$_{0-4}$-(Q)$_{0-1}$-(alkyl)$_{0-4}$-$NR^DR^E$, -(alkyl)$_{0-4}$-(Q)$_{0-1}$-(alkyl)$_{0-4}$-C(O)—$OR^F$, -(alkyl)$_{0-4}$-(Q)$_{0-1}$-(alkyl)$_{0-4}$-C(O)—$NR^DR^E$, -(alkyl)$_{0-4}$-C(O)-(alkyl)$_{0-4}$-C(O)$OR^F$, —O-(alkyl)-$OSI(alkyl)_3$, —O—(alkyl)-$OR^D$ or —O-(alkyl)-formyl;
wherein $R^C$ is selected from the group consisting of alkyl, cycloalkyl, cycloalkyl-alkyl, aryl, aralkyl, heteroaryl, heteroaryl-alkyl, heterocycloalkyl and heterocycloalkyl-alkyl; wherein the cycloalkyl, cycloalkyl-alkyl, aryl, aralkyl, heteroaryl, heteroaryl-alkyl, heterocycloalkyl or heterocycloalkyl-alkyl group is optionally substituted with one or more substituents independently selected from halogen, hydroxy, alkyl, alkoxy, —SH, —S(alkyl), $SO_2$, $NO_2$, CN, $CO_2H$, $R^C$, —$SO_2$—$NR^DR^E$, $NR^DR^E$, $NR^D$—$SO_2$—$R^F$, -(alkyl)$_{0-4}$-C(O)—$NR^DR^E$, -(alkyl)$_{0-4}$-$NR^D$—C(O)—$R^F$, -(alkyl)$_{0-4}$-(Q)$_{0-1}$-(alkyl)$_{0-4}$-$NR^DR^E$, -(alkyl)$_{0-4}$-(Q)$_{0-1}$-(alkyl)$_{0-4}$-C(O)—$OR^F$, —(alkyl)$^{0-4}$-(Q)$_{0-1}$-(alkyl)$_{0-4}$-C(O)—$NR^DR^E$ or -(alkyl)$_{0-4}$-C(O)-(alkyl)$_{0-4}$-C(O)—$OR^F$;
wherein Q is selected from the group consisting of O, S, NH, N(alkyl) and —CH=CH—;
wherein each $R^D$ and $R^E$ is independently selected from the group consisting of hydrogen and alkyl; alternatively $R^D$ and $R^E$ are taken together with the nitrogen atom to which they are bound to form a 3 to 10 membered, preferably 4 to 8 membered, ring selected from the group consisting of heteroaryl or heterocycloalkyl; wherein the heteroaryl or heterocycloalkyl group is optionally substituted with one or more substituents independently selected from halogen, hydroxy, oxo, alkyl, alkoxy, carboxy, amino, alkylamino, dialkylamino, nitro or cyano;
wherein $R^F$ is selected from the group consisting of hydrogen, alkyl, cycloalkyl, cycloalkyl-alkyl, aryl, aralkyl, heteroaryl, heteroaryl-alkyl, heterocycloalkyl and heterocycloalkyl-alkyl; wherein the cycloalkyl, aryl, heteroaryl, heteroaryl-alkyl, heterocycloalkyl or heterocycloalkyl-alkyl group is optionally substituted with one or more substituents independently selected from halogen, hydroxy, alkyl, alkoxy, carboxy, amino, alkylamino, dialkylamino, nitro or cyano;
$R^2$ is selected from the group consisting of hydroxy, alkyl, alkenyl, cycloalkyl, aryl, —C(O)-aryl, aralkyl, heteroaryl and heteroaryl-alkyl; wherein the alkyl, cycloalkyl, aryl, aralkyl, heteroaryl or heteroaryl-alkyl group is optionally substituted with one or more substituents independently selected from halogen, hydroxy, alkyl, alkoxy, —SH, —S(alkyl), $SO_2$, $NO_2$, CN, $CO_2H$, $R^C$, —$OR^C$, —C(O)—$R^C$, —C(O)O-(alkyl)-$NR^DR^E$, —C(O)—$NR^D$-(alkyl)-$NR^D$ $R^E$, —C(O)-(heterocycloalkyl)-$NR^DR^E$, —C(O)-(heterocycloalkyl)-$R^F$, —$SO_2$—$NR^DR^E$, —$NR^DR^E$, $NR^D$—$SO_2$—$R^F$, -(alkyl)$_{0-4}$-C(O)$NR^DR^E$, (alkyl)$_{0-4}$-$NR^D$—C(O)—$R^F$, -(alkyl)$_{0-4}$-(Q)$_{0-1}$-(alkyl)$_{0-4}$-$NR^DR^E$, -(alkyl)$_{0-4}$-(Q)$_{0-1}$-(alkyl)$_{0-4}$-C(O)—

$NR^DR^E$, -(alkyl)$_{0-4}$-C(O)-(alkyl)$_{0-4}$-C(O)—OR$^F$, —O-(alkyl)-OSi(alkyl)$_3$, —O-(alkyl)-OR$^D$ or —O-(alkyl)-formyl;

alternatively, $R^1$ and $R^2$ are taken together with the carbon atom to which they are bound to form C(O);

provided that when $R^1$ and $R^2$ are taken together with the carbon atom to which they are bound to form C(O) and X is selected from the group consisting of O and S, then Y is selected from the group consisting of CR$^A$R$^B$, CR$^A$R$^B$(CR$^A$R$^B$)$_{1-2}$, CR$^A$R$^B$C(O) and CH$_2$C(O)CH$_2$;

provided further that when $R^1$ and $R^2$ are taken together with the carbon atom to which they are bound to form C(O) and Y is selected from the group consisting of O and S, then X is selected from the group consisting of CR$^A$R$^B$;

n is an integer selected from 0 to 4;

each $R^3$ is independently selected from the group consisting of halogen, hydroxy, R$^C$, amino, alkylamino, dialkylamino, nitro, cyano, —C(O)R$^G$, —C(O)OR$^G$, —OC(O)R$^G$, —OC(O)OR$^G$, —OC(O)N(R$^G$)$_2$, —N(R$^G$)C(O)R$^G$, —OSi(R$^G$)$_3$, —OR$^G$, —SO$_2$N(R$^G$)$_2$, —O-(alkyl)$_{1-4}$-C(O)R$^G$ and —O-(alkyl)$_{1-4}$-C(O)OR$^G$;

wherein each R$^G$ is independently selected from hydrogen, alkyl, aryl, aralkyl and 1,7,7-trimethyl-2-oxabicyclo[2.2.1]heptan-3-one; wherein the alkyl, aryl or aralkyl group is optionally substituted with one or more substituents independently selected from alkyl, halogenated alkyl, alkoxy, halogen, hydroxy, nitro, cyano, —OC(O)-alkyl or —C(O)O-alkyl;

alternatively two R$^G$ groups are taken together with the nitrogen atom to which they are bound to form a heterocycloalkyl group; wherein the heterocycloalkyl group is optionally substituted with one or more substituents independently selected from halogen, hydroxy, alkyl, alkoxy, carboxy, amino, alkylamino, dialkylamino, nitro or cyano;

m is an integer selected from 0 to 4;

each $R^4$ is independently selected from the group consisting of halogen, hydroxy, R$^C$, amino, alkylamino, dialkylamino, nitro, cyano, —C(O)R$^G$, —C(O)OR$^G$, —OC(O)R$^G$, —OC(O)OR$^G$, —OC(O)N(R$^G$)$_2$, —N(R$^G$)C(O)R$^G$, —OSi(R$^G$)$_3$, —OR$^G$, —SO$_2$N(alkyl)$_2$, —O-(alkyl)$_{1-4}$-C(O)R$^G$ and —O-(alkyl)$_{1-4}$-C(O)OR$^G$;

provided that when ---- is a double bond, X is CH$_2$, Y is O, Z is O and $R^1$ and $R^2$ are taken together with the carbon atom to which they are bound to form C(O), then at least one of n or m is an integer selected from 1 to 4; preferably, n is an integer from 1 to 4 and m is an integer from 1 to 4;

provided further that when ---- is a single bond, X is O, Y is CH(alkyl), Z is O, $R^1$ is hydrogen and $R^2$ is alkyl, then at least one of n or m is an integer selected from 1 to 4; preferably, n is an integer from 1 to 4 and m is an integer from 1 to 4;

provided further that when ---- is a single bond, X is O, Y is CH(alkyl), Z is O, $R^1$ is hydrogen, $R^2$ is alkyl, n is 1 and m is 1, then $R^3$ and $R^4$ are other than methoxy or ethoxy, preferably $R^3$ and $R^4$ are other than alkoxy;

provided further that when ---- is a double bond, X is O, Y is CH$_2$, Z is O, $R^1$ and $R^2$ are taken together with the carbon atom to which they are bound to form C(O), n is 0 and m is 2, then each $R^4$ is not hydroxy or alkoxy;

or a pharmaceutically acceptable salt thereof.

The present invention is further directed to a compound of formula (D)

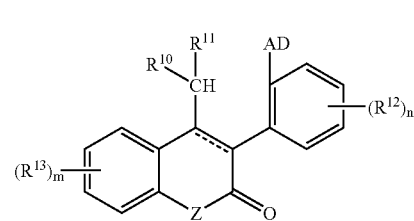

wherein
---- represents a single or double bond,
A is selected from the group consisting of O and S;
D is selected from the group consisting of hydrogen, methyl, acetyl, benzyl, benzoyl, SEM, MOM, BOM, TBS, TMS, pivaloyl and —C(O)R; wherein R is selected from alkyl, aryl, and substituted aryl; wherein the substituents on the aryl group are one or more independently selected from halogen, hydroxy, alkyl, alkoxy, amino, alkylamino, di(alkyl)amino, nitro or cyano;
each $R^{10}$ and $R^{11}$ is independently selected from hydrogen, halogen, hydroxy, alkyl, hydroxy substituted alkyl, alkoxy, —CH(OH)-aryl, —CHO, —C(O)—alkyl, —C(O)-aryl, —C(O)O-alkyl, —C(O)O-aryl, SEM, MOM, BOM, —CH$_2$CH$_2$OCH$_3$, —CH$_2$CH$_2$—O-benzyl and pivaloyl; wherein the alkyl group, whether alone or as part of a larger substituents group is optionally substituted with one or more substituents independently selected from hydroxy, halogen or phenyl; wherein the aryl group, whether alone or as part of a larger substituents group is optionally substituted with one or more substituents independently selected from hydroxy, alkoxy or alkoxy-carbonyl;
provided that $R^{10}$ and $R^{11}$ are not each hydrogen or each hydroxy;
Z is selected from the group consisting of O and S;
n is an integer selected from 0 to 4;
each $R^{12}$ is independently selected from the group consisting of halogen, hydroxy, alkyl, alkoxy, trialkylsilyl, acyloxy, benzoyloxy, aryloxy, aralkyloxy, SEMoxy, MOMoxy and pivaloyloxy;
m is an integer selected from 0 to 4;
each $R^{13}$ is independently selected from the group consisting of halogen, hydroxy, alkyl, alkoxy, trialkylsilyl, acyloxy, benzoyloxy, aryloxy, aralkyloxy, SEMoxy, MOMoxy and pivaloyloxy;
or a pharmaceutically acceptable salt thereof.

The present invention is further directed to a compound of formula (DI)

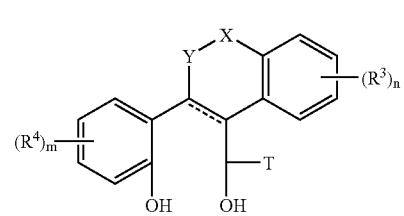

wherein
---- represents a single or double bond,
X is selected from the group consisting of O and S and Y is selected from the group consisting of CR$^A$R$^B$, CR$_A$R$^B$(CR$^A$R$^B$)$_{1-2}$ (preferably CR$^A$R$^B$(CR$^A$R$^B$)$_{1-2}$ is selected from —CR^AR^B(CH_2)_{1-2}, —CH_2CR^AR^BCH_2—, —CR^AR^B—CH (OH)—CR^AR^B— or —CR^AR^B—CH_2—CR^AR^B—), CR^AR^B C(O), CR^AR^BC(O)CR^AR^B (preferably CH_2C(O)CH_2 and C(O); alternatively Y is selected from the group consisting of O and S and X is selected from the group consisting of CR^AR^B and C(O);

provided that when X is S, then Y is selected from the group consisting of CR^AR^B, CR^AR^B(CR^AR^B)_{1-2} and CH_2C (O)CH_2; provided further that when Y is S, then X is selected from the group consisting of CR^AR^B;

wherein each R^A and R^B is independently selected from hydrogen, hydroxy, alkyl or alkoxy; provided that R^A and R^B are not each hydroxy;

T is selected from the group consisting of -(aryl)-O-(alkyl)-NR^DR^E and -(aryl)-O-(alkyl)-OH;

n is an integer selected from 0 to 4;

each R^3 is independently selected from the group consisting of halogen, hydroxy, R^C, amino, alkylamino, dialkylamino, nitro, cyano, —C(O)R^G, —C(O)OR^G, —OC(O)R^G, —OC(O)OR^G, —OC(O)N(R^G)_2, —N(R^G)C(O)R^G, —OSi (R^G)_3, —OR^G, —SO_2N(R^G)_2, —O-(alkyl)_{1-4}-C(O)R^G and —O-(alkyl)_{1-4}-C(O)OR^G;

wherein R^C is selected from the group consisting of alkyl, cycloalkyl, cycloalkyl-alkyl, aryl, aralkyl, heteroaryl, heteroaryl-alkyl, heterocycloalkyl and heterocycloalkyl-alkyl; wherein the cycloalkyl, cycloalkyl-alkyl, aryl, aralkyl, heteroaryl, heteroaryl-alkyl, heterocycloalkyl or heterocycloalkyl-alkyl group is optionally substituted with one or more substituents independently selected from halogen, hydroxy, alkyl, alkoxy, —SH, —S(alkyl), SO_2, NO_2, CN, CO_2H, R^C, —SO_2—NR^DR^E, NR^DR^E, NR^D—SO_2—R^F, -(alkyl)_{0-4}-C(O)—NR^DR^E, -(alkyl)_{0-4}-NR^D—C(O)—R^F, -(alkyl)_{0-4}-(Q)_{0-1}-(alkyl)_{0-4}-NR^DR^E, -(alkyl)_{0-4}-(Q)_{0-1}-(alkyl)_{0-4}-C(O)—OR^F, -(alkyl)^{0-4}-(Q)_{0-1}-(alkyl)_{0-4}-C(O)—NR^DR^E or -(alkyl)_{0-4}-C(O)-(alkyl)_{0-4}-C(O)—OR^F;

wherein Q is selected from the group consisting of O, S, NH, N(alkyl) and —CH═CH—;

wherein R^D and R^E are each independently selected from the group consisting of hydrogen and alkyl; alternatively R^D and R^E are taken together with the nitrogen atom to which they are bound to form a 3 to 10 membered, preferably 4 to 8 membered, ring selected from the group consisting of heteroaryl or heterocycloalkyl; wherein the heteroaryl or heterocycloalkyl group is optionally substituted with one or more substituents independently selected from halogen, hydroxy, oxo, alkyl, alkoxy, carboxy, amino, alkylamino, dialkylamino, nitro or cyano;

wherein R^F is selected from the group consisting of hydrogen, alkyl, cycloalkyl, cycloalkyl-alkyl, aryl, aralkyl, heteroaryl, heteroaryl-alkyl, heterocycloalkyl and heterocycloalkyl-alkyl; wherein the cycloalkyl, aryl, heteroaryl, heteroaryl-alkyl, heterocycloalkyl or heterocycloalkyl-alkyl group is optionally substituted with one or more substituents independently selected from halogen, hydroxy, alkyl, alkoxy, carboxy, amino, alkylamino, dialkylamino, nitro or cyano;

wherein each R^G is independently selected from hydrogen, alkyl, aryl, aralkyl and 1,7,7-trimethyl-2-oxabicyclo[2.2.1]heptan-3-one; wherein the alkyl, aryl or aralkyl group is optionally substituted with one or more substituents independently selected from alkyl, halogenated alkyl, alkoxy, halogen, hydroxy, nitro, cyano, —OC(O)-alkyl or —C(O)O-alkyl;

alternatively two R^G groups are taken together with the nitrogen atom to which they are bound to form a heterocycloalkyl group; wherein the heterocycloalkyl group is optionally substituted with one or more substituents independently selected from halogen, hydroxy, alkyl, alkoxy, carboxy, amino, alkylamino, dialkylamino, nitro or cyano;

m is an integer selected from 0 to 4;

each R^4 is independently selected from the group consisting of halogen, hydroxy, R^C, amino, alkylamino, dialkylamino, nitro, cyano, —C(O)R^G, —C(O)OR^G, —OC(O)R^G, —OC(O)OR^G, —OC(O)N(R^G)_2, —N(R^G)C(O)R^G, —OSi (R^G)_3, —OR^G, —SO_2N(alkyl)_2, —O-(alkyl)_{1-4}-C(O)R^G and —O-(alkyl)_{1-4}-C(O)OR^G;

or a pharmaceutically acceptable salt thereof.

The present invention is further directed to a process for the preparation of a compound of formula (DX)

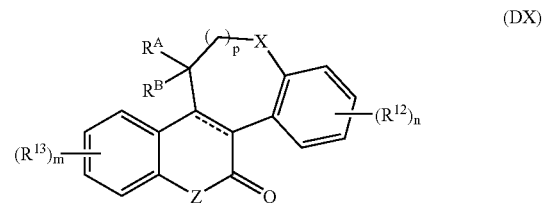

wherein

---- represents a single or double bond,

X is selected from the group consisting of O and S;

p is an integer from 0 to 2;

R^A and R^B are each independently selected from hydrogen, hydroxy, alkyl or alkoxy; provided that R^A and R^B are not each hydroxy;

Z is selected from the group consisting of O and S;

n is an integer from 0 to 4;

each R^{12} is independently selected from the group consisting of halogen, hydroxy, alkyl, alkoxy, trialkylsilyl, acyloxy, benzoyloxy, aryloxy, aralkyloxy, SEMoxy, MOMoxy and pivaloyloxy;

m is an integer selected from 0 to 4;

each R^{13} is independently selected from the group consisting of halogen, hydroxy, alkyl, alkoxy, trialkylsilyl, acyloxy, benzoyloxy, aryloxy, aralkyloxy, SEMoxy, MOMoxy and pivaloyloxy;

or a pharmaceutically acceptable salt thereof;

comprising

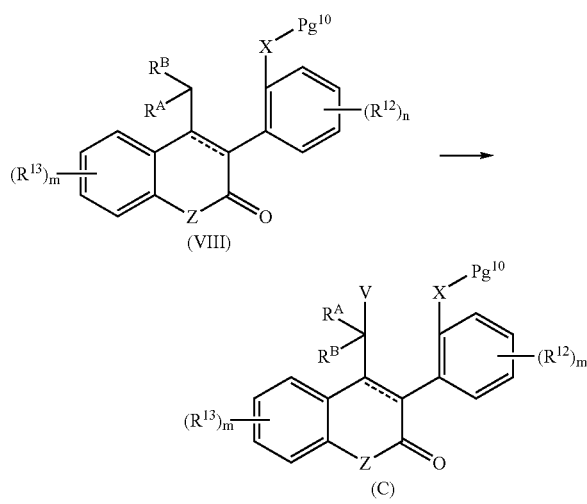

reacting a suitable substituted compound of formula (VIII), a known compound or compound prepared by known methods, wherein $Pg^{10}$ is a protecting group, with an organic base selected from the group consisting of NaHMDS, LiHMDS, KHMDS, LDA and di(lower alkyl)amino lithium, to yield the corresponding compound of formula (C), wherein V is the corresponding base cation;

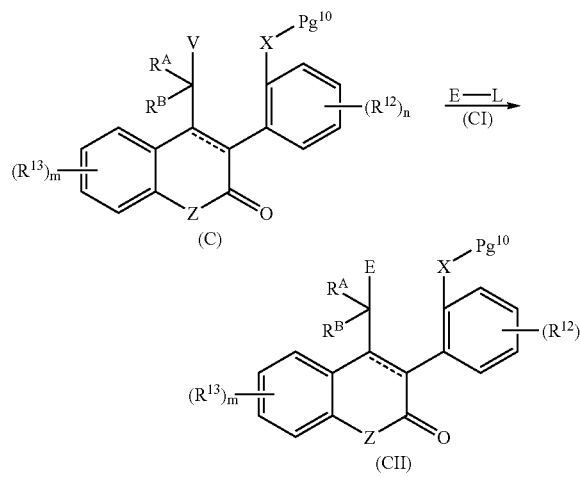

reacting the compound of formula (C) with a suitably substituted compound of formula (CI), wherein E is an electrophile and L is a leaving group, to yield the corresponding compound of formula (CII);

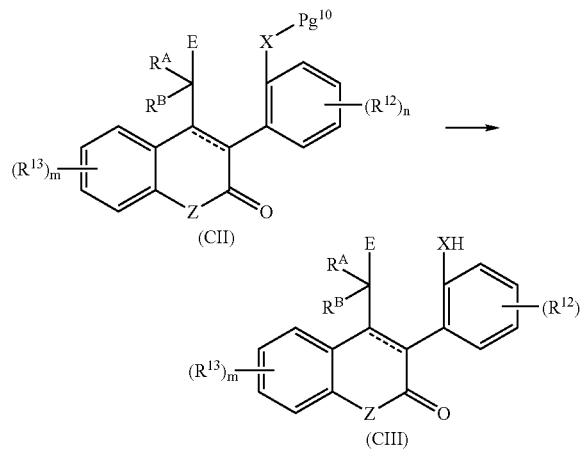

de-protecting the compound of formula (CII), to yield the corresponding compound of formula (CIII);

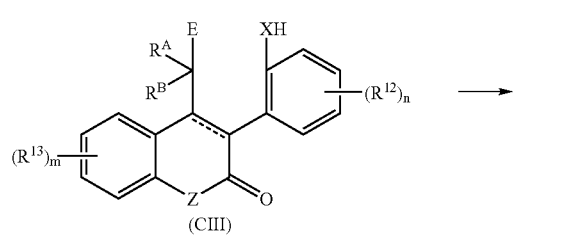

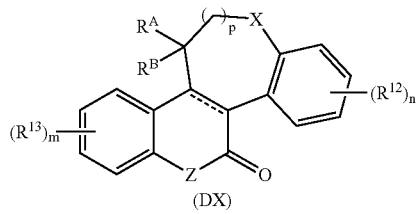

cyclizing the compound of formula (CIII), to yield the corresponding compound of formula (DX).

The present invention is further directed to a process for the preparation of a compound of formula (DXI)

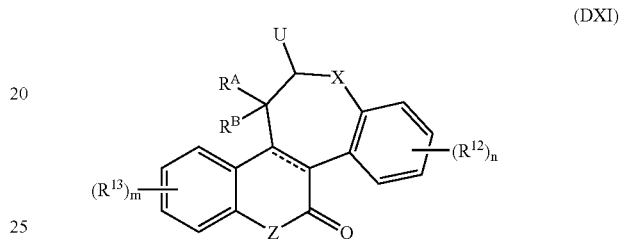

wherein
---- represents a single or double bond,
X is selected from the group consisting of O and S;
U is selected from the group consisting of hydrogen and alkyl;
$R^A$ and $R^B$ are each independently selected from hydrogen, hydroxy, alkyl or alkoxy; provided that $R^A$ and $R^B$ are not each hydroxy;
Z is selected from the group consisting of O and S;
n is an integer from 0 to 4;
each $R^{12}$ is independently selected from the group consisting of halogen, hydroxy, alkyl, alkoxy, trialkylsilyl, acyloxy, benzoyloxy, aryloxy, aralkyloxy, SEMoxy, MOMoxy and pivaloyloxy;
m is an integer selected from 0 to 4;
each $R^{13}$ is independently selected from the group consisting of halogen, hydroxy, alkyl, alkoxy, trialkylsilyl, acyloxy, benzoyloxy, aryloxy, aralkyloxy, SEMoxy, MOMoxy and pivaloyloxy;
or a pharmaceutically acceptable salt thereof;
comprising

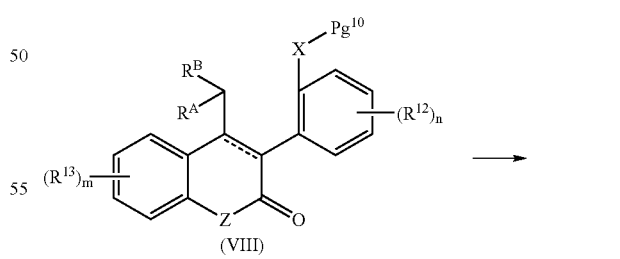

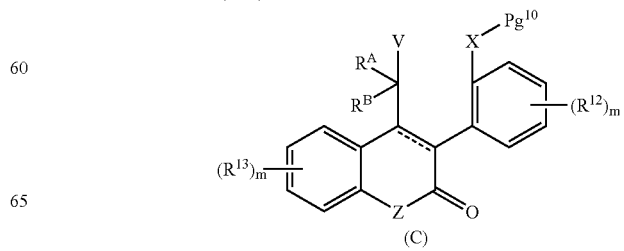

reacting a suitable substituted compound of formula (VIII), a known compound or compound prepared by known methods, wherein $Pg^{10}$ is a protecting group, with an organic base selected from the group consisting of NaHMDS, LiHMDS, KHMDS, LDA and di(lower alkyl)amino lithium, to yield the corresponding compound of formula (C), wherein V is the corresponding base cation;

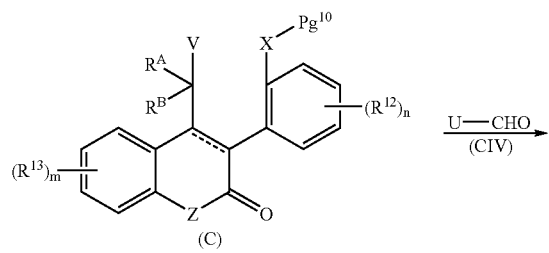

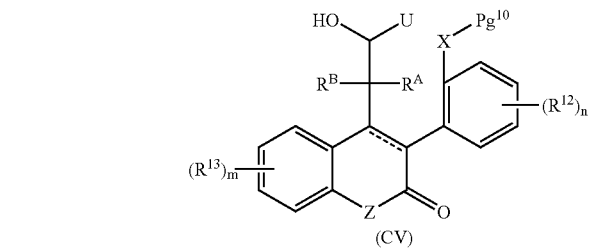

reacting the compound of formula (C) with a suitably substituted aldehyde, a compound of formula (CIV), to yield the corresponding compound of formula (CV);

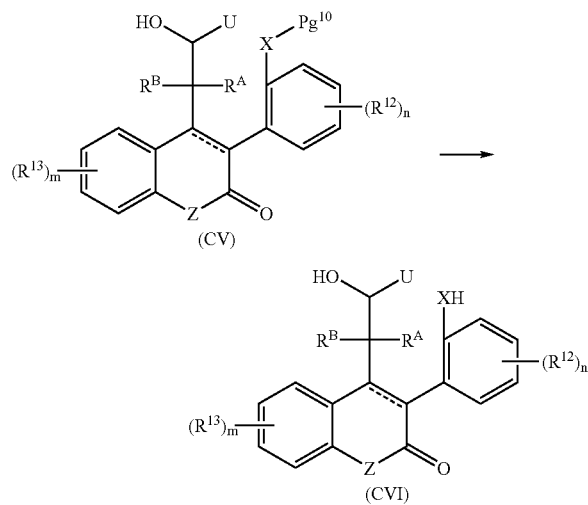

de-protecting the compound of formula (CV), to yield the corresponding compound of formula (CVI);

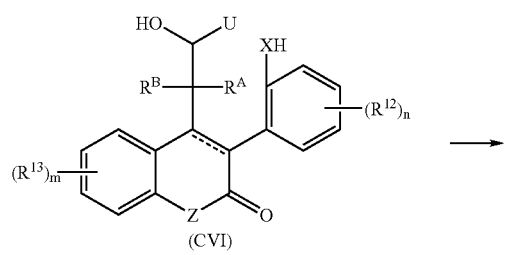

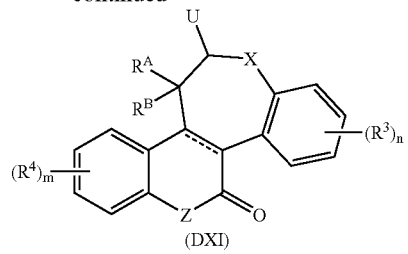

cyclizing the compound of formula (CIVI), to yield the corresponding compound of formula (DXI).

The present invention is further directed to a process for the preparation of a compound of formula (C)

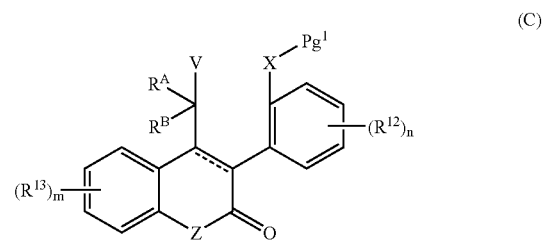

wherein
---- represents a single or double bond,
X is selected from the group consisting of O and S;
$Pg^1$ is a protecting group selected from alkyl, allyl, benzyl, benzoyl, SEM, MOM, BOM and pivaloyl;
V is a base cation selected from the group consisting of Li, Na and K;
$R^A$ and $R^B$ are each independently selected from hydrogen, hydroxy, alkyl or alkoxy; provided that $R^A$ and $R^B$ are not each hydroxy;
Z is selected from the group consisting of O and S;
n is an integer from 0 to 4;
each $R^{12}$ is independently selected from the group consisting of halogen, hydroxy, alkyl, alkoxy, trialkylsilyl, acyloxy, benzoyloxy, aryloxy, aralkyloxy, SEMoxy, MOMoxy and pivaloyloxy;
m is an integer selected from 0 to 4;
each $R^{13}$ is independently selected from the group consisting of halogen, hydroxy, alkyl, alkoxy, trialkylsilyl, acyloxy, benzoyloxy, aryloxy, aralkyloxy, SEMoxy, MOMoxy and pivaloyloxy;
or a pharmaceutically acceptable salt thereof;
comprising

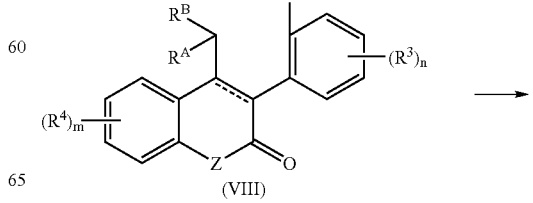

-continued

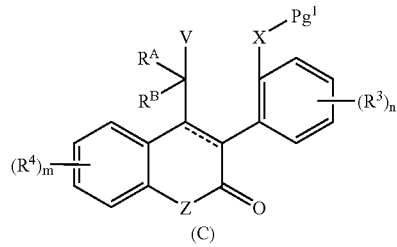

(C)

reacting a suitable substituted compound of formula (VIII), a known compound or compound prepared by known methods, wherein Pg$^1$ is as defined above, with an organic base selected from the group consisting of LiHMDS, LDA, NaHMDS, KHMDS and di(lower alkyl)amino lithium, to yield the corresponding compound of formula (C).

The present invention is further directed to the product prepared according to any of the processes disclosed herein.

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention are methods of treating a disorder mediated by one or more estrogen receptors in a subject in need thereof comprising administering to the subject a therapeutically effective amount of any of the compounds or pharmaceutical compositions described above.

Illustrating the invention is a method of contraception comprising administering to a subject in need thereof co-therapy with a therapeutically effective amount of a compound of formula (I) with a progestogen or progestogen antagonist.

Another example of the invention is the use of any of the compounds described herein in the preparation of a medicament for treating: (a) hot flashes, (b) vaginal dryness, (c) osteopenia, (d) osteoporosis, (e) hyperlipidemia, (f) loss of cognitive function, (g) a degenerative brain disorder, (h) cardiovascular disease, (i) cerebrovascular disease (j) breast cancer, (k) endometrial cancer, (l) cervical cancer, (m) prostate cancer, (n) benign prostatic hyperplasia, (o) endometriosis, (p) uterine fibroids, (q) osteoarthritis and for (r) contraception in a subject in need thereof.

DETAILED DESCRIPTION OF THE INVENTION

The present invention is directed to a compound of formula (I)

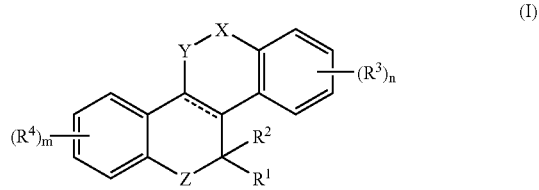

(I)

wherein ----, X, Y, Z, R$^1$, R$^2$, n, R$^3$, m, and R$^4$ are as herein defined, useful for the treatment and/or prevention of disorders mediated by an estrogen receptor. More particularly, the compounds of the present invention are useful for the treatment and/or prevention of disorders mediated by the estrogen-α and/or estrogen-β receptors. More preferably, the compounds of the present invention are tissue selective estrogen receptor modulators.

The compounds of the present invention are further useful in the treatment and/or prevention of disorders associated with the depletion of estrogen, hormone sensitive cancers and hyperplasia, endometriosis, uterine fibroids, osteoarthritis and as contraceptive agents, alone or in combination with a progestogen or progestogen antagonist.

More particularly, the compounds of the present invention are useful in the treatment and/or prevention of a condition or disorder selected from the group consisting of hot flashes, vaginal dryness, osteopenia, osteoporosis, hyperlipidemia, loss of cognitive function, degenerative brain diseases, cardiovascular diseases, cerebrovascular diseases, cancer or hyperplasia of the breast tissue, cancer or hyperplasia of the endometrium, cancer or hyperplasia of the cervix, cancer or hyperplasia of the prostate, endometriosis, uterine fibroids and osteoarthritis; and as a contraceptive agent. Preferably, the disorder is selected from the group consisting of osteoporosis, hot flashes, vaginal dryness, breast cancer, and endometriosis.

In the compound of formula (I), the relative orientation of the groups R$^1$ and R$^2$ is not intended to be fixed, rather both possible orientations of the groups are intended to be included within the definition of the compound of formula (I).

Wherein the compound of formula (I) Y is CR$^A$R$^B$C(O), the group is incorporated into the core structure such that the carbonyl portion of the group is bound to the X atom.

The present invention is further directed to compounds of formula (D).

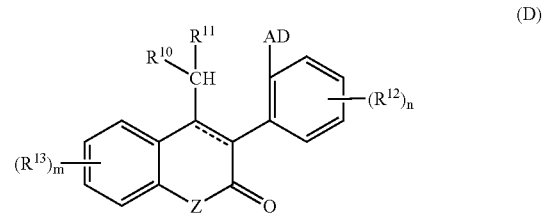

(D)

wherein ----, A, D, Z, R$^{10}$, R$^{11}$, n, R$^{12}$, m and R$^{13}$ are as herein defined, useful as intermediates in the preparation of the compounds of formula (I).

The present invention is further directed to a compounds of formula (DI)

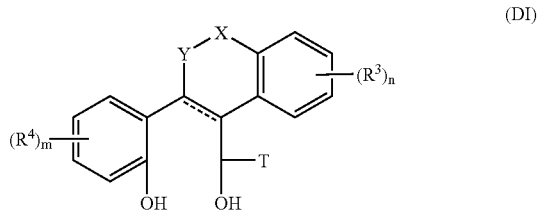

(DI)

wherein ----, X, Y, T, n, R$^3$, m and R$^4$ are as herein defined, useful as intermediates in the preparation of the compounds of formula (I).

In an embodiment of the present invention is a compound of formula (I) wherein ---- represents a single or double bond, X is selected from the group consisting of O and S and Y is selected from the group consisting of $CR^A R^B$, $CR^A R^B (CH_2)_{1-2}$, $CR^A R^B C(O)$ and $C(O)$; alternatively Y is selected from the group consisting of O and S and X is selected from the group consisting of $CR^A R^B$ and $C(O)$;

provided that when X is S, then Y is selected from the group consisting of $CR^A R^B$ and $CR^A R^B (CH_2)_{1-2}$; provided further that when Y is S, then X is selected from the group consisting of $CR^A R^B$;

wherein each $R^A$ and $R^B$ is independently selected from hydrogen, hydroxy, alkyl or alkoxy; provided that $R^A$ and $R^B$ are not each hydroxy;

Z is selected from the group consisting of O and S;

$R^1$ is selected from the group consisting of hydrogen, alkyl, cycloalkyl, aryl, aralkyl, heteroaryl and heteroaryl-alkyl; wherein the cycloalkyl, aryl, aralkyl, heteroaryl or heteroaryl-alkyl group is optionally substituted with one or more substituents independently selected from halogen, hydroxy, alkyl, alkoxy, —SH, —S(alkyl), $SO_2$, $NO_2$, CN, $CO_2H$, $R^C$, —$OR^C$, —$SO_2$—$NR^D R^E$, —$NR^D R^E$, $NR^D$—$SO_2$—$R^F$, -(alkyl)$_{0-4}$-C(O)$NR^D R^E$, (alkyl)$_{0-4}$-$NR^D$—C(O)—$R^F$, -(alkyl)$_{0-4}$-(Q)$_{0-1}$-(alkyl)$_{0-4}$-$NR^D R^E$, -(alkyl)$_{0-4}$-(Q)$_{0-1}$-(alkyl)$_{0-4}$-C(O)—$OR^F$, -(alkyl)$^{0-4}$-(Q)$_{0-1}$-(alkyl)$_{0-4}$-C(O)—$NR^D R^E$ or -(alkyl)$_{0-4}$-C(O)-(alkyl)$_{0-4}$-C(O)—$OR^F$;

wherein $R^C$ is selected from the group consisting of alkyl, cycloalkyl, cycloalkyl-alkyl, aryl, aralkyl, heteroaryl, heteroaryl-alkyl, heterocycloalkyl and heterocycloalkyl-alkyl; wherein the cycloalkyl, cycloalkyl-alkyl, aryl, aralkyl, heteroaryl, heteroaryl-alkyl, heterocycloalkyl or heterocycloalkyl-alkyl group is optionally substituted with one or more substituents independently selected from halogen, hydroxy, alkyl, alkoxy, —SH, —S(alkyl), $SO_2$, $NO_2$, CN, $CO_2H$, $R^C$, —$SO_2$—$NR^D R^E$, $NR^D R^E$, $NR^D$—$SO_2$—$R^F$, -(alkyl)$_{0-4}$-C(O)—$NR^D R^E$, -(alkyl)$_{0-4}$-$NR^D$—C(O)—$R^F$, -(alkyl)$_{0-4}$-(Q)$_{0-1}$-(alkyl)$_{0-4}$-$NR^D R^E$, -(alkyl)$_{0-4}$-(Q)$_{0-1}$-(alkyl)$_{0-4}$-C(O)—$OR^F$, -(alkyl)$^{0-4}$-(Q)$_{0-1}$-(alkyl)$_{0-4}$-C(O)—$NR^D R^E$ or -(alkyl)$_{0-4}$-C(O)-(alkyl)$_{0-4}$-C(O)—$OR^F$;

wherein Q is selected from the group consisting of O, S, NH, N(alkyl) and —CH=CH—;

wherein $R^D$ and $R^E$ are each independently selected from the group consisting of hydrogen and alkyl; alternatively $R^D$ and $R^E$ are taken together with the nitrogen atom to which they are bound to form a 4 to 8 membered ring selected from the group consisting of heteroaryl or heterocycloalkyl; wherein the heteroaryl or heterocycloalkyl group is optionally substituted with one or more substituents independently selected from halogen, hydroxy, alkyl, alkoxy, carboxy, amino, alkylamino, dialkylamino, nitro or cyano;

wherein $R^F$ is selected from the group consisting of hydrogen, alkyl, cycloalkyl, cycloalkyl-alkyl, aryl, aralkyl, heteroaryl, heteroaryl-alkyl, heterocycloalkyl and heterocycloalkyl-alkyl; wherein the cycloalkyl, aryl, heteroaryl, heteroaryl-alkyl, heterocycloalkyl or heterocycloalkyl-alkyl group is optionally substituted with one or more substituents independently selected from halogen, hydroxy, alkyl, alkoxy, carboxy, amino, alkylamino, dialkylamino, nitro or cyano;

$R^2$ is selected from the group consisting of hydroxy, alkyl, cycloalkyl, aryl, aralkyl, heteroaryl and heteroaryl-alkyl; wherein the cycloalkyl, aryl, aralkyl, heteroaryl or heteroaryl-alkyl group is optionally substituted with one or more substituents independently selected from halogen, hydroxy, alkyl, alkoxy, —SH, —S(alkyl), $SO_2$, $NO_2$, CN, $CO_2H$, $R^C$, —$OR^C$, —$SO_2$—$NR^D R^E$, $NR^D R^E$, $NR^D$—$SO_2$—$R^F$, -(alkyl)$_{0-4}$-C(O)$NR^D R^E$, (alkyl)$_{0-4}$-$NR^D$—C(O)—$R^F$, -(alkyl)$_{0-4}$-(Q)$_{0-1}$-(alkyl)$_{0-4}$-$NR^D R^E$, -(alkyl)$_{0-4}$-(Q)$_{0-1}$-(alkyl)$_{0-4}$-C(O)—$OR^F$, -(alkyl)$^{0-4}$-(Q)$_{0-1}$-(alkyl)$_{0-4}$-C(O)—$NR^D R^E$ or -(alkyl)$_{0-4}$-C(O)-(alkyl)$_{0-4}$-C(O)—$OR^F$;

alternatively, $R^1$ and $R^2$ are taken together with the carbon atom to which they are bound to form C(O);

provided that when $R^1$ and $R^2$ are taken together with the carbon atom to which they are bound to form C(O) and X is selected from the group consisting of O and S, then Y is selected from the group consisting of $CR^A R^B$ and $CR^A R^B (CH_2)_{1-2}$;

provided further that when $R^1$ and $R^2$ are taken together with the carbon atom to which they are bound to form C(O) and Y is selected from the group consisting of O and S, then X is selected from the group consisting of $CR^A R^B$;

n is an integer selected from 0 to 4;

each $R^3$ is independently selected from the group consisting of halogen, hydroxy, $R^C$, amino, alkylamino, dialkylamino, nitro, cyano, $SO_2$, —$C(O)R^G$, —$C(O)OR^G$, —$OC(O)R^G$, —$OC(O)OR^G$, —$OC(O)N(R^G)_2$, —$N(R^G)C(O)R^G$, —$OSi(R^G)_3$, —$OR^G$, —$SO_2 N(R^G)_2$, —O-(alkyl)$_{1-4}$-$C(O)R^G$ and —O-(alkyl)$_{1-4}$-$C(O)OR^G$;

wherein each $R^G$ is independently selected from hydrogen, alkyl, aryl, aralkyl and 1,7,7-trimethyl-2-oxabicyclo[2.2.1]heptan-3-one; wherein the alkyl, aryl or aralkyl group is optionally substituted with one or more substituents independently selected from alkyl, halogenated alkyl, alkoxy, halogen, hydroxy, nitro, cyano, —OC(O)alkyl or —C(O)O-alkyl;

alternatively two $R^G$ groups are taken together with the nitrogen atom to which they are bound to form a heterocycloalkyl group; wherein the heterocycloalkyl group is optionally substituted with one or more substituents independently selected from halogen, hydroxy, alkyl, alkoxy, carboxy, amino, alkylamino, dialkylamino, nitro or cyano;

m is an integer selected from 0 to 4;

each $R^4$ is independently selected from the group consisting of halogen, hydroxy, $R^C$, amino, alkylamino, dialkylamino, nitro, cyano, $SO_2$, —$C(O)R^G$, —$C(O)OR^G$, —$OC(O)R^G$, —$OC(O)OR^G$, —$OC(O)N(R^G)_2$, —$N(R^G)C(O)R^G$, —$OSi(R^G)_3$, —$OR^G$, —$SO_2 N(alkyl)_2$, —O-(alkyl)$_{1-4}$—$C(O)R^G$ and —O-(alkyl)$_{1-4}$-$C(O)OR^G$;

provided that when ---- is a double bond, X is $CH_2$, Y is O, Z is O and $R^1$ and $R^2$ are taken together with the carbon atom to which they are bound to form C(O), then at least one of n or m is an integer selected from 1 to 4; preferably, n is an integer from 1 to 4 and m is an integer from 1 to 4;

provided further that when ---- is a single bond, X is O, Y is CH(alkyl), Z is O, $R^1$ is hydrogen and $R^2$ is alkyl, then at least one of n or m is an integer selected from 1 to 4; preferably, n is an integer from 1 to 4 and m is an integer from 1 to 4;

provided further that when ---- is a single bond, X is O, Y is CH(alkyl), Z is O, $R^1$ is hydrogen, $R^2$ is alkyl, n is 1 and m is 1, then $R^3$ and $R^4$ are other than methoxy or ethoxy, preferably $R^3$ and $R^4$ are other than alkoxy;

provided further that when ---- is a double bond, X is O, Y is $CH_2$, Z is O, $R^1$ and $R^2$ are taken together with the carbon atom to which they are bound to form C(O), n is 0 and m is 2, then each $R^4$ is not hydroxy or alkoxy.

or a pharmacetucailly acceptable salt thereof.

In an embodiment of the present invention, ---- represents a double bond.

In an embodiment of the present invention, when X is S, then Y is selected from the group consisting of $CR^A R^B$, $CR^A R^B (CH_2)_{1-2}$, $CR^A R^B C(O)CR^A R^B$ (preferably $CH=2C(O)CH_2$) and $CH_2 CH_2 CH_2$; preferably Y is $CR^A R^B$ or $CR^A R^B (CH_2)_{1-2}$. In another embodiment of the present invention, when when Y is S, then X is $CR^A R^B$. In yet another embodiment of the present invention Y is selected from the group consisting of —$CR^AR^B$—$CH_2$—, —$CH_2CR^AR^BCH_2$—, —$CR^AR^B$—CH(OH)—$CR^AR^B$— and —$CR^AR^B$—$CH_2$—$CR^AR^B$—.

In an embodiment of the present invention ---- represents a double bond; X is O; Z is O; and Y is selected from the group consisting of —$CH_2$—, —$CH_2CH_2$—, —$CH_2CH_2CH_2$—, —CH(lower alkoxy)-, —CH(OH)—, —CH(lower alkyl)-, —$CH_2C(O)$—, —$CH_2C(O)CH_2$— and —$CH_2CH(OH)CH_2$—; preferably Y is selected from the group consisting of —$CH_2$—, —$CH_2CH_2$—, —$CH_2CH_2CH_2$, —$CH(OCH_3)$—, —CH(OH)—, —CH$((CH(CH_3)_2))$—, —$CH_2C(O)$—, —$CH_2C(O)CH_2$— and $CH_2CH(OH)CH_2$—; more preferably, Y is selected from the group consisting of —$CH_2$—, —$CH_2CH_2$—, —$CH_2CH_2CH_2$—, —$CH(OCH_3)$— and —CH(OH)—; more preferably still, Y is selected from the group consisting of —$CH_2$—, —$CH_2CH_2$—, —$CH_2CH_2CH_2$— and —CH(OH).

In another embodiment of the present invention ---- represents a double bond; X is O; Z is O; and Y is selected from the group consisting of —$CH_2$—, —$CH_2CH_2$—, —CH(lower alkoxy)-, —CH(OH)—, —CH(lower alkyl)- and —$CH_2C(O)$—; preferably Y is selected from the group consisting of —$CH_2$—, —$CH_2CH_2$—, —$CH(OCH_3)$—, —CH(OH)—, —CH$((CH(CH_3)_2))$— and —$CH_2C(O)$—; more preferably Y is selected from the group consisting of —$CH_2$—, —$CH(OCH_3)$— and —CH(OH)—; more preferably still Y is selected from the group consisting of —$CH_2$— and —CH(OH)—.

In an embodiment of the present invention are compounds of formula (I) wherein X is O, Y is $CR^AR^B$ and Z is O. In another embodiment of the present invention are compounds of formula (I) wherein X is $CR^AR^B$, Y is O and Z is O. In yet another embodiment of the present invention are compounds of formula (I) wherein X is O, Y is $CR^AR^BC(O)$ and Z is O. In yet another embodiment of the present invention are compounds of formula (I) wherein X is O, Z is O and Y is —$CH_2C(O)CH_2$—. In yet another embodiment of the present invention are compounds of formula (I) wherein X is O, Z is O and Y is selected from the group consisting of —$CH_2$—, —$CH_2CH_2$— and —$CH_2CH_2CH_2$—.

In an embodiment of the present invention X is selected from the group consisting of O and S, preferably X is O. In another embodiment of the present invention Y is selected from the group consisting of O and S, preferably Y is O. Preferably Z is O.

In an embodiment of the present invention X is $CR^AR^B$. In another embodiment of the present invention Y is selected from the group consisting of $CR^AR^B$, $CR^AR^BCH_2$ and $CR^AR^BC(O)$.

In an embodiment of the present invention $R^A$ and $R^B$ are each independently selected from the group consisting of hydrogen, hydroxy, alkyl and alkoxy; provided that $R^A$ and $R^B$ are not each hydroxy. In a preferred embodiment of the present invention $R^A$ and $R^B$ are each independently selected from the group consisting of hydrogen hydroxy, isopropyl and methoxy; provided that both $R^A$ and $R^B$ are not hydroxy. In yet another embodiment of the present invention, $R^A$ and $R^B$ are each independently selected from the group consisting of hydrogen, hydroxy and methoxy.

In an embodiment of the present invention, $R^1$ is selected from the group consisting of hydrogen, lower alkyl, lower alkenyl, aryl, —C(O)-aryl, aralkyl, heteroaryl and heteroaryl-(lower alkyl); wherein the lower alkyl, aryl, aralkyl, heteroaryl or heteroaryl-(lower alkyl) group is optionally substituted with one to two substituents independently selected from halogen, hydroxy, lower alkyl, lower alkoxy, —SH, —S(lower alkyl), $SO_2$, $NO_2$, CN, —C(O)-(lower alkyl), $CO_2H$, $R^C$, —$SO_2$—$NR^DR^E$, —$NR^DR^E$, $NR^D$—$SO_2$—$R^F$, -(alkyl)$_{0-4}$-C(O)$NR^DR^E$, —C(O)O-(lower alkyl)-$NR^DR^E$, —C(O)—NH-(lower alkyl)-$NR^DR^E$, —C(O)—(N containing heterocycloalkyl (wherein said N containing heterocycloalkyl is bound through the N atom))-$NR^DR^E$, —C(O)—(N containing heterocycloalkyl (wherein said N containing heterocycloalkyl is bound through the N atom))-$R^F$, -(alkyl)$_{0-4}$-$NR^D$—C(O)—$R^F$, -(alkyl)$_{0-4}$-(Q)$_{0-1}$-(alkyl)$_{0-4}$-$NR^DR^E$, -(alkyl)$_{0-4}$-(Q)$_{0-1}$-(alkyl)$_{0-4}$-C(O)—$OR^F$, -(alkyl)$_{0-4}$-(Q)$_{0-1}$-(alkyl)$_{0-4}$-C(O)—$NR^DR^E$, -(alkyl)$_{0-4}$-C(O)-(alkyl)$_{0-4}$-C(O)—$OR^F$, —O-(lower alkyl)-OSi(lower alkyl)$_3$, —O-(lower alkyl)-$OR^D$ or —O-(lower alkyl)-formy.

In another embodiment of the present invention $R^1$ is selected from the group consisting of hydrogen and lower alkyl, preferably $R^1$ is selected from the group consisting of hydrogen and methyl. In another embodiment of the present invention, $R^1$ is hydrogen.

In an embodiment of the present invention $R^1$ is hydrogen and $R^2$ is in the R stereo-configuration. In another embodiment of the present invention $R^1$ is hydrogen and $R^2$ is in the S stereo-configuration.

In an embodiment of the present invention $R^1$ is selected from the group consisting of hydrogen, lower alkyl, aryl, aralkyl, heteroaryl and heteroaryl-(lower alkyl); wherein the aryl, aralkyl, heteroaryl or heteroaryl-(lower alkyl) group is optionally substituted with one to two substituents independently selected from halogen, hydroxy, lower alkyl, lower alkoxy, —SH, —S(lower alkyl), $SO_2$, $NO_2$, CN, $CO_2H$, $R^C$, —$SO_2$—$NR^DR^E$, $NR^DR^E$, $NR^D$—$SO_2$—$R^F$, -(alkyl)$_{0-4}$-C(O)$NR^DR^E$, (alkyl)$_{0-4}$-$NR^D$—C(O)$R^F$, -(alkyl)$_{0-4}$-(Q)$_{0-1}$-(alkyl)$_{0-4}$-$NR^DR^E$, -(alkyl)$_{0-4}$-(Q)$_{0-1}$-(alkyl)$_{0-4}$-C(O)—$OR^F$, -(alkyl)$_{0-4}$-(Q)$_{0-1}$-(alkyl)$_{0-4}$-C(O)—$NR^DR^E$ or -(alkyl)$_{0-4}$-C(O)-(alkyl)$_{0-4}$-C(O)—$OR^F$.

Preferably $R^1$ is selected from the group consisting of hydrogen, lower alkyl, aryl, aralkyl, heteroaryl and heteroaryl-(lower alkyl); wherein the aryl, aralkyl, heteroaryl or heteroaryl-(lower alkyl) group is optionally substituted with one to two substituents independently selected from halogen, hydroxy, lower alkyl, lower alkoxy, —SH, —S(lower alkyl), $SO_2$, $NO_2$, CN, $CO_2H$, $R^C$ or $NR^DR^E$, More preferably, $R^1$ is selected from the group consisting of hydrogen and lower alkyl. More preferably still, $R^1$ is selected from the group consisting of hydrogen and methyl.

In an embodiment of the present invention $R^C$ is selected from the group consisting of lower alkyl, aryl, aralkyl, heteroaryl, heteroaryl-(lower alkyl), heterocycloalkyl and heterocycloalkyl-(lower alkyl); wherein the aryl, aralkyl, heteroaryl, heteroaryl-(lower alkyl), heterocycloalkyl or heterocycloalkyl-(lower alkyl) group is optionally substituted with one to two substituents independently selected from halogen, hydroxy, lower alkyl, lower alkoxy, —SH, —S(alkyl), $SO_2$, $NO_2$, CN, $CO_2H$, $R^C$, —$SO_2$—$NR^DR^E$, $NR^D$—$SO_2$—$R^F$, -(alkyl)$_{0-4}$-C(O)—$NR^DR^E$, -(alkyl)$_{0-4}$-$NR^D$—C(O)—$R^F$, -(alkyl)$_{0-4}$-(Q)$_{0-1}$-(alkyl)$_{0-4}$-$NR^DR^E$, -(alkyl)$_{0-4}$-(Q)$_{0-1}$-(alkyl)$_{0-4}$-C(O)—$OR^F$, -(alkyl)$^{0-4}$-(Q)$_{0-1}$-(alkyl)$_{0-4}$-C(O)—$NR^DR^E$ or -(alkyl)$_{0-4}$-C(O)-(alkyl)$_{0-4}$-C(O)—$OR^F$.

Preferably, $R^C$ is selected from the group consisting of lower alkyl, aryl, aralkyl, heteroaryl, heteroaryl-(lower alkyl), heterocycloalkyl and heterocycloalkyl-(lower alkyl); wherein the aryl, aralkyl, heteroaryl, heteroaryl-(lower alkyl), heterocycloalkyl or heterocycloalkyl-(lower alkyl) group is optionally substituted with one to two substituents independently selected from halogen, hydroxy, lower alkyl, lower alkoxy, —SH, —S(alkyl), $SO_2$, $NO_2$, CN, $CO_2H$, $R^C$ or $NR^DR^E$.

More preferably $R^C$ is selected from the group consisting of lower alkyl, and aralkyl. More preferably still, $R^C$ is selected from the group consisting of methyl, isopropyl and benzyl.

In an embodiment of the present invention, Q is selected from the group consisting of O, S and —CH═CH—. Preferably, Q is selected from the group consisting of O and —CH═CH—, more preferably, Q is O.

In an embodiment of the present invention $R^D$ and $R^E$ are each independently selected from the group consisting of hydrogen and lower alkyl. In another embodiment of the present invention, $R^D$ and $R^E$ are taken together with the nitrogen atom to which they are bound to form a 4 to 8 membered ring selected from the group consisting of heteroaryl or heterocycloalkyl; wherein the heteroaryl or heterocycloalkyl group is optionally substituted with one to two substituents independently selected from halogen, hydroxy, lower alkyl, lower alkoxy, carboxy, amino, (lower alkyl)-amino, di(lower alkyl)amino, nitro or cyano. In another embodiment of the present invention, $R^D$ and $R^E$ are taken together with the nitrogen atom to which they are bound to form a 5 to 6 membered ring selected from the group consisting of heteroaryl or heterocycloalkyl; wherein the heteroaryl or heterocycloalkyl group is optionally substituted with one to two substituents independently selected from halogen, hydroxy, lower alkyl, lower alkoxy, carboxy, amino, (lower alkyl)-amino, di(lower alkyl)amino, nitro or cyano.

In another embodiment of the present invention, $R^D$ and $R^E$ are each independently selected from the group consisting of hydrogen, methyl, ethyl and isopropyl.

In another embodiment of the present invention, $R^D$ and $R^E$ are taken together with the nitrogen atom to which they are bound to form a 5 to 6 membered ring selected from the group consisting of heteroaryl or heterocycloalkyl; wherein the heteroaryl or heterocycloalkyl group is optionally substituted with one to two substituents independently selected from halogen, hydroxy, oxo, lower alkyl, lower alkoxy, carboxy, amino, (lower alkyl)-amino, di(lower alkyl)amino, nitro or cyano. Preferably, $R^D$ and $R^E$ are taken together with the nitrogen atom to which they are bound to form a 5 to 6 membered ring selected from the group consisting of azepanyl, morpholinyl, pyridyl, piperidinyl, piperazinyl, pyrrolidinyl, piperidinyl-2,6-dione and pyrrolidinyl-2,5-dione.

In an embodiment of the present invention $R^F$ is selected from the group consisting of hydrogen, lower alkyl, aryl, aralkyl, heteroaryl, heteroaryl-(lower alkyl), heterocycloalkyl and heterocycloalkyl-(lower alkyl); wherein the aryl, heteroaryl, heteroaryl-(lower alkyl), heterocycloalkyl or heterocycloalkyl-(lower alkyl) group is optionally substituted with one to two substituents independently selected from halogen, hydroxy, lower alkyl, lower alkoxy, carboxy, amino, (lower alkyl)-amino, di(lower alkyl)amino, nitro or cyano. Preferably $R^F$ is selected from the group consisting of hydrogen, lower alkyl, aryl and heteroaryl; wherein the aryl is optionally substituted with a halogen. More preferably, $R^F$ is selected from the group consisting of hydrogen, methyl, 4-fluorophenyl and 2-pyridyl.

In an embodiment of the present invention $R^2$ is selected from the group consisting of hydroxy, lower alkyl, aryl, aralkyl, heteroaryl and heteroaryl-(lower alkyl); wherein the aryl, aralkyl, heteroaryl or heteroaryl-(lower alkyl) group is optionally substituted with one to two substituents independently selected from halogen, hydroxy, lower alkyl, lower alkoxy, —SH, —S(lower alkyl), $SO_2$, $NO_2$, CN, $CO_2H$, $R^C$, —$OR^C$, —$SO_2$—$NR^DR^E$, —$NR^DR^E$, -(alkyl)$_{0-4}$-C(O)$NR^DR^E$, (alkyl)$_{0-4}$-$NR^D$—C(O)—$R^F$, -(alkyl)$_{0-4}$-(Q)$_{0-1}$-(alkyl)$_{0-4}$-$NR^DR^E$, -(alkyl)$_{0-4}$-(Q)$_{0-1}$-(alkyl)$_{0-4}$-C(O)—$OR^F$, -(alkyl)$_{0-4}$-(Q)$_{0-1}$-(alkyl)$_{0-4}$-C(O)—$NR^DR^E$ or -(alkyl)$_{0-4}$-C(O)-(alkyl)$_{0-4}$-C(O)—$OR^F$.

Preferably, $R^2$ is selected from the group consisting of hydroxy, lower alkyl, aryl, aralkyl, heteroaryl and heteroaryl-(lower alkyl); wherein the aryl, aralkyl, heteroaryl or heteroaryl-(lower alkyl) group is optionally substituted with one to two substituents independently selected from halogen, hydroxy, lower alkyl, lower alkoxy, —SH, —S(lower alkyl), $SO_2$, $NO_2$, CN, $CO_2H$, $R^C$, —$OR^C$ or —$NR^DR^E$.

More preferably, $R^2$ is selected from the group consisting of hydroxy, aryl, 4-(1-heterocycloalkyl-alkoxy)-phenyl, 4-(di(alkyl)amino-alkoxy)-phenyl, 4-(di(alkyl)amino)-phenyl and 4-aralkyloxy-phenyl. More preferably still, $R^2$ is selected from the group consisting of hydroxy, phenyl, 4-(1-piperidinyl-ethoxy)-phenyl, 4-(1-pyrrolidinyl-ethoxy)-phenyl, 4-(4-morpholinyl-ethoxy)-phenyl, 4-(1-azepanyl-ethoxy)-phenyl, 4-(diethylamino-ethoxy)-phenyl, 4-(dimethylamino-ethoxy)-phenyl, 4-(dimethylamino)-phenyl, 4-benzyloxy-phenyl and 4-(1-piperidinyl-n-propoxy)-phenyl. More preferably still, $R^2$ is selected from the group consisting of phenyl, 4-(1-piperidinyl-ethoxy)-phenyl, 4-(1-pyrrolidinyl-ethoxy)-phenyl, 4-(4-morpholinyl-ethoxy)-phenyl, 4-(1-azepanyl-ethoxy)-phenyl, 4-(diethylamino-ethoxy)-phenyl, 4-(dimethylamino-ethoxy)-phenyl, 4-(dimethylamino)-phenyl and 4-(1-piperidinyl-n-propoxy)-phenyl. More preferably still, $R^2$ is selected from the group consisting of phenyl, 4-(1-piperidinyl-ethoxy)-phenyl, 4-(1-pyrrolidinyl-ethoxy)-phenyl, 4-(4-morpholinyl-ethoxy)-phenyl, 4-(1-azepanyl-ethoxy)-phenyl, 4-(diethylamino-ethoxy)-phenyl, 4-(dimethylamino-ethoxy)-phenyl and 4-(dimethylamino)-phenyl. More preferably still, $R^2$ is selected from the group consisting of phenyl, 4-(1-piperidinyl-ethoxy)-phenyl, 4-(1-pyrrolidinyl-ethoxy)-phenyl, 4-(4-morpholinyl-ethoxy)-phenyl, 4-(1-azepanyl-ethoxy)-phenyl, 4-(dimethylamino-ethoxy)-phenyl and 4-(dimethylamino)-phenyl.

In another embodiment of the present invention $R^2$ is selected from the group consisting of -(alkyl)$^{0-4}$-(Q)$_{0-1}$-(alkyl)$_{0-4}$-$NR^DR^E$ and -(alkyl)$_{0-4}$-(Q)$_{0-1}$-(alkyl)$_{0-4}$-C(O)$OR^F$. In yet another embodiment of the present invention, $R^2$ is selected from the group consisting of -(alkyl)$_{0-4}$-(Q)$_{0-1}$-(alkyl)$_{0-4}$-$NR^DR^E$; wherein $R^D$ and $R^E$ are taken together with the nitrogen atom to which they are bound to form a 5 to 7 membered ring selected from the group consisting of heteroaryl and heterocycloalkyl.

In yet another embodiment of the present invention, $R^2$ is selected from the group consisting of hydroxy, lower alkyl, lower alkenyl, aryl, —C(O)-aryl, aralkyl, heteroaryl and heteroaryl-(lower alkyl); wherein the lower alkyl, aryl, aralkyl, heteroaryl or heteroaryl-(lower alkyl) group is optionally substituted with one to two substituents independently selected from halogen, hydroxy, lower alkyl, lower alkoxy, —SH, —S(lower alkyl), $SO_2$, $NO_2$, CN, —C(O)-(lower alkyl), $CO_2H$, $R^C$, —$OR^C$, —$SO_2$—$NR^DR^E$, —$NR^DR^E$, -(alkyl)$_{0-4}$-C(O)$NR^DR^E$, —C(O)O-(lower alkyl)-$NR^DR^E$, —C(O)—NH-(lower alkyl)-$NR^DR^E$, —C(O)—(N containing heterocycloalkyl (wherein said N containing heterocycloalkyl is bound through the N atom))-$NR^DR^E$, —C(O)—(N containing heterocycloalkyl, bound through the N atom)-$R^F$, (alkyl)$_{0-4}$-$NR^D$(O)—$R^F$, -(alkyl)$_{0-4}$-(Q)$_{0-1}$-(alkyl)$_{0-4}$-$NR^DR^E$, -(alkyl)$_{0-4}$-(Q)$_{0-1}$-(alkyl)$_{0-4}$-C(O)—$OR^F$, -(alkyl)$_{0-4}$-(Q)$_{0-1}$-(alkyl)$_{0-4}$-C(O)—$NR^DR^E$, -(alkyl)$_{0-4}$-C (O)-(alkyl)$_{0-4}$-C(O)—OR$^F$, —O-(lower alkyl)-OSi(lower alkyl)$_3$, —O-(lower alkyl)-OR$^D$ or —O-(lower alkyl)-formyl.

Preferably, R$^2$ is selected from the group consisting of hydroxy, lower alkenyl, carboxy-lower alkyl, hydroxy-lower alkyl, aryl, 4-(1-N containing heterocycloalkyl (wherein said N containing heterocycloalkyl is bound through the N atom)-alkoxy)-phenyl, 4-(di(lower alkyl) amino-alkoxy)-phenyl, 4-(di(lower alkyl)amino)-phenyl, 4-aralkyloxy-phenyl, lower alkoxy-carbonyl-lower alkyl, 4-(lower alkoxy-lower alkoxy)-phenyl, di(lower alkyl) amino-(lower alkoxy)-carbonyl-(lower alkyl), (N containing heterocycloalkyl (wherein said N containing heterocycloalkyl is bound through the N atom))-(lower alkoxy)-carbonyl-(lower alkyl), (N containing heterocyloalkyl (wherein said N containing heterocycloalkyl is bound through the N atom))-(lower alkyl)-amino-carbonyl-(lower alkyl), (N containing heteroaryl)-(N containing heterocycloalkyl (wherein said N containing heterocycloalkyl is bound through the N atom))-C(O)-(lower alkyl), (halo-substituted aryl)-(N containing heterocycloalkyl (wherein said N containing heterocycloalkyl is bound through the N atom))-carboxy-(lower alkyl), 4-((N containing heterocycloalkyl)-(lower alkoxy))-phenyl-carbonyl, 2-hydroxy-2-(4-N containing heterocycloalkyl-lower alkoxy)-phenyl)-ethyl, 4-(tri(lower alkyl)silyloxy-(lower alkoy)phenyl, 4-(hydroxy-lower alkoxy)-phenyl, 4-(formyl-lower alkoxy)-phenyl, 4-(carboxy-lower alkoxy)-phenyl, 4-(lower alkoxy-carbonyl-lower alkoxy)-phenyl, 4-(piperidinyl-2,6-dione-lower alkoxy)-phenyl, 4-(pyrrolidinyl-2,5-dione-(lower alkyl)phenyl, R-4-(pyrrolidinyl-2,5-dione-(lower alkoxy)-phenyl and S-4-(pyrrolidinyl-2,5-dione-(lower alkoxy)-phenyl.

More preferably, R$^2$ is selected from the group consisting of hydroxy, allyl, carboxymethyl, hydroxy-ethyl, 3-hydroxy-n-propyl, phenyl, 3-(1-piperidinyl-ethoxy)-phenyl, 4-(1-piperidinyl-ethoxy)-phenyl, S-4-(piperidinyl-ethoxy)-phenyl, R-4-(piperidinyl-ethoxy)-phenyl, 4-(1-pyrrolidinyl-ethoxy)-phenyl, 4-(4-morpholinyl-ethoxy)-phenyl, 4-(1-azepanyl-ethoxy)-phenyl, R-4-(1-azepanyl-ethoxy)-phenyl, S-4-(1-azepanyl-ethoxy)-phenyl, 4-(diethylamino-ethoxy)-phenyl, 4-(dimethylamino-ethoxy)-phenyl, R-4-(dimethylamino-ethoxy-phenyl, S-4-(dimethylamino-ethoxy)-phenyl, 4-(diisopropylamino-ethoxy)-phenyl, R-4-(diisopropylamino-ethoxy)-phenyl, S-4-(diisopropylamino-ethoxy)-phenyl, 4-(dimethylamino)-phenyl, 4-benzyloxy-phenyl, 4-(1-piperidinyl-n-propoxy)-phenyl, 4-(t-butyl-dimethyl-silyloxy-ethoxy)-phenyl, 4-(methoxy-ethoxy)-phenyl, methoxy-carbonyl-methyl, isopropoxy-carbonyl-methyl, dimethylamino-ethoxy-carbonyl-methyl, piperidinyl-ethoxy-carbonyl-methyl, pyrrolidinyl-ethoxy-carbonyl-methyl, morpholinyl-ethoxy-carbonyl-methyl, dimethylamino-n-propoxy-carbonyl-methyl and morpholinyl-ethyl-amino-carbonyl-methyl, morpholinyl-n-propyl-amino-carbonyl-methyl, pyrrolidinyl-ethyl-amino-carbonyl-methyl, 4-(2-pyridyl)-piperazinyl-carbonyl-methyl, 4-(4-fluorophenyl)-piperazinyl-carboxy-methyl, 4-(piperidinyl-ethoxy)-phenyl-carbonyl, 2-hydroxy-2-(4-(piperidinyl-ethoxy)-phenyl)-ethyl, 4-(2-hydroxy-ethoxy)-phenyl, R4-(2-hydroxy-ethoxy)-phenyl, S-4-(hydroxy-ethoxy)-phenyl, 4-(3-hydroxy-n-propoxy)-phenyl, R4-(3-hydroxy-n-propoxy)-phenyl, S-4-(3-hydroxy-n-propoxy)-phenyl, 4-(formyl-methoxy)-phenyl, 4-(carboxy-methoxy)-phenyl, 4-carboxy-ethoxy)-phenyl, 4-(methoxy-carbonyl-methoxy)-phenyl, 4-(methoxy-carbonyl-ethoxy)-phenyl, R4-(piperidinyl-2,6-dione-ethoxy)-phenyl, R-4-(pyrrolidinyl-2,5-dione-ethoxy)-phenyl, S-4-(pyrrolidinyl-2,5-dione-ethoxy)-phenyl, R-4-(pyrrolidinyl-2,5-dione-n-propoxy)-phenyl and S-4-(pyrrolidinyl-2,5-dione-n-propoxy)-phenyl.

More preferably still, R$^2$ is selected from the group consisting of phenyl, 4-(1-piperidinyl-ethoxy)-phenyl, R-4 (piperidinyl-ethoxy)-phenyl, S-4-(piperidinyl-ethoxy)-phenyl, 4-(1-pyrrolidinyl-ethoxy)-phenyl, 4-(4-morpholinyl-ethoxy)-phenyl, 4-(1-azepanyl-ethoxy)-phenyl, R-4-(azepanyl-ethoxy)-phenyl, S-4-(azepanyl-ethoxy)-phenyl, 4-(diethylamino-ethoxy)-phenyl, 4-(dimethylamino-ethoxy)-phenyl, R-4-(dimethylamino-ethoxy)-phenyl, S-4-(dimethylamino-ethoxy)-phenyl, R-4-(diisopropylamino-ethoxy)-phenyl, S-4-(diisopropylamino-ethoxy)-phenyl, 4-(dimethylamino)-phenyl, 4-(3-hydroxy-n-propoxy)-phenyl and 4-(methoxy-cabonyl-methoxy).

More preferably still, R$^2$ is selected from the group consisting of phenyl, 4-(1-piperidinyl-ethoxy)-phenyl, R-4-(piperidinyl-ethoxy)-phenyl, S4-(piperidinyl-ethoxy)-phenyl, 4-(1-pyrrolidinyl-ethoxy)-phenyl, 4-(4-morpholinyl-ethoxy)-phenyl, 4-(1-azepanyl-ethoxy)-phenyl, R-4-(azepanyl-ethoxy)-ohenyl, S-4-(azepanyl-ethoxy)-phenyl, 4-(diethylamino-ethoxy)-phenyl, 4-(dimethylamino-ethoxy)-phenyl, R-4-(dimethylamino-ethoxy)-phenyl, S-4-(dimethylamino-ethoxy)-phenyl, R-4-(diisopropylamino-ethoxy)-phenyl, S-4-(diisopropylamino-ethoxy)-phenyl, 4-(dimethylamino)-phenyl, 4-(3-hydroxy-n-propoxy)-phenyl and 4-(methoxy-cabonyl-methoxy).

More preferably still, R$^2$ is selected from the group consisting of phenyl, 4-(1-piperidinyl-ethoxy)-phenyl, R-4-(piperidinyl-ethoxy)-phenyl, S-4-(piperidinyl-ethoxy)-phenyl), 4-(1-pyrrolidinyl-ethoxy)-phenyl, 4-(4-morpholinyl-ethoxy)-phenyl, 4-(1-azepanyl-ethoxy)-phenyl, R-4-(azepanyl-ethoxy)-ohenyl, S-4-(azepanyl-ethoxy)-phenyl, 4-(dimethylamino-ethoxy)-phenyl, R-4-(dimethylamino-ethoxy)-phenyl, S-4-(dimethylamino-ethoxy)-phenyl, R-4-(diisopropylamino-ethoxy)-phenyl, S-4-(diisopropylamino-ethoxy)-phenyl, 4-(dimethylamino)-phenyl, 4-(3-hydroxy-n-propoxy)-phenyl and 4-(methoxy-cabonyl-methoxy).

In yet another embodiment of the present invention R$^2$ is selected from the group consisting of aryl substituted with —O-(alkyl)-NR$^D$R$^E$.

In an embodiment of the present invention are compounds of formula (I) wherein R$^1$ and R$^2$ are taken together with the carbon atom to which they are bound to form C(O).

In another embodiment of the present invention, R$^1$ and R$^2$ are taken together with the carbon atom to which they are bound to form C(O) and Y is selected from the group consisting of CR$^A$R$^B$, CR$^A$R$^B$(CH$_2$)$_{1-2}$, CR$^A$R$^B$C(O), CH$_2$C(O)CH$_2$ and CH$_2$CR$^A$R$^B$CH$_2$, preferably CR$^A$R$^B$, CR$^A$R$^B$(CH$_2$)$_{1-2}$, CR$^A$R$^B$C(O) and CH$_2$C(O)CH$_2$. More preferably, R$^1$ and R$^2$ are taken together with the carbon atom to which they are bound to form C(O) and Y is selected from the group consisting of CH$_2$, CH$_2$CH$_2$, CH$_2$CH$_2$CH$_2$, CH$_2$C(O) and CH$_2$C(O)CH$_2$.

In an embodiment of the present invention, n is an integer selected from 0 to 2. Preferably, n is an integer selected from 0 to 1. In another embodiment of the present invention, n is 1.

In an embodiment of the present invention, an R$^3$ substituent is bound at the 2-position of the core ring structure.

In an embodiment of the present invention R$^3$ is selected from the group consisting of halogen, hydroxy, R$^C$, amino, (lower alkyl)-amino, di(lower alkyl)amino, nitro, cyano, —OC(O)R$^G$, —OC(O)OR$^G$, —OC(O)N(R$^G$)$_2$, —OSi(R$^G$)$_3$, —OR$^G$, —O-(alkyl)$_{1-4}$-C(O)R$^G$ and —O-(alkyl)$_{1-4}$C(O)OR$^G$.

Preferably, $R^3$ is selected from the group consisting of hydroxy, $R^C$, —OC(O)$R^G$, —OC(O)O$R^G$, —OC(O)N($R^G$)$_2$, —OSi($R^G$)$_3$, —O$R^G$, —O-(alkyl)$_{1-4}$-C(O)$R^G$ and —O-(alkyl)$_{1-4}$-C(O)O$R^G$.

More preferably, $R^3$ is selected from the group consisting of halogen, hydroxy, lower alkoxy, tri(lower alkyl)-silyloxy, —OC(O)-(lower alkyl), —OC(O)—C(phenyl)-OC(O)-(lower alkyl), —OC(O)-(1,7,7-trimethyl-2-oxabicyclo[2.2.1]heptan-3-one) and —OC(O)—C(CH$_3$)(CF$_3$)-phenyl. More preferably still $R^3$ is selected from the group consisting of fluoro, hydroxy, methoxy, t-butyl-dimethyl-silyloxy, —OC(O)-methyl, —OC(O)-t-butyl, —OC(O)—C(phenyl)-OC(O)CH$_3$, —OC(O)-(1,7,7-trimethyl-2-oxabicyclo[.2.1]heptan-3-one) and —OC(O)—C(CH$_3$)(CF$_3$)-phenyl. More preferably still, $R^3$ is selected from the group consisting of hydroxy, methoxy and —OC(O)-t-butyl. More preferably still, $R^3$ is selected from the group consisting of hydroxy and —C(O)-t-butyl.

In an embodiment of the present invention $R^G$ is selected from hydrogen, lower alkyl (preferably methyl), aryl, aralkyl and 1,7,7-trimethyl-2-oxabicyclo[2.2.1]heptan-3-one; wherein the alkyl, aryl or aralkyl group is optionally substituted with one to two substituents independently selected from lower alkyl, halogenated lower alkyl, lower alkoxy, halogen, hydroxy, nitro, cyano, —OC(O)-(lower alkyl) and —C(O)O-(lower alkyl).

In another embodiment of the present invention two $R^G$ groups are taken together with the nitrogen atom to which they are bound to form a 5 to 6 membered heterocycloalkyl group; wherein the heterocycloalkyl group is optionally substituted with one to two substituents independently selected from halogen, hydroxy, lower alkyl, lower alkoxy, carboxy, amino, (lower alkyl)-amino, di(lower alkyl)amino, nitro or cyano.

Preferably, $R^G$ is selected from the group consisting of lower alkyl, aralkyl and 1,7,7-trimethyl-2-oxabicyclo[2.2.1]heptan-3-one; wherein the aralkyl group is optionally substituted with lower alkyl, halogenated alkyl or —OC(O)-(lower alkyl). More preferably, $R^G$ is selected from the group consisting of methyl, t-butyl, —C(CH$_3$)(CF$_3$)-phenyl, —CH(OC(O)CH$_3$)-phenyl and 1,7,7-trimethyl-2-oxabicyclo[2.2.1]heptan-3-one.

In an embodiment of the present invention, m is an integer selected from 0 to 2. Preferably, m is an integer selected from 0 to 1. In another embodiment of the present invention, m is 1.

In an embodiment of the present invention, an $R^4$ substituent is bound at the 8- or 9-position of the core ring structure.

In an embodiment of the present invention $R^4$ is selected from the group consisting of halogen, hydroxy, $R^C$, amino, (lower alkyl)-amino, di(lower alkyl)amino, nitro, cyano, —OC(O)$R^G$, —OC(O)O$R^G$, —OC(O)N($R^G$)$_2$, —OSi($R^G$)$_3$, —O$R^G$, —O-(alkyl)$_{1-4}$-C(O)$R^G$ and —O-(alkyl)$_{1-4}$-C(O)O$R^G$.

Preferably $R^4$ is selected from the group consisting of hydroxy, $R^C$, —OC(O)$R^G$, —OC(O)O$R^G$, —OC(O)N($R^G$)$_2$, —OSi($R^G$)$_3$, —O$R^G$, —O-(alkyl)$_{1-4}$-C(O)$R^G$ and —O-(alkyl)$_{1-4}$-C(O)O$R^G$.

More preferably, $R^4$ is selected from the group consisting of hydroxy, lower alkyl, lower alkoxy, tri(lower alkyl)-silyloxy, —OC(O)-(lower alkyl), —OC(O)—C(phenyl)-OC(O)-(lower alkyl), —OC(O)-(1,7,7-trimethyl-2-oxabicyclo[2.2.1]heptan-3-one) and —OC(O)—C(CH$_3$)(CF$_3$)-phenyl. More preferably still, $R^4$ is selected from the group consisting of hydroxy, methyl, methoxy, t-butyl-dimethyl-silyloxy, —OC(O)-methyl, —OC(O)-t-butyl, —OC(O)—C(phenyl)-OC(O)CH$_3$, —OC(O)-(1,7,7-trimethyl-2-oxabicyclo[.2.1]heptan-3-one) and —OC(O)—C(CH$_3$)(CF$_3$)-phenyl. More preferably still, $R^4$ is selected from the group consisting of fluoro, hydroxy, methoxy and —OC(O)-t-butyl. More preferably still, $R^4$ is selected from the group consisting of hydroxy and —OC(O)-t-butyl.

In an embodiment of the present invention ---- represents a single or double bond, X is selected from the group consisting of O and S and Y is selected from the group consisting of $CR^AR^B$, $CR^AR^B$($R^AR^B$)$_{1-2}$, (preferably $CR^AR^B(CR^AR^B)_{1-2}$ is selected from —$CR^AR^B$(CH$_2$)$_{1-2}$, —CH$_2CR^AR^B$CH$_2$—, —$CR^AR^B$—CH(OH)—$CR^AR^B$— or —$CR^AR^B$—CH$_2$—$CR^AR^B$—), $CR^AR^B$C(O) and $CR^AR^B$C(O)$CR^AR^B$ (preferably CH$_2$C(O)CH$_2$); alternatively Y is selected from the group consisting of O and S and X is selected from the group consisting of $CR^AR^B$ and C(O);

provided that when X is S, then Y is selected from the group consisting of $CR^AR^B$, $CR^AR^B(CR^AR^B)_{1-2}$ and CH$_2$C(O)CH$_2$; provided further that when Y is S, then X is selected from the group consisting of $CR^AR^B$;

wherein each $R^A$ and $R^B$ is independently selected from hydrogen, hydroxy, alkyl or alkoxy; provided that $R^A$ and $R^B$ are not each hydroxy;

Z is selected from the group consisting of O and S;

$R^1$ and $R^2$ are taken together with the carbon atom to which they are bound to form C(O);

provided that when X is selected from the group consisting of O and S, then Y is selected from the group consisting of $CR^AR^B$, $CR^AR^B(CR^AR^B)_{1-2}$ $CR^AR^B$C(O) and CH$_2$C(O)CH$_2$;

provided further that when Y is selected from the group consisting of O and S, then X is selected from the group consisting of $CR^AR^B$;

n is an integer selected from 0 to 4;

each $R^3$ is independently selected from the group consisting of halogen, hydroxy, $R^C$, amino, alkylamino, dialkylamino, nitro, cyano, —C(O)$R^G$, —C(O)O$R^G$, —OC(O)$R^G$, —OC(O)O$R^G$, —OC(O)N($R^G$)$_2$, —N($R^G$)C(O)$R^G$, —OSi($R^G$)$_3$, —O$R^G$, —SO$_2$N($R^G$)$_2$, —O-(alkyl)$_{1-4}$-C(O)$R^G$ and —O-(alkyl)$_{1-4}$C(O)O$R^G$;

wherein $R^C$ is selected from the group consisting of alkyl, cycloalkyl, cycloalkyl-alkyl, aryl, aralkyl, heteroaryl, heteroaryl-alkyl, heterocycloalkyl and heterocycloalkyl-alkyl; wherein the cycloalkyl, cycloalkyl-alkyl, aryl, aralkyl, heteroaryl, heteroaryl-alkyl, heterocycloalkyl or heterocycloalkyl-alkyl group is optionally substituted with one or more substituents independently selected from halogen, hydroxy, alkyl, alkoxy, —SH, —S(alkyl), SO$_2$, NO$_2$, CN, CO$_2$H, $R^C$, —SO$_2$—NR$^D$R$^E$, NR$^D$R$^E$, NR$^D$—SO$_2$—R$^F$, -(alkyl)$_{0-4}$-C(O)—NR$^D$R$^E$, -(alkyl)$_{0-4}$-NR$^D$—C(O)—R$^F$, -(alkyl)$_{0-4}$-(Q)$_{0-1}$-(alkyl)$_{0-4}$-NR$^D$R$^E$, -(alkyl)$_{0-4}$-(Q)$_{0-1}$-(alkyl)$_{0-4}$-C(O)—OR$^F$, -(alkyl)$^{0-4}$-(Q)$_{0-1}$-(alkyl)$_{0-4}$-C(O)—NR$^D$R$^E$ or -(alkyl)$_{0-4}$-C(O)-(alkyl)$_{0-4}$-C(O)—OR$^F$;

wherein Q is selected from the group consisting of O, S, NH, N(alkyl) and —CH=CH—;

wherein each $R^D$ and $R^E$ is independently selected from the group consisting of hydrogen and alkyl; alternatively $R^D$ and $R^E$ are taken together with the nitrogen atom to which they are bound to form a 3 to 10 membered, preferably 4 to 8 membered, ring selected from the group consisting of heteroaryl or heterocycloalkyl; wherein the heteroaryl or heterocycloalkyl group is optionally substituted with one or more substituents independently selected from halogen, hydroxy, oxo, alkyl, alkoxy, carboxy, amino, alkylamino, dialkylamino, nitro or cyano;

wherein $R^F$ is selected from the group consisting of hydrogen, alkyl, cycloalkyl, cycloalkyl-alkyl, aryl, aralkyl, heteroaryl, heteroaryl-alkyl, heterocycloalkyl and heterocycloalkyl-alkyl; wherein the cycloalkyl, aryl, heteroaryl, heteroaryl-alkyl, heterocycloalkyl or heterocycloalkyl-alkyl group is optionally substituted with one or more substituents independently selected from halogen, hydroxy, alkyl, alkoxy, carboxy, amino, alkylamino, dialkylamino, nitro or cyano;

wherein each $R^G$ is independently selected from hydrogen, alkyl, aryl, aralkyl and 1,7,7-trimethyl-2-oxabicyclo[2.2.1]heptan-3-one; wherein the alkyl, aryl or aralkyl group is optionally substituted with one or more substituents independently selected from alkyl, halogenated alkyl, alkoxy, halogen, hydroxy, nitro, cyano, —OC(O)-alkyl or —C(O)O-alkyl;

alternatively two $R^G$ groups are taken together with the nitrogen atom to which they are bound to form a heterocycloalkyl group; wherein the heterocycloalkyl group is optionally substituted with one or more substituents independently selected from halogen, hydroxy, alkyl, alkoxy, carboxy, amino, alkylamino, dialkylamino, nitro or cyano;

m is an integer selected from 0 to 4;

each $R^4$ is independently selected from the group consisting of halogen, hydroxy, $R^C$, amino, alkylamino, dialkylamino, nitro, cyano, —C(O)$R^G$, —C(O)O$R^G$, —OC(O)$R^G$, —OC(O)O$R^G$, —OC(O)N($R^G$)$_2$, —N($R^G$)C(O)$R^G$, —OSi($R^G$)$_3$, —O$R^G$, —SO$_2$N(alkyl)$_2$, —O-(alkyl)$_{1-4}$-C(O)$R^G$ and —O-(alkyl)$_{1-4}$-C(O)O$R^G$;

provided that when ----is a double bond, X is CH$_2$, Y is O, Z is O and $R^1$ and $R^2$ are taken together with the carbon atom to which they are bound to form C(O), then at least one of n or m is an integer selected from 1 to 4; preferably, n is an integer from 1 to 4 and m is an integer from 1 to 4;

provided further that when ----is a double bond, X is O, Y is CH$_2$, Z is O, $R^1$ and $R^2$ are taken together with the carbon atom to which they are bound to form C(O), n is 0 and m is 2, then each $R^4$ is not hydroxy or alkoxy.

or a pharmacetucailly acceptable salt thereof.

In an embodiment of the present invention are compounds of formula (D) wherein ----represents a single or double bond, A is selected from the group consisting of O and S;

D is selected from the group consisting of hydrogen, methyl, acetyl, benzoyl, SEM, MOM, BOM, TBS, pivaloyl and —C(O)R; wherein R is selected from alkyl, aryl, and substituted aryl; wherein the substituents on the aryl group are one or more independently selected from halogen, hydroxy, alkyl, alkoxy, amino, alkylamino, di(alkyl)amino, nitro or cyano;

each $R^{10}$ and $R^{11}$ is independently selected from hydrogen, halogen, hydroxy, alkyl, hydroxy substituted alkyl, alkoxy, —CH(OH)-aryl, —CHO, —C(O)-aryl, —C(O)O-alkyl, —C(O)O-aryl and pivaloyl; provided that $R^{10}$ and $R^{11}$ are not each hydroxy;

Z is selected from the group consisting of O and S;

n is an integer selected from 0 to 4;

each $R^{12}$ is independently selected from the group consisting of hydroxy, alkoxy, trialkylsilyl, acyloxy, benzoyloxy, aryloxy, aralkyloxy, SEMoxy, MOMoxy and pivaloyloxy;

m is an integer selected from 0 to 4;

each $R^{13}$ is independently selected from the group consisting of hydroxy, alkoxy, trialkylsilyl, acyloxy, benzoyloxy, aryloxy, aralkyloxy, SEMoxy, MOMoxy and pivaloyloxy;

In an embodiment of the present invention are compounds of formula (D) wherein A is O and Z is O.

In an embodiment of the present invention $R^{10}$ and $R^{11}$ are each independently selected from the group consisting of hydrogen, halogen, hydroxy substituted alkyl, halogen substituted alkyl, —CHO, —CH(OH)-phenyl, aryl (wherein the aryl group is optionally substituted with a hydroxy, alkoxy or alkoxycarbonyl), —C(O)-alkyl, —C(O)(halogen substituted alkyl), —C(O)-phenyl, —C(O)O-alkyl, —C(O)-(alkyl)-O-(alkyl), —C(O)O-phenyl, -(alkyl)-O-(alkyl) and -(alkyl)-O-(alkyl)-Si(alkyl)$_3$. In a preferred embodiment of the present invention $R^{10}$ is selected from the group consisting of hydrogen and bromo, preferably hydrogen; and $R^{11}$ is selected from the group consisting of hydrogen, bromo, iodo-methyl, chloromethyl, —CHO, —CH$_2$OH, CH(OH)CH$_2$CH$_2$CH$_3$, —CH(OH)-phenyl, 4-hydroxy-phenyl, 4-methoxy-phenyl, 4-(methoxy-carbonyl)-phenyl, —C(O)—CH$_2$—Cl, —C(O)OCH$_3$, —C(O)—CH$_2$—O—CH$_3$, —C(O)O-phenyl, —CH$_2$—O—CH$_3$ and —CH$_2$—O—CH$_2$CH$_2$—Si(CH$_3$)$_3$.

In another embodiment of the present invention $R^{10}$ and $R^{11}$ are each independently selected from the group consisting of hydrogen, halogen, hydroxy substituted alkyl, —CHO, —CH(OH)-phenyl, —C(O)-phenyl, —C(O)O-alkyl and —C(O)O-phenyl. In a preferred embodiment of the present invention $R^{10}$ is hydrogen and $R^{11}$ is selected from the group consisting of hydrogen, bromine, —CHO, —CH$_2$OH, CH(OH)CH$_2$CH$_2$CH$_3$, —CH(OH)-phenyl, —C(O)OCH$_3$ and —C(O)O-phenyl.

In an embodiment of the present invention $R^{12}$ and $R^{13}$ are each independently selected from the group consisting of halogen, hydroxy, lower alkyl, lower alkoxy, aralkyloxy, SEMoxy MOMoxy, pivaloyloxy and —OSi(lower alkyl)$_3$. In another embodiment of the present invention $R^{12}$ and $R^{13}$ are each independently selected from the group consisting of halogen, hydroxy, methyl, methoxy, ethoxy, isopropyloxy, benzoyloxy, SEMoxy MOMoxy, pivaloyloxy and t-butyl-dimethyl-silyloxy. In yet another embodiment of the present invention $R^{12}$ and $R^{13}$ are each independently selected from the group consisting of hydroxy, methoxy, ethoxy, isopropyloxy, benzoyloxy, SEMoxy MOMoxy and pivaloyloxy. In yet another embodiment $R^{12}$ and $R^{13}$ are each independently selected from the group consisting of hydroxy, methoxy, benzyloxy, benzoyloxy, MOMoxy, SEMoxy and pivaloyloxy.

In an embodiment of the present invention D is selected from the group consisting of hydrogen, methyl, methylcarbonyl, benzoyl, SEM, MOM and pivaloyl. In another embodiment of the present invention D is selected from the group consisting of hydrogen, methyl, benzoyl, SEM, MOM and pivaloyl.

In an embodiment of the present invention are compounds of formula (DI) wherein Y is selected form the group consisting of —CH$_2$— and —CH$_2$CH$_2$—.

In another embodiment of the present invention are compounds of formula (DI) wherein T is selected from the group consisting of -(aryl)-O-(alkyl)-NR$^D$R$^E$ and -(aryl)-O-(alkyl)-OH. Preferably, T is selected from the group consisting of 4-(piperidinyl-ethoxy)-phenyl and 4-(3-hydroxy-prop-1-yl-oxy)-phenyl. In yet another embodiment of the present invention, T is selected from the group consisting of -(phenyl)-O-(lower alkyl)-NR$^D$R$^E$.

In an embodiment of the present invention is a process for the preparation of a compound of formula (DX), as described in more detail in Scheme 16, which follows herein.

In another embodiment of the present invention is a process for the preparation of a compound of formula (DXI), as described in more detail in Scheme 17, which follows herein.

In another embodiment of the present invention is a process for the preparation of a compound of formula (C), as described in more detail in Schemes 16 and 17, which follow herein.

In yet another embodiment of the present invention, is a process for the preparation of a compound of formula (I) comprising reacting a compound of formula (DX) or a compound of formula (DXI) according to the process outlined in Scheme 3, Scheme 10, Scheme 12 or Scheme 15, which follow herein.

In an embodiment of the present invention, is a compound prepared according to any of the processes described herein.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

As used herein, the term "degenerative brain disease" shall include cognitive disorder, dementia, regardless of underlying cause and Alzheimer's disease.

As used herein, the term "cardiovascular disease" shall include elevated blood lipid levels, coronary arthrosclerosis and coronary heart disease.

As used herein, the term "cerebrovascular disease" shall include abnormal regional cerebral blood flow and ischemic brain damage.

As used herein, the term "progestogen antagonist" shall include mifepristone (RU486), J-867 (Jenapharm/TAP Pharmaceuticals), J-956 (Jenapharm/TAP Pharmaceuticals), ORG-31710 (Organon), ORG-32638 (Organon), ORG-31806 (Organon), onapristone (ZK98299) and PRA248 (Wyeth).

As used herein, unless otherwise noted, "halogen" shall mean chlorine, bromine, fluorine and iodine.

As used herein, unless otherwise noted, the term "alkyl" whether used alone or as part of a substituent group, include straight and branched chain compositions of one to eight carbon atoms. For example, alkyl radicals include methyl, ethyl, propyl, isopropyl, butyl, isobutyl, sec-butyl, t-butyl, pentyl and the like. Unless otherwise noted, "lower" when used with alkyl means a carbon chain composition of 1-4 carbon atoms. Similarly, the group "-(alkyl)$_{0-4}$-", whether alone or as part of a large substituent group, shall me the absence of an alkyl group or the presence of an alkyl group comprising one to four carbon atoms. Suitable examples include, but are not limited to —CH$_2$—, —CH$_2$CH$_2$—, CH$_2$—CH(CH$_3$)—, CH$_2$CH$_2$CH$_2$—, —CH$_2$CH(CH$_3$)CH$_2$—, CH$_2$CH$_2$CH$_2$CH$_2$—, and the like As used herein, unless otherwise noted, the term "alkenyl" shall mean a carbon chain comprising one to eight carbon atom and containing at least one double bond. Suitable examples include but are not limited to, allyl, crotyl, 2-butenyl, 2-pentenyl, and the like. Unless otherwise noted, "lower" when used with alkenyl shall mean an alkenyl carbon chain comprising one to four carbon atoms, such as allyl, and the like.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like. Unless otherwise noted, "lower" when used with alkoxy means an alkoxy group (an oxygen ether radical as described above) comprising one to four carbon atoms. Suitable examples include, but are not limited to methoxy, ethoxy, isopropoxy, n-propoxy, and the like.

As used herein, unless otherwise noted, "aryl" shall refer to unsubstituted carbocyclic aromatic groups such as phenyl, naphthyl, and the like.

As used herein, unless otherwise noted, "aralkyl" shall mean any lower alkyl group substituted with an aryl group such as phenyl, naphthyl and the like. Suitable examples include benzyl, phenylethyl, phenylpropyl, naphthylmethyl, and the like.

As used herein, unless otherwise noted, the term "cycloalkyl" shall mean any stable 3-8 membered monocyclic, saturated ring system, for example cyclopropyl, cyclobutyl, cyclopentyl, cyclohexyl, cycloheptyl and cyclooctyl.

As used herein, unless otherwise noted, the term "cycloalkyl-alkyl" shall mean any lower alkyl group substituted with a cycloalkyl group. Suitable examples include, but are not limited to cyclohexyl-methyl, cyclopentyl-methyl, cyclohexyl-ethyl, and the like.

As used herein, unless otherwise noted, the terms "acyloxy" shall mean a radical group of the formula —O—C(O)—R where R is alkyl, aryl or aralkyl, wherein the alkyl, aryl or aralkyl is optionally substituted. As used herein, the term "carboxylate" shall mean a radical group of the formula —C(O)O—R where R is alkyl, aryl or aralkyl, wherein the alkyl, aryl or aralkyl is optionally substituted.

As used herein, unless otherwise noted, "heteroaryl" shall denote any three to ten membered monocyclic or bicyclic aromatic ring structure containing at least one heteroatom selected from the group consisting of O, N and S, optionally containing one to four additional heteroatoms independently selected from the group consisting of O, N and S. Preferably, the heteroaryl group is a five or six membered monocyclic aromatic ring structure containing at least one heteroatom selected from the group consisting of O, N and S, optionally containing one to three additional heteroatoms independently selected from the group consisting of O, N and S; or a nine or ten membered bicyclic aromatic ring structure containing at least one heteroatom selected from the group consisting of O, N and S, optionally containing one to four additional heteroatoms independently selected from the group consisting of O, N and S. The heteroaryl group may be attached at any heteroatom or carbon atom of the ring such that the result is a stable structure.

Examples of suitable heteroaryl groups include, but are not limited to, pyrrolyl, furyl, thienyl, oxazolyl, imidazolyl, purazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like.

As used herein, unless otherwise noted, the term "heteroaryl-alkyl" shall mean any lower alkyl group substituted with a heteroaryl group. Suitable examples include, but are not limited to pyridyl-methyl, isoquinolinyl-methyl, thiazolyl-ethyl, furyl-ethyl, and the like.

As used herein, the term "heterocycloalkyl" shall denote any three to ten membered monocyclic or bicyclic, saturated, partially unsaturated or partially aromatic ring structure containing at least one heteroatom selected from the group consisting of O, N and S, optionally containing one to four additional heteroatoms independently selected from the group consisting of O, N and S. Preferably, the heterocycloalkyl is a five to seven membered monocyclic, saturated or partially unsaturated ring structure containing at least one heteroatom selected from the group consisting of O, N and S, optionally containing one to three additional heteroatoms independently selected from the group consisting of O, N and S; or a nine to ten membered saturated, partially unsaturated or partially aromatic bicyclic ring system containing at least one heteroatom selected from the group consisting of O, N and S, optionally containing one to four additional heteroatoms independently selected from the group consisting of O, N and S. The heterocycloalkyl group may be attached at any heteroatom or carbon atom of the ring such that the result is a stable structure.

Examples of suitable heteroaryl groups include, but are not limited to, pyrrolinyl, pyrrolidinyl, dioxalanyl, imidazolinyl, imidazolidinyl, pyrazolinyl, pyrazolidinyl, piperidinyl, dioxanyl, morpholinyl, dithianyl, thiomorpholinyl, piperazinyl, trithianyl, indolinyl, chromenyl, 3,4-methylenedioxyphenyl, 2,3-dihydrobenzofuryl, and the like.

Preferred heterocycloalkyl groups include morpholinyl, piperidinyl, piperazinyl, pyrrolidinyl, azepanyl and 2-oxabicyclo[2.2.1]heptane.

As used herein, unless otherwise noted, the term "heterocycloalkyl-alkyl" shall mean any lower alkyl group substituted with a heterocycloalkyl group. Suitable examples include, but are not limited to piperidinyl-methyl, piperazinyl-methyl, piperazinyl-ethyl, morpholinyl-methyl, and the like.

As used herein the term "N containing heterocycloalkyl (wherein said N containing heterocycloalkyl is bound through the N atom)" shall mean any heterocycloalkyl as described above which contains at least one N atom and which is bound through said N atom. Suitable examples include, but are not limited to, 1-piperidinyl, 4-piperazinyl, 1-pyrrolidinyl, 4-morpholinyl, 1-azepanyl, and the like.

As used herein, the notation "*" shall denote the presence of a stereogenic center.

When a particular group is "substituted" (e.g., cycloalkyl, aryl, heteroaryl, heterocycloalkyl), that group may have one or more substituents, preferably from one to five substituents, more preferably from one to three substituents, most preferably from one to two substituents, independently selected from the list of substituents. Additionally when aralkyl, heteroaryl-alkyl, heterocycloalkyl-alkyl or cycloalkyl-alkyl group is substituted, the substituent(s) may be on any portion of the group (i.e. the substituent(s) may be on the aryl, heteroaryl, heterocycloalkyl, cycloalkyl or the alkyl portion of the group.)

With reference to substituents, the term "independently" means that when more than one of such substituents is possible, such substituents may be the same or different from each other.

Under standard nomenclature used throughout this disclosure, the terminal portion of the designated side chain is described first, followed by the adjacent functionality toward the point of attachment. Thus, for example, a "phenyl$C_1$-$C_6$alkylaminocarbonyl$C_1$-$C_6$alkyl" substituent refers to a group of the formula

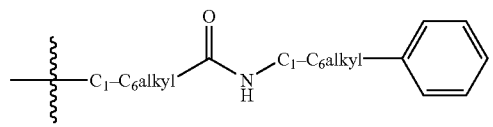

Unless otherwise noted, when naming substituents such as $R^3$ and $R^4$ groups, the following numbering of the core structure will be applied. The capital letters A, B, C and D will be used to designate specific rings of the tetracyclic core structure.

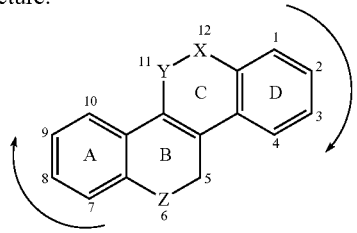

As used herein, the term "leaving group" shall mean any group which leaves a substrate during a reaction in which the substrate is cleaved. Suitable examples include, but are not limited to, Cl, Br, I, tosylate, mesylate, triflate, hydroxy, and the like.

As used herein, the term "electrophile" shall mean an atom or molecule which takes a pair of electron. Suitable example include, but are not limited to, Br, Cl, I, $CH_3$, SEM, MOM, BOM, —C(O)$CH_2$—O$CH_3$, —C(O)—$CH_2$—Cl, —C(O)—$CH_2$—Br, —C(O)—$CH_2$-(lower alkyl), —C(O)—$CH_2$-(benzyl), —C(O)—$CH_2$-(aryl), —$CH_2$—C(O)O-(lower alkyl), and the like.

Abbreviations used in the specification, particularly the Schemes and Examples, are as follows

| | |
|---|---|
| Ac = | Acetyl group (—C(O)—$CH_3$) |
| AD = | Alzheimer's disease |
| AIBN = | 2,2'-Azobisisobutyronitrile |
| $BF_3 \cdot Et_2O$ = | Boron trifluoride etherate |
| BOM = | Benzyloxy methyl |
| BOMCl = | Benzyloxy methyl chloride |
| BOMoxy = | Benzyloxy methyl-oxy |
| Bz = | Benzoyl |
| CSA = | Camphor sulfonic acid |
| DCC = | 1,3-Dicyclohexylcarbodiimide |
| DCE = | 1,1-Dichloroethane |
| DCM = | Dichloromethane |
| DEAD = | Diethylazodicarboxylate |
| DIAD = | Diisopropylazodicarboxylate |
| Dibal-H or DIBAL = | Diisobutyl aluminum hydride |
| DIC = | Diisopropylcarbodiimide |
| DIPEA or DIEA = | Diisopropylethylamine |
| DMAP = | N,N-Dimethylaminopyridine |
| DMF = | Dimethyl formamide |
| DTT = | Dithiothreitol |
| ERT = | Estrogen replacement therapy |
| Et = | ethyl (i. e. —$CH_2CH_3$) |
| EtOAc = | Ethyl acetate |
| EtOH = | Ethanol |
| FBS = | Fetal bovine serum |
| HEPES = | 4-(2-Hydroxyethyl)-1-piperazine ethane sulfonic acid |
| HPLC = | High pressure liquid chromatography |
| HRT = | Hormone replacement therapy |
| IPA or iPrOH = | Isopropyl alcohol |
| $iPr_2NH$ = | Diisopropylamine |
| LAH = | Lithium aluminum hydride |
| LDA = | Lithium Diisopropylamide |
| LHMDS or LiHMDS or $(TMS)_2NLi$ or $LiN(TMS)_2$ = | Lithium Hexamethyldisilazinamide |
| KHMDS = | Potassium Hexamethyldisilazinamide |
| Me = | methyl (—$CH_3$) |
| MeOH = | Methanol |
| MOM = | Methoxy methyl |
| MOMCl = | Methoxy methyl chloride |
| MOMoxy = | Methoxy methyl-oxy |
| NaHMDS = | Sodium Hexamethyldisilazinamide |
| NBS = | N-Bromosuccinimide |
| n-BuLi = | n-butyl lithium |
| $nBu_3SnH$ = | n-Tributyltin hydride |
| NCS = | N-chlorosuccinimide |
| OAc = | Acetoxy |
| OTBS = | t-Butyl-dimethyl-silyloxy |
| PBS = | Phosphate buffered solution |
| PCC = | Pyridinium chlorochromate |
| PDC = | Pyridinium dichromate |
| Ph = | Phenyl |
| PIV or Piv = | Pivaloyl |
| PMB = | Para-methoxy-benzyl |
| $P(Ph)_3$ = | Triphenylphosphine |
| PPTS = | Pyridinium p-toluenesulfonate |
| Rochelle Solution = | Aqueous solution of potassium sodium tartrate tetrahydrate |
| SEM = | 2-(Trimethylsilyl)ethoxy methyl |
| SEMCl = | 2-(Trimethylsilyl)ethoxy methyl chloride |
| SEMoxy = | 2-(Trimethylsilyl)ethoxy methyl-oxy |
| SERM = | Selective estrogen receptor modulator |
| TBAF = | Tetra(n-butyl)ammonium fluoride |
| TBDMS = | Tert-butyldimethylsilane |
| TBS = | Tert-butyl-dimethyl-silyl |
| TBSCl = | Tert-butyl-dimethyl-silyl chloride |
| TEA or $Et_3N$ = | Triethylamine |
| TFA = | Trifluoroacetic acid |
| THF = | Tetrahydrofuran |
| TIPSCl = | Triisopropylsilyl chloride |
| TIPSOTf = | Triisopropylsilyl trifluoromethane sulfonate |
| TMS = | Trimethylsilyl |
| $TMSCHN_2$ = | Trimethylsilyl diazomethane |
| TPAP = | Tetra-n-propylammonium perruthenate |
| TsOH = | Tosic acid |

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. Wherein the present invention directed to co-therapy comprising administration of one or more compound(s) of formula I and a progestogen or progestogen antagonist, "therapeutically effective amount" shall mean that amount of the combination of agents taken together so that the combined effect elicits the desired biological or medicinal response. For example, the therapeutically effective amount of co-therapy comprising administration of a compound of formula I and progestogen would be the amount of the compound of formula I and the amount of the progestogen that when taken together or sequentially have a combined effect that is therapeutically effective. Further, it will be recognized by one skilled in the art that in the case of co-therapy with a therapeutically effective amount, as in the example above, the amount of the compound of formula I and/or the amount of the progestogen or progestogen antagonist individually may or may not be therapeutically effective.

As used herein, the term "co-therapy" shall mean treatment of a subject in need thereof by administering one or more compounds of formula I with a progestogen or progestogen antagonist, wherein the compound(s) of formula I and progestogen or progestogen antagonist are administered by any suitable means, simultaneously, sequentially, separately or in a single pharmaceutical formulation. Where the compound(s) of formula I and the progestogen or progestogen antagonist are administered in separate dosage forms, the number of dosages administered per day for each compound may be the same or different. The compound(s) of formula I and the progestogen or progestogen antagonist may be administered via the same or different routes of administration. Examples of suitable methods of administration include, but are not limited to, oral, intravenous (iv), intramuscular (im), subcutaneous (sc), transdermal, and rectal. Compounds may also be administered directly to the nervous system including, but not limited to, intracerebral, intraventricular, intracerebroventricular, intrathecal, intracisternal, intraspinal and/or perispinal routes of administration by delivery via intracranial or intravertebral needles and/or catheters with or without pump devices. The compound(s) of formula I and the progestogen or progestogen antagonist may be administered according to simultaneous or alternating regimens, at the same or different times during the course of the therapy, concurrently in divided or single forms.

As used herein, the term "composition" is intended to encompass a product comprising the specified ingredients in the specified amounts, as well as any product which results, directly or indirectly, from combinations of the specified ingredients in the specified amounts.

Compounds of formula (I) wherein X is O or S, Y is CH$_2$ and Z is O or S may be prepared via synthesis through a key intermediate, a compound of formula (II) or (III)

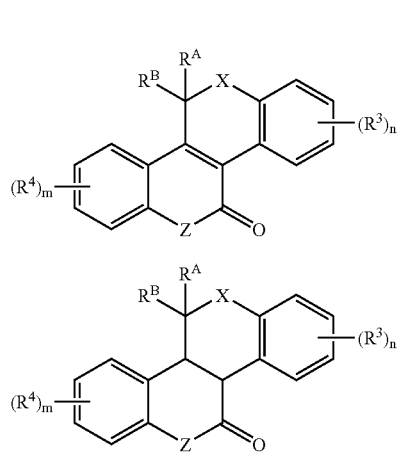

which, in turn, may be prepared according to the processes outlined in Scheme 1 and 2.

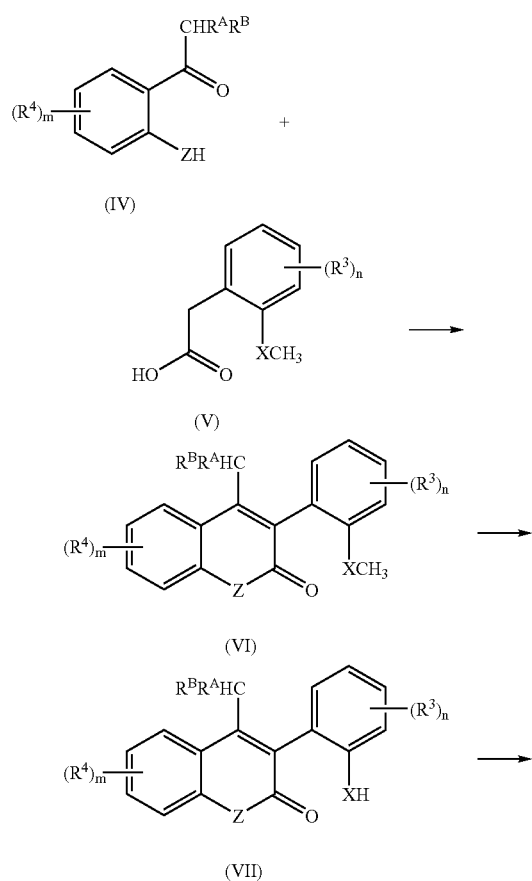

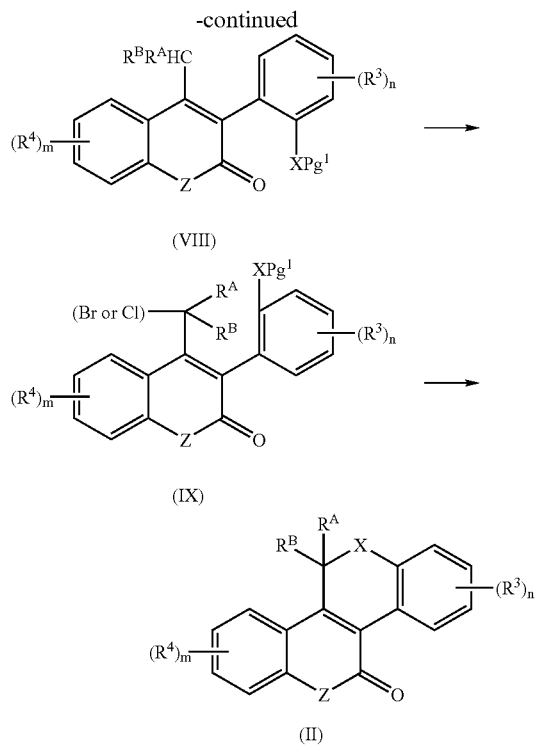

More particularly, a suitably substituted compound of formula (IV), where Z is O or S, a known compound or compound prepared by known methods, is reacted with a suitably substituted compound of formula (V), and where X is O or S, a known compound or compound prepared by known methods, in the presence of an organic base such as TEA, DIPEA, pyridine, and the like, in an organic solvent such as acetic anhydride, propionic anhydride, butyric anhydride, and the like, at an elevated temperature in the range of about 80° C. to about 120° C., to yield the corresponding compound of formula (VI).

The compound of formula (VI) is reacted with a de-methylating reagent such as TMS iodide, BBr$_3$, AlCl$_3$ with ethanethiol, and the like, in an chlorinated solvent such as methylene chloride, chloroform, dichloroethane, and the like, to yield the corresponding compound of formula (VII).

Alternatively, the compound of formula (VI) is reacted with a de-methylating reagent such as pyridine hydrochloride, pyridine hydrobromide, pyridine hydroiodide, and the like, optionally in an organic solvent such as xylene, acetic acid, and the like, at an elevated temperature in the range of about 170° C. to about 220° C., to yield the corresponding compound of formula (VII).

The compound of formula (VII) is reacted with a suitably selected protecting reagent such as acetyl chloride, acetic anhydride, benzoyl chloride, BOMCl, MOMCl, SEMCl and the like, in the presence of an base such as pyridine, TEA, DIPEA, K$_2$CO$_3$, and the like, in an organic solvent such as methylene chloride, chloroform, acetone, acetonitrile, dichloroethane, and the like, to yield the corresponding compound of formula (VII), wherein Pg$^1$ represents a protecting group. For example, wherein the compound of formula (VII) is reacted with acetyl chloride or acetic anhydride, Pg$^1$ is an acetyl group; wherein the compound of formula (VII) is reacted with benzoyl chloride, Pg$^1$ is a benzoyl group; wherein the compound of formula (VII) is reacted with BOMCl, MOMCl or SEMCl, $Pg^1$ is BOM, MOM or SEM, respectively.

When $Pg^1$ is acetyl or the like, the compound of formula (VII) is reacted with a radical brominating agent such as NBS, $CBrCl_3$, $NaBrO_3$ in combination with $NaHSO_3$, and the like or a radical chlorinating agent, such as NCS, $SO_2Cl_2$, $Cl_2$ gas, t-butyl hypochloride, and the like, preferably a radical brominating agent such as NBS, in the presence of a radical initiator such as benzoyl peroxide, AIBN, and the like and/or in the presence of a light source, such as a tungsten lamp, a 120 Watt light bulb, bright sunshine, and the like, optionally at an elevated temperature in the range of about 50° C. to about 120° C., to yield the corresponding compound of formula (VIII).

Wherein the compound of formula (VII) is reacted with a radical brominating reagent such as NBS, the reaction is carried out in a halogenated organic solvent such as carbon tetrachloride, chloroform, dichloromethane, and the like. Wherein the radical brominating reagent is $NaBrO_3$, the reaction is carried out in an organic solvent such as ethyl acetate, cyclohexane, and the like. Wherein the compound of formula (VII) is reacted with a radical chlorinating reagent, the reaction is carried out in an organic solvent such as ethyl acetate, chloroform, dichloromethane, and the like.

When $Pg^1$ is a benzoyl group, pivaloyl, BOM, MOM, SEM, or the like, the compound of formula (VII) is reacted with bromine or a source of bromine or a source of chlorine such as NBS, NCS, and the like, in the presence of a base such as LHMDS, LDA, KHMDS, NaHMDS, and the like, at a reduced temperature in the range of about 30° C. to about −78° C., to yield the corresponding compound of formula (IX).

The compound of formula (IX) is de-protected to yield the corresponding compound of formula (II). When $Pg^1$ is acetyl or benzoyl, the compound of formula (IX) is de-protected with a base such as potassium carbonate, sodium carbonate, cesium carbonate, and the like, in a solvent such as methanol, ethanol, isopropanol, or in a mixture thereof such as methanol:acetone, ethanol:acetone, methanol:acetonitrile, and the like, to yield the corresponding compound of formula (II).

When $Pg^1$ is methyl, benzyl, BOM, MOM or SEM, the compound of formula (IX) is de-protected with acid such as TFA, HF, HCl, $H_2SO_4$, and the like, or a Lewis acid such as tin tetrachloride, titanium tetrachloride, boron trichloride, boron tribromide, and the like, or when $Pg^1$ is SEM with a de-protecting agent such as $LiBF_4$, TBAF, and the like, in a solvent such as THF, acetonitrile, methylene chloride, chloroform, isopropanol, methanol, and the like, at a temperature in the range of about 0° C. to about 50° C., and then treated with a base such as potassium carbonate, sodium carbonate, cesium carbonate, potassium hydroxide, sodium hydroxide, and the like, or an alkali metal alkoxide such as sodium ethoxide, sodium methoxide, sodium t-butoxide, potassium ethoxide, potassium methoxide, potassium t-butoxide, in a solvent such as methanol, ethanol, isopropanol, THF, or in a mixture thereof such as methanol:acetone, ethanol:acetone, methanol:acetonitrile, and the like, to yield the corresponding compound of formula (II).

Alternatively, the compound of formula (VI) is reacted with bromine or a source of bromine or chlorine such as NBS, NCS, and the like, in the presence of a base such as LHMDS, LDA, KHMDS, NaHMDS, and the like, at a reduced temperature in the range of about 30° C. to about −78° C., to yield the corresponding compound of formula (IX).

One skilled in the art will recognize that it may be necessary and/or desirable to protect one or more of the $R^3$ and/or $R^4$ groups at any of the steps within the process described above. This may be accomplished using known protecting groups and know protection and de-protection reagents and conditions, for example such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991.

One skilled in the art will further recognize that the process as described in Scheme 1 above may be applied to compounds of formula (IV) and compounds of formula (V) wherein the $R^3$ group(s) are substituted with $R^{12}$ group(s) and the $R^4$ group(s) are substituted with $R^{13}$ groups, respectively, wherein $R^{12}$ and $R^{13}$ are as herein defined, to yield the corresponding compound of formula (IIa)

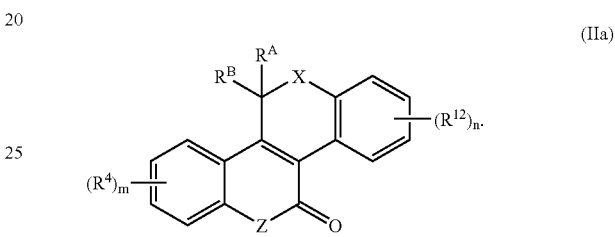

The compound of formula (IIa) is then optionally reacted according to known methods (including for example, those disclosed herein) to displace the $R^{12}$ and $R^{13}$ group(s) with suitably selected, desired $R^3$ and $R^4$ group(s).

The compound of formula (II) may be selectively hydrogenated to yield the corresponding compound of formula (III), as shown in Scheme 2.

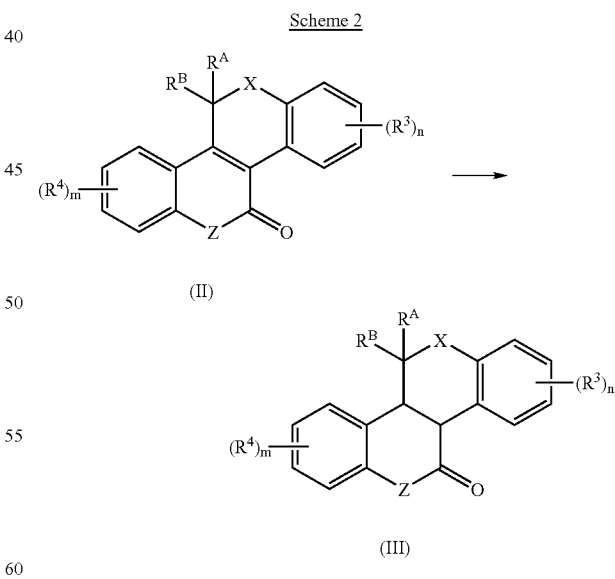

Accordingly, the compound of formula (II) is reacted with hydrogen gas, at a pressure in the range of about 20 psi to about 100 psi, in the presence of a metal catalyst such as Pd on C, Pt on C, Raney nickel, $Pd(OH)_2$, and the like, to yield the corresponding compound of formula (III), as predominately the cis isomer.

Alternatively, the compound of formula (III) is reacted with a hydride such as LAH, Cu hydride, SmI$_2$, Stryker's Reagent ([(Ph$_3$P)CuH]$_6$), and the like, in an solvent such as THF, diethyl ether, and the like, at a temperature in the range of about –20° C. to about 60° C., to yield the corresponding compound of formula (III), as predominately the trans isomer.

Alternatively still, the compound of formula (II) is reacted with triethyl silane, in the presence of an acid such as TFA, BF$_3$ etherate, Tin tertachloride, and the like, in an organic solvent such as methylene chloride, toluene, and the like, to yield the corresponding compound of formula (III), as a mixture of cis and trans isomers.

One skilled in the art will further recognize that the process outlined in Scheme 2 above may be similarly used to prepared compounds of formula (IIIb)

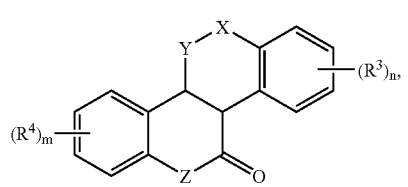

by substituting a suitably substituted compound of formula (IIb)

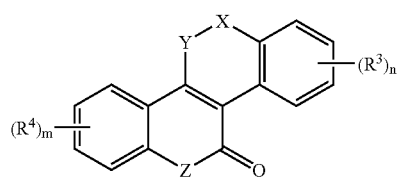

a known compound or compound prepared by known methods, for the compound of formula (II).

Compounds of formula (I) wherein X is O or S, Y is CR$^A$R$^B$ and Z is O or S may be prepared from the intermediate compound of formula (II) according to the process outlined in Scheme 3.

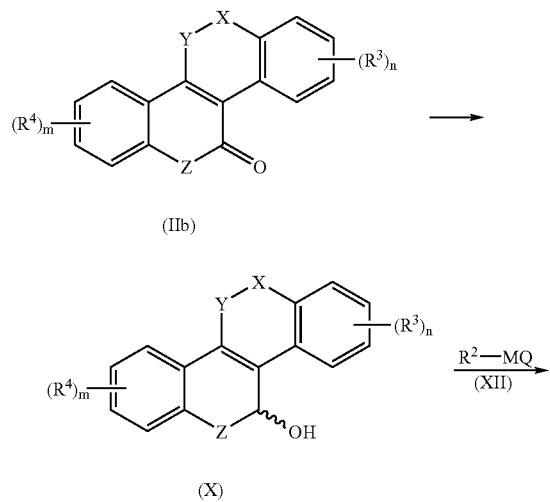

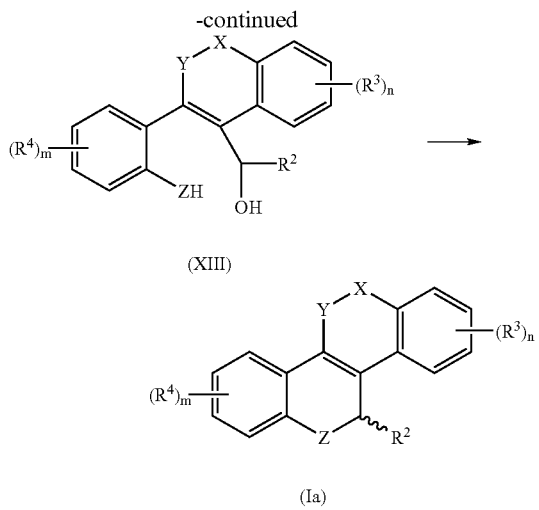

Accordingly, the compound of formula (IIb), a known compound or compound prepared by known methods, is reacted with diisobutyl-aluminum hydride, L-selectride, and the like, in an organic solvent such as toluene, benzene, THF, methylene chloride, and the like, at a reduced temperature in the range of about 0° C. to about –80° C., to yield the corresponding compound of formula (X).

The compound of formula (X) is reacted with a suitably substituted compound of formula (XII), wherein MQ is lithium or a magnesium halide such as MgCl, MgBr or MgI, prepared from the corresponding known alkyl or aryl halide by known methods, in an organic solvent such as THF, diethyl ether, dioxane, hexane, and the like, to yield the corresponding compound of formula (XIII).

The compound of formula (XIII) is treated with a protic acid such as HCl, H$_2$SO$_4$, p-toluene sulfonic acid, camphor sulfonic acid (CSA), TFA, and the like or a Lewis acid such as BF$_3$ etherate, AlCl$_3$, SnCl$_4$, and the like, in a solvent such as toluene, methylene chloride, acetonitrile and the like, to yield the corresponding compound of formula (Ia).

Alternatively, the compound of formula (XIII) is treated with a reagent such as triphenylphosphine, tributylphosphine, and the like, or an azodicarboxamide such as DEAD, DIAD, and the like, in a solvent such as toluene, THF, and the like, to yield the corresponding compound of formula (Ia).

One skilled in the art will recognize that it may be necessary and/or desirable to protect one or more of the R$^3$ and/or R$^4$ groups at any of the steps within the process described above. This may be accomplished using known protecting groups and know protection and de-protection reagents and conditions, for example such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991.

One skilled in the art will further recognize that in the process outlined in Scheme 3, when Y is —CH$_2$C(O)CH$_2$— and the compound of formula (IIb) is reacted with a protecting group reagent, to protect any substituent group (for example an R$^3$ or R$^4$ group), the C(O) on the —CH$_2$C(O)CH$_2$— may also react with the protecting group reagent to form —CH=C(OPg)CH$_2$— wherein Pg is the protecting group. Upon de-protection, the —CH=C(OPg)CH$_2$— is also de-protected to yield —CH$_2$C(O)CH$_2$—.

Alternatively, the compound of formula (III) is substituted for the compound of formula (IIb) in Scheme 3 above, to yield the compound of formula (Ib)

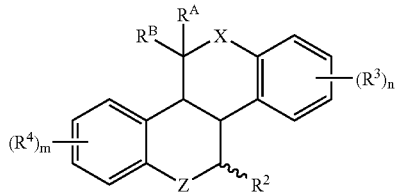

(Ib)

wherein $R^2$ as defined above.

One skilled in the art will recognize that the compound of formula (Ib) may alternatively be prepared by selectively hydrogenating a suitably substituted compound of formula (Ia), wherein Y is $CR^A R^B$, using reagents and conditions as described in Scheme 2.

One skilled in the art will further recognize that the compound of formula (IIIb) may be similarly substituted for the compound of formula (IIb) in Scheme 3 above, to yield the corresponding compound of formula (Iq)

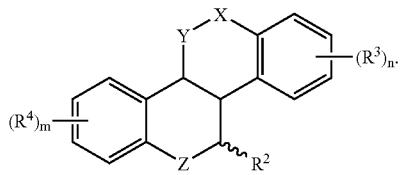

(Iq)

Compounds of formula (I) wherein one or more $R^3$ and/or $R^4$ are acyloxy may be prepared by reacting a suitably substituted compound of formula (I), wherein the $R^3$ and/or $R^4$ group(s) are hydroxy with a suitably substituted acid chloride, a suitably substituted carboxylic acid or a suitably substituted anhydride. For example, a compound of formula (I) wherein $R^3$ and $R^4$, at the 2 and 8 positions respectively, are acyloxy may be prepared according to the process outlined in Scheme 4.

Scheme 4

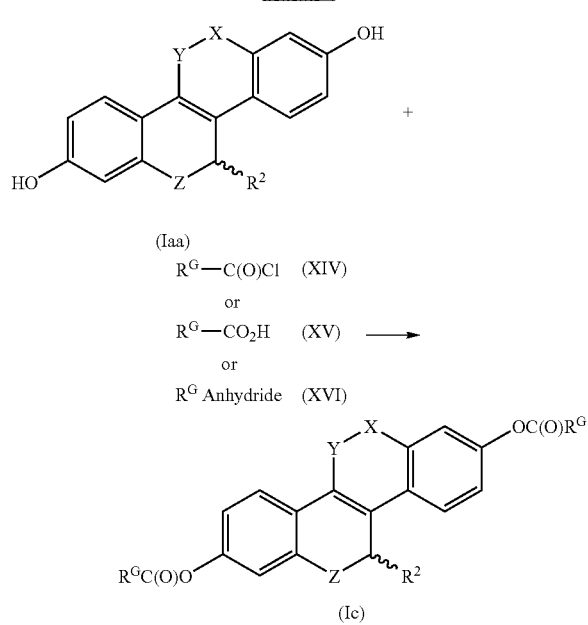

Accordingly, a suitably substituted compound of formula (Iaa) prepared as in Scheme 3 (wherein n is 1, R3 is hydroxy, m is 1 and R4 is hydroxy), is reacted with a suitably substituted acid chloride, a compound of formula (XIV), or a suitably substituted anhydride, a compound of formula (XVI), wherein $R^G$ is as defined above, a known compound or compound prepared by known methods, in the presence of an organic amine such as TEA, DIPEA, pyridine, and the like, in a halogenated organic solvent such as DCM, methylene chloride, chloroform, and the like, or in a hydrocarbon solvent such as benzene, toluene, and the like, to yield the corresponding compound of formula (Ic).

Alternatively, the compound of formula (Iaa) is reacted with a suitably substituted carboxylic acid, a compound of formula (XV), wherein $R^G$ is as defined above, a known compound or compound prepared by known methods, in the presence of a coupling reagent such as DCC, DIC, and the like, in an organic solvent such as DMF, THF, methylene chloride, and the like, to yield the corresponding compound of formula (Ic).

One skilled in the art will recognize that any $R^3$ and/or $R^4$ group(s) terminating with a hydroxy group may be similar converted according to the process outlined in Scheme 4 above. One skilled in the art will further recognize that wherein one or more of the $R^3$ and/or $R^4$ groups are hydroxy groups protected with a silyl protecting group such as TBS, the corresponding compound of formula (Ia) is reacted with a tetra-alkyl ammonium fluoride such as TBAF, and the like, and then reacted with a suitably substituted acid chloride of formula (XIV), in an organic solvent such as THF, diethyl ether, and the like, to yield the corresponding compound of formula (Ic).

One skilled in the art will further recognize that reacting the compound of formula (Iaa) with ≦about 1 equivalent of a suitably substituted compound of formula (XIV), a suitably substituted compound of formula (XV) or a suitably substituted compound of formula (XVI), will yield a mixture of compounds wherein only $R^3$, only $R^4$ and both $R^3$ and $R^4$ are converted to the group —OC(O)$R^G$. This mixture of compounds is preferably separated by known methods to recover the desired compound. Further, reacting the compound of formula (Iaa) with ≧about 2 equivalents of a suitably substituted compound of formula (XIV), a suitably substituted compound of formula (XV) or a suitably substituted compound of formula (XVI), will yield the compound of formula (Ic) wherein both $R^3$ and $R^4$ are converted to the group —OC(O)$R^G$.

Alternatively, the compound of formula (Iba), a compound of formula (Ib) wherein n is 1, $R^3$ is hydroxy, m is 1 and $R^4$ is hydroxy) may substituted for the compound of formula (Iaa) and reacted as described in Scheme 4, to yield the corresponding compound of formula (Id)

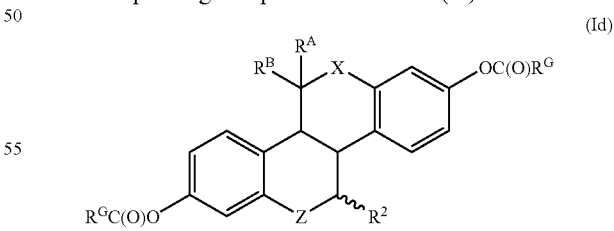

(Id)

One skilled in the art will further recognize that the above reaction can be tailored to the preparation of compound of formula (I) and (II) wherein the position of the $R^3$ and $R^4$ group may be varied about the A and D rings respectively, and where the number of $R^3$ and $R^4$ groups is varied.

Further, one skilled in the art will recognize that if different acyloxy groups are desired at the $R^3$ and $R^4$ positions, the acyloxy groups may be sequentially coupled onto the core structure through conversion of a hydroxy group as described in Scheme 4 above, with suitable protection and de-protection of reactive groups as necessary.

Compounds of formula (I) wherein X is O, Y is $CH_2$ or C(O) and Z is O or S may be from the intermediate compound of formula (XIX).

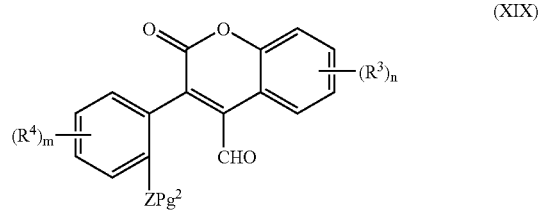

(XIX)

The compound of formula (XIX) may be prepared according to the process outlined in Scheme 5.

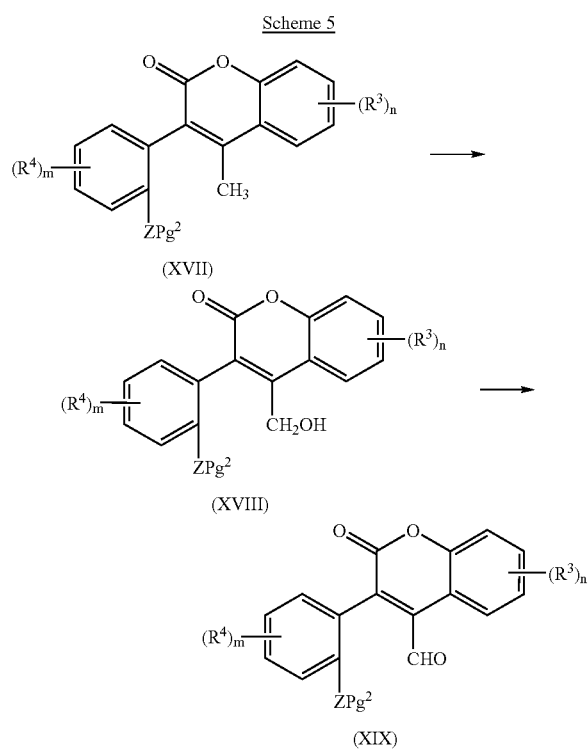

Accordingly, a suitably substituted compound of formula (XVII), wherein $Pg^2$ is a suitable protecting group such as benzyloxy, methoxy, SEM, MOM, acetoxy, and the like, a known compound or compound prepared by known methods is reacted with an oxidizing agent such as $SeO_2$, PCC, PDC, and the like, in an organic solvent such as toluene, xylene, ethyl acetate, dichloromethane, and the like, to yield the corresponding compound of formula (XVIII).

The compound of formula (XVIII) is further oxidized with an oxidizing agent such as $SeO_2$, PCC, PDC, and the like, in an organic solvent such as toluene, xylene, ethyl acetate, dichloromethane, and the like, to yield the corresponding compound of formula (XIX).

One skilled in the art will recognize that when the compound of formula (XVII) is reacted with 2 or more equivalents of the oxidizing agent, the compound of formula (XVII) is converted directly to the compound of formula (XIX) (i.e. The intermediate alcohol compound of formula, (XVIII) need not be isolated).

Alternatively, the compound of formula (XIX) may be prepared according to the process outlined in Scheme 6.

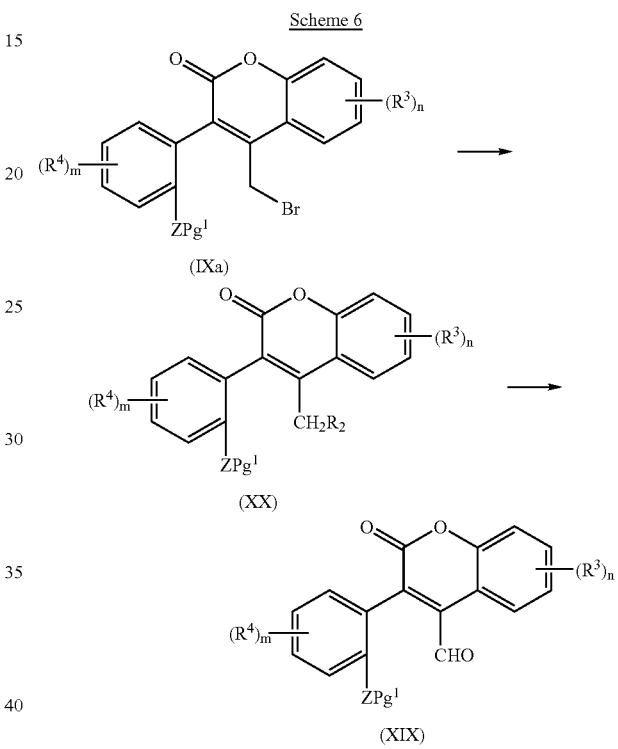

Accordingly, a suitably substituted compound of formula (IXa), a compound of formula (IX) wherein $R^A$ and $R^B$ are each hydrogen, wherein Z is O and wherein $Pg^1$ is a suitable protecting group such as benzyloxy, methoxy, SEM, MOM, acetoxy, and the like, a known compound or compound prepared by known methods is reacted with a radical brominating agent such as NBS, $CBrCl_3$, $NaBrO_3$ in combination with $NaHSO_3$, and the like or a radical chlorinating agent, such as NCS, $SO_2Cl_2$, $Cl_2$ gas, t-butyl hypochloride, and the like, preferably a radical brominating agent such as NBS, in the presence of a radical initiator such as benzoyl peroxide, AIBN, and the like and/or in the presence of a light source, such as a tungsten lamp, a 120 Watt light bulb, bright sunshine, and the like, optionally at an elevated temperature in the range of about 50° C. to about 120° C., to yield the corresponding compound of formula (XX).

The compound of formula (XX) is hydrolyzed with water, in the presence of a base such as sodium carbonate, sodium bicarbonate, and the like, to yield the corresponding compound of formula (XIX).

Compounds of formula (I) wherein X is O, Y is $CH_2$ or C(O) and Z is O or S may be prepared from the intermediate compound of formula (XIX) according to the process outlined in Scheme 7.

Scheme 7

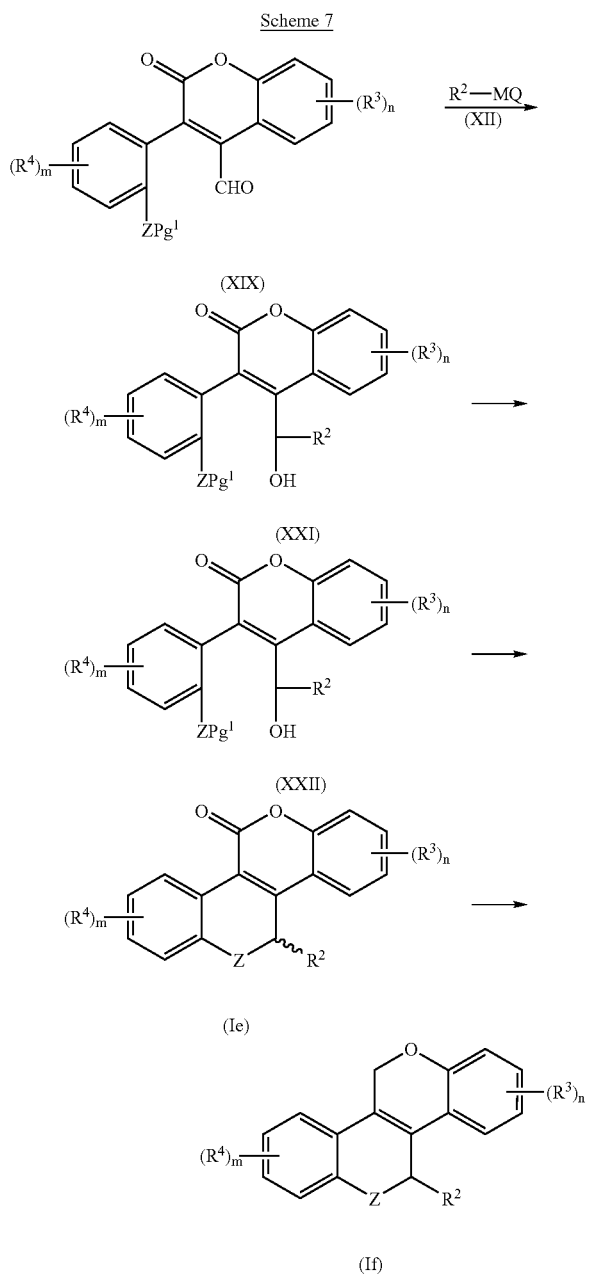

Accordingly, a compound of formula (XIX), is reacted with a suitably substituted compound of formula (XII), where MQ is lithium of a magnesium halide such as such as MgCl, MgBr or MgI, prepared from the corresponding known alkyl or aryl halide by known methods, in an organic solvent such as THF, diethyl ether, dioxane, hexane, and the like, to yield the corresponding compound of formula (XXI).

The compound of formula (XXI) is reacted with a protic acid such as HCl, $H_2SO_4$, p-toluene sulfonic acid, camphor sulfonic acid (CSA), TFA, and the like or a Lewis acid such as $BF_3$ etherate, $AlCl_3$, $SnCl_4$, and the like, in a solvent such as toluene, methylene chloride, acetonitrile and the like, to yield the corresponding compound of formula (Ie).

The compound of formula (Ie) may optionally be selectively reduced by reacting with a reducing agent such as LAH/$AlCl_3$, and the like, in an organic solvent such as THF, diethyl ether, dioxane, and the like, to yield the corresponding compound of formula (If).

One skilled in the art will recognize that it may be necessary and/or desirable to protect one or more of the $R^3$ and/or $R^4$ groups at any of the steps within the process described above. This may be accomplished using known protecting groups and know protection and de-protection reagents and conditions, for example such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991.

One skilled in the art will further recognize that the compounds of (Ie) and/or (If) may be optionally further selectively hydrogenated at the bridge bond of the B and C rings, as previously described, with protection of reactive groups as necessary, to yield the corresponding compound of formula (Ig).

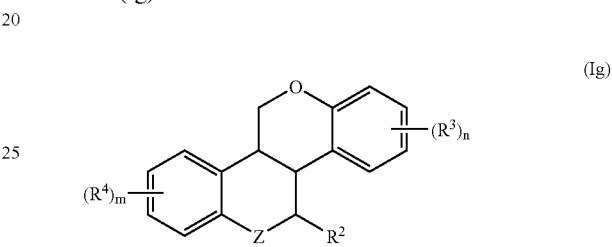

Alternatively, the compound of formula (XIX) may be substituted with the corresponding compound wherein the bridge bond of the B and C rings is fully saturated and then reacted according to the process outlined in Scheme 7, to yield the corresponding compound of formula (Ig) or (Ih).

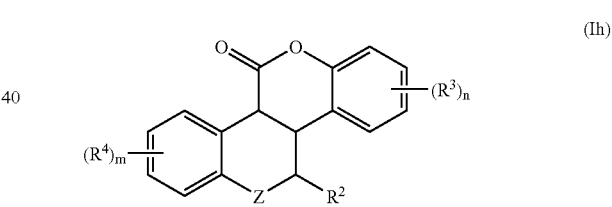

Compounds of formula (I) wherein X is $CR^AR^B$, Y is O and Z is O or S may be prepared via synthesis of intermediate compounds of formula (XXIII) and (XXIV)

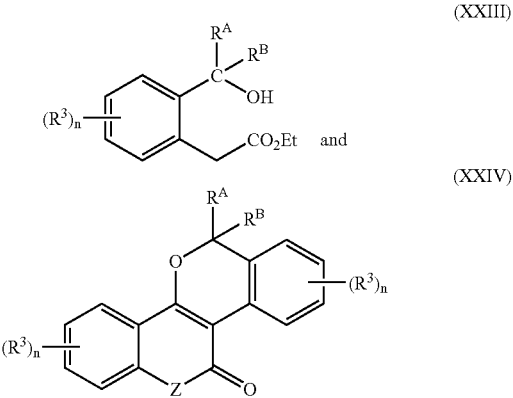

which in turn may be prepared according to the processes outlined in Scheme 8 and 9. Accordingly, compounds of formula (XXIII) wherein one or both $R^A$ and $R^B$ are other than hydrogen may be prepared according to the process outlined in Scheme 8.

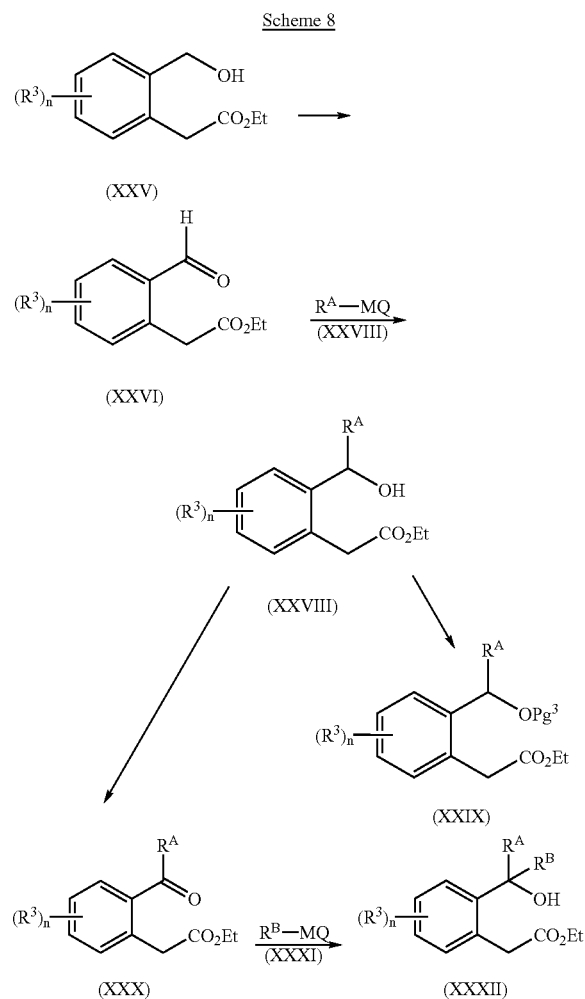

Accordingly, a suitably substituted compound of formula (XXV) is reacted with an oxidizing agent such as $MnO_2$, PDC, TPAP, and the like, in an organic solvent such as DCM, acetonitrile, DCE, and the like, to yield the corresponding compound of formula (XXVI).

The compound of formula (XXVI) is reacted with a compound of formula (XXVII), wherein MQ is lithium or a magnesium halide such as MgCl, MgBr or MgI, prepared from the corresponding known alkyl or aryl halide by known methods, in an organic solvent such as THF, diethyl ether, dioxane, hexane, and the like, to yield the corresponding compound of formula (XXVIII).

The compound of formula (XXVIII) is protected by reacting with a suitable protecting group, via known chemistry, to yield the corresponding compound of formula (XXIX), wherein $Pg^3$ is a suitable protecting group such as benzyloxy, methoxy, MOM, SEM, and the like.

Alternatively, the compound of formula (XXVIII) is reacted with an oxidizing agent such as $MnO_2$, PDC, TPAP, and the like, in an organic solvent such as DCE, DCM, acetonitrile, and the like, to yield the corresponding compound of formula (XXX).

The compound of formula (XXX) is reacted with a suitably substituted compound of the formula (XXXI), wherein MQ is lithium or a magnesium halide such as MgCl, MgBr or MgI, prepared from the corresponding known alkyl or aryl halide by known methods, in an organic solvent such as THF, diethyl ether, dioxane, hexane, and the like, to yield the corresponding compound of formula (XXXII).

Compounds of formula (XXIII) wherein $R^A$ and $R^B$ are each hydrogen, (i.e. compounds of formula (XXV)) may be prepared by reducing a suitably substituted compound of the formula (XXXIII)

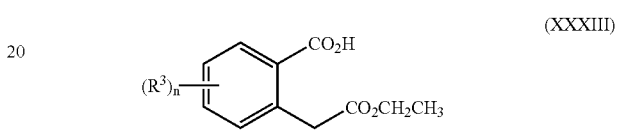

in a two step process. Accordingly, the compound of formula (XXXIII) is reacted with oxalyl chloride, in an organic solvent such as THF, DCM, and the like, and then reacted with a reducing agent such as sodium borohydride, and the like, in an alcohol such as methanol, ethanol, and the like. Alternatively, the compound of formula (XXXIII) is reacted with an anhydride such as acetic anhydride, and the like, in an organic solvent such as THF, DCM, and the like, and then reacted with a reducing agent such as sodium borohydride, and the like, in an alcohol such as methanol, ethanol, and the like, to yield the corresponding compound of formula (XXIII).

Alternatively, the compound of formula (XXXIII) is converted to the corresponding compound of formula (XXV) by reacting the compound of formula (XXXIII) with borane THF complex, in an organic solvent such as THF, and the like, at a reduced temperature in the range of about −78° C. to about room temperature.

The compound of formula (XXIV) may be prepared according to the process outlined in Scheme 9.

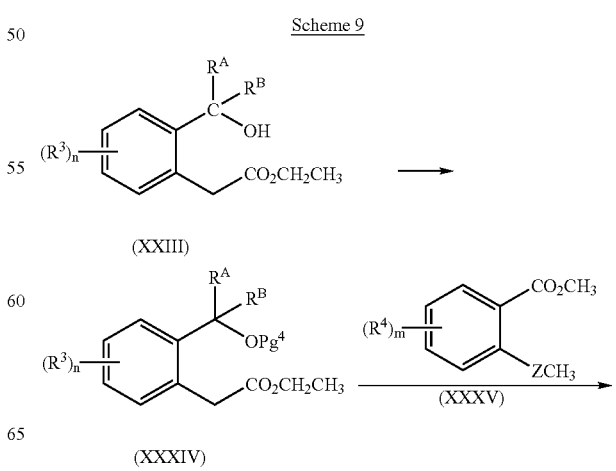

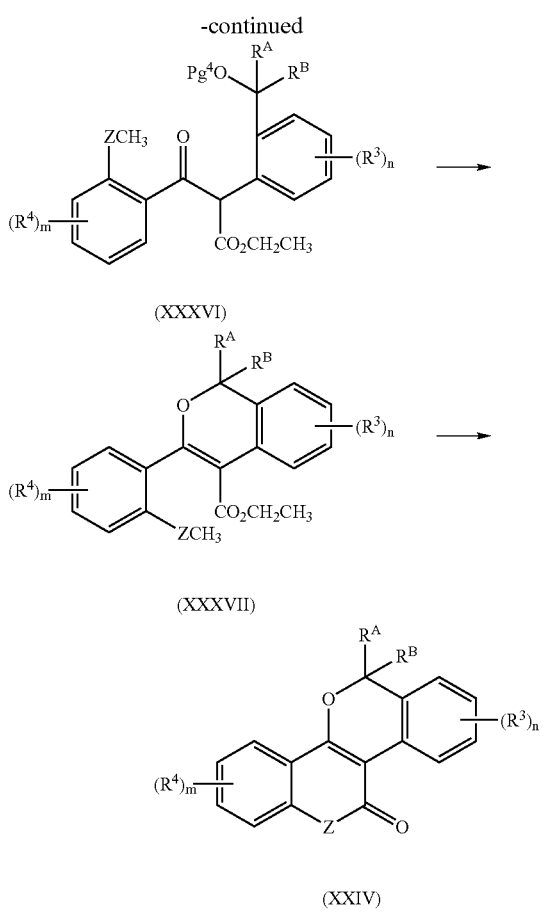

(XXXVI)

(XXXVII)

(XXIV)

Accordingly, a suitably substituted compound of formula (XXIII), a known compound or compound prepared by known methods, for example as in Scheme 8 above, is protected with a suitable protecting group, by known methods, to yield the corresponding compound of formula (XXXIV), wherein $Pg^4$ is a suitable protecting group such as benzyloxy, methoxy, SEM, MOM, and the like.

The compound of formula (XXXIV) is reacted with a suitably substituted compound of formula (XXXV), a known compound or compound prepared by known methods, in the presence of a base such as LDA, LHMDS, sodium hydride, and the like, in an organic solvent such as diethyl ether, THF, and the like, at a reduced temperature in the range of about −78° C. to about 30° C., to yield the corresponding compound of formula (XXXVI).

The compound of formula (XXXVI) is de-protected by known methods, to yield the corresponding compound of formula (XXXVII).

The compound of formula (XXXVII) is reacted with a de-methylating reagent such as pyridine hydrochloride, pyridine hydrobromide, pyridine hydroiodide, and the like, optionally in an organic solvent such as xylene, acetic acid, and the like, at an elevated temperature in the range of about 170° C. to about 220° C., to yield the corresponding compound of formula (XXIV).

One skilled in the art will recognize that for preparation of compounds of formula (I) wherein one of $R^A$ or $R^B$ is hydrogen, the compound of formula (XXIX) may be substituted for the compound of formula (XXXIV) in the process outlined in Scheme 9.

One skilled in the art will further recognize that in the process outlined in Scheme 9, where the compound of formula (XXXVI) is de-protected to yield the compound of formula (XXXVII), it is possible that the compound of formula (XXXVI) does not fully convert to the compound of formula (XXXVII), but rather forms the intermediate compound of formula (XXXVIII).

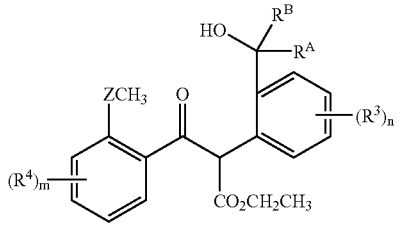

(XXXVIII)

The compound of formula (XXXVIII) may then be converted to the compound of formula (XXXVII) according to known methods. For Example, wherein $R^A$ and/or $R^B$ is hydrogen, the compound of formula (XXXVIII) is reacted under Mitsunobu conditions to yield the corresponding compound of formula (XXXVII).

Alternatively, if both $R^A$ and $R^B$ are other than hydrogen, the compound of formula (XXXVIII) is reacted with an acid such as HCl, TsOH, PPTS, and the like, in an organic solvent or mixture such as THF, THF/$H_2O$, dichloromethane, toluene/$H_2O$, and the like, to yield the corresponding compound of formula (XXXVII)

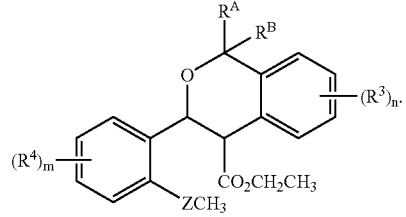

(XXXVII)

which may be further converted to yield the desired compound of formula (I) according to the processes as herein described.

The compound of formula (XXIV) is then optionally, further substituted at the 5 position of the core structure, to yield the desired compound of formula (I), according to the process outlined in Scheme 10.

Scheme 10

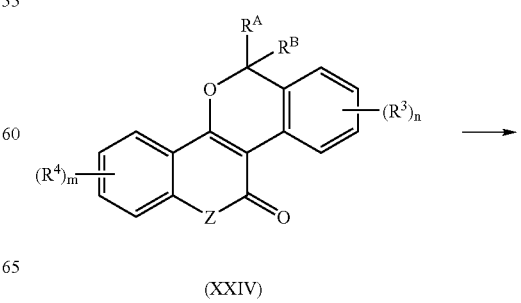

(XXIV)

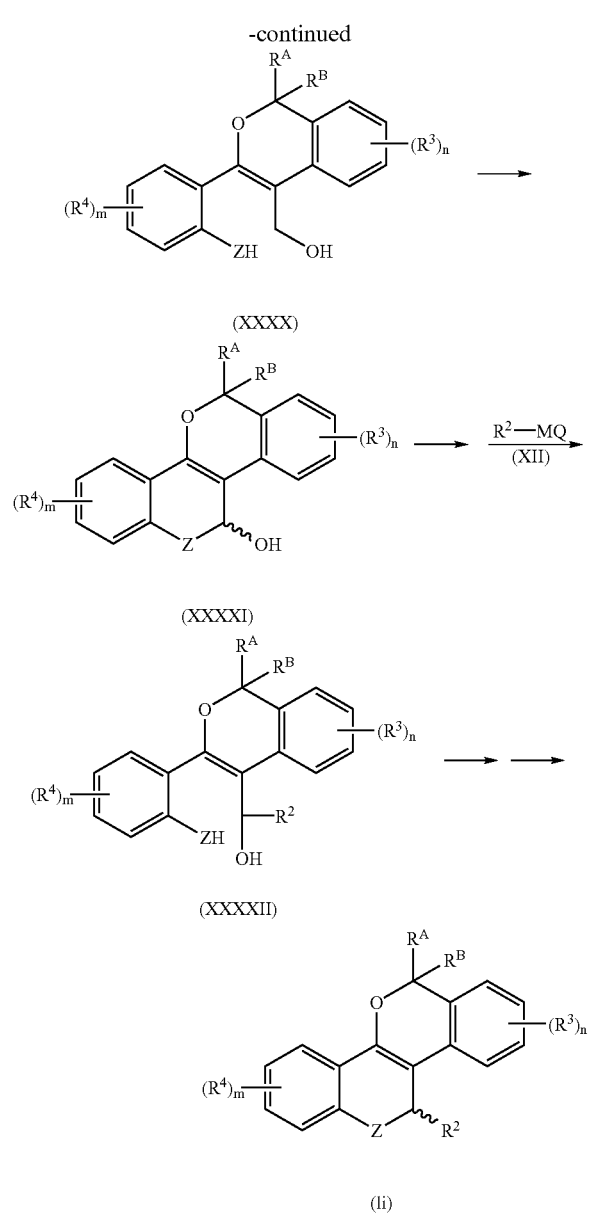

the like, and an azodicarboxamide such as DEAD, DIAD, and the like, in a solvent such as toluene, THF, and the like, to yield the corresponding compound of formula (Ii).

One skilled in the art will recognize that it may be necessary and/or desirable to protect one or more of the $R^3$ and/or $R^4$ groups at any of the steps within the process described above. This may be accomplished using known protecting groups and know protection and de-protection reagents and conditions, for example such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991.

Wherein the compound of formula (Ii) one or more $R^3$ and/or $R^4$ groups is hydroxy, the hydroxy groups may be optionally converted to desired groups according to the processes previously described, for example by reacting the compound of formula (Ii) with a suitably substituted acid chloride, a suitably substituted carboxylic acid or suitably substituted anhydride, as described in Scheme 4.

One skilled in the art will further recognize that the compound of formula (XXIV), the compound of formula (Ii) or the compound of formula (Ii) wherein any $R^3$ and/or $R^4$ hydroxy groups have been further functionalized may be selectively hydrogenated to yield the corresponding compound wherein the bond at the bridge of the B and C rings is fully saturated, according to the process as previously outlined.

Compounds of formula (I) wherein X is $CR^A R^B$ and Y is S may be prepared by modifying the processes outlined in Scheme 9 and 10. More particularly, the compound of formula (XXXVI), prepared as in Scheme 9, is reacted with a thionating reagent such as $CF_3SO_3Si(CH_3)_3/(CH_3)_3Si$—S—$Si(CH_3)_3$, and the like, in an organic solvent such as methylene chloride, chloroform, dichloromethane, and the like, to yield the corresponding compound of formula (XXXVIa).

(XXXVIa)

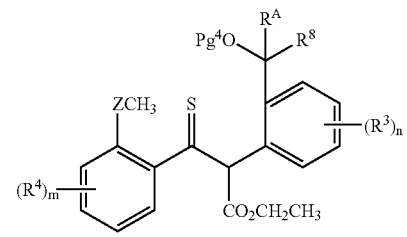

The compound of formula (XXXVIa) is then substituted for the compound of formula (XXXVI) and further reacted as described in Scheme 9, to yield the corresponding compound of formula (XXIVa), (XXIVa)

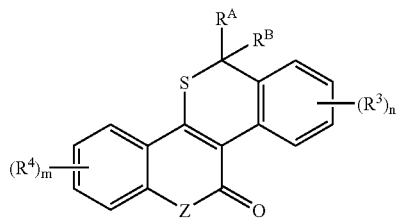

More specifically, a suitably substituted compound of formula (XXIV) is reacted with a reducing agent such as diisobutyl aluminum hydride, LAH, and the like, in an organic solvent such as toluene, benzene, THF, and the like, at a reduced temperature in the range of about −50° C. to about −80° C., to yield the corresponding compound of formula (XXXX).

The compound of formula (XXXX) is oxidized under oxidizing conditions such as Swern oxidation, Dess-Martin periodinane, TPAP, and the like, in an organic solvent such as dichloromethane, acetonitrile, DCE, and the like, to yield the corresponding compound of formula (XXXXI).

The compound of formula (XXXXI) is reacted with a suitably substituted compound of formula (XII), wherein MQ is lithium or a magnesium halide such as MgCl, MgBr or MgI, prepared from the corresponding known alkyl or aryl halide by known methods, in an organic solvent such as THF, diethyl ether, dioxane, hexane, and the like, to yield the corresponding compound of formula (XXXXI).

The compound of formula (XXXXII) is treated with a reagent such as triphenylphosphine, tributylphosphine, and which is in turn substituted for the compound of formula (XXIV) in the process described in Scheme 10, to yield the corresponding compound of formula (I) wherein Y is S.

Compounds of formula (I) wherein X is O or S, Z is O or S and Y is —CR$^A$R$^B$CH$_2$— or —CR$^A$R$^B$CH$_2$CH$_2$, wherein R$^A$ and R$^B$ are not hydroxy, may be prepared according to the process outlined in Scheme 11.

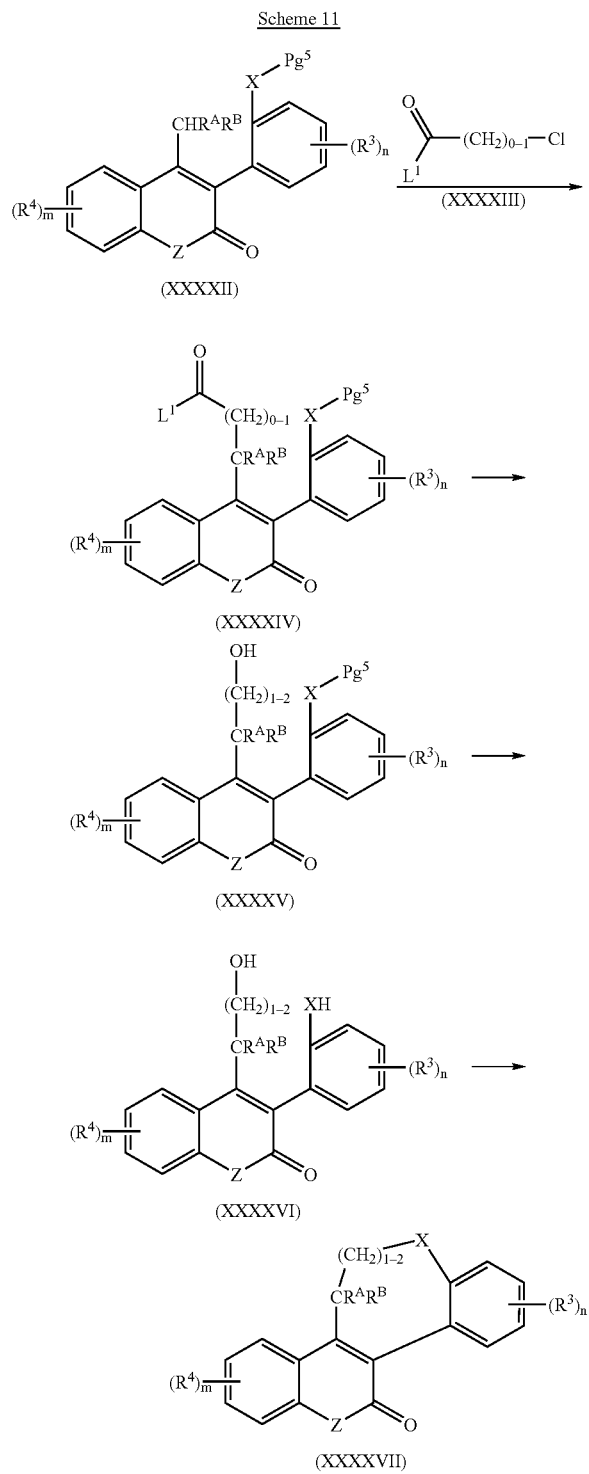

More particularly, a suitably substituted compound of formula (XXXXII), where Pg$^5$ is a suitable protecting groups such as alkyl (such as methyl), benzyl, SEM, MOM, BOM, pivaloyl, and the like, a known compound or compound prepared by known methods, is reacted with a suitably substituted compound of formula (XXXXIII), wherein L$^1$ is H or alkoxy, such as methoxy, ethoxy, and the like, in the presence of a base such as (TMS)$_2$NLi, LDA, NaHMDS, KHMDS, and the like, in the presence of a formylating reagent such as phenyl formate, 2,4,6-trichlorophenylformate, BrCH$_2$COOCH$_3$, ClCH$_2$COOCH$_3$, and the like, in an organic solvent such as THF, diethyl ether, dioxane, and the like, to yield the corresponding compound of formula (XXXXIV).

The compound of formula (XXXXIV) is reacted with a reducing agent such as NaBH$_4$, borane, LAH, and the like, in an organic solvent such as THF, diethyl ether, dioxane, and the like, to yield the corresponding compound of formula (XXXXV).

The compound of formula (XXXXV) is de-protected by known methods, to yield the corresponding compound of formula (XXXXVI).

The compound of formula (XXXXVI) is treated with a protic acid such as HCl, H$_2$SO$_4$, p-toluene sulfonic acid, camphor sulfonic acid (CSA), TFA, and the like or a Lewis acid such as BF$_3$ etherate, AlCl$_3$, SnCl$_4$, and the like, in a solvent such as toluene, methylene chloride, acetonitrile and the like, to yield the corresponding compound of formula (XXXVII).

Alternatively, the compound of formula (XXXXVI) is treated with a reagent such as triphenylphosphine, tributylphosphine, and the like, or an azodicarboxamide such as DEAD, DIAD, and the like, in a solvent such as toluene, THF, and the like, to yield the corresponding compound of formula (XXXXVII).

Compounds of formula (I) wherein X is selected from O, Y is CR$^A$R$^B$C(O) and Z is O or S may be prepared by reacting a suitably substituted compound of formula (XXXXIV) wherein L$^1$ is phenoxy and wherein Pg$^5$ is SEM or MOM, with an acid such as hydrochloric acid, H$_2$SO$_4$, TFA, and the like, in an organic solvent such as isopropanol, THF, or a mixture thereof such as isopropanol:THF, and the like to yield the corresponding compound of formula (XXXIX).

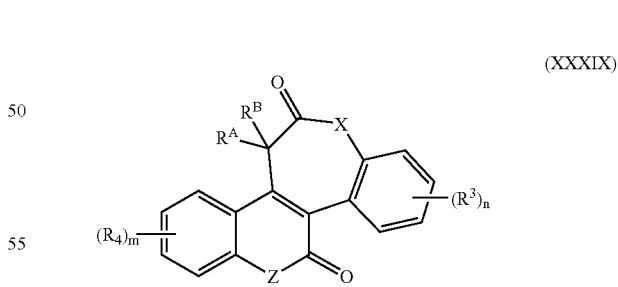

The compound of formula (XXXIX) is then further reacted to yield the desired compound of formula (I) according to the processes described herein.

One skilled in the art will recognize that the compound of formula (XXXXVII) may be further reacted to the corresponding compound of formula (I) or (II) according to the processes previously described. For example, by substituting the compound of formula (XXXXVII) for the compound of formula (II) in Scheme 2 or 3, or substituting the compound of formula (XXXXVII) for the compound of formula (XXIV) in Scheme 10.

One skilled in the art will recognize that it may be necessary and/or desirable to protect one or more of the $R^3$ and/or $R^4$ groups at any of the steps within the process described above. This may be accomplished using known protecting groups and know protection and de-protection reagents and conditions, for example such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991.

One skilled in the art will further recognize that wherein one or more $R^3$ and/or $R^4$ groups are hydroxy, the hydroxy groups may be optionally converted to desired groups according to the processes previously described.

One skilled in the art will further recognize that compounds of formula (I) wherein the bond at the bridge of the B and C rings is unsaturated (i.e. a double bond) may be converted to the corresponding compound of formula (I) wherein the bond at the bridge of the B and C rings is fully saturated (i.e. a single bond) as previously described, for example by selective hydrogenation, for example with hydrogen gas, with protection of reactive functional groups, as necessary. Alternatively, the bond at the bridge of the B and C rings may be selectively hydrogenated in any intermediate in the synthesis of the compound of formula (I) provided that reactive functional groups are suitably protected.

Compounds of formula (I) wherein $R^1$ and $R^2$ are each other than hydrogen may be prepared according to the process outlined in Scheme 12.

Accordingly, a suitably substituted compound of formula (XXXXVIII), a known compound or compound prepared by known methods, for example according to the processes described herein, is reacted with a suitably substituted compound of formula (XXXXIX), wherein MQ is lithium or a magnesium halide such as MgCl, MgBr or MgI, prepared from the corresponding known alkyl or aryl halide by known methods, in an organic solvent such as THF, diethyl ether, dioxane, hexane, and the like, to yield the corresponding compound of formula (L).

The compound of formula (L) is reacted with a suitably substituted compound of formula (XII), wherein MQ is lithium or a magnesium halide such MgCl, MgBr or MgI, prepared from the corresponding known alkyl or aryl halide by known methods, in an organic solvent such as THF, diethyl ether, dioxane, hexane, and the like, to yield the corresponding compound of formula (LI).

The compound of formula (LI) is treated with a protic acid such as HCl, $H_2SO_4$, p-toluene sulfonic acid, camphor sulfonic acid (CSA), TFA, and the like or a Lewis acid such as $BF_3$ etherate, $AlCl_3$, $SnCl_4$, and the like, in a solvent such as toluene, methylene chloride, acetonitrile and the like, to yield the corresponding compound of formula (Ij).

Alternatively, the compound of formula (LI) is treated with a reagent such as triphenylphosphine, tributylphosphine, and the like, or an azodicarboamide such as DEAD, DIAD, and the like, in a solvent such as toluene, THF, and the like, to yield the corresponding compound of formula (Ij).

Compounds of formula (D) may be prepared from suitably substituted compounds of formula (VIII) wherein $R^3$ corresponds to $R^{12}$, $R^4$ corresponds to $R^{13}$ and $R^A$ and $R^B$ are each hydrogen. More particularly, the compound of formula (VIII) is reacted with a strong base such as LDA, LiN$(TMS)_2$, and the like, and then reacted with a suitably selected eletrophile such as an alkyl aldehyde, an aryl aldehyde, an alkyl acid chloride, methylchloroformate, phenylchloroformate, α-chloroacetyl chloride, and the like, to yield the corresponding compound of formula (D).

Compounds of formula (I) wherein X is O or S, Z is O or S and Y is —$CH_2CH_2$—, may be prepared according to the process outlined in Scheme 13.

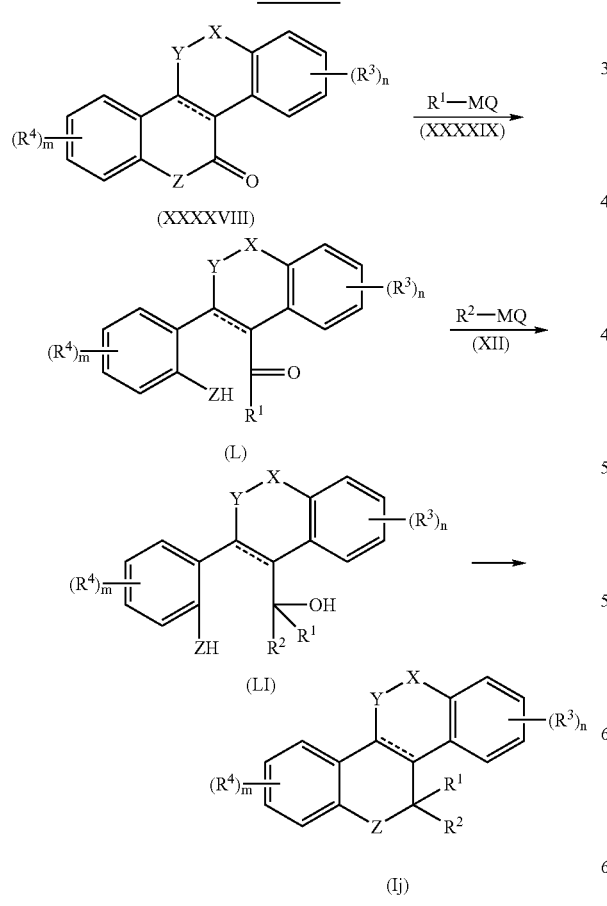

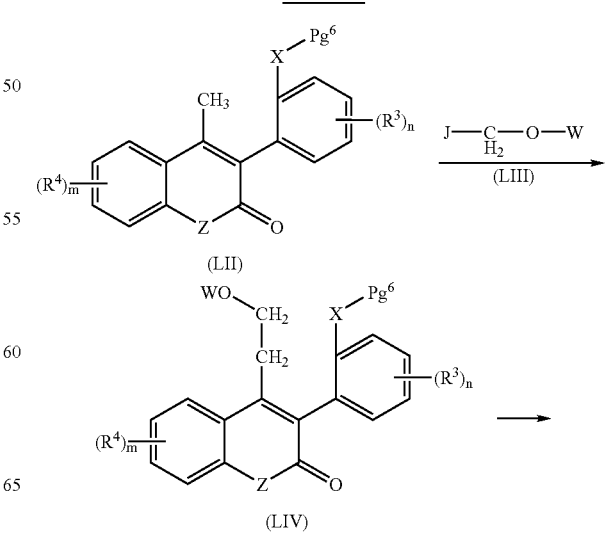

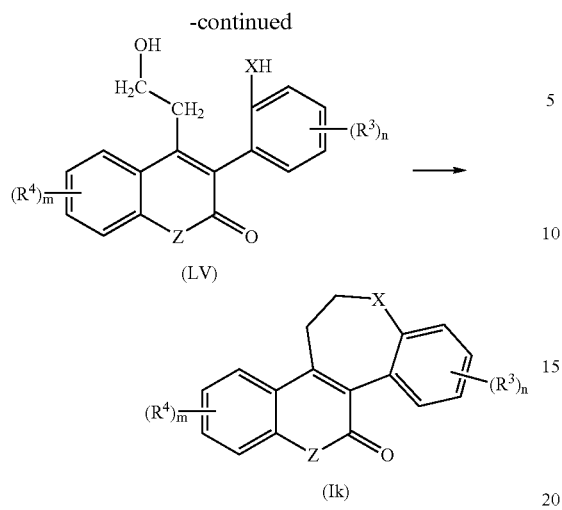

More particularly, a suitably substituted compound of formula (LII) where Pg⁶ is a suitable protecting groups such as benzyl, alkyl (such as methyl), SEM, MOM, BOM, substituted benzyl, PMB and the like, a known compound or compound prepared by known methods, is reacted with a suitably substituted compound of formula (LIII), wherein J is Cl, Br, iodide or another suitable leaving group, and W is a group such as alkyl (such as methyl, ethyl, and the like), benzyl, —CH₂CH₂TMS, —CH₂CH₂OCH₃, —CH₂O-benzyl, and the like, in the presence of a base such as (TMS)₂NLi, LDA, NaHMDS, KHMDS, and the like, to yield the corresponding compound of formula (LIV).

The compound of formula (LIV) is de-protected by known methods, for example by treating the compound of formula (LIV) with a protic such as HCl, H₂SO₄, TFA or with a Lewis acid such as BCl₃, BBr₃, TiCl₄, SnCl₄ or with a derivative of such a Lewis acid such catechol borane bromide, dimethy borane bromide, and the like, to yield the corresponding compound of formula (LV).

The compound of formula (LV) is treated with a protic acid such as HCl, H₂SO₄ and the like or with a Lewis acid such as BF₃ etherate, AlCl₃, SnCl₄, PCl₃, POCl₃, PCl₅ and the like, in a solvent such as toluene, methylene chloride, acetonitrile and the like, to yield the corresponding compound of formula (Ik).

Alternatively, the compound of formula (LV) is treated with a reagent such as triphenylphosphine, tributylphosphine, and the like, or with an azodicarboxamide such as DEAD, DIAD, and the like, in a solvent such as toluene, THF, and the like, to yield the corresponding compound of formula (Ik).

Compounds of formula (I) wherein X is O or S, Z is O or S and Y is —CH₂CH₂CH₂— may be prepared according to the process outlined in Scheme 14.

Scheme 14

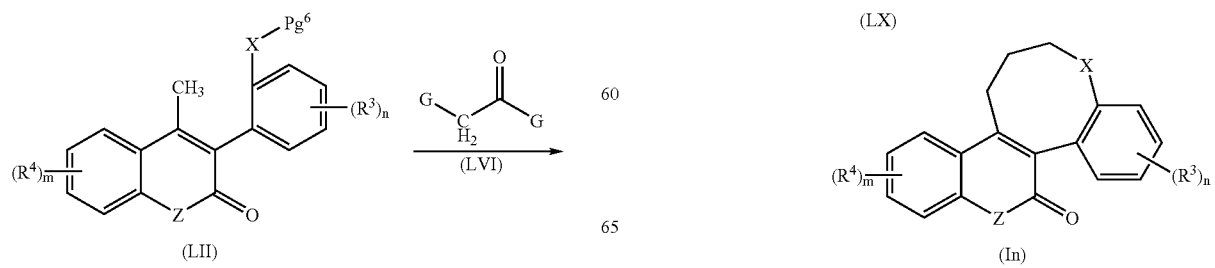

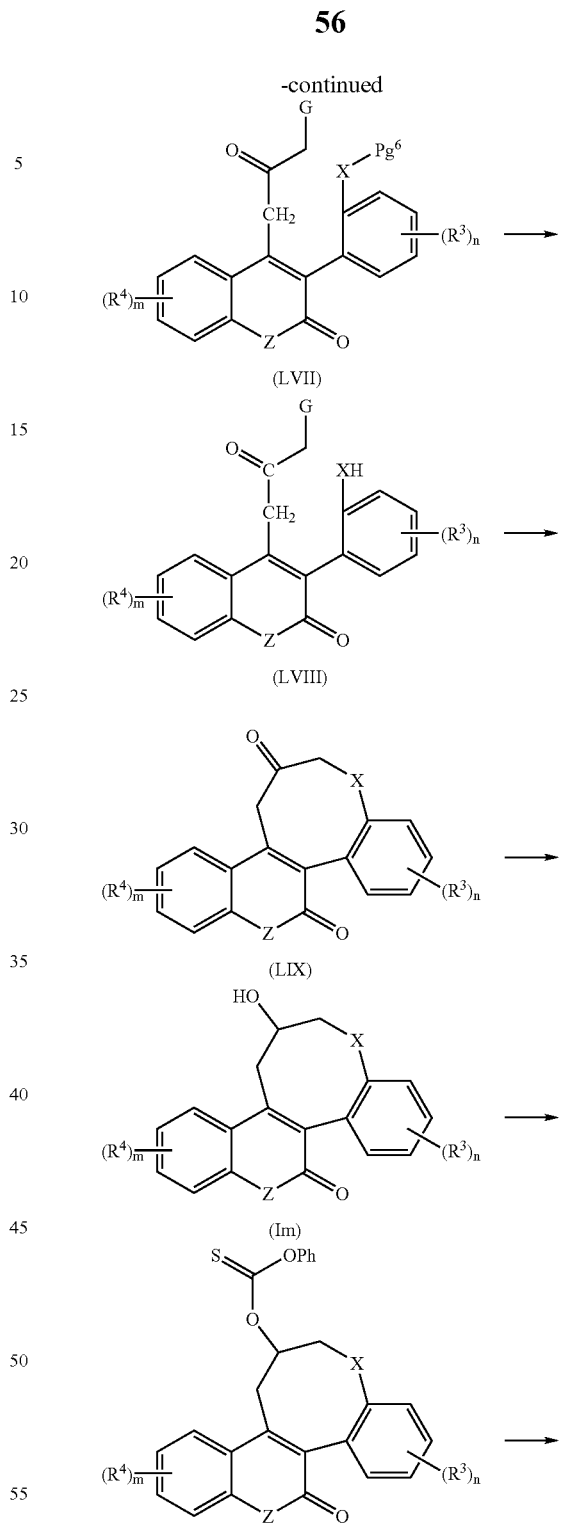

More particularly, a suitably substituted compound of formula (LII), where pg$^6$ is a suitable protecting groups such as benzyl, alkyl (such as methyl), SEM, MOM, BOM, substituted benzyl, PMB and the like, a known compound or compound prepared by known methods, is reacted with a suitably substituted compound of formula (LVI), wherein the two G groups are leaving groups, such as Cl, Br, Idodine, hydroxy, and the like, and wherein the two G groups are the same or different, a known compound or compound prepared by known methods, in the presence of a base such as (TMS)$_2$NLi, LDA, NaHMDS, KHMDS, and the like, to yield the corresponding compound of formula (LVII).

One skilled in the art will recognize that when the two G groups are different, they are selected such that the G group bound to the C(O) is more reactive than the G group bound to the CH$_2$ group.

The compound of formula (LVII) is de-protected by known methods, for example by treating the compound of formula (LVII) with a protic acid such as HCl, H$_2$SO$_4$, TFA and the like, or with a Lewis acid such as BCl$_3$, BBr$_3$, TiCl$_4$, SnCl$_4$, and the like or with a derivatives of a Lewis acid such as catechol borane bromide, dimethy borane bromide, and the like, to yield the corresponding compound of formula (LVIII).

The compound of formula (LVIII) is treated with a base such as potassium carbonate, sodium carbonate, cesium carbonate, potassium hydroxide, sodium hydroxide, and the like, or with an alkali metal alkoxide such as sodium ethoxide, sodium methoxide, sodium t-butoxide, potassium ethoxide, potassium methoxide, potassium t-butoxide, and the like, in a solvent such as methanol, ethanol, isopropanol, THF, and the like, or in a mixture of solvents thereof such as methanol:acetone, ethanol:acetone, methanol:acetonitrile, and the like, to yield the corresponding compound of formula (LIX).

The compound of formula (LIX) is reacted with a base such as NaBH$_4$, borane, LAH, and the like, in an organic solvent such as THF, diethyl ether, dioxane, and the like, to yield the corresponding compound of formula (Im).

The compound of formula (Im) is deoxygenated using Barton or modified Barton protocol (see for example, K. C. Nicolaou, R. A. Daines, J. Uenishi, W. S. Li, D. P. Papahatjis and T. K. Chakraborty, *J. Am. Chem. Soc.*, 1988, 110, pp. 4672-4683; which procedure involves conversion of the alcohol on the compound of formula (Im) to a thiocarbonate, as in the compound of formula (LX), followed by treatment with tributyltinhydride in presence of radical initiator like benzoyl peroxide, AIBN, and the like) to yield the corresponding compound of formula (In).

One skilled in the art will recognize that compounds of formula (I) wherein X is O or S, Z is O or S and Y is —CR$^A$R$^B$—CH(OH)—CR$^A$R$^B$— or —CR$^A$R$^B$— CH$_2$—CR$^A$R$^B$— may be similarly prepared according to the process outlined in Scheme 13 above, with substitution of a suitably substituted compound (LIIa) and (LVIa)

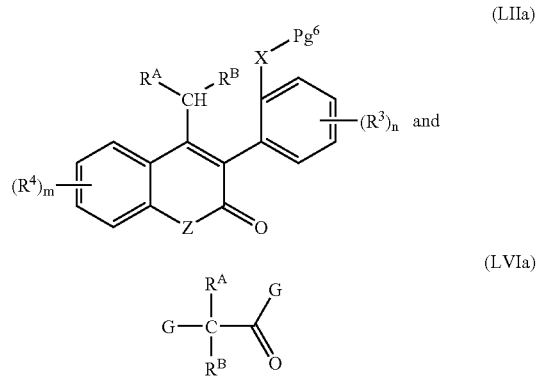

for the corresponding compounds of formula (LII) and (LIII), respectively.

Compounds of formula (I) wherein X is O or S, Y is CR$^A$R$^B$, CH$_2$CH$_2$ or CH$_2$CH$_2$CH$_2$ and Z is O or S may be prepared from a suitably substituted compound of formula (xA) according to the process outlined in Scheme 15.

Scheme 15

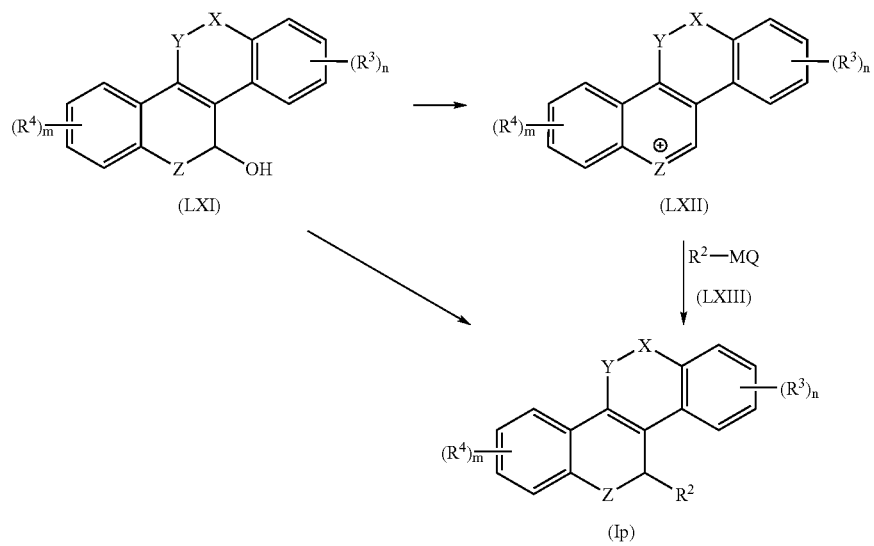

Accordingly, a suitably substituted compound of formula (LXI), a known compound or compound prepared by known methods, is reacted with a Lewis acid such $BF_3OEt_2$, $SnCl_4$, $TiCl_4$, perchloric acid and like, in an organic solvent such as $CH_2Cl_2$, $CHCl_3$ and the like, to yeld the corresponding, reactive intermediate compound of formual (LXII).

The compound of formula (LXII) is reacted with a suitably substituted compound of formula (LXIII), wherein MQ is a magnesium halide such as MgCl, MgBr or MgI (which magnesium halide may be prepared from the corresponding known alkyl or aryl halide by known methods), in an organic solvent such as THF, diethyl ether, dioxane, hexane, and the like, to yield the corresponding compound of formula (Ip).

Alternatively, the compound of formula (LXI) is reacted with enol ether, or an allyllic reagent such as 1,1-bis-trimethylsilyloxy-ethene, 1,1-bis-trimethylsilyloxy-propene, (1-methoxy-vinyloxy)-trimethyl-silane, allyl-trimethyl-silane, allyl-trimethyl-stannane, but-2-enyl-trimethyl-silane, but-2-enyl-trimethyl-stannane and trimethyl-vinyloxy-silane, and the like to yield the corresponding comound of formula (Ip).

One skilled in the art will further recognize that compounds of formula (I) wherein Y is selected from the group consisting of $CR^A R^B (CR^A R^B)_{1-2}$ and $CR^A R^B C(O) CR^A R^B$ may be similarly prepared according to processes described herein, by selecting and substituting, suitably substituted reagents for those described herein.

The present invention is further directed to a process for the preparation of a compound of formula (DX), as described in more detail in Scheme 16.

Scheme 16

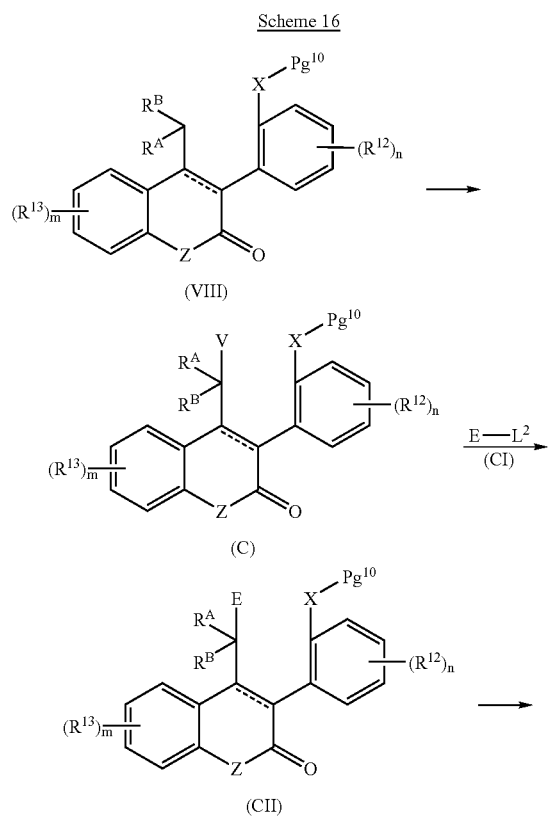

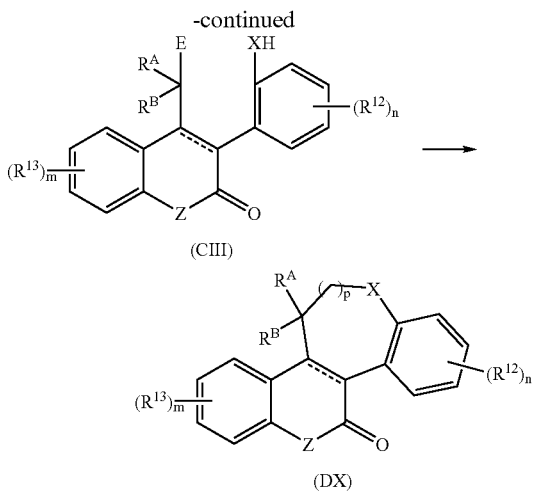

Accordingly, a suitably substituted compound of formula (VIII), a known compound or compound prepared by known methods, wherein $R^A$, $R^B$, n, $R^3$, m, $R^4$ and Z are as previously defined, wherein X is O or S and wherein $Pg^{10}$ is a suitable protecting group such as alkyl (such as methyl), benzyl, benzoyl, SEM, MOM, BOM, pivaloyl, and the like (see for example *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991), is reacted with a base such as LiHMDS, LDA, KHMDS, NaHMDS, and the like; preferably at a temperature of less than or equal to about room temperature, more preferably at a temperature in the range of about 30° C. to about −100° C., more preferably still, at reduced temperature in the range of about −10° C. to about −30° C.; in an aprotic organic solvent such as THF, dioxane, diethyether, and the like; to yield the corresponding compound of formula (C), wherein V is the corresponding base cation, Li, K or Na (i.e. when the base is LiHMDs or LDA, V is Li; when the base is KHMDS, V is K; when the base is NaHMDS, V is Na).

The compound of formula (C) is reacted with a suitably substituted compound of formula (CI), wherein E is an electrophile (i.e. an atom or molecule capable of forming a carbon cation or partial carbon cation), such as Br, Cl, I, $CH_3$, SEM, MOM, BOM, Br—$CH_2CH_2$—$OCH_3$, and the like, and wherein $L^2$ is a suitable leaving group such as Cl, Br, I, tosylate, mesylate, and the like, to yield the corresponding compound of formula (CII). The compound of formula (CI) may also be a source of Br or Cl such as NBS, NCS, and the like.

The compound of formula (CII) is de-protected by known methods (*Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991), to yield the corresponding compound of formula (CIII).

The compound of formula (CIII) is cyclized according to known methods, to yield the corresponding compound of formula (DX), wherein p is an integer from 0 to 2. When the electrophile E is Br, Cl, I and the like, the compound of formula (CIV) is treated with a base such as sodium carbonate, sodium bicarbonate, potassium carbonate, potassium bicarbonate, NaOH, KOH, TEA, and the like, preferably to a pH in the range of about pH10 to about pH11, to yield the corresponding compound of formula DX, wherein p is 0. When the elctrophile E is SEM, MOM, BOM, Br—CH₂CH₂—OCH₃, and the like, the compound of formula (CIV) is reacted with a protic acid such as HCl, H₂SO₄, p-toluene sulfonic acid, camphor sulfonic acid (CSA), TFA, and the like or a Lewis acid such as BF₃ etherate, AlCl₃, SnCl₄, and the like, in a solvent such as toluene, methylene chloride, acetonitrile and the like; or with a reagent such as triphenylphosphine, tributylphosphine, and the like, or an azodicarboamide such as DEAD, DIAD, and the like, in a solvent such as toluene, THF, and the like, to yield the corresponding compound of formula (DX), wherein p is 1-2.

One skilled in the art will recognize that the compound of formula (C) may alternatively be reacted with a suitably substituted compound of formula (CIa) wherein when the electrophile E is —C(O)CH₂—OCH₃, —C(O)—CH₂—Cl, —C(O)—CH₂—Br, —C(O)—CH₂-(lower alkyl), —CH₂—C(O)O-(lower alkyl), to yield the corresponding compound of formula (CII) which is then further reacted with a protic acid such as HCl, H₂SO₄, p-toluene sulfonic acid, camphor sulfonic acid (CSA), TFA, and the like or a Lewis acid such as BF₃ etherate, AlCl₃, SnCl₄, and the like, in a solvent such as toluene, methylene chloride, acetonitrile and the like; or with a reagent such as triphenylphosphine, tributylphosphine, and the like, or an azodicarboamide such as DEAD, DIAD, and the like, in a solvent such as toluene, THF, and the like, to yield the corresponding compound of formula (DXa), wherein —(CH₂)ₚ— is substituted with —C(O)—CH₂ wherein the CH₂ portion is bound to the X.

The present invention is further directed to a process for the preparation of a compound of formula (DXI), as described in more detail in Scheme 17.

Scheme 17

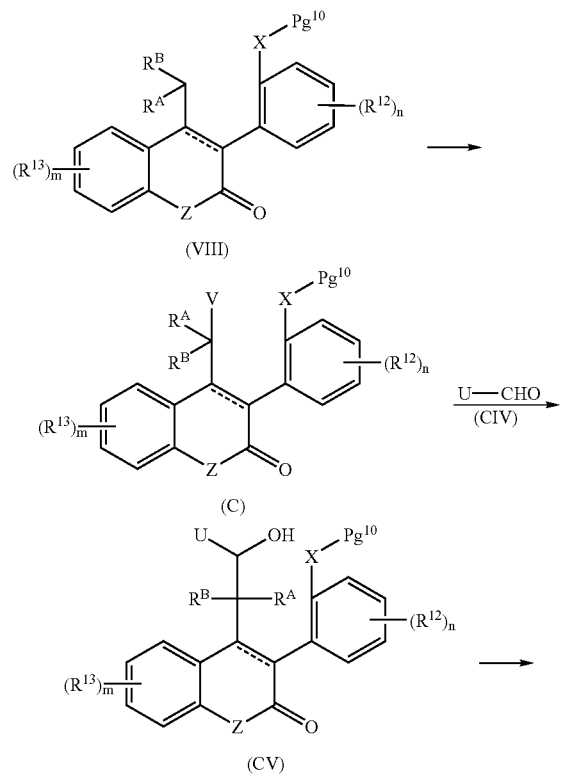

(VIII)

(C)

(CV)

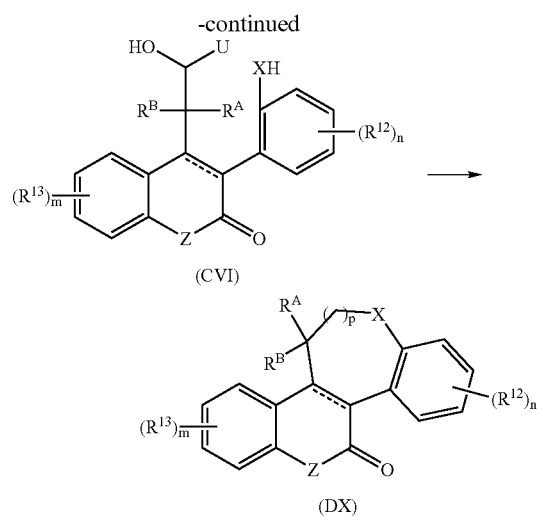

(CVI)

(DX)

Accordingly, a suitably substituted compound of formula (VIII), a known compound or compound prepared by known methods, wherein $R^A$, $R^B$, n, $R^3$, m, $R^4$ and Z are as previously defined, wherein X is O or S and wherein $Pg^{10}$ is a suitable protecting group such as alkyl (such as methyl), benzyl, benzoyl, SEM, MOM, BOM, pivaloyl, and the like (see for example T. W. Greene & P. G. M. Wuts, *Protective Groups in Organic Synthesis*, John Wiley & Sons), is reacted with a base such as LiHMDS, LDA, KHMDS, NaHMDS, and the like; preferably at a temperature of less than or equal to about room temperature, more preferably at a temperature in the range of about 30° C. to about −100° C., more preferably still, at reduced temperature in the range of about −10 to about −30° C.; in an aprotic organic solvent such as THF, dioxane, diethyether, and the like; to yield the corresponding compound of formula (C), wherein V is the corresponding base cation, Li, K or Na (i.e. when the base is LiHMDs or LDA, V is Li; when the base is KHMDS, V is K; when the base is NaHMDS, V is Na).

The compound of formula (C) is reacted with a suitably substituted compound of formula (C) is reacted with a suitably substituted aldehyde, a compound of formula (CIV), wherein U is hydrogen or lower alkyl, to yield the corresponding compound of formula (CV).

The compound of formula (CV) is de-protected by known methods (*Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991), to yield the corresponding compound of formula (CVI).

The compound of formula (CVI) is is cyclized according to known methods, to yield the corresponding compound of formula (DX), wherein p is 1. More particularly, the compound of formula (CIV) is reacted with a protic acid such as HCl, H₂SO₄, p-toluene sulfonic acid, camphor sulfonic acid (CSA), TFA, and the like or a Lewis acid such as BF₃ etherate, AlCl₃, SnCl₄, and the like, in a solvent such as toluene, methylene chloride, acetonitrile and the like; or with a reagent such as triphenylphosphine, tributylphosphine, and the like, or an azodicarboamide such as DEAD, DIAD, and the like, in a solvent such as toluene, THF, and the like; to yield the corresponding compound of formula (DX), wherein p is 1.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The utility of the compounds of the instant invention to treat disorders mediated by an estrogen receptor may be determined according to the procedures described in Examples—172, 173, 174 and 175 herein.

The present invention therefore provides a method of treating disorders mediated by an estrogen receptor in a subject in need thereof which comprises administering any of the compounds as defined herein in a quantity effective to treat said disorder. The compound may be administered to a patient by any, conventional route of administration, including, but not limited to, intravenous, oral, subcutaneous, intramuscular, intradermal and parenteral. The quantity of the compound which is effective for treating a disorder mediated by an estrogen receptor is between 0.01 mg per kg and 20 mg per kg of subject body weight.

The present invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 5 to about 1000 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating a disorder mediated by an estrogen receptor described in the present invention may also be carried out using a pharmaceutical composition comprising any of the compounds as defined herein and a pharmaceutically acceptable carrier. The pharmaceutical composition may contain between about 5 mg and 1000 mg, preferably about 10 to 500 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms may include suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyl-eneoxidepolyl-ysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of a disorder mediated by an estrogen receptor is required.

The daily dosage of the products may be varied over a wide range from about 1 to about 1,000 mg per adult human per day. For oral administration, the compositions are preferably provided in the form of tablets containing, 1.0, 5.0, 10.0, 15.0, 25.0, 50.0, 100, 250 and 500 milligrams of the active ingredient for the symptomatic adjustment of the dosage to the patient to be treated. An effective amount of the drug is ordinarily supplied at a dosage level of from about 0.01 mg/kg to about 20 mg/kg of body weight per day. Preferably, the range is from about 0.1 mg/kg to about 10 mg/kg of body weight per day, and especially from about 0.5 mg/kg to about 10 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The following Examples are set forth to aid in the understanding of the invention, and are not intended and should not be construed to limit in any way the invention set forth in the claims which follow thereafter.

EXAMPLE 1

Acetic acid 3-(2,4-dimethoxyphenyl)-7-hydroxy4-methyl-2-oxo-2H-chromen-7-yl ester

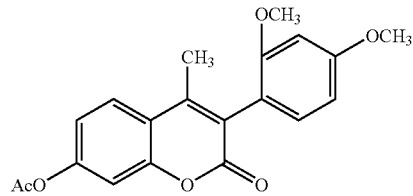

A mixture of 2,4-dihydroxyacetophenone (2.233 g, 14.67 mmol, 1 eq), 2, 4-dimethoxyphenylacetic acid (2.88 9, 14.67 mmol, 1 eq), acetic anhydride (7.5 mL, 78 mmol, 5 eq) and triethylamine (1.49 mL, 2.05 mmol, 1 eq) was stirred and heated to reflux under nitrogen for 48 hours. After cooling to room temperature the dark syrupy reaction mixture was poured into ice water (~450 mL). The suspension of sticky, semisolid product was neutralized by slowly adding solid $NaHCO_3$ to the mixture. The mixture was then allowed to solidify overnight. The dark solid was isolated by filtration, washed with water, sucked dry, and recrystallized from acetic acid to yield the title compound as an ivory crystalline solid. A second crop (0.95 g, 18.3%) was isolated from the mother liquor.

mp: 146-148° C. MS (Cl) m/z 355 $(M+H)^{+1}$H NMR (300 MHz, $CDCl_3$): δ 7.67 (1H, d, J=8.7 Hz), 7.13-7.06 (3H, m), 6.58 (1H, d, J=12.3 Hz), 6.56 (1H, s), 3.85 (3H, s), 3.76 (3H, s), 2.36 (3H, s), 2.24 (3H, s) IR (KBr): 1762, 1731, 1610, 1574, 1506, 1462, 1312, 1264, 1212 $cm^{-1}$ Anal. Calc $C_{20}H_{18}O_6$: C, 67.79; H, 5.12. Found: C, 67.75; H, 4.99.

EXAMPLE 2

Acetic acid 3-(2,4-dimethoxyphenyl)-8-hydroxy4-methyl-2-oxo-2H-chromen-7-yl ester

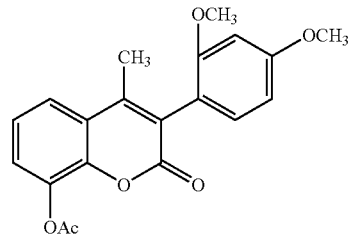

The title compound was prepared according to the procedure described in Example 1 with substitution of 2,3 dihydroxyacetophenone for the 2,4-dihydroxyacetophenone reagent.

mp 140-141° C. MS (Cl) m/z 355, $(M+H)^+$, 377 $(M+Na)^+$ 1H NMR (300 MHz, $CDCl_3$): δ 7.55 (1H, d, d, J=4.2, 5.32 Hz), 7.29 (1H, d, J=1.29 Hz), 7.27 (1H, d, J=4.37 Hz), 7.08) 1H, d, J=8.13 Hz), 6.57-6.55 (2H, m), 3.86 (3H, s), 3.76 (3H, s), 2.43 (3H, s), 2.24 (3H, s).

EXAMPLE 3

3-(2,4-Dimethoxyphenyl)-7-fluoro-4-methyl-2-oxo-2H-chromen-7-yl ester

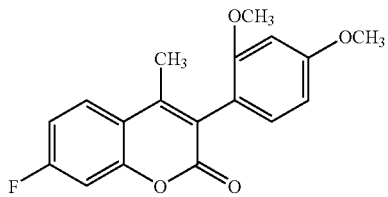

The title compound was prepared according to the procedure described in Example 1 with substitution of 4-fluoro-2-hydroxyacetophenone for the 2,4-dihydroxyacetophenone reagent.

mp 156-157° C. MS (Cl) m/z 315 (M+H)$^+$, 337 (M+Na)$^{+1}$ H NMR (300 MHz, CDCl$_3$): δ 7.64 (1H, d, d, J=5.98, 8.77 Hz), 7.11-7.01 (3H, m), 6.58 (1H, d, d, J=2.30, 8.10 Hz), 6.57 (1H, s), 3.86 (3H, s), 3.77 (3H, s), 2.24 (3H, s) IR (KBr): 1712, 1617, 1527, 1505, 1215, 1118 cm$^{-1}$ Anal. Calc. C$_{18}$H$_{15}$O$_4$: C, 68.78; H, 4.84. Found: C, 68.67; H, 4.70.

EXAMPLE 4

3-(2-Benzyloxy-3-methoxyphenyl)-7-methoxy4-methyl-chromen-2-one

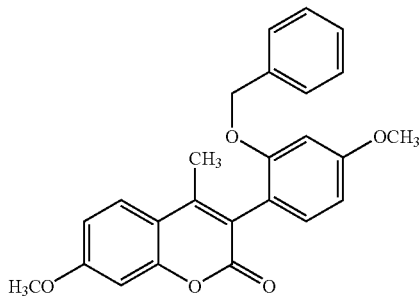

The title compound was prepared as a tan foamy solid according to the procedure described in Example 1 with substitution of 2-benzyloxy-4-methoxyphenylacetic acid for the 2,3-dimethoxyphenylacetic acid reagent.

MS (Cl) m/z 403 (M+H)$^+$, 425 (M+Na)$^+$, 827 (2M+Na)$^{+1}$ H NMR (300 MHz, CDCl$_3$): δ 7.53 (1H, d, J=9. Hz), 7.30-7.23 (5H, m), 7.11 (1H, d, J=8.96 Hz), 6.88-6.85 (2H, m), 5.06 (2H, d, J=2.00 Hz), 3.88 (3H, s), 3.81 (3H, s), 2.22 (3H, s) IR (KBr): 1712, 1619, 1603, 1579, 1564, 1509 cm$^{-1}$ Anal. Calc C$_{25}$H$_{22}$O$_5$/0.1 H$_2$O: C, 74.28; H, 5.54. Found: C, 74.10; H, 5.38.

EXAMPLE 5

3-(2,4-Dihydroxyphenyl)-7-hydroxy-4-methyl-chromen-2-one

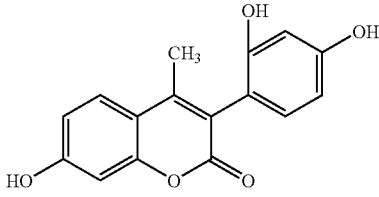

A mixture of acetic acid 3-(2,4-dimethoxyphenyl)-7-hydroxy-4-methyl-2-oxo-2H-chromen-7-yl ester, prepared as in Example 1 (0.177 g, 0.5 mmol, 1 eq) and dry pyridine hydrochloride (0.9 g, 8.8 mmol, 16 eq) was stirred and heated in an oil bath to a melt, at 210° C. under a closed nitrogen atmosphere in a loosely stoppered round bottom flask for 1 hour. After cooling to room temperature the reaction mixture was triturated with water and the aqueous solution was extracted several times with ethyl acetate until the latter was colorless. Combined organic extracts were washed with brine, dried (anhydrous sodium sulphate), filtered and evaporated to yield the title compound as a pinkish crystalline solid.

mp 282-283° C. MS (Cl) m/z 285 (M+H)$^+$, 306 (M+Na)$^+$; loop negative 283 (M–H) $^1$H NMR (300 MHz, DMSO-d$_6$): δ 10.47 (1H, brs), 9.34 (2H, s), 7.62 (1H, d, J=8.8 Hz), 6.81 (2H, d,d, J=2.5, 8.3 Hz), 6.72 (1H, d, J=2.2 Hz), 6.35 (1H, d, J=2.1 Hz), 6.27 (1H, d,d, J=2.1, 8.2 Hz) 2.13 (3H, s) IR (KBr): 3454, 3264, 1673, 1616, 1562, 1509, 1461, 1379, 1350, 1282, 1157, 1106 cm$^{-1}$ Anal. Calc. C$_{16}$H$_{12}$O$_5$/0.25 H$_2$O: C, 66.55; H, 4.36. Found: C, 66.63; H, 4.53.

EXAMPLE 6

3-(2,3-Dihydroxyphenyl)-7-hydroxy-4-methyl-chromen-2-one

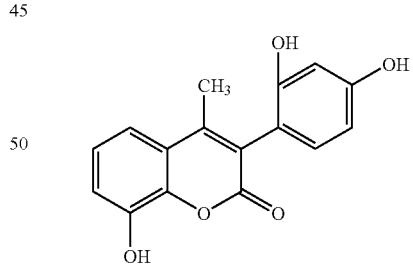

The title compound was prepared according to the procedure described in Example 5 with substitution of acetic acid 3-(2,4-dimethoxyphenyl)-8-hydroxy-4-methyl-2-oxo-2H-chromen-7-yl ester, prepared in Example 2, for acetic acid 3-(2,4-dimethoxyphenyl)-7-hydroxy-4-methyl-2-oxo-2H-chromen-7-yl ester.

mp 273-274° C. MS (Cl) m/z 285 (M+H)$^+$, 307 (M+Na)$^+$, loop negative 283 (M–H) $^1$H NMR (300 MHz, DMSO-d6): δ 10.10 (1H, s), 9.32 9 1H, s), 9.24 (1H, s), 7.23-7.07 (3H, m), 6.85 (1H, d, J=8.23 Hz), 6.37 (1H, d, J=2.27 Hz), 6.29 (1H, d, d, J=2.30, 8.24 Hz), 2.17 (3H, s)

EXAMPLE 7

3-(2,4-Dihydroxyphenyl)-7-fluoro-4-methyl-chromen-2-one

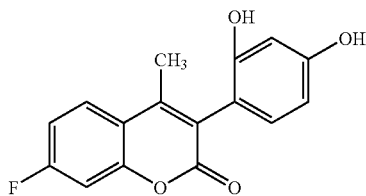

The title compound was prepared according to the procedure outlined in Example 5 with substitution of 3-(2,4-dimethoxyphenyl)-7-fluoro-4-methyl-2-oxo-2H-chromen-7-yl ester, prepared in Example 3, for acetic acid 3-(2,4-dimethoxyphenyl)-7-hydroxy-4-methyl-2-oxo-2H-chromen-7-yl ester.

mp 266-268° C. MS (Cl) m/z 287 (M+H)$^+$, 309 (M+Na)$^+$; loop negative 285 (M−H) $^1$H NMR (300 MHz, acetone-d6): δ 8.36 (1H, s), 8.12 (1H, s), 7.91-7.85 (1H, m), 7.37-7.10 (2H, m), 6.98 (1H, d, J=8.24 Hz), 6.50 (1H, d, J=8.32 Hz), 6.46 (1H, d, d, J=2.37, 8.24 Hz), 2.31 (3H, s) IR (KBr): 3329, 3164, 1685, 1611, 1570, 1272, 1116 cm$^{-1}$ Anal. Calc. $C_{18}H_{11}FO_4/0.1 H_2O$: C, 66.71; H, 3.92. Found: C, 66.63; H, 4.06.

EXAMPLE 8

3-(2-Hydroxy-4-methoxyphenyl)-7-hydroxy-4-methyl-chromen-2one

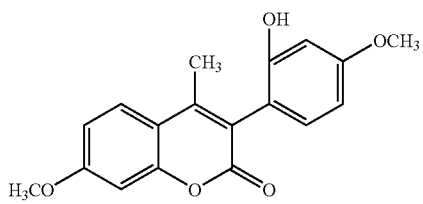

A solution of 3-(2-benzyloxy-3-methoxyphenyl)-7-methoxy-4-methyl-chromen-2-one (0.98 g, 2.44 mmol), prepared as in Example 4, in glacial acetic acid (8 mL) was treated with concentrated hydrochloric acid (3.5 mL) and the mixture stirred and heated to 60° C. for about 20 hours. Reaction monitoring by mass spectrum and thin layer chromatography revealed the presence of the starting material, so additional acetic acid (4 mL) and hydrochloric acid (3 mL) were added and stirring and heating continued for another 20 hours. The reaction mixture was then evaporated to dryness in vacuum and the residue diluted with water. The precipitated crystalline pinkish, solid, crude title compound was isolated by filtration, washed with water and dried. The resulting product was triturated with ether, filtered and washed with additional ether to yield the title product as a solid.

mp 213-214° C. MS (Cl) m/z 313 (M+H)$^+$; (M−H, loop negative) $^1$H NMR (300 MHz, DMSO-d6): δ 9.40 (1H, brs), 7.73 (1H, d, J=8.68 Hz), 7.01-6.96 (3H, m), 6.47 (1H, s), 6.46 (1H, d, J=6.60 Hz), 3.88 (3H, s), 3.74 (3H, s), 2.16 (3H, s) IR (KBr): 3300, 1669, 1603, 1562 cm$^{-1}$. Anal. Calc. $C_{18}H_{16}O_5$: C, 69.22; H, 5.16. Found: C, 69.42; H, 5.18.

EXAMPLE 9

Acetic acid 3-acetoxy-4-(7-acetoxy-4-methyl-2-oxo-2H-chromen-3-yl)-phenyl ester

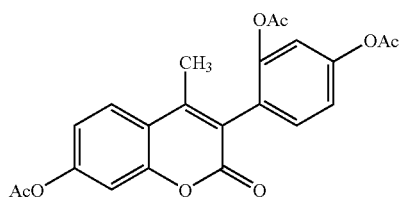

A mixture of 3-(2,4-dihydroxyphenyl)-7-hydroxy-4-methyl-chromen-2-one (0.72 g, 2.533 mmol), prepared as in Example 5, acetic anhydride (2 mL, about 20 mmol) and pyridine (0.2 mL, about 2.2 mmol) was heated to 70° C. under nitrogen for 18 hours. The resulting mixture was cooled. To then mixture was then added water and the mixture stirred at room temperature for 30 minutes, then extracted with dichloromethane. The organic extracts were washed with brine, dried (anhydrous sodium sulphate), filtered and evaporated to a foam. The foam was crystallized by triturating the foam with ethyl acetate/ether to yield the title product as a beige, crystalline solid.

mp 145-145° C. MS (Cl) m/z 411 (M+H)$^+$, 432 (M+Na)$^+$ $^1$H NMR (300 MHz, CDCl$_3$): δ 7.70 (1H, d, J=8.7 Hz), 7.26 (1H, d, J=2.3 Hz), 7.16-7.10 (4H, m), 2.37 (3H, s), 2.32 (3H, s), 2.28 (3H, s), 2.11 (3H, s) IR (KBr): 1763, 1726, 1611, 1573, 1501, 1428, 1373, 1202 cm$^{-1}$ Anal. Calc. $C_{22}H_{18}O_8$: C, 64.39; H, 4.42. Found: C, 64.16; H, 4.23.

EXAMPLE 10

Acetic acid 5-acetoxy-2-(8-acetoxy-4-methyl-2-oxo-2H-chromen-3-yl)-phenyl ester

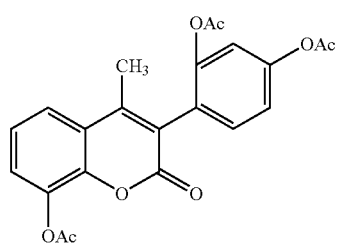

The title compound was prepared according to the procedure described in Example 9 with substitution of 3-(2,3-dihydroxyphenyl)-7-hydroxy-4-methyl-chromen-2-one, prepared as in Example 6, for 3-(2,4-dihydroxyphenyl)-7-hydroy-4-methyl-chromen-2-one.

mp 119-120° C. MS m/z 369 [(M−Ac)+H]$^+$ 411 (M+H)$^+$, 433(M+Na)$^+$ $^1$H NMR (300 MHz, CDCl$_3$): δ 7.59-7.54 (1H, m), 7.34-7.29 (2H, m), 7.25 (1H, d, J=8.41 Hz), 2.43 (3H, s), 2.32 (3H, s), 2.29 (3H, s), 2.11 (3H, s) IR (KBr): 1769, 1720, 1610, 1578, 1501, 1462, 1371, 1202 cm$^{-1}$ Anal. Calc. $C_{18}H_{11}FO_4/0.1 H_2O$: C, 66.71; H, 3.92. Found: C, 66.63; H, 4.06.

EXAMPLE 11

Acetic acid 5-acetoxy-2-(7-fluoro-4-methyl-2-oxo-2H-chromen-3-yl)-phenyl ester

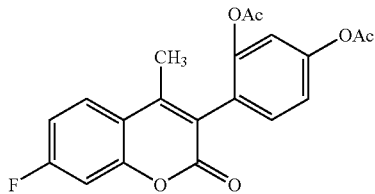

The title compound was prepared according to the procedure described in Example 9 with substitution of 3-(2,4-dihydroxyphenyl)-7-fluoro-4-methyl-chromen-2-one, prepared as in Example 7, for 3-(2,4-dihydroxyphenyl)-7-hydroxy-4-methyl-chromen-2-one.

mp 148-149° C. MS (Cl) m/z 329 [(M−Ac)+H]$^+$ 371(M+H)$^+$, 393 (M+Na)$^+$ $^1$H NMR (300 MHz, CDCl$_3$): δ 7.70-7.65 (1H, m), 7.27 (2H, d, J=8.06 Hz), 7.14-7.05 (3H, m), 2.32 (3H, s), 2.28 (3H, s), 2.109 (3H, s) IR (KBr): 1765, 1726, 1706, 1612, 1529, 1500, 1429, 1372, 1273, 1191 cm$^{-1}$ Anal. Calc. C$_{20}$H$_{15}$FO$_6$: C, 64.87; H, 4.08. Found: C, 64.69; H, 3.94.

EXAMPLE 12

Acetic acid 3-methoxy-2-(7-methoxy-4-methyl-2oxo-2H-chromen-3-yl)-phenyl ester

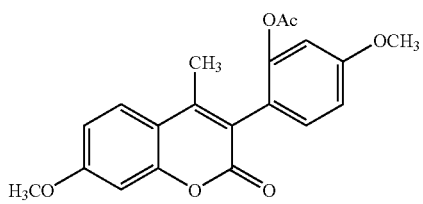

The title compound was prepared as a light pink solid according to the procedure described in Example 9 with substitution of 3-(2-hydroxy-4-methoxyphenyl)-7-hydroxy-4-methyl-chromen-2-one, prepared as in Example 8, for 3-(2,4-dihydroxyphenyl)-7-hydroxy-4-methyl-chromen-2-one.

mp 125-126° C. MS (Cl) m/z 355 (M+H)$^+$ 1H NMR (300 MHz, CDCl$_3$): δ 7.57 (1H, d, J=8.76 Hz), 7.17 (1H, d, J=8.54 Hz), 6.91-6.86 (3H, m), 6.78 (1H, d, J=2.52 Hz), 3.89 (3H, s), 3.84 (3H, s), 2.24 (3H, s), 2.09 (3H, s) IR (KBr): 1765, 1716, 1618, 1605, 1564, 1508, 1206 cm$^{-1}$ Anal. Calc. C$_{20}$H$_{18}$O$_6$: C, 67.79; H, 5.12. Found: C, 67.94, H, 5.14.

EXAMPLE 13

Acetic acid 3-acetoxy-4-(7-acetoxy-4-bromomethyl-2-oxo-2H-chromen-3-yl)-phenyl ester

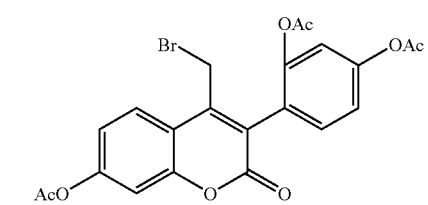

A mixture of acetic acid 3-acetoxy-4-(7-acetoxy-4-methyl-2-oxo-2H-chromen-3-yl)phenyl ester (0.767 g, 1.87 mmol, 1 eq), N-bromosuccinimide (0.349 g, 1.962 mmol, 1.05 eq) and benzoyl peroxide (0.035 g, 0.145 mmol) in carbon tetrachloride (30 mL) was stirred and heated to reflux under nitrogen in presence of a 100 W tungsten lamp for 20 hours. Reaction monitoring by MS and TLC showed the presence unreacted starting material, and additional N-bromosuccinimide (0.060 g, 0.34 mmol) and benzoyl peroxide (0.008 g) were added to the reaction mixture and the reaction was heated at reflux under nitrogen for an additional 2 hours. The mixture was evaporated to dryness, dissolved in hot dichloromethane and purified by column chromatography on silica gel using 3% ethyl acetate/hexane as an eluent to yield the title product as a tan crystalline solid.

mp 171-172° C. MS (cl) m/z 488 (M+H)$^+$, 512 (M+Na)$^+$ $_1$H NMR (300 MHz, CDCl$_3$): δ 7.81 (1H, d, J=8.7 Hz), 7.49 (1H, d, J=8.3 Hz), 7.19-7.13 (4H, m), 4.40 (1H, d, J=10.6 Hz), 4.27 (1H, d, J=10.7 Hz), 2.38 (3H, s), 2.33 (3H, s), 2.11 (3H, s) IR (KBr): 1766, 1725, 1613, 1571, 1499, 1426, 1369, 1194 cm$^{-1}$ Anal. Calc. C$_{22}$H$_{17}$BrO$_8$: C, 54.01; H, 3.50. Found: C, 54.03; H, 3.42.

EXAMPLE 14

Acetic acid 5-acetoxy-2-(8-acetoxy-4-bromomethyl-2-oxo-2H-chromen-3-yl)-phenyl ester

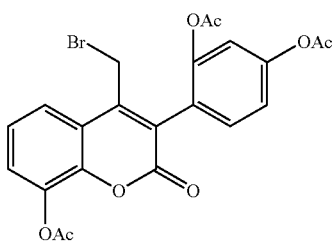

The title compound was prepared as a crystalline solid according the procedure described in Example 13 with substitution of acetic acid 5-acetoxy-2-(8-acetoxy-4-methyl-2-oxo-2H-chromen-3-yl)-phenyl ester, prepared as in Example 10, for acetic acid 3-acetoxy-4-(7-acetoxy-4-methyl-2-oxo-2H-chromen-3-yl)-phenyl ester.

EXAMPLE 15

Acetic acid 2-(4-bromomethyl-7-methoxy-2-oxo-2H-chromen-3-yl)-5-methoxy-phenyl ester

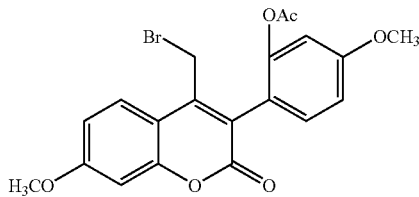

The title compound was prepared as a crystalline solid according the procedure described in Example 13 with substitution of acetic acid 3-methoxy-2-(7-methoxy-4-methyl-2-oxo-2H-chromen-3-yl)-phenyl ester, prepared a in Example 15, for acetic acid 3-acetoxy-4-(7-acetoxy-4-methyl-2-oxo-2H-chromen-3-yl)-phenyl ester.

mp 132-133° C. MS (Cl) m/z 435 (M+H)$^+$, 391 [(M−Ac)+H]$^+$ $^1$H NMR (300 MHz, CDCl$_3$): δ 7.68 (1H, d, J=8.80 Hz), 7.40 (1H, d, J=8.58 Hz), 6.97-6.91 (3H, m), 6.88 (1H, d, J=2.28 Hz), 6.80 (1H, d, J=2.40 Hz), 4.39 (1H, d, J=10.39 Hz), 4.27 (1H, d, J=10.38 Hz), 3.90 (3H, s), 3.86 (3H, s), 2.09 (3H, s) IR(KBr): 1785, 1721, 1605, 1564, 1512, 1453, 1289, 1213, 1105 cm$^{-1}$ Anal. Calc. C$_{20}$H$_{17}$BrO$_6$: C, 55.44; H, 3.96. Found: C, 55.45; H, 4.02.

EXAMPLE 16

Acetic acid 3-acetoxy-4-(4-bromomethyl-7-fluoro-2-oxo-2H-chromen-3-yl)-phenyl ester

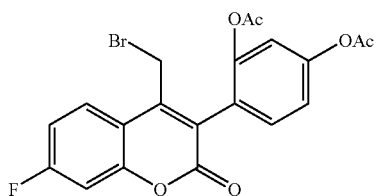

The title compound was prepared as a crystalline solid according the procedure described in Example 13 with substitution of acetic acid 5-acetoxy-2-(7-fluoro-4-methyl-2-oxo-2H-chromen-3-yl)-phenyl ester, prepared as in Example 11, for acetic acid 3-acetoxy-4-(7-acetoxy-4-methyl-2-oxo-2H-chromen-3-yl)-phenyl ester.

mp 230-231° C. MS (Cl) m/z 451 (M+H)$^+$, 471 (M+Na)$^+$, 409 [(M−Ac)+H]$^+$ $^1$H NMR (300 MHz, CDCl$_3$): δ 7.80 (1H, d, d, J=3.37, 9.62 Hz), 7.49 (1H, d, J=8.35 Hz), 7.21-7.11 (4H, m), 4.39 (1H, d, J=10.61 Hz), 4.27 (1H, d, J=10.68), 2.33 (3H, s), 2.10 (3H, s) IR (KBr): 1758, 1727, 1617, 1581, 1371, 1215 cm$^{-1}$.

EXAMPLE 17

2,8-Dihydroxy-11H-chromeno[4,3-c]chromen-5-one
Compound #1

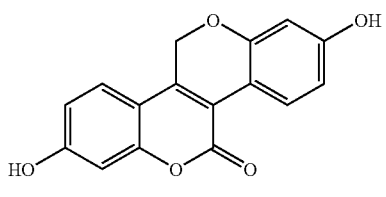

Method A:

To a stirred solution of 3-(2-hydroxy-4-methoxyphenyl)-7-hydroxy-4-methyl-chromen-2-one (0.100 g, 0.204 mmol), prepared as in Example 13, in a mixture of methanol (5 mL) and acetone (2 mL) was added at room temperature anhydrous potassium carbonate (0.08474 g, 0.6 mmol). The solution immediately turned yellow. The solution was stirred for 2 hours, evaporated to dryness, the residue was dissolved in water (15 mL) and then acidified with dilute hydrochloric acid to about pH 1. The precipitated yellow solid was isolated by filtration, washed with water and dried to yield the title compound.

mp>350° C. MS (Cl) m/z 283 (M+H)$^+$, 305 (M+Na)$^+$, 321 (M+K)$^+$; loop negative 281 (M−H) $^1$H NMR (300 MHz, DMSO-d6): δ 10.65 (1H, brs), 9.85 (1H, brs), 8.19 (1H, d, J=8.0 Hz), 7.62 (1H, d, J=8.1 Hz), 6.82 (1H, d, J=8.2 Hz), 6.76 (1H, s), 6.47 (1H, d, J=7.75 Hz), 6.38 (1H, s), 5.33 (2H, s) IR (KBr): 3373, 1699, 1620, 1597, 1508, 1464, 1299, 1264, 1166 cm$^{-1}$ Anal. Calc. C$_{16}$H$_{10}$O$_5$/0.2 H$_2$O: C, 67.23; H, 3.67. Found: C, 67.31; H, 3.55.

EXAMPLE 18

2,8-Dihydroxy-11H-chromeno[4,3-c]chromen-5-one
Compound #1

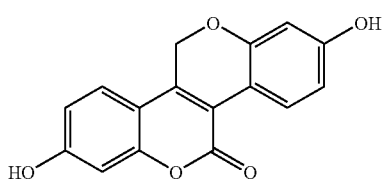

Method B:

The title product was prepared according to the procedure described in Example 5 with substitution of 2,8-dimethoxy-11H-chromeno[4,3c]chromen-5-one, prepared as in Example 21, for acetic acid 3-(2,4-dimethoxyphenyl)-7-hydroxy-4-methyl-2-oxo-2H-chromen-7-yl ester.

m.p.>360° C.

EXAMPLE 19

2,7-Dihydroxy-11H-chromeno[4,3-c]chromen-4-one Compound #84

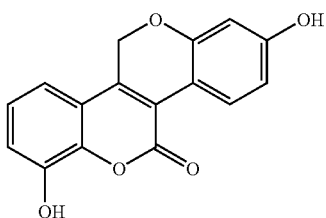

The title compound was prepared according the procedure described in Example 17 with substitution of acetic acid 5-acetoxy-2-(8-acetoxy-4-bromomethyl-2-oxo-2H-chromen-3-yl)-phenyl ester, prepared as in Example 10, for 3-(2-hydroxy-4-methoxyphenyl)-7-hydroxy-4-methyl-chromen-2-one.

EXAMPLE 20

8-Fluoro-2-hydroxy-11H-chromeno[4,3-c]chromen-5-one Compound #37

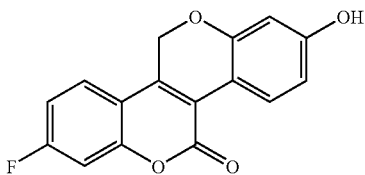

The title compound was prepared as a yellow solid according the procedure described in Example 17 with substitution of acetic acid 3-acetoxy-4-(4-bromomethyl-7-fluoro-2-oxo-2H-chromen-3-yl)-phenyl ester, prepared as in Example 16, for 3-(2-hydroxy-4-methoxyphenyl)-7-hydroxy-4-methyl-chromen-2-one.

mp 259-260° C. MS (Cl) m/z 285 (M+H)$^+$, 307 (M+Na)$^+$; loop negative 281 (M−H) $^1$H NMR (300 MHz, DMSO-d6): δ 9.99 (1H, s), 8.22 (1H, d, J=8.70 Hz), 7.87 (1H, d, d, J=6.12, 8.90 Hz), 7.46 (1H, d, d, J=2.52, 9.53 Hz), 7.31 (1H, d, t, J=2.56, 8.77 Hz), 6.51 (1H, d, d, J=2.45, 8.71 Hz), 6.41 (1H, d, J=2.41 Hz), 5.40 (2H, s) IR (KBr): 3341, 1697, 1621 1506, 1455, 1275, 1110 cm$^{-1}$ Anal. Calc. $C_{16}H_9FO_4$: C, 67.61; H, 3.19. Found: C, 65.252; H, 3.38.

EXAMPLE 21

2,8-DiMethoxy-11H-chromeno[4,3-c]chromen-5-one Compound #2

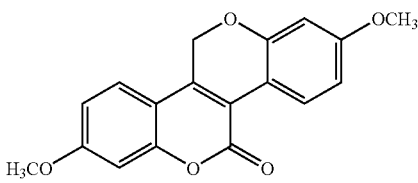

The title compound was prepared as a light yellow solid according the procedure described in Example 17 with substitution of acetic acid 2-(4-bromomethyl-7-methoxy-2-oxo-2H-chromen-3-yl)-5-methoxy-phenyl ester, prepared as in Example 15, for 3-(2-hydroxy-4-methoxyphenyl)-7-hydroxy-4-methyl-chromen-2-one.

mp 200-201° C. MS (Cl) m/z 311 (M+H)$^+$, 333 (M+Na)$^+$ $^1$H NMR (300 MHz, CDCl$_3$): δ 8.49 (1H, d, J=8.83 Hz), 7.37 (1H, d, J=8.46 Hz), 6.90 (1H, d, d, J=2.67, 8.84 Hz), 6.53 (1H, d, J=2.36 Hz), 5.27 (2H, s), 3.89 (3H, s), 3.83 (3H, s) IR (KBr): 1712, 1621 1573, 1504, 1168 cm$^{-1}$ Anal. Calc. for $C_{18}H_{14}O_5$: C, 69.67; H, 4.55. Found: C, 69.42; H, 4.54.

EXAMPLE 22

2,8-Bis-(tert-butyl-dimethyl-silyloxy)-11H-chromeno[4,3-c]chromen-5-one Compound #3

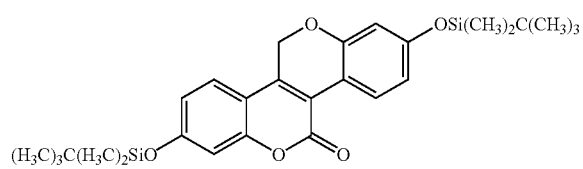

A slurry of 2,8-dihydroxy-11H-chromeno[4,3-c]chromen-5-one (0.322 g, 1.1412 mmol, 1 eq), prepared as in Example 17, in dichloromethane (10 mL) was treated with triethylamine (0.8 mL, 5.70 mmol, 5 eq), followed by the addition of t-butyldimethylsilyl chloride (0.585 g, 3.88 mmol, 3.4 eq). The reaction mixture was stirred at room temperature under nitrogen for 18 hours. (The slurry was observed to become a clear solution after about 30 minutes of stirring.) The reaction mixture was diluted with hexane (~35 mL) and washed once with brine. The aqueous washing was re-extracted with hexane. The combined organic extracts were dried (anhydrous sodium sulphate), filtered and evaporated in vacuum to yield a yellow solid residue. The solid residue was recrystallized from hexane to yield the title compound as a light yellow crystalline solid.

mp 150-151° C. MS (Cl) m/z 533 (M+Na)$^+$ $^1$H NMR (300 MHz, CDCl$_3$): δ 8.43 (1H, d, J=8.6 Hz), 7.33 (1H, d, J=8.3 Hz), 6.84 (1H, s), 6.83 (1H, d, J=9.1 Hz), 6.57 (1H, d, d, J=2.4, 8.7 Hz), 6.47 (1H, d, J=2.22 Hz), 5.26 (2H, s), 1.00 (9H, s), 0.99 (9H, s), 0.26 (3H, s), 0.23 (6H, s) IR (KBr): 2957, 2927, 2883, 2855, 1713, 1618, 1567, 1498, 1287 cm$^{-1}$ Anal. Calc. for $C_{24}H_{38}O_5Si_2$: C, 65.84; H, 7.50. Found: C, 65.53; H, 7.43.

EXAMPLE 23

2-(tert-Butyl-dimethyl-silyloxy)-8-fluoro-11H-chromeno[4,3-c]chromen-5-one Compound #85

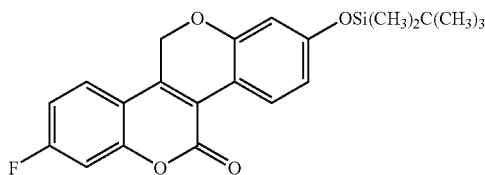

The title product was prepared as a colorless crystalline solid according to the procedure described in Example 22 with substitution of 8-fluoro-2-hydroxy-11H-chromeno[4,3-c]chromen-5-one, prepared as in Example 20, for 2,8-dihydroxy-11H-chromeno[4,3-c]chromen-5-one.

mp 197-198° C. MS (Cl) m/z 399 (M+H)$^+$, 421 (M+Na)$^+$, 819 (2M+Na)$^+$ $^1$H NMR (300 MHz, CDCl$_3$): δ 8.42 (1H, d, J=8.83 Hz), 7.45 (1H, d, d, J=5.79, 8.46 Hz), 7.13-7.04 (2H, m), 6.58 (1H, d, d, J=2.48, 8.71 Hz), 6.48 (1H, d, J=2.45 Hz), 5.27 (2H, s), 0.99 (9H, s), 0.24 (6H, s) IR (KBr): 1724, 1619 1503, 1302, 1262, 1173, 832 cm$^{-1}$ Anal. Calc. C$_{22}$H$_{23}$FO$_4$Si: C, 66.31; H, 5.82. Found: C, 66.05; H, 5.80.

EXAMPLE 24

2,8-Bis-(tert-Butyl-dimethyl-silanlyoxy)-5,11-dihydro-chromeno[4,3-c]-chromen-5-ol Compound #4

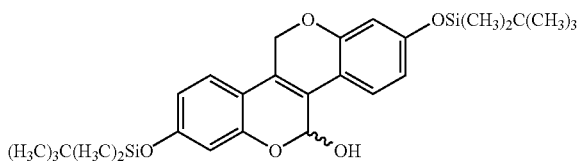

A solution of 2,8-bis-(tert-butyl-dimethyl-silyloxy)-11H-chromeno[4,3-c]chromen-5-one (5.016 g, 9.82 mmol, 1 eq) in toluene (525 mL) was cooled to −78° C. in a 1 L 3-neck round bottom flask equipped with a mechanical stirrer, a nitrogen inlet and a dropping funnel. To the reaction mixture was slowly added a toluene solution of diisobutylaluminum hydride (19 mL of 1.5 M, 28.48 mmol, 2.9 eq), with the temperature of the reaction mixture maintained at less than −70° C. The reaction was stirred for 5 hours, quenched with addition of methanol (25 mL) followed by 10% citric acid solution (~140 mL). The resulting solution was diluted with dichloromethane (525 mL), the solution washed with a saturated solution of Rochelle salt (250 mL), then washed with brine, dried on anhydrous sodium sulphate, filtered and evaporated to yield the crude compound as a yellow solid. The solid was recrystallized from a dichloromethane:hexane mixture (1:1) to yield the title product as an ivory, crystalline solid.

mp 188-190° C. MS (Cl) m/z 511 (M+H)$^+$, 533 (M+Na)$^+$, 495 [(M−H$_2$O)+H]$^+$, 1043 (2M+Na)$^+$ $^1$H NMR (300 MHz, CDCl$_3$): δ 7.15 (1H, d, J=8.4 Hz), 6.96 (1H, J=8.4 Hz), 6.59 (1H, d, J=2.24 Hz), 6.54 (1H, d, d, J=2.31, 11.62 Hz), 6.46 (1H, d, d, J=2.31, 8.35 Hz), 6.41 (1H, d, J=2.31 Hz), 6.11 (1H, d, J=8.1 Hz, collapsed to a s upon D$_2$O exchange), 3.01 (1H, d, J=8.2 Hz, D$_2$O exchangeable), 0.98 (18H, s,). 0.22 (6H, s), 0.21 (6H, s) IR (KBr): 3407, 2950, 2928, 2857, 1612, 1572, 1496, 1276, 1252, 1166, 1126, 1020, 838, 777 cm$^{-1}$.

EXAMPLE 25

2-(tert-Butyl-dimethyl-silanlyoxy)-8-fluoro-5,11-dihydro-chromeno[4,3-c]-chromen-5-ol Compound #86

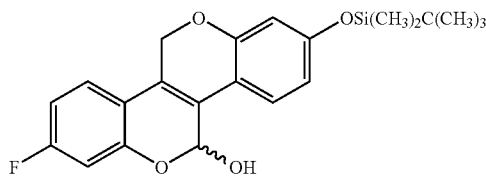

The title product was prepared as a colorless crystalline solid according to the procedure described in Example 24 with substitution of 2-(tert-Butyl-dimethyl-silyloxy)-8-fluoro-11H-chromeno[4,3-c]chromen-5-one, prepared as in Example 20, for 2,8-Dihydroxy-11H-chromeno[4,3-c]chromen-5-one.

mp 166-167° C. MS (Cl) m/z 401 (M+H)$^+$, 423 (M+Na)$^+$, 383 [(M−H$_2$O)+H]$^+$ $^1$H NMR (300 MHz, CDCl$_3$): δ 8.42 (1H, d, J=8.83 Hz), 7.45 (1H, d, d, J=5.79, 8.46 Hz), 7.13-7.04 (2H, m), 6.58 (1H, d, d, J=2.48, 8.71 Hz), 6.48 (1H, d, J=2.45 Hz), 5.27 (2H, s), 0.99 (9H, s), 0.24 (6H, s) IR (KBr): 3441, 1616, 1590 1566, 1504, 1294, 1283, 1142, 1028 cm$^{-1}$ Anal. Calc. C$_{22}$H$_{23}$FO$_4$Si/0.4 H$_2$O: C, 64.81; H, 6.38. Found: C, 64.71; H, 6.19.

EXAMPLE 26

5-(tert-Butyl-dimethyl-silyloxy)-2-(7-(tert-butyl-dimethyl-silyloxy)-4-{hydroxy-[4-(2-piperidine-1-yl-ethoxy)-phenyl]-methyl}-2H-chromen-3-yl)-phenol

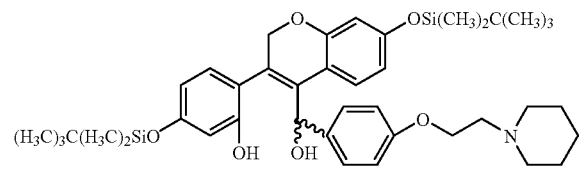

In a single neck, 50 mL round bottom flask was dissolved and stirred 4-[2-(piperidin-1-yl)-ethoxy]-iodobenzene (0.828 g, 2.5 mmol, 3 eq), in tetrahydrofuran (10 mL) under argon, and the mixture cooled to −22° C. After 5 minutes of stirring, an ether solution of isopropylmagnesium bromide (1.244 mL of 2.13 M, 2.65 mmol, 3 eq) was added via syringe. The reaction mixture was then stirred for 2 hours at about −22° C. A tetrahydrofuran solution of 2,8-bis-(tert-Butyl-dimethyl-silanlyoxy)-5,11-dihydro-chromeno[4,3-c]-chromen-5-ol (0.512 g, 1 mmol, 1 eq, in 10 mL), prepared as in Example 24, was then added, the cooling bath was removed and the reaction mixture was allowed to warm to room temperature overnight. After about 18 hours, the reaction was worked-up with addition of saturated ammonium acetate solution (15 mL) and extraction with ethyl ether (2×25 mL). The combined organic extracts were washed with brine and water, dried with anhydrous sodium sulphate, filtered and evaporated to yield a sticky semisolid residue. The title product was isolated as a viscous, colorless, semisolid foam via chromatography on silica gel eluted with 3% methanol/dichloromethane.

MS (Cl) m/z 718 (M+H)$^+$, loop negative 716 (M–H)]$^1$H NMR (300 MHz, CDCl$_3$): δ 7.06 (4H, m), 6.62 (2H, d, J=8.4 Hz), 6.45-6.34 (3H, m), 5.38 (1H, brs,), 4.81 (2H, brs), 4.05 (2H, t), 2.80 (2H, t), 2.57 (4H, brs), 1.47 (4H, m), 1.46 (2H, m), 0.96 (9H, s), 0.93 (9H, s), 0.19 (6H, s), 0.14 (6H, s).

EXAMPLE 27

2-[4-{[4-(2-Azepan-1-yl-ethoxy)-phenyl]hydroxymethyl}-7-(tert-Butyl-dimethyl-silyloxy)-2H-chromen-3-yl]-5-(tert-butyl-dimethyl-silyloxy)-phenol

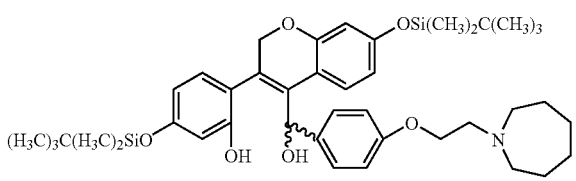

The title product was prepared according to the procedure described in Example 26 with substitution of 4-[2-(azapan-1-yl)-ethoxy]-phenyl magnesium bromide (generated in situ from 4-[2-(azapan-1-yl)-ethoxy]-iodobenzene and isopropyl magnesium bromide) as the Grignard reagent, for the Grignard reagent 4-[2-(piperidin-1-yl)-ethoxy]-phenyl magnesium bromide.

MS (Cl) m/z 732 (M+H)$^+$, loop negative 730 (M–H) $^1$H NMR (300 MHz, CDCl$_3$): δ 7.09-7.03 (4H, m), 6.66 (2H, d, J=8.32 Hz), 6.45-6.28 (4H, m), 5.60 (1H, brs,), 4.81 (2H, brs), 4.03 (2H, t), 2.97 (2H, m), 2.83 (4H, m), 1.61-1.53 (8H, m), 0.96 (9H, s), 0.93 (9H, s), 0.19 (6H, s), 0.15 (6H).

EXAMPLE 28

5-(tert-Butyl-dimethyl-silyloxy)-2-(7-(tert-butyl-dimethyl-silyloxy)-4-{hydroxy-[4-(2-morpholin-1-yl-ethoxy)-phenyl]-methyl}-2H-chromen-3-yl)-phenol

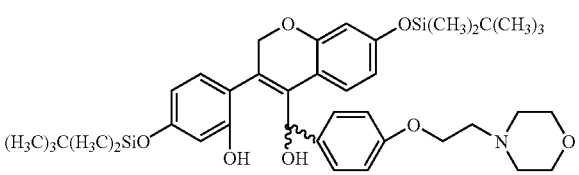

The title compound was prepared according to the procedure described in Example 26 with substitution of 4-[2-(mopholin-1-yl)-ethoxyphenyl]-magnesium bromide (generated in situ from 4-[2-(morpholin-1-yl)-ethoxy]-iodobenzene and isopropyl magnesium bromide) as the Grignard reagent, for the Grignard reagent 4-[2-(piperidin-1-yl)-ethoxyphenyl]-magnesium bromide.

MS (Cl) m/z 720 (M+H)$^+$, 742 (M+Na)$^+$; loop negative 718 (M–H) $^1$H NMR (300 MHz, CDCl$_3$): δ 7.06-7.02 (4H, m), 6.77 (2H, d, J=7.98 Hz), 6.43-6.18 (4H, m), 5.67 (1H, brs,), 4.81 (2H, brs), 4.05 (2H, t), 3.72 (4H, m), 2.77 (2H, t), 2.56 (4H, m), 0.96 (9H, s), 0.93 (9H, s), 0.19 (6H, s), 0.15 (6H,s).

EXAMPLE 29

5-tert-Butyl-dimethyl-silyloxy)-2-(7-(tert-butyl-dimethyl-silyloxy)-4-{hydroxy-[4-(2-pyrroidine-1-yl-ethoxy)-phenyl]-methyl}-2H-chromen-3-yl)-phenol

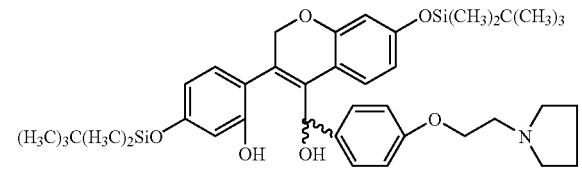

The title product was prepared according to the procedure described in Example 26 with substitution of 4-[2-(pyrrolidin-1-yl)-ethoxy]-phenyl magnesium bromide (generated in situ from 4-[2-(pyrrolidin-1-yl)-ethoxy]-iodobenzene and isopropyl magnesium bromide) as the Grignard reagent, for the Grignard reagent 4-[2-(piperidin-1-yl)-ethoxy]-phenyl magnesium bromide.

MS (Cl) m/z 704 (M+H)$^+$, 726 (M+Na)$^+$, loop negative 702 (M–H)

EXAMPLE 30

5-tert-Butyl-dimethyl-silyloxy)-2-(7-(tert-butyl-dimethyl-silyloxy)-4-{hydroxy-[4-(2-diethylamino-ethoxy)-phenyl]-methyl}-2H-chromen-3-yl)-phenol

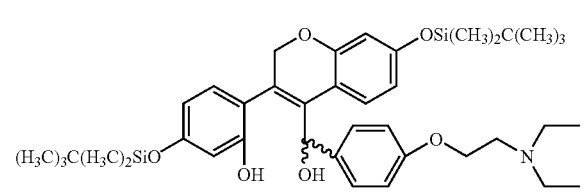

The title product was prepared according to the procedure described in Example 26 with substitution of 4-(2-diethylaminoethoxy)-phenyl magnesium bromide (generated in situ from 4-(2-diethylaminoethoxy)-iodobenzene and isopropyl magnesium bromide) as the Grignard reagent, for the Grignard reagent 4-[2-(piperidin-1-yl)-ethoxyphenyl]-magnesium bromide.

MS (Cl) m/z 706 (M+H)$^+$, 728 (M+Na)$^+$, loop negative 704 (M–H)

EXAMPLE 31

5-(tert-Butyl-dimethyl-silyloxy)-2-(7-(tert-butyl-dimethyl-silyloxy)-4-{hydroxy-[4-(2-dimethy-lamino-ethoxy)-phenyl]-methyl}-2H-chromen-3-yl)-phenol

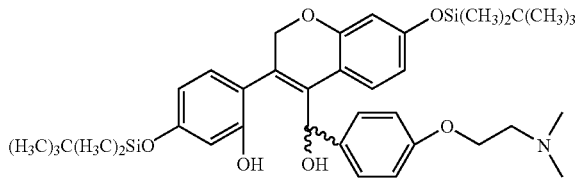

The title product was prepared according to the procedure described in Example 26 with substitution of 4-(2-diethylaminoethoxy)-phenyl magnesium bromide (generated in situ from 4-(2-diethylaminoethoxy)-iodobenzene and isopropyl magnesium bromide) as the Grignard reagent, for the Grignard reagent 4-[2-(piperidin-1-yl)-ethoxy]-phenyl magnesium bromide.

MS (Cl) m/z 678 (M+H)$^+$, 700 (M+Na)$^+$; loop negative 706 (M–H) $^1$HNMR (300 MHz, CDCl$_3$ δ 7.09 (4H, m), 6.94 (2H, d, J=8.10 Hz), 6.58-6.33 4H, m), 5.50 (1H, brs,), 4.82 (2H, brs), 4.00 (2H, t), 2.78 (2H, m), 2.38 (6H, s), 0.98 (9H, s), 0.94 (9H, s), 0.20 (6H, s), 0.15 (6H, s).

EXAMPLE 32

5-(tert-Butyl-dimethyl-silyloxy)-2-[7-(tert-butyl-dimethyl-silyloxy)-4-(hydroxy-phenyl]-methyl)-2H-chromen-3-yl)]-phenol

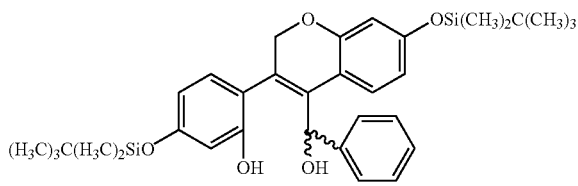

The title product was prepared according to the procedure described in Example 26 with substitution of phenyl magnesium bromide as the Grignard reagent for the Grignard reagent 4-[2-(piperidin-1-yl)-ethoxy]-phenyl magnesium bromide (generated in situ from 4-[2-(piperidin-1-yl)-ethoxy]-iodobenzene and isopropyl magnesium bromide).

MS (Cl) m/z 591 (M+H)$^+$, 613 (M+Na)$^+$, 573 M–H$_2$O+ H)$^+$; loop negative, 589 (M–H).

EXAMPLE 33

5-(tert-Butyl-dimethyl-silyloxy)-2-[7-(tert-butyl-dimethyl-silyloxy)-4-[(4-dimethylamino-(phenyl)-hydroxy-methyl]-2H-chromen-3-yl)]-phenol

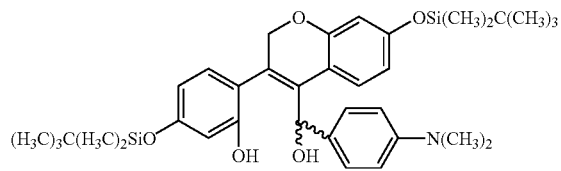

The title product was prepared according to the procedure described in Example 26 with substitution of 4-(dimethylamino)-phenyl magnesium bromide as the Grignard reagent for the Grignard reagent 4-[2-(piperidin-1-yl)-ethoxy]-phenyl magnesium bromide (generated in situ from 4-[2-(piperidin-1-yl)-ethoxy]-iodobenzene and isopropyl magnesium bromide).

MS (Cl) m/z 634 (M+H)$^+$, 616 (M–H$_2$O+H)$^+$.

EXAMPLE 34

2-(7-(tert-butyl-dimethyl-silyloxy)-4{hydroxy-[4-(2-piperidin-1-yl-ethoxy)-phenyl]-methyl}-2H-chromen-3-yl-5-fluoro-phenol

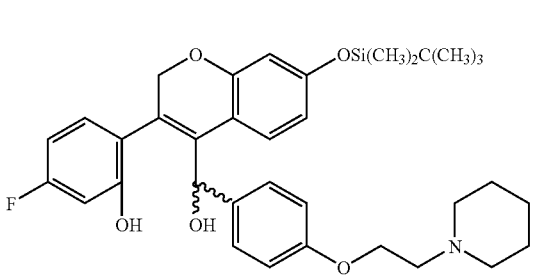

The title compound was prepared according to the procedure described in Example 26, with substitution of 2-(tert-Butyl-dimethyl-silanlyoxy)-8-fluoro-5,11-dihydro-chromeno[4,3-c]-chromen-5-ol, prepared as in Example 25, for 2, 8-bis-(tert-Butyl-dimethyl-silanlyoxy)-5,11-dihydro-chromeno[4,3-c]-chromen-5-ol.

MS (Cl) m/z 606 (M+H$^+$), 648 (M+Na)$^+$; loop negative 604 (M–H)

EXAMPLE 35

1-(2-{4-[2,8-Bis-(tert-butyl-dimethyl-silyloxy)-5,11-dihydro-chromeno[4,3-c]-chromen-5-yl]-phenoxy}-ethyl)-piperidine Compound #8

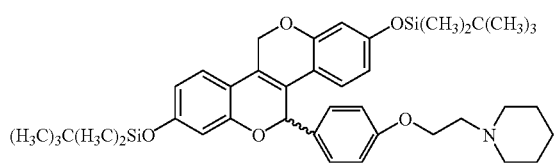

To a stirred solution of 5-(tert-butyl-dimethyl-silyloxy)-2-(7-(tert-butyl-dimethyl-silyloxy)-4-{hydroxy-[4-(2-piperidine-1-yl-ethoxy)-phenyl]-methyl}-2H-chromen-3-yl)-phenol (1.0633 g, 1.48 mmol, 1 eq), prepared as in Example 26, in tetrahydrofuran (50 mL) under argon at room temperature were added powdered molecular sieve (4 Å, 0.250 g) and triphenyl phosphine (0.7829 g, 2.99 mmol, 2 eq) followed by diethyl diazodicarboxylate (0.52 g=0.466 mL, 2.96 mmol). The reaction mixture was let run overnight (about 18 hours). The reaction mixture was evaporated to dryness, triturated with ether and the resulting colorless solid of triphenyl phosphine oxide removed by filtration. The filtrate was evaporated to dryness to yield a residue which was purified by column chromatography on silica gel using 2% methanol in dichloromethane as an eluent to yield the title product as a viscous semisolid.

MS (Cl) m/z 700 (M+H)$^+$ $^1$H NMR (300 MHz, CDCl$_3$) δ: 7.30 (2H, d, J=8.7 Hz), 6.87 (1H, d, J=8.30 Hz), 6.79 (2H, d, J=1.91, 6.82 Hz), 6.70 (1H, d, J=8.42 Hz), 6.39 (2H, m), 6.29 (2H, m), 6.14 (1H, s), 5.30 (1H, d, J=13.90 Hz), 5.10 (1H, d, d, J=1.654, 13.90 Hz), 4.04 (2H, t, J=5.97 Hz), 2.48 (2H, t, J=6.0 Hz), 2.48 (4H, m), 1.58 (4H, m), 1.43 (2H, m), 0.95 (9H, s), 0.93 (9H, s), 0.18 (6H, s), 0.16 (6H, s).

EXAMPLE 36

1-(2{-4-[2,8-Bis-(tert-butyl-dimethyl-silyloxy)-5,11-dihydro-chromeno[4,3-c]-chromen-5-yl]-phenoxy}-ethyl)-azepane Compound #16

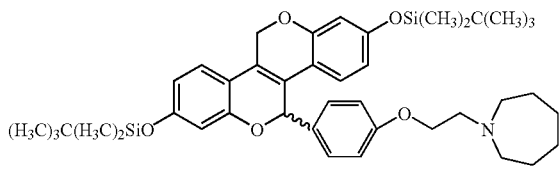

The title product was prepared according to the procedure described in Example 35 with substitution of 5-(tert-Butyl-dimethyl-silyloxy)-2-(7-(tert-butyl-dimethyl-silyloxy)-4-{hydroxy-[4-(2-diethylamino-ethoxy)-phenyl]-methyl}-2H-chromen-3-yl)-phenol, prepared as in Example 27 for 5-(tert-butyl-dimethyl-silyloxy)-2-(7-(tert-butyl-dimethyl-silyloxy)-4-{hydroxy-[4-(2-piperidine-1-yl-ethoxy)-phenyl]-methyl}-2H-chromen-3-yl)-phenol.

MS (Cl) m/z 714 (M+H)$^+$ $^1$H NMR (300 MHz, CDCl$_3$): δ 731 (2H, d, J=8.72 Hz), 6.87 (1H, d, J=8.32 Hz), 6.79 (2H, d, J=8.70 Hz), 6.70 (1H, d, J=8.44 Hz), 6.14 (1H, s), 5.30 (1H, d, J=13.88 Hz), 5.10 (1H, d, d, J=1.55, 13.88 Hz 4.01 (2H, t, J=6.20 Hz), 2.91 (2H, t, J=6.20 Hz), 2.81-2.73 (4H, m), 1.70-1.60 (8H, m), 0.95 (9H, s), 0.93 (9H, s), 0.18 (6H, s), 0.16 (6H, s)

EXAMPLE 37

1-(2{-4-[2,8-Bis-(tert-butyl-dimethyl-silyloxy)-5,11-dihydro-chromeno[4,3-c]-chromen-5-yl]-phenoxy}-ethyl)-morpholine Compound #12

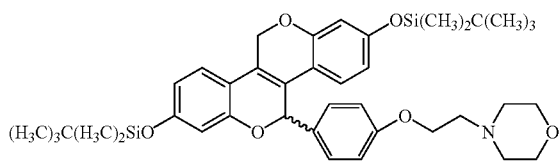

The title product was prepared according to the procedure described in Example 35 with substitution of 2-[4-{[4-(2-Azepan-1-yl-ethoxy)-phenyl]hydroxymethyl}-7-(tert-Butyl-dimethyl-silyloxy)-2H-chromen-3-yl]-5-(tert-butyl-dimethyl-silyloxy)-phenol, prepared as in Example 28, for 5-(tert-butyl-dimethyl-silyloxy)-2-(7-(tert-butyl-dimethyl-silyloxy)-4-{hydroxy-[4-(2-piperidine-1-yl-ethoxy)-phenyl]-methyl}-2H-chromen-3-yl)-phenol.

MS (Cl) m/z 702 (M+H)$^+$ $^1$H NMR (300 MHz, CDCl$_3$): δ 7.31 (2H, d, J=8.65 Hz), 6.88 (1H, d, J=8.33 Hz), 6.79 (2H, d, J=8.74 Hz), 6.70 (1H, d, J=8.43 Hz), 6.41-6.27 (4H, m), 6.15 (1H, brs), 5.30 (1H, d, J=13.77 Hz), 5.10 (1H, d, d, J=1.52, 13.77 Hz), 4.04 (2H, t) 3.74-3.69 (4H, m), 2.75 (2H, t), 2.55-2.52 (4H, m), 0.95 (9H, s), 0.93 (9H, s), 0.18 (6H, s), 0.16 (6H, s).

EXAMPLE 38

1-(2{-4-[2,8-Bis-(tert-butyl-dimethyl-silyloxy)-5,11-dihydro-chromeno[4,3-c]-chromen-5-yl]-phenoxy}-ethyl)-pyrrolidine Compound #10

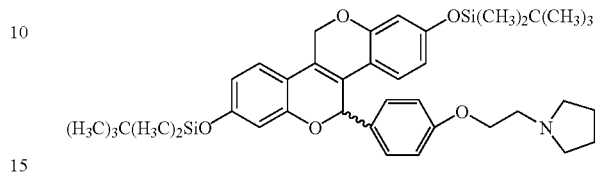

The title product was prepared according to the procedure described in Example 35 with substitution of 5-(tert-Butyl-dimethyl-silyloxy)-2-(7-(tert-butyl-dimethyl-silyloxy)-4-{hydroxy-[4-(2-pyrroidine-1-yl-ethoxy)-phenyl]-methyl}-2H-chromen-3-yl)-phenol, prepared as in Example 29, for 5-(tert-butyl-dimethyl-silyloxy)-2-(7-(tert-butyl-dimethyl-silyloxy)4-{hydroxy-[4-(2-piperidine-1-yl-ethoxy)-phenyl]-methyl}-2H-chromen-3-yl)-phenol.

MS (Cl) m/z 686 (M+H)$^+$ $^1$H NMR (300 MHz, CDCl$_3$): δ 731 (2H, d, J=8.59 Hz), 6.87 (1H, d, J=8.32 Hz), 6.80 (2H, d, J=8.70 Hz), 6.70 (1H, d, J=8.41 Hz), 6.15 (1H, s), 5.30 (1H, d, J=13.88 Hz), 5.10 (1H, d, J=14.04 Hz), 4.05 (2H, t, J=5.88 Hz), 2.87 (2H, t, J=5.98 Hz), 2.61 (4H, brs), 0.95 (9H, s), 0.93 (9H, s), 0.18 (6H, s), 0.16 (6H, s).

EXAMPLE 39

(2-{4-[2,8-Bis-(tert-butyl-dimethyl-silyloxy)-5,11-dihydro-chromeno[4,3-c]-chromen-5-yl]-phenoxy}-ethyl)-diethylamine Compound #18

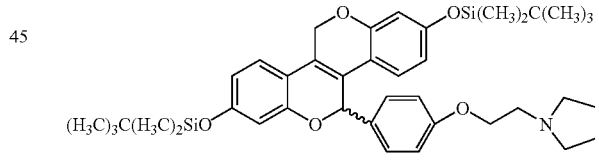

The title product was prepared according to the procedure described in Example 35 with substitution of 5-(tert-Butyl-dimethyl-silyloxy)-2-(7-(tert-butyl-dimethyl-silyloxy)-4-{hydroxy-[4-(2diethylamino-ethoxy)-phenyl]-methyl}-2H-chromen-3-yl)-phenol, prepared as in Example 30, for 5-(tert-butyl-dimethyl-silyloxy)-2-(7-(tert-butyl-dimethyl-silyloxy)-4-{hydroxy-[4-(2-piperidine-1-yl-ethoxy)-phenyl]-methyl}-2H-chromen-3-yl)-phenol.

MS (cl) m/z 688 (M+H)$^+$ $^1$H NMR (300 MHz, CDCl$_3$): δ 7.31 (2H, d, J=8.59 Hz), 6.87 (1H, d, J=8.32 Hz), 6.77 (2H, d, J=8.70 Hz), 6.70 (1H, d, J=8.42 Hz), 6.41-6.27 (4H, m), 6.15 (1H, s), 5.30 (1H, d, J=13.85 Hz), 5.10 (1H, d, J=13.89 Hz), 3.97 (2H, t, J=6.41 Hz), 2.82 (2H, t, J=6.39 Hz), 2.60 (4H, q, J=7.14 Hz), 1.03 (6H, t, J=7.14 Hz), 0.96 (9H, s), 0.93 (9H, s), 0.18 (6H, s), 0.16 (6H, s).

EXAMPLE 40

(2-{4-[2,8-Bis-(tert-butyl-dimethyl-silyloxy)-5,11-dihydro-chromeno[4,3-c]-chromen-5-yl]-phenoxy}-ethyl)-dimethylamine Compound #20

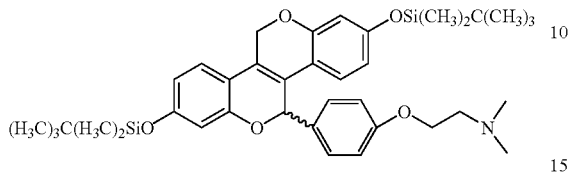

The title product was prepared according to the procedure described in Example 35 with substitution of 5-(tert-Butyl-dimethyl-silyloxy)-2-(7-(tert-butyl-dimethyl-silyloxy)-4-{hydroxy-[4-(2-dimethylamino-ethoxy)-phenyl]-methyl}-2H-chromen-3-yl)-phenol, prepared as in Example 31, for 5-(tert-butyl-dimethyl-silyloxy)-2-(7-(tert-butyl-dimethyl-silyloxy)-4-{hydroxy-[4-(2-piperidine-1-yl-ethoxy)-phenyl]-methyl}-2H-chromen-3-yl)-phenol.

MS (CI) m/z 660 (M+H)+ $^1$H NMR (300 MHz, CDCl$_3$): δ 7.31 (2H, d, J=8.69 Hz), 6.87 (1H, d, J=8.32 Hz), 6.81 (2H, d, J=8.68 Hz), 6.70 (1H, d, J=8.42 Hz), 6.41-6.27 (4H, m), 6.14 (1H, s), 5.30 (1H, d, J=13.83 Hz), 4.91 (1H, d, d, J=1.50, 13.88 Hz), 3.99 (2H, t, J=5.79 Hz), 2.68 (2H, t, J=5.79 Hz), 2.29 (6H, s), 0.95 (9H, s), 0.93 (9H, s), 0.18 (6H, s), 0.16 (6H, s).

EXAMPLE 41

2,8-Bis-(tert-butyl-dimethyl-silyloxy)-5-phenyl-5,11-dihydro-chromeno[4,3-c]-chromene Compound #5

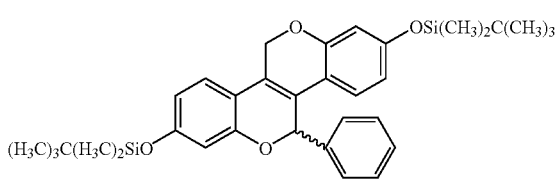

The title product was prepared according to the procedure described in Example 35 with substitution of 5-(tert-Butyl-dimethyl-silyloxy)-2-(7-(tert-butyl-dimethyl-silyloxy)-4-(hydroxy-phenyl]-methyl)-2H-chromen-3-yl)]-phenol, prepared as in Example 32, for 5-(tert-butyl-dimethyl-silyloxy)-2-(7-(tert-butyl-dimethyl-silyloxy)-4-{hydroxy-[4-(2-piperidine-1-yl-ethoxy)-phenyl]-methyl}-2H-chromen-3-yl)-phenol.

MS (CI) m/z 573 (M+H)+, (M+Na)+ $^1$H NMR (300 MHz, CDCl3): δ 7.41 (2H, m), 7.28 (2H, m), 6.87 (1H, d, J=8.30 Hz), 6.54 (1H, d, J=8.40 Hz), 6.41 (1H, d, J=2.30 Hz), 6.40 (1H, d, d, J=2.34, 7.94 Hz), 6.21 (s, 1H, s), 5.31 (1H, d, J=13.90 Hz), 5.10 (1H, d, d, J=1.44, 13.90 Hz), 0.96 (9H, s), 0.93 (9H, s), 0.19 (6H, s), 0.16 (6H, s).

EXAMPLE 42

2,8-Bis-(tert-butyl-dimethyl-silyloxy)-5-(4-dimethylamino)-phenyl-5,11-dihydro-chromeno[4,3-c]-chromene Compound #23

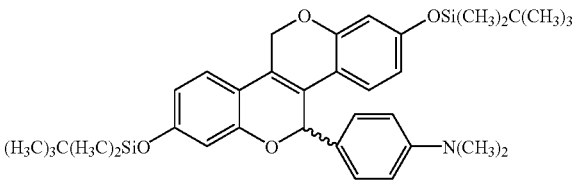

Crude 5-(tert-Butyl-dimethyl-silyloxy)-2-[7-(tert-butyl-dimethyl-silyloxy)-4-[(4-dimethylamino-(phenyl)hydroxymethyl]-2H-chromen-3-yl)]-phenol, prepared as in Example 34, when attempted to purify using silica gel chromatography and ethyl acetate/hexane as the eluent yielded the title compound as the cyclodehydrated product.

MS (CI) m/z 573 (M+H)+, (M+Na)+ $^1$H NMR (300 MHz, CDCl3): δ 7.41 (2H, m), 7.28 (2H, m), 6.87 (1H, d, J=8.30 Hz), 6.54 (1H, d, J=8.40 Hz), 6.41 (1H, d, J=2.30 Hz), 6.40 (1H, d, d, J=2.34, 7.94 Hz), 6.21 (s, 1H, s), 5.31 (1H, d, J = 13.90 Hz), 5.10 (1H, d, d, J=1.44, 13.90 Hz), 2.89 (6H, s), 0.96 (9H, s), 0.93 (9H, s), 0.19 (6H, s), 0.16 (6H, s).

EXAMPLE 43

1-(2-{4-{2-(tert-butyl-dimethyl-silyloxy)-8-fluoro-5,11-dihydro-chromeno[4,3c]-chromen-5-yl]-phenoxy}-ethyl)-piperidine Compound #87

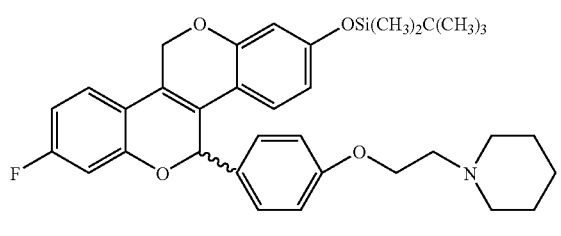

The title product was prepared according to the procedure described in Example 26, with substitution of 2-(7-(tert-butyl-dimethyl-silyloxy)-4{hydroxy-[4-(2-piperidin-1-yl-ethoxy)-phenyl]-methyl}-2H-chromen-3-yl-5-fluoro-phenol, prepared as in Example 34, for 2,8-bis-(tert-Butyl-dimethyl-silanlyoxy)-5,11-dihydro-chromeno[4,3-c]-chromen-5-ol.

MS (CI) m/z 588 (M+H)+. $^1$H NMR (300 MHz, CDCl$_3$): δ 7.30 (2H, d, J=8.67 Hz), 6.94 (1H, ABq, J=8.49 Hz), 6.80 (2H, d, J=8.68 Hz), 6.70 (1H, d, J=8.42 Hz), 6.59 (1H, d, t, J=2.55, 8.47 Hz), 6.51 (1H, d, d, J=2.51, 9.82 Hz), 6.41 (1H, d, J=2.34 Hz), 6.23 (1h, d, d, J=2.36, 8.37 Hz), 6.18 (1H,s), 5.31 (1H, d, J=14.07 Hz), 5.08 (1H, d, d, J=1.37, 13.87 Hz), 4.04 (2H, t, J=6.02 Hz), 2.73 (2H, t, J=6.03 Hz), 2.47 (4H, m), 1.88 (4H, m), 1.43 (2H, m) 0.96 (9H, s), 0.19 (6H, s).

EXAMPLE 44

5-[4-(2-Piperidin-1-yl-ethoxy)-phenyl]-5,11-dihydrochromeno[4,3-c]chromene-2,8-diol Compound #9

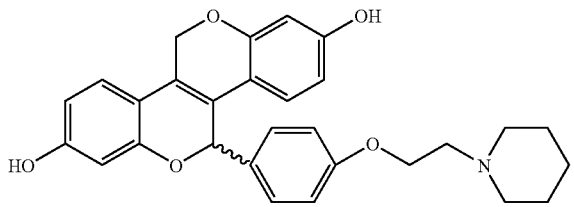

To a stirred solution of 1-(2-{4-[2,8-Bis-(tert-butyl-dimethyl-silyloxy)-5,11-dihydro-chromeno[4,3-c]-chromen-5-yl]-phenoxy}-ethyl)-piperidine (0.19 g, 0.2714 mmol, 1 eq), prepared as in Example 35, in tetrahydrofuran (15 mL) under nitrogen was added tetra-n-butyl ammonium fluoride (1M in tetrahydrofuran, 1.36 mL, 1.36 mmol, 5 eq) and the mixture was stirred for 3 hours. The reaction mixture was diluted with ethyl (30 mL) and then washed with saturated aqueous ammonium chloride solution (35 mL). The precipitated inorganic salts were removed by filtration and washed with ethyl acetate. The combined organic phases were washed with saturated aqueous sodium bicarbonate solution (50 mL), dried (anhydrous sodium sulphate), filtered and evaporated to dryness to yield the crude product. The crude product was purified by column chromatography on silica gel using a 1:1 mixture of hexane and 10% ammoniated methanol containing 10% ammonium hydroxide to yield the purified title product as a brownish, foamy solid.

MS (Cl) m/z 472 (M+H)+, 470 (M−H, loop negative) $^1$H NMR (300 MHz, d-6 acetone): δ 8.46 (2H, br hump), 7.24 (2H, d, d, J=1.93, 6.6 Hz), 6.91 (1H, d, J=8.40 Hz), 6.71 (3H, d, J=6.6 Hz), 6.29 (1H, d, d, J=2.43, 8.34 Hz), 6.25 (1H, d, J=2.40 Hz), 6.20 (1H, d, d, J=2.43, 8.32 Hz), 6.13 (2H, d, J=2.36 Hz), 5.25 (1H, d, J=14.15 Hz), 4.93 (1H, d, d, J=1.66, 14.13 Hz), 3.89 (2H, t, J=6.02 Hz), 2.51 (2H, t, J=6.02 Hz), 2.30 (4H, m), 1.37 (4H, m), 1.26 (2H, m)

EXAMPLE 45

5-[4-(2-Azepan-1-yl-ethoxy)-phenyl]-5,11-dihydrochromeno[4,3-c]chromene-2,8-diol Compound #17

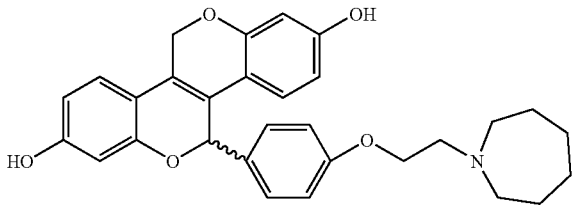

The title product was prepared according to the procedure described in Example 44 with substitution of 1-(2-{4-[2,8-Bis-(tert-butyl-dimethyl-silyloxy)-5,11-dihydro-chromeno[4,3-c]-chromen-5-yl]-phenoxy}-ethyl)-azepane, prepared as in Example 36, for 1-(2-{4-[2,8-Bis-(tert-butyl-dimethyl-silyloxy)-5,11-dihydro-chromeno[4,3-c]-chromen-5-yl]-phenoxy}-ethyl)-piperidine.

MS (Cl) m/z 486 (M+H)+; loop negative 484 (M−H) $^1$H NMR (300 MHz, d-6 acetone) δ 7.32 (2H, d, J=8.70 Hz), 7.03 (1H, d, J=8.37 Hz), 6.84 (3H, d, J=8.60 Hz), 6.43-6.26 (5H, m), 5.37 (1H, d, J=14.14 Hz), 5.06 (1H, d, d, J=1.67, 14.14 Hz), 4.00 (2H, t, J=6.14 Hz), 2.85 (2H, t, J=6.11 Hz), 1.56 (8H, m).

EXAMPLE 46

5-[4-(2-Morphlin-4-yl-ethoxy)-phenyl]-5,11-dihydrochromeno[4,3-c]chromene-2,8-diol Compound #13

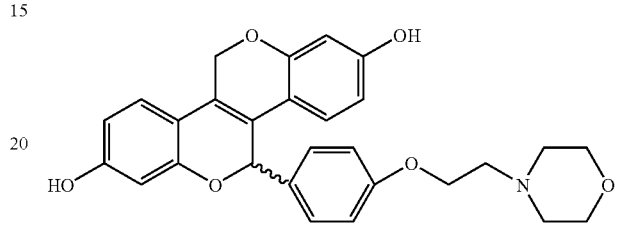

The title product was prepared according to the procedure described in Example 44 with substitution of 1-(2-{4-[2,8-Bis-(tert-butyl-dimethyl-silyloxy)-5,11-dihydro-chromeno[4,3-c]-chromen-5-yl]-phenoxy}-ethyl)-morpholine, prepared as in Example 37, for 1-(2-{4-[2,8-Bis-(tert-butyl-dimethyl-silyloxy)-5,11-dihydro-chromeno[4,3-c]-chromen-5-yl]-phenoxy}-ethyl)-piperidine.

MS (Cl) m/z 474 (M+H)+; loop negative 472 (M−H) $^1$H NMR (300 MHz, d-6 acetone) δ 8.58 (2H, br hump), 7.37 (2H, d, J=8.68 Hz), 7.04 (1H, d, J=8.73 Hz), 6.84 (3H, d, J=8.73 Hz), 6.42 (1H, d, d, J=2.37, 8.34 Hz), 6.38 (2H, d, 2.37 Hz), 6.33 (1H, d, d, J=2.41, 8.33 Hz), 6.27 (2H, d, J=2.33 Hz), 6.27 (1H, s), 5.38 (1H, d, J=14.11 Hz), 5.06 (1H, d, d, J=1.56, 14.13 Hz), 4.06 (2H, t, J=5.81 Hz), 3.57 (4H, t, J=4.01 Hz), 2.92 (4H, brs), 2.69 (2H, t, J=3.45).

EXAMPLE 47

5-[4-(2-Pyrrolidin-1-yl-ethoxy)-phenyl]-5,11-dihydrochromeno[4,3-c]chromene-2,8-diol Compound #11

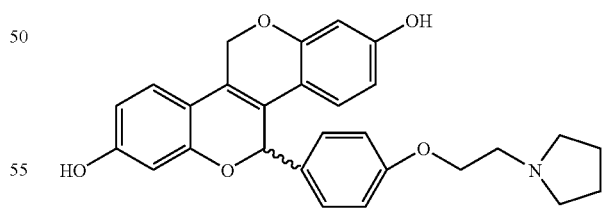

The title product was prepared according to the procedure described in Example 44 with substitution of 1-(2-{4-[2,8-Bis-(tert-butyl-dimethyl-silyloxy)-5,11-dihydro-chromeno[4,3-c]-chromen-5-yl]-phenoxy}-ethyl)-pyrrolidine, prepared as in Example 38, for 1-(2-{4-[2,8-Bis-(tert-butyl-dimethyl-silyloxy)-5,11-dihydro-chromeno[4,3-c]-chromen-5-yl]-phenoxy}-ethyl)-piperidine.

MS (Cl) m/z 458 (M+H)+; loop negative 456 (M−H) $^1$H NMR (300 MHz, d-6 acetone) δ 7.36 (2H, d, J=8.63 Hz), 7.01 (1H, d, J=8.34 Hz), 6.84-6.79 (3H, m), 6.44-6.26 (5H, m), 5.36 (1H, d, J=14.14 Hz), 5.05 (1H, d, d, J=1.22, 14.13 Hz), 4.82 (2H, br hump), 4.03 (2H, t, J=5.85 Hz), 2.81 (2H, t, J=5.83), 2.54 (4H, m) 1.71-1.68 (4H, m).

EXAMPLE 48

5-[4-(2-Diethylamino-ethoxy)-phenyl]-5,11-dihydro-chromeno[4,3-c]chromene-2,8-diol Compound #19

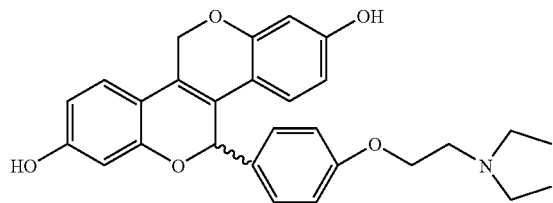

The title product was prepared according to the procedure described in Example 44 with substitution of (2-{4-[2,8-Bis-(tert-butyl-dimethyl-silyloxy)-5,11-dihydro-chromeno[4,3-c]-chromen-5-yl]-phenoxy}-ethyl)-diethylamine, prepared as in Example 39, for 1-(2-{4-[2,8-Bis-(tert-butyl-dimethyl-silyloxy)-5,11-dihydro-chromeno[4,3-c]-chromen-5-yl]-phenoxy}-ethyl)-piperidine.

MS (CI) m/z 460 (M+H)⁺; loop negative 458 (M−H) ¹H NMR (300 MHz, d-6 acetone) δ 7.36 (2H, d, J=8.65 Hz), 7.02 (1H, d, J=8.36 Hz), 6.82 (3H, d, d, J=2.34, 8.47), 6.43-6.26 (5H, m), 5.50 (2H, br hump), 5.37 (1H, d, J=14.12 Hz), 5.06 (1H, d, d, J=1.46, 14.12 Hz), 4.82 (2H, br hump), 3.99 (2H, t, J=6.23 Hz), 2.81 (2H, t, J=6.16 Hz), 2.57 (4H, q, J=7.12 Hz) 0.99 (6H, t, J=7.11).

EXAMPLE 49

5-[4-(2-Dimethylamino-ethoxy)-phenyl]-5,11-dihydrochromeno[4,3-c]chromene-2,8-diol Compound #21

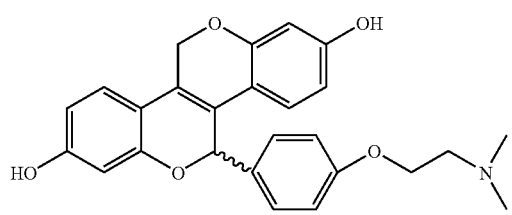

The title product was prepared according to the procedure described in Example 44 with substitution of (2-{4-[2,8-Bis-(tert-butyl-dimethyl-silyloxy)-5,11-dihydro-chromeno[4,3-c]-chromen-5-yl]-phenoxy}ethyl)-dimethylamine, prepared as in Example 40, for 1-(2-{4-[2,8-Bis-(tert-butyl-dimethyl-silyloxy)-5,11-dihydro-chromeno[4,3-c]-chromen-5-yl]-phenoxy}-ethyl)-piperidine.

MS (CI) m/z 432 (M+H)⁺; loop negative 430 (M−H) ¹H NMR (300 MHz, d-6 acetone) δ 7.37 (2H, d, J=8.63 Hz), 7.03 (1H, d, J=8.36 Hz), 6.84 (3H, d, J=8.49 HZ), 6.43-6.27 (5H, m), 5.38 (1H, d, J=14.11 Hz), 5.06 (1H, d, d, J=1.39, 14.11 Hz), 4.02 (2H, t, J=5.88 Hz), 2.63 (2H, t, J=5.85 Hz), 2.23 (6H, brs).

EXAMPLE 50

5-[4-Dimethylamino-phenyl]-5,11-dihydro-chromeno[4,3-c]chromene-2,8-diol Compound #26

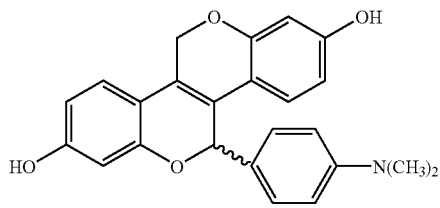

The title product was prepared according to the procedure described in Example 44 with substitution of 2,8-Bis-(tert-butyl-dimethyl-silyloxy)-5-(4-dimethylamino)-phenyl-5,11-dihydro-chromeno[4,3-c]-chromene, prepared as in Example 42, for 1-(2-{4-[2,8-Bis-(tert-butyl-dimethyl-silyloxy)-5,11-dihydro-chromeno[4,3-c]-chromen-5-yl]-phenoxy}-ethyl)-piperidine.

MS (CI) m/z 388 (M+H)⁺; loop negative 386 (M−H) ¹H NMR (300 MHz, d-5 methanol) δ 7.21 (2H, d, J=8.79 Hz), 6.92 (1H, d, J=8.36 Hz), 6.71 (1H, d, J=8.41 HZ), 6.64 (2H, d, J=8.83 Hz), 6.33 (1H, d, d, J=2.42, 7.70 Hz), 6.30 (1H, d, J=2.39 Hz), 6.23 (1H, d, d, J=2.43, 8.36 Hz), 6.12 (1H, d, J=2.41 Hz), 6.08 (1H, s), 5.26 (1H, d, J=13.95 Hz), 5.03 (1H, d, d, J=1.62, 13.95 Hz), 2.86 ((6H, s).

EXAMPLE 51

5-Phenyl-5,11-dihydro-chromeno[4,3-c]chromene-2,8-diol: Compound #6

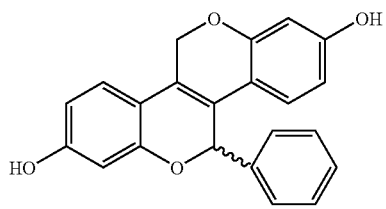

The title product was prepared according to the procedure described in Example 44 with substitution of 2,8-Bis-(tert-butyl-dimethyl-silyloxy)-5-phenyl-5,11-dihydro-chromeno[4,3-c]-chromene, prepared as in Example 41, for 1-(2-{4-[2,8-Bis-(tert-butyl-dimethyl-silyloxy)-5,11-dihydro-chromeno[4,3-c]-chromen-5-yl]-phenoxy}-ethyl)-piperidine.

MS (CI) m/z 345 (M+H)⁺; loop negative 343 (M−H,) ¹H NMR (500 MHz, acetone-d6): δ 8.49 (1H, brs), 8.47 (1H, s), 7.46 (2H, d, d, J=1.76, 8.10 Hz), 7.31-7.26 (3H, m), 7.04 (1H, d, J=8.38 Hz), 6.87 (1H, d, J=8.38 Hz), 6.47 (1H, d, d, J=2.43, 8.38 Hz), 6.38 (1H, d, d, J=2.43, 8.38 Hz), 6.33 (1H, brs), 6.29 (1H, d, J=2.43), 5.38 (1H, d, J=14.08 Hz), 5.06 (1H, d, d, J=1.67, 14.08 Hz).

EXAMPLE 52

8-Fluoro-5-[4-(2-piperidin-1-yl-ethoxy)-phenyl]-5,11-dihydro-chromeno[4,3c]chromen-2-ol Compound #46

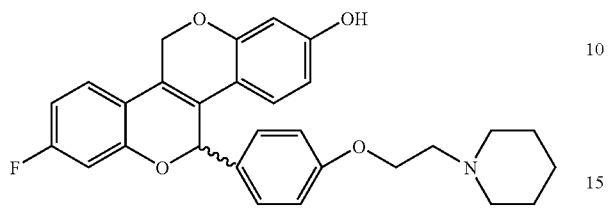

The title compound was prepared according to the procedure described in Example 44, with substitution of 1-(2-{-[2,8-Bis-(tert-butyl-dimethyl-silyloxy)-8-fluoro-5,11-dihydro-chromeno[4,3c]chromen-5-yl]-phenoxy}-ethyl)-piperidine, prepared as in Example 42 for 1-(2-{4-[2,8-Bis-(tert-butyl-dimethyl-silyloxy)-5,11-dihydro-chromeno[4,3-c]-chromen-5-yl]-phenoxy}-ethyl)-piperidine.

MS (Cl) m/z 474 (M+H)$^+$; loop negative 472 (M−H) $^1$H NMR (300 MHz, CDCl$_3$): δ 7.24 (2H, d, J=8.36 Hz), 7.19 (1H, br hump), 6.90 (1H, ABq, J=8.45 Hz), 6.67 (2H, d, J=8.66 Hz), 6.62 (2H, d, 8.43), 6.57 (1H, d, d, J=2.53, 8.49 Hz), 6.49 (1H, d, d, J=2.47, 9.79 Hz), 6.33 (1H, d, J=2.24 Hz), 6.14 (1H, s), 5.24 (1H, d, J=13.86 Hz), 5.03 (1H, d, 13.19 Hz), 4,00 (2H, t, J=5.69 Hz), 2.70 (2H, m), 2.54 (4H, brs), 1.60 (4H, brm), 1.43 (2H, brm).

EXAMPLE 53

8-Fluoro-11-isopropyl-5-[4-(2-Piperidin-1-yl-ethoxy)-phenyl]-5,11-dihydrochromeno[4,3-c]chromen-2-ol Compound #47

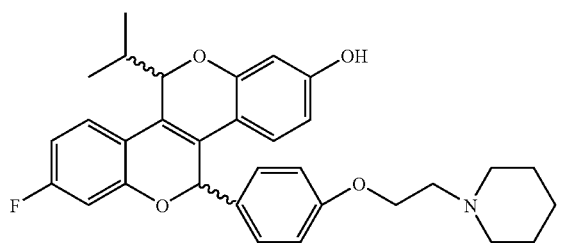

During the purification of the compound prepared in Example 52 by column chromatography, the title compound was isolated in small amount as an accompanying minor component, derived from the silylated precursor [MS (Cl) m/z 630, present as a minor side product in the major component prepared as in Example 52, which in turn was derived from a precursor formed as a minor side product during the preparation of the title compound of Example 34, through the side reaction with isopropyl magnesium bromide.

MS (Cl) m/z 516 (M+H)$^+$; loop negative 514 (M−H) $^1$H NMR (300 MHz, CDCl$_3$): δ 7.34 (2H, d, J=8.34 Hz), 7.03 (1H, ABq, J=8.53 Hz), 6.75 (2H, d, J=8.79 Hz), 6.61 (2H, d, J=8.34 Hz), 6.57 (1H, d, 2.40 Hz), 6.50 (1H, d, d, J=2.61, 6.12 Hz), 6.429 (1H, d, J=2.40 Hz), 6.24 (1H, d, d, J=2.42, 8.34 Hz), 6.04 (1H, s), 4.92 (1H, d, 7.30 Hz), 4.08 (2H, t, J=5.79 Hz), 2.83 (2H, m), 2.59 (4H, brs), 2.28 (1H, m), 1.64 (4H, brm), 1.46 (2H, brm), 1.25 (1H, s), 1.07 (3H, d, J=6.90 Hz), 1.03 (3H, d, J=6.54 Hz).

EXAMPLE 54

2,2-Dimethyl-propionic acid, 8-(2,2-dimethyl-propionyloxy)-5-[4-(2-piperidin-1-yl-ethoxy)-phenyl]-5,11-dihydro-chromeno[4,3-c]chromen-2-yl ester Compound #22

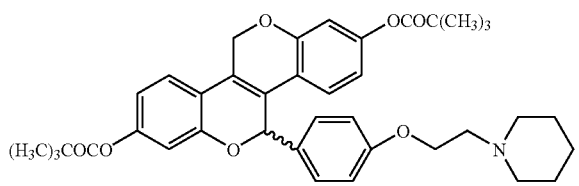

To an ice-cooled and stirred slurry of 5-[4-(2-Piperidin-1-yl-ethoxy)-phenyl]-5,11-dihydrochromeno[4,3-c]chromene-2,8-diol (0.200 g, 0.424 mmol), prepared as in Example 44, in dichloromethane (10 mL) under nitrogen, was added triethylamine (0.2 mL, 1.43 mmol, 3.5 eq). After about 10 minutes the reaction mixture was observed to become clear. To the reaction mixture was then slowly added (over a period of about 5 minutes) 2,2-dimethylpropionyl chloride (i.e., pivaloyl chloride, 0.157 mL, 1.3 mmol, 3.18 eq.). The cooling bath was then removed and the reaction mixture was allowed to warm to room temperature overnight. To the reaction mixture was then added saturated NaHCO$_3$ solution (20 mL) and the resulting solution was stirred at room temperature for 1 hour. The organic layer was separated and the aqueous layer re-extracted with dichloromethane (2×20 mL). The combined organic extracts were washed with brine, dried (anhydrous sodium sulphate), filtered and evaporated in vacuo. The residue was purified by chromatography on silica gel using 2% methanol/dichloromethane as an eluent to yield the title product as an ivory, crystalline solid.

MS (Cl) m/z 640 (M+H)$^+$ $^1$H NMR (300 MHz, CDCl$_3$): δ 7.30 (2H, d, J=8.7 Hz), 7.01 (1H, d, J=8.4 Hz), 6.83-6.78 (3H, m), 6.64 (1H, d,d, J=2.3, 8.5 Hz), 6.63 (1H, d, J=2.3 Hz), 6.54-6.49 (2H, m), 6.21 (1H, s), 5.37 (1H, d, J=14 Hz), 5.16 (1H, d, J=14 Hz), 4.05 (2H, t, J=6.0 Hz), 2.74 (1H, t, J=6.0 Hz), 2.49 (4H, brs), 1.59 (4H, m), 1.37 (2H, m), 1.32 (9H, s), 1.30 (9H, s) IR (KBr): 2972, 2934, 2872, 1754, 1611, 1585, 1510, 1498, 1220, 1175, 1157, 1127, 1109, 1026 cm$^{-1}$ Anal. Calc. C$_{39}$H$_{45}$NO$_7$/0.6H$_2$O: C, 73.22; H, 7.09; N, 2.19. Found: C, 72.25; H, 7.06; N, 2.08.

EXAMPLE 55

2,2-Dimethyl-propionic acid, 8-(2,2-dimethyl-propionyloxy)-5-methyl-5-[4-(2-pyrrolidin-1-yl-ethoxy)-phenyl]-5,11-dihydro-chromeno[4,3-c]chromen-2-yl ester Compound #30

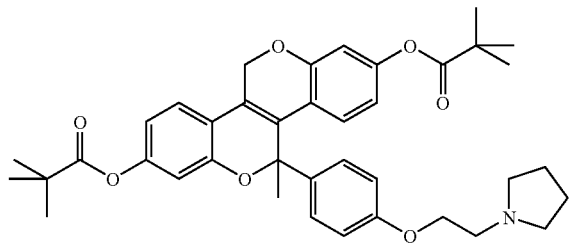

Step A: 5-(tert-butyl-dimethyl-silyloxy)-2-(7-(tert-butyl-dimethyl-silyloxy)-4-{1-hydroxy-1-[4-(2-pyrrolidin-1-yl-ethoxy)-phenyl]-ethyl}-2H-chromen-3-yl)-phenol To a solution of 1-[2-(4-bromophenoxy)-ethyl]-pyrrolidine (331 mg, 1.22 mmol) in THF (7.5 mL) at −78° C., was added n-butyl lithium (2.5 M in hexane, 478 µL, 1.19 mmol). The mixture was stirred at −78° C. for 0.5 hours. To this mixture was then added 2,8-bis-(tert-butyl-dimethyl-silyloxy)-11H-chromeno[4,3-c]chromen-5-one (153 mg, 0.30 mmol) in THF (3 mL), prepared as in Example 22. The reaction mixture was then stirred at −78° C. for 1.5 hours. To this mixture was added methyl magnesium bromide (3 M in diethyl ether, 1 mL, 2.99 mmol) at −78° C. and the reaction mixture stirred at room temperature overnight. The reaction was quenched with aqueous $NH_4Cl$ and extracted with ethyl acetate. The organic layer was washed with brine and dried over $MgSO_4$. The solvent was evaporated to yield the crude product as a yellow oil. The crude product was carried to the next step without further purification.
MS m/z (M+)=719

Step B: 1-(2-{4-[2,8-bis-(tert-butyl-dimethyl-silyloxy)-5-methyl-5,11-dihydro-chromeno[4,3-c]chromen-5-yl]-phenoxy}-ethyl)-pyrrolidine 5-(Tert-butyl-dimethyl-silyloxy)-2-(7-(tert-butyl-dimethyl-silyloxy)-4-{1-hydroxy-1-[4-(2-pyrrolidin-1-yl-ethoxy)-phenyl]-ethyl}-2H-chromen-3-yl)phenol, prepared as in STEP A above, was dissolved in toluene (8 mL) and treated with diluted HCl (0.4 mL of concentrated HCl:$H_2O$=1:2 v/v). The reaction mixture was vigorously stirred at room temperature for 1.5 h. The mixture was then diluted with water and ethyl acetate. The layers were separated and the organic layer washed successively with saturated $NaHCO_3$, brine and dried over $MgSO_4$. The desiccant was filtered off, and the filtrate concentrated. Flash chromatography with ethyl acetate:hexane:$CH_3OH$ (containing 1% $NH_4OH$)=49:49:2 as the eluent to yield the title compound as a light oil.

$^1$H NMR (300 MHz; $CDCl_3$): δ 0.80 (s, 30 H), 1.72-1.76 (m, 4 H), 1.97 (s, 3 H), 2.59-2.61 (m, 4 H), 2.84 (t, 2H J=5.9), 4.03 (t, 2 H J=5.9), 5.04 (ABq, 2 H, $J_{AB}$=13.8; $\Delta v_{AB}$=22 Hz), 6.29 (dd, 1 H, J=2.4, 8.6 Hz), 6.41 (d, 1 H, J=2.2 Hz), 6.52-6.57 (m, 3 H), 6.78 (d, 2 H, J=8.8 Hz), 6.89 (d, 1 H, J=8.4 Hz), 7.38 (d, 2 H, J=8.8 Hz) MS m/z (M$^+$)=700.

Step C: 5-methyl-5-[4-(2-pyrrolidin-1-yl-ethoxy)-phenyl]-5,11-dihydro-chromeno[4,3-c]chromene-2,8-diol To a solution of 1-(2-{4-[2,8-bis-(tert-butyl-dimethyl-silyloxy)-5-methyl-5,11-dihydro-chromeno[4,3-c]chromen-5-yl]-phenoxy)ethyl)-pyrrolidine (84.5 mg, 0.12 mmol) in THF (7 mL) was added tetrabutylammonium fluoride (1M in THF, 241.4 µL, 0.24 mmol). The mixture was stirred at room temperature for 40 min. Saturated $NH_4Cl$ was added followed by addition of ethyl acetate. The resulting layers were separated, the organic layer was washed with brine, and dried over $MgSO_4$. The solvent was evaporated and the residue dried under vacuum for 2 h at room temperature to yield the title compound which was carried on to the next step without further purification.
MS m/z (M$^+$)=472, (M$^-$)=470.

Step D: 2,2-dimethyl-propionic acid 8-(2,2-dimethyl-propionyloxy)-5-methyl-5-[4-(2-pyrrolidin-1-yl-ethoxy)-phenyl]-5,11-dihydro-chromeno[4,3,-c]chromen-2-yl ester To a suspension of 5-methyl-5-[4-(2-pyrrolidin-1-yl-ethoxy)-phenyl]-5,11-dihydro-chromeno[4,3-c]chromene-2,8-diol, prepared as in STEP C above, in dichloromethane (5 mL) (DCM) at 50° C. was added triethylamine ($Et_3N$) (67 mg, 0.66 mmol) and stirred for 5 min. Trimethylacetyl chloride (75.7 mg, 0.63 mmol) was then added to the reaction mixture and the mixture stirred at room temperature overnight. To the reaction mixture was then added saturated $NaHCO_3$ (10 mL) and the mixture stirred for 1 h. The reaction mixture was then extracted with DCM, washed with brine and dried over $MgSO_4$. After removal of the dessicant, the solution was solution was concentrated and the resulting residue eluted through a short silica column with 2% methanol in DCM. The solvent was evaporated to yield the title compounds as a thick yellow oil.

$^1$H NMR (300 MHz; $CDCl_3$): δ 1.23 (s, 18 H), 1.72-1.76 (m, 4 H), 1.97 (s, 3 H), 2.59-2.61 (m, 4 H), 2.84 (t, 2 H, J=5.9 Hz), 4.03 (t, 2 H, J=5.9 Hz) 5.04 (ABq, 2 H, $J_{AB}$=13.8; $\Delta v_{AB}$=22 Hz), 6.29 (dd, 1 H, J=2.4, 8.6 Hz), 6.41 (d, 1 H, J=2.2 Hz), 6.52-6.57 (m, 3 H), 6.78 (d, 2 H, J=8.8 Hz), 6.89 (d, 1 H J=8.4 Hz), 7.38 (d, 2 H, J=8.8 Jz) MS m/z (M$^+$)=640, 662

EXAMPLE 56

11-[4-(2-azepan-1-yl-ethoxy)-phenyl]8-(2,2-dimethyl-propionyloxy)-11-methyl-5,11-dihydro-chromeno[4,3-c]chromen-2-yl ester Compound #33

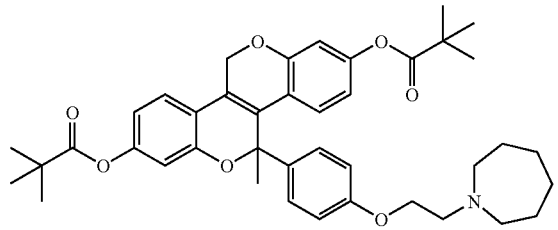

Step A: 2-[4-{1-[4-(2-azepan-1-yl-ethoxy)-phenyl]-1-hydroxy-ethyl}-7-(tert-butyl-dimehyl-silyloxy)-2H-chromen-3-yl]-5-(tert-butyl-dimethyl-silyloxy)-phenol To a solution of 1-[2-(4-bromophenoxy)ethyl]-azepane (356 mg, 1.19 mmol) in THF (7.5 mL) at −78° C., was added n-butyl lithium (2.5 M in hexane, 466 µL, 1.17 mmol). The reaction mixture was stirred at −78° C. for 0.5 hours. To the mixture was then added 2,8-bis-(tert-butyl-dimethyl-silyloxy)-11H-chromeno[4,3-c]chromen-5-one, prepared as in Example 22, (149 mg, 0.29 mmol) in THF (3 mL) and the reaction mixture stirred at −78° C. for 1.5 hours. To the mixture was then methyl magnesium bromide (3 M in diethyl ether, 1 mL, 3 mmol) at −78° C. and then stirred at room temperature overnight. The reaction was quenched with aqueous NH$_4$Cl and extracted with ethyl acetate. The organic layer was washed with brine and dried over MgSO$_4$. The remaining solvent was evaporated to yield the crude title product as a yellow oil, which was carried on to the next step without further purification.

MS m/z (M$^+$)=746

Step B: 1-(2-{4-[2,8-bis-(tert-butyl-dimethyl-silyloxy)-5-methyl-5,11-dihydro-chromeno[4,3-c]chromen-5-yl]-phenoxy}-ethyl)-azepane 2-[4-{1-[4-(2-azepan-1-yl-ethoxy)-phenyl]-1-hydroxy-ethyl}-7-(tert-butyl-dimehyl-silyloxy)-2H-chromen-3-yl]-5-(tert-butyl-dimethyl-silyloxy)-phenol, prepared as in STEP A above, was dissolved in toluene (8 mL) and treated with diluted HCl (0.4 mL of concentrated HCl:H$_2$O=1:2 v/v). The reaction mixture was vigorously stirred at room temperature for 1.5 h, then diluted with water and ethyl acetate. The resulting layers were separated and organic layer washed successively with saturated NaHCO$_3$, brine and dried over MgSO$_4$. The desiccant was filtered off, and the filtrate concentrated. Flash chromatography with ethyl acetate:hexane:CH$_3$OH (containing 1% NH$_4$OH)=49:49:2 as the eluent yielded the title compound as a light yellow oil.

$^1$H NMR (300 MHz; CDCl$_3$): δ 0.77 (s, 30 H), 1.52-1.59 (m, 8 H), 1.97 (s, 3 H), 2.71-2.75 (m, 4 H), 2.90 (t, 2 H, J=6.0 Hz), 3.99 (t, 2 H J=6.0 Hz), 5.04 (ABq, 2 H, J$_{AB}$=13.8; Δv$_{AB}$=22 Hz), 6.29 (dd, 1 H, J=2.4, 8.6 Hz), 6.41 (d, 1 H, J=2.2 Hz), 6.53 (m, 3H), 6.77 (d, 2 H, J=8.8 Hz), 6.88 (d, 1 H, J=8.4 Hz, 7.38 (d,2 H, J=8.8 Hz) MS m/z (M$^+$)=728.

Step C: 5-[4-(2-azepan-1-yl-ethoxy)-phenyl]-5-methyl-5,11-dihydro-chromeno[4,3-c]chromene-2,8diol To a solution of 1-(2-{4-[2,8-bis-(tert-butyl-dimethyl-silyloxy)-5-methyl-5,11-dihydro-chromeno[4,3-c]chromen-5-yl]-phenoxy}-ethyl)-azepane (77.5 mg, 0.11 mmol) in THF (7 mL) was added tetrabutylammonium fluoride (1M in THF, 213 µL, 0.21 mmol). The mixture was stirred at room temperature for 40 min. Saturated NH$_4$Cl was then added followed by addition of ethyl acetate. The resulting layers were separated, organic layer was washed with brine, and dried over MgSO$_4$. The remaining solvent was evaporated and the residue dried under vacuum for 2 h at room temperature to yield the title compound, which was carried on to the next step without further purification.

MS m/z (M$^+$)=472, (M$^-$)=470

Step D: 11-[4-(2-azepan-1-yl-ethoxy)-phenyl]-8-(2,2-dimethyl-propionyloxy)-11-methyl-5,11-dihydro-chromeno[4,3-c]chromen-2-yl ester To a suspension of 5-[4-(2azepan-1-yl-ethoxy)-phenyl]-5,11-dihydro-chromeno[4,3-c]chromene-2,8-diol, prepared as in STEP C above, in dichloromethane (5 mL) (DCM) at 5° C. was added triethylamine (TEA) (59 mg, 0.59 mmol) and stirred for 5 min. To the reaction mixture was then added trimethylacetyl chloride (66.7 mg, 0.55 mmol) and the mixture was then stirred at room temperature overnight. To the reaction mixture was then added saturated NaHCO$_3$ (10 mL) and stirred for 1 h. The reaction mixture was extracted with DCM, washed with brine and dried over MgSO$_4$. After removal of the dessicant, the organic solution was concentrated and the residue was purified via silica gel chromatography with 2% methanol in DCM as the eluent, to yield the title compound as a thick yellow oil.

$^1$H NMR (300 MHz; CDCl$_3$): δ 1.23 (s, 18 H), 1.52-1.59 (m, 8 H), 1.97 (s, 3 H), 2.72-2.75 (m, 4 H), 2.90 (t, 2 H, J=6.0 Hz), 3.99 (t, 2 H J=6.0 Hz), 5.04 (ABq, 2 H, J$_{AB}$=13.8; Δv$_{AB}$=22 Hz), 6.29 (dd, 1 H, J=2.4, 8.6 Hz), 6.41 (d, 1 H, J=2.2 Hz), 6.51-6.56 (m, 3H), 6.77 (d, 2 H, J=8.8 Hz), 6.88 (d, 1 H, J=8.4 Hz), 7.38 (d, 2 H, J=8.8 Hz) MS m/z (M$^+$)=668.

EXAMPLE 57

2,2-Dimethyl-propionic acid 8-(2,2-dimethyl-propionyloxy)-11-methyl-11-[4-(2-piperidin-1-yl-ethoxy)-phenyl]-5,11-dihydro-chromeno[4,3-c]chromen-2-yl ester Compound #41

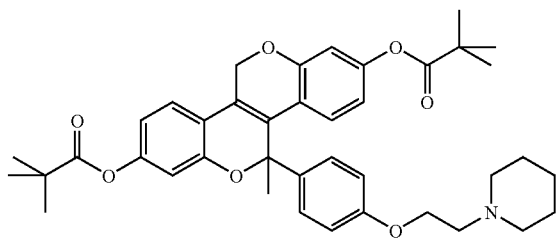

Step A: 5-(tert-butyl-dimethyl-silyloxy)-2-(7-(tert-butyl-dimethyl-silyloxy)-4-{1-hydroxy-1-[4-(2-piperidin-1-yl-ethoxy)-phenyl]-ethyl}-2H-chromen-3-yl)-phenol To a solution of 1-[2-(4-bromophenoxy)-ethyl]-piperidine (360 mg, 1.27 mmol) in THF (7.5 mL) at −78° C., was added n-butyl lithium (1.6 M in hexane, 773 µL, 1.24 mmol). The reaction mixture was stirred at −78° C. for 0.5 hours. To the reaction mixture was then added 2,8-bis-(tert-butyl-dimethyl-silyloxy)-11H-chromeno[4,3-c]chromen-5-one, prepared as in Example 22, (158 mg, 0.31 mmol) in THF (3 mL) and the mixture was stirred at −78° C. for 1.5 hours. To the reaction mixture was then added methyl magnesium bromide (3 M in diethyl ether, 1 mL, 3 mmol) at −78° C. and the reaction stirred at room temperature overnight. The reaction was quenched with aqueous NH$_4$Cl and extracted with ethyl acetate. The organic layer was washed with brine and dried over MgSO$_4$. The organic layer was concentrated to yield the crude title product as a yellow oil, which was carried into the next step without further purification.

MS m/z (M$^+$)=732

Step B: 1-(2-{4-[2,8-bis-(tert-butyl-dimethyl-silyloxy)-5-methyl-5,11-dihydro-chromeno[4,3-c]chromen-5-yl]-phenoxy}-ethyl)-piperidine 5-(Tert-butyl-dimethyl-silyloxy)-2-(7-(tert-butyl-dimethyl-silyloxy)-4-{1-hydroxy-1-[4-(2-piperidin-1-yl-ethoxy)-phenyl]-ethyl}-2H-chromen-3-yl)phenol, prepared as in STEP A above, was dissolved in toluene (8 mL) and treated with diluted HCl (0.4 mL of concentrated HCl: H$_2$O=1:2 v/v). The reaction mixture was vigorously stirred at room temperature for 1.5 h, then diluted with water and ethyl acetate. The layers were separated and the organic layer washed successively with saturated NaHCO$_3$, brine and then dried over MgSO$_4$. The desiccant was filtered off, and the filtrate concentrated. Flash chromatography with ethyl acetate:hexane:CH$_3$OH (containing 1% NH$_4$OH)=49:49:2 as the eluent yielded the title compound as a light yellow oil.

$^1$H NMR (300 MHz; CDCl$_3$): δ 0.78 (s, 30 H), 1.33-1.35 (m, 2 H), 1.57-1.63 (m, 4 H), 2.05 (s, 3 H), 2.49-2.51 (m, 4 H), 2.76 (t, 2 H, J=6.0 Hz), 4.08 (t, 2 H, J=6.0 Hz), 5.11 (ABq, 2 H, J$_{AB}$=13.8; Δv$_{AB}$=31 Hz), 6.37 (dd, 1 H, J=2.4, 8.6 Hz), 6.48 (d, 1 H, J=2.2 Hz), 6.60-6.64 (m, 3H), 6.84 (d, 2 H, J=8.8 Hz), 6.96 (d, 1 H, J=8.4 Hz), 7.44 (d, 2 H, J=8.8 Hz) MS m/z (M$^+$)=716, 739.

Step C: 5-methyl-5-[4-(2-piperidin-1-yl-ethoxy)-phenyl]-5,11-dihydro-chromeno[4,3-c]chromene-2,8-diol To a solution of 1-(2-{4-[2,8-bis-(tert-butyl-dimethyl-silyloxy)-5-methyl-5,11-dihydro-chromeno[4,3-c]chromen-5-yl]-phenoxy}-ethyl)-pepiridine (54 mg, 0.076 mmol) in THF (7 mL) was added tetrabutylammonium fluoride (1M in THF, 151 µL, 0.15 mmol). The mixture was stirred at room temperature for 40 min. Saturated NH$_4$Cl was then added followed by addition of ethyl acetate. The resulting layers were separated; the organic layer was washed with brine, and dried over MgSO$_4$. After concentration of the organic layer, the residue was dried under vacuum for 2 h at room temperature to yield the title compound which was carried on to the next step without further purification.

MS m/z (M$^+$) 486, (M$^-$) 484

Step D: 2,2-dimethyl-propionic acid 8-(2,2-dimethyl-propionyloxy)-11-methyl-11-[4-(2-piperidin-1-yl-ethoxy)-phenyl]-5,11-dihydro-chromeno[4,3-c]chromen-2-yl ester To a suspension of 5-methyl-5-[4-(2-piperidin-1-yl-ethoxy)-phenyl]-5,11-dihydro-chromeno[4,3-c]chromene-2,8-diol, prepared as om STEP C above, in dichloromethane (5 mL) (DCM) at 5° C. was added TEA (42 mg, 0.42 mmol) and the reaction mixture stirred for 5 min. Trimethylacetyl chloride (47 mg, 0.39 mmol) was then added to the reaction mixture and the mixture stirred at room temperature overnight. To the reaction mixture was then added saturated NaHCO$_3$ (10 mL) and stirred for 1 h. The resulting mixture was extracted with DCM, washed with brine and dried over MgSO$_4$. The organic layer was concentrated and the residue was purified via silica gel with 2% methanol in DCM as the eluent, to yield the title compound as a thick yellow oil.

$^1$H NMR (300 MHz; CDCl$_3$): δ 1.31 (s, 18 H), 1.33-1.35 (m, 2 H), 1.57-1.63 (m, 4 H), 2.05 (s, 3 H), 2.49-2.51 (m, 4 H), 2.76 (t, 2 H, J=6.0 Hz), 4.08 (t, 2 H, J=6.0 Hz), 5.11 (ABq, 2 H, J$_{AB}$=13.8 Hz; Δv$_{AB}$=31 Hz), 6.37 (dd, 1 H, J=2.4, 8.6 Hz), 6.48 (d, 1 H, J=2.2 Hz), 6.26 (m, 3H), 6.84 (d, 2 H, J=8.8 Hz), 6.96 (d, 1 H, J=8.4 Hz), 7.44 (d, 2 H, J=8.8 Hz) MS m/z (M$^+$)=654, 667.

EXAMPLE 58

2,2-Dimethyl-propionic acid 8-(2,2-dimethyl-propionyloxy)-11-methyl-11-[4-(3-piperidin-1-yl-propoxy)-phenyl]-5,11-dihydro-chromeno[4,3-c]chromen-2-yl ester Compound #43

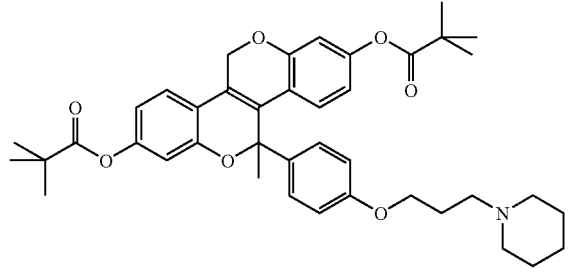

Step A: 5-(tert-butyl-dimethyl-silyloxy)-2-(7-(tert-butyl-dimethyl-silyloxy)-4-{1-hydroxy-1-[4-(3-piperidin-1-yl-propoxy)-phenyl]-ethyl}-2H-chromen-3-yl)-phenol To a solution of 1-[3-(4-bromo-phenoxy)-propyl]-piperidine (393 mg, 1.32 mmol) in THF (7.5 mL) at −78° C., was added n-butyl lithium (1.6 M in hexane, 804 µL, 1.29 mmol). The reaction mixture was then stirred at −78° C. for 0.5 hour. To the reaction mixture was then added 2,8-bis-(tert-butyl-dimethyl-silyloxy)-11H-chromenol[4,3-c]chromen-5-one, prepared as in Example 22, (164 mg, 0.32 mmol) in THF (3 mL) and the reaction mixture stirred at −78° C. for 1.5 hours. To the reaction mixture was then added methyl magnesium bromide (3 M in diethyl ether, 1 mL, 3 mmol) at −78° C. and then stirred at room temperature overnight. The reaction was quenched with aqueous NH$_4$Cl and then extracted with ethyl acetate. The organic layer was washed with brine and dried over MgSO$_4$. After removal of the dessicant, the residue was concentrated to yield the crude title product as a yellow oil, which was carried on to the next step without further purification.

MS m/z (M$^+$)=746-

Step B: 1-(3-{4-[2,8-bis-(tert-butyl-dimethyl-silyloxy)-5-methyl-5,11-dihydro-chromenol[4,3-c]chromen-5-yl]-phenoxy}-propyl)-piperidine 5-(tert-butyl-dimethyl-silyloxy)-2-(7-(tert-butyl-dimethyl-silyloxy)-4-{1-hydroxy-1-[4-(3-piperidin-1-yl-propoxy)-phenyl]-ethyl}-2H-chromen-3-yl)-phenol, prepared as in STEP A above, was dissolved in toluene (8 mL) and then treated with diluted HCl (0.4 mL of concentrated HCl:H$_2$O=1:2 v/v). The reaction mixture was vigorously stirred at room temperature for 1.5 h. The mixture was then diluted with water and ethyl acetate. The resulting layers were separated and the organic layer washed successively with saturated NaHCO$_3$, brine and then dried over MgSO$_4$. The desiccant was filtered off, and the filtrate was concentrated. Flash chromatography with ethyl acetate:hexane:CH$_3$OH (containing 1% NH$_4$OH)=49:49:2 as the eluent yielded the title compound as a light yellow oil.

$^1$H NMR (300 MHz; CDCl$_3$): δ 0.78 (s, 30 H), 1.51-1.53 (m, 2 H), 1.78-1.82 (m, 4 H), 2.05 (s, 3 H), 2.14-2.19 (m, 2 H), 2.74-2.79 (m, 4 H), 2.86-2.92 (m, 2 H), 4.00 (t, 2 H, J=5.9 Hz), 5.14 (ABq, 2 H, J$_{AB}$=13.8 Hz; Δv$_{AB}$=21 Hz), 6.37 (dd, 1 H, J=2.4, 8.6 Hz), 6.48 (d, 1 H, J=2.2 Hz), 6.59-6.64 (m, 3 H), 6.82 (d, 2 H, J=8.8 Hz), 6.97 (d, 1 H, J=8.4 Hz), 7.46 (d, 2 H, J=8.8 Hz)

Step C: 5-methyl-5-[4-(3-piperidin-1-yl-propoxy)-phenyl]-5,11-dihydro-chromeno[4,3-c]chromene-2,8-diol To a solution of 1-(3-{4-[2,8-bis-(tert-butyl-dimethyl-silyloxy)-5-methyl-5,11-dihydro-chromenol[4,3-c]chromen-5-yl]-phenoxy}-propyl)-piperidine (97.5 mg, 0.134 mmol) in THF (7 mL) was added, tetrabutylammonium fluoride (1M in THF, 268 µL, 0.27 mmol). The reaction mixture was stirred at room temperature for 40 min. To the reaction mixture was then added saturated NH$_4$Cl followed by addition of ethyl acetate. The resulting layers were separated, the organic layer was washed with brine, and then dried over MgSO$_4$. After concentration of the organic layer, the residue was dried under vacuum for 2 h at room temperature to yield the title compound which was carried on to the next step without further purification.

MS m/z (M$^+$) 500, (M$^-$) 498

Step D: 2,2-dimethyl-propionic acid 8-2,2-dimethyl-propionyloxy)-11-methyl-11-[4-(3-piperidin-1-yl-propoxy)-phenyl]-5,11-dihydro-chromeno[4,3-c]chromen-2-yl ester To a suspension of 5-methyl-5-[4-(2-piperidin-1-yl-propoxy)-phenyl]-5,11-dihydro-chromeno[4,3-c]chromene-2,8-diol, prepared as in STEP C above, in dichloromethane (5 mL) (DCM) at 5° C. was added Et$_3$N (74.5 mg, 0.74 mmol) and stirred for 5 min. Trimethylacetyl chloride (84 mg, 0.70 mmol) was then added and the reaction mixture stirred at room temperature overnight. To the reaction mixture was then added saturated NaHCO$_3$ (10 mL) and then stirred for 1 h. The reaction mixture was then extracted with DCM, washed with brine and dried over MgSO$_4$. After removal of the dessicant, the organic layer was concentrated and the resulting residue was purified via silica gel chromatography with 2% methanol in DCM as the eluent to yield the title compound as a thick yellow oil.

MS m/z (M+H) 668 $^1$H NMR (300 MHz; CDCl$_3$): δ 1.30 (s, 18 H), 1.51-1.53 (m, 2 H), 1.78-1.82 (m, 4 H), 2.05 (s, 3 H), 2.14-2.19 (m, 2 H), 2.74-2.79 (m, 4 H), 2.86-2.92 (m, 2 H), 4.00 (t, 2 H, J=5.9 Hz), 5.14 (ABq, 2 H, J$_{AB}$=13.8 Hz; Δv$_{AB}$=21 Hz), 6.37 (dd, 1 H, J=2.4, 8.6 Hz), 6.48 (d, 1 H, J=2.2 Hz), 6.59-6.64 (m, 3 H), 6.82 (d, 2 H, J=8.8 Hz), 6.97 (d, 1 H, J=8.4 Hz), 7.46 (d, 2 H, J=8.8 Hz)

EXAMPLE 59

2,2-Dimethyl-propionic acid 8-(2,2-dimethyl-propionyloxy)-11-methyl-11-[3-(2-piperidin-1-yl-ethoxy)-phenyl]-5,11-dihydro-chromeno[4,3-c]chromen-2-yl ester Compound #38

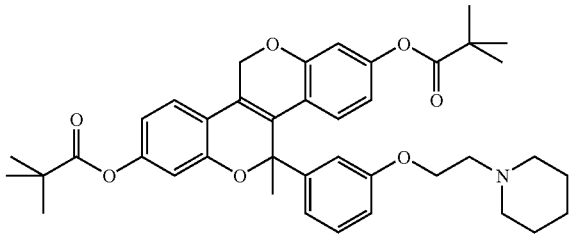

Step A: 5-(tert-butyl-dimethyl-silyloxy)-2-(7-(tert-butyl-dimethyl-silyloxy)-4-{1-hydroxy-1-[3-(2-piperidin-1-yl-ethoxy)-phenyl]-ethyl}-2H-chromen-3-yl)-phenol To a solution of 1-[3-(4-bromophenoxy)-ethyl]-piperidine (343 mg, 1.21 mmol) in THF (7.5 mL) at −78° C., was added n-butyl lithium (2.5 M in hexane, 471 µL, 1.18 mmol) and the reaction mixture was stirred at −78° C. for 0.5 hours. To the reaction mixture was then added a solution of 2,8-bis-(tert-butyl-dimethyl-silyloxy)-11H-chromeno[4,3-c]chromen-5-one, prepared as in Example 22, (150 mg, 0.29 mmol) in THF (3 mL). The reaction mixture was stirred at −78° C. for 1.5 hours. To the reaction mixture was then added methyl magnesium bromide (3 M in diethyl ether, 1 mL, 3 mmol) at −78° C. and then stirred at room temperature overnight. The reaction was quenched with aqueous NH$_4$Cl and extracted with ethyl acetate. The organic layer was washed with brine and dried over MgSO$_4$. After removal of the dessicant, the organic layer was concentrated to yield crude the title compound as a yellow oil, which was carried on to the next step without further purification.

MS m/z (M$^+$)=732

Step B: 1-(2-{3-[2,8-bis-(tert-butyl-dimethyl-silyloxy)-5-methyl-5,11-dihydro-chromenol[4,3-c]chromen-5-yl]-phenoxy}-ethyl)-piperidine 5-(Tert-butyl-dimethyl-silyloxy)-2-(7-(tert-butyl-dimethyl-silyloxy)-4-{1-hydroxy-1-[3-(2-piperidin-1-yl-ethoxy)-phenyl]-ethyl}-2H-chromen-3-yl)phenol, prepared as in STEP A above, was dissolved in toluene (8 mL) and treated with diluted HCl (0.4 mL of concentrated HCl:H$_2$O=1:2 v/v) and the reaction mixture was vigorously stirred at room temperature for 1.5 h. The reaction mixture was then diluted with water and ethyl acetate. The resulting layers were separated and the organic layer washed successively with saturated NaHCO$_3$, brine and then dried over MgSO$_4$. The desiccant was filtered off, and the filtrate was concentrated. Flash chromatography with ethyl acetate:hexane: CH$_3$OH (containing 1% NH$_4$OH)=49:49:2 as the eluent yielded the title compound as a light yellow oil.

MS m/z (M$^+$) 715, 736

Step C: 5-methyl-5-[3-(2-piperidin-1-yl-ethoxy)-phenyl]-5,11-dihydro-chromeno[4,3-c]chromene-2,8-diol To a solution of 1-(2-3-[2,8-bis-(tert-butyl-dimethyl-silyloxy)-5-methyl-5,11-dihydro-chromenol[4,3-c]chromen-5-yl]-phenoxy}-ethyl)-pepiridine (34 mg, 0.048 mmol) in THF (7 mL) was added, tetrabutylammonium fluoride (1M in THF, 95 µL, 0.095 mmol). The mixture was stirred at room temperature for 40 min. To the reaction mixture was then added saturated NH₄Cl followed by addition of ethyl acetate. The resulting layers were separated, the organic layer was washed with brine, and then dried over MgSO₄. The dessicant was filtered off, the organic layer was concentrated and the resulting residue was dried under vacuum for 2 h at room temperature to yield the title compound which was carried on to the next step without further purification.

MS m/z (M⁺) 486, (M⁻) 484

Step D: 2,2-dimethyl-propionic acid 8-(2,2-dimethyl-propionyloxy)-11-methyl-11-[3-(2-piperidin-1-yl-ethoxy)-phenyl]-5,11-dihydro-chromeno[4,3-c]chromen-2-yl ester To a suspension of 5-methyl-5-[3-(2-piperidin-1-yl-ethoxy)-phenyl]-5,11-dihydro-chromeno[4,3-c]chromene-2,8-diol, prepared as in STEP C above, in dichloromethane (5 mL) (DCM) at 5° C. was added Et₃N (27 mg, 0.26 mmol) and the reaction mixture stirred for 5 min. Trimethylacetyl chloride (30 mg, 0.25 mmol) was then added and the reaction mixture was stirred at room temperature overnight. To the reaction mixture was then added saturated NaHCO₃ (10 mL) and stirred for 1 h. The reaction mixture was then extracted with DCM, washed with brine and dried over MgSO₄. The dessicant was removed and the organic layer concentrated. The resulting residue was purified via silca gel chromatography with 2% methanol in DCM as the eluent, to yield the title compound as a thick yellow oil.

MS m/z (M⁺) 654

EXAMPLE 60

4-Bromomethyl-3-(2,4dibenzoyl-phenyl)-7-benzoyl-chromen-2-one

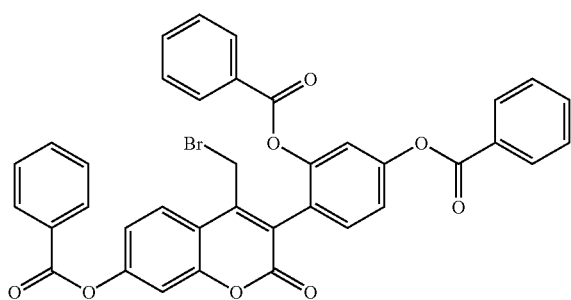

LiHMDS (1.0 M, 378 µL, 2.5 eq., 0.378 mmol) in THF was added drop-wise via syringe into a solution of 3-(2,4-dihydroxy-phenyl)-7-hydroxy-4-methyl-chromen-2-one (90 mg, 1.0 eq., 0.151 mmol) in THF (1 mL) at −78° C. under N₂. The reaction mixture was observed to turn a reddish color. After addition, the reaction mixture was stirred for an additional 0.5 h at −78° C. To the reaction mixture, was then added bromine (12 µL, 1.5 eq., 0.227 mmol) at 78° C. The color of the mixture was observed to turn from red to light yellow. The reaction mixture was then stirred for an additional 0.5 h at −78° C. The reaction was quenched with saturated NaHSO₃ solution, warmed to room temperature and stirred vigorously at room temperature for 15 min. THF was removed by rotavap in vacuo. Ethyl acetate (20 mL) and water (5 mL) were then added to the reaction residue, resulting in two phases. The aqueous phase was extracted twice with ethyl acetate. The combined organic layer was washed with brine, dried over anhydrous Na₂SO₄, filtered and concentrated to yield the crude title compound as a yellow solid. The crude material was purified by flash column chromatography using hexanes and ethyl acetate at 3:1 solution as eluent to yield the title compound as a light yellow solid.

The product was determined to contain the benzoic acid 3-benzoyloxy-4-(7-benzoyloxy-4-bromomethyl-2-oxo-2H-chromen-3-yl)-phenyl ester compound and the benzoic acid, 3-benzoyloxy-4-(7-benzoyloxy-4-dibromomethyl-2-oxo-2H-chromen-3-yl)-phenyl ester.

R$_f$=0.60 in 3:1 hexane:ethyl acetate (UV) ¹H NMR (CDCl₃, TMS standard), 8.22 (m, J=14.4 Hz, 5H), 8.04 (d, J=6.9 Hz, 1H), 7.85 (d, J=9.6 Hz, 1H), 7.69 (m, 4H), 7.42 (m, 5H), 7.30 (m, 5H), 4.48 (ABq, J=10.8 Hz, 2H) MS (M+1), 699, 697.

EXAMPLE 61

2,8-Dihydroxy-11H-chromeno[4,3-c]chromen-5-one Compound #1

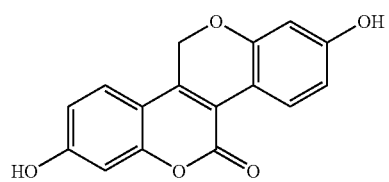

Method C:

4-Bromomethyl-3-(2,4-dibenzoyl-phenyl)-7-benzoyl-chromen-2-one (67 mg, 1.0 eq., 0.099 mmol) was dissolved in acetone (1 mL) and methanol (0.5 mL) under N₂. K₂CO₃ (41 mg, 3.0 eq., 0.298 mmol) powder was then added in one portion into the solution. The reaction mixture was stirred at room temperature overnight. The color of the reaction was observed to turn from light yellow to orange. The solvent was removed, the residue was dissolved in water and the resulting mixture acidified to about pH 1 by drop-wise addition of 6 N HCl. CH₂Cl₂ was added into the reaction mixture and the aqueous phase was extracted with CH₂Cl₂ twice. The combined organic layer was washed with water and brine, dried over anhydrous Na₂SO₄, filtered and concentrated to yield crude title compound as a brown solid. A 5:1 mixture of hexane:ethyl acetate was added to the crude product. The supernatant solution was removed by a pipet and the remaining insoluble solid was dried in vacuo to yield the title compound as a solid.

R$_f$=0.2, hexane:ethyl acetate=3:1, UV

EXAMPLE 62

3-[2,4-Bis-2-trimethylsilanylethoxymethoxy)-pheny]-4-methyl-7-(2-trimethylsilanyl-ethoxymethoxy)-chromen-2-one

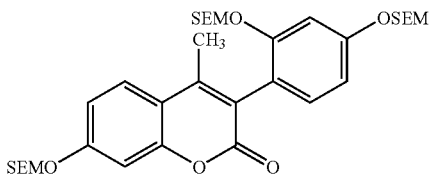

A mixture of 3-(2,4-dihydroxyphenyl)-7-hydroxy-4-methyl-chromen-2-one (4.7 g, 16.5 mmol), SEMCl (14.6 ml, 82.9 mmol) and $K_2CO_3$ (18.6 g, 367.1 mmol) in acetone (600 mL) was heated to 50° C. under nitrogen for 1 hour. The resulting mixture was cooled, filtered and evaporated to form a thick oil. The oil was purified by $SiO_2$ using 5-10 ethyl acetate/hexane as solvent gradient to yield the title compound as an oil.

MS(Cl) m/z 675 (M+H)$^+$, 697 (M+Na)$^+$ $^1$H-NMR(CDCl$_3$, 300 MHz) δ(ppm) 7.6(d, J=6 Hz, 1H), 7.2-6.8(m, 5H), 5.1-5.4(m, 6H), 3.6-3.9(m, 6H), 2.25(s, 3H), 0.2-0.1(m, 27H).

EXAMPLE 63

3-[2,4-Bis-(2-trimethylsilanylethoxymethoxy)-phenyl]-4-bromomethyl-7-(2-trimethylsilanyl-ethoxymethoxy)-chromen-2-one

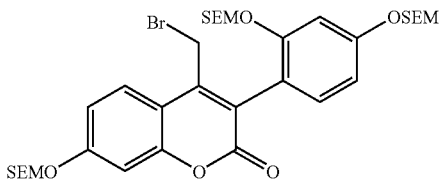

A 250 mL 3-neck round bottom flask was equipped with a magnetic stirrer, a rubber stopper and an argon inlet/outlet adapter. This vessel was charged with THF (20 mL) via syringe, iPr$_2$NH (1.8 mL, 14.0 mmol) via syringe and cooled to −10° C. in an ice/methanol bath. n-Butyl lithium (1.85 M (titrated) via syringe, 6.3 mL, 11.7 mmol) in hexane was added dropwise via syringe at −10° C., stirred for 15 min at −10° C. To the solution was added 3-[2,4-bis-(2-trimethylsilanyl-ethoxymethoxy)-phenyl]-4-methyl-7-(2-trimethylsilanyl-ethoxymethoxy)-chromen-2-one (5.1 g, 7.8 mol) in THF (20 mL) drop-wise via syringe. The mixture was stirred at −10° C. for 2.5 h. This mixture was added dropwise via syringe to a solution of Br$_2$(0.76 mL, 2 eq) in −78° C. THF (100 mL) via syringe that was contained in a 1-L 3-neck round bottom flask equipped with mechanical stirrer and septum under N$_2$. After the addition was complete, the mixture was stirred for 5 min at −78° C. and then diluted with EtOAc (0.5 L) via syringe, saturated NaHCO$_3$ (50 mL) via syringe and saturated Na$_2$SO$_3$ (100 mL) via syringe. The dry ice/acetone bath was removed and the mixture was allowed to warm to room temperature while stirring. The organic phase was separated and the aqueous phase was back-extracted with EtOAc (2×0.2 L). The combined organic phase was washed with brine (2×0.5 L) and concentrated in vacuo to yield the title compound as a crude semi-solid.

MS M/z M+H=770; M+Na=793 $^1$H-NMR(CDCl$_3$, 300 MHz) δ(ppm): 7.8-6.8 (m, 6H), 5.6-5.1 (m, 6H), 4.4-4.2 (Abq, J=16 Hz, 2H), 3.8-3.6 (m, 6H), 0.8-0.11 (m, 6H)

EXAMPLE 64

3-[2,4-Bis-(2-trimethylsilanyl-ethoxymethoxy)-phenyl]-4-methyl-7-(2-trimethyl silanyl-ethoxymethoxy)-chromen-2-one

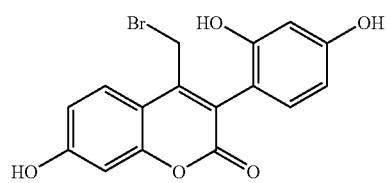

Into 1N HCl (10 mL) (1N HCl solution made using concentrated HCl in 1:1 THF:IPA) was dissolved 3-[2,4-bis-(2-trimethylsilanyl-ethoxymethoxy)-phenyl]-4-bromomethyl-7-(2-trimethylsilanyl-ethoxymethoxy)-chromen-2-one (200 mg, 0.544 mmol) and the resulting mixture was stirred for 24 h at room temperature. The reaction mixture was then diluted with EtOAc (100 mL) and the organic layer washed with water (2×20 mL) and brine (30 mL). The organic layer was dried over Na$_2$SO$_4$, filtered and the organic solvent evaporated to yield the title compound, 3-[2,4-Bis-(2-trimethylsilanyl-ethoxymethoxy)-phenyl]-4-methyl-7-(2-trimethyl silanyl-ethoxymethoxy)-chromen-2-one as a crude solid.

MS(Cl) m/z 362(M+H$^+$); 384 (M+Na$^+$) $^1$H-NMR(CDCl$_3$, 300 MHz) δ(ppm): 7.8-6.8 (m, 6H), 4.8-4.6 (Abq, J=14.6 Hz, 2H).

EXAMPLE 65

2,8-Dihydroxy-11H-chromeno[4,3-c]chromen-5-one
Compound #1

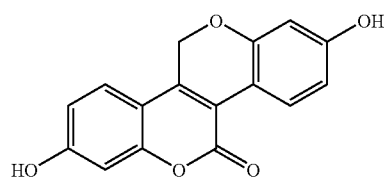

Method D:

2,8-Dihydroxy-11H-chromeno[4,3-c]chromen-5-one (90 mg, 0.25 mmol) was dissolved in MeOH (2.5 mL). K$_2$CO$_3$ (35 mg, 0.2 mmol) was added and the resulting mixture was stirred for 10 min at room temperature. The reaction mixture was diluted with EtOAc (50 mL), filtered and the organic solvent evaporated to dryness. The semisolid obtained was purified SiO$_2$ using 50% EtOAc in hexanes to yield the title compound as a solid.

MS(Cl) m/z 283 (M+H$^+$), 306 (M+Na$^+$)

EXAMPLE 66

1-(2-{4-[2,8-Bis-(tert-butyl-dimethyl-silyloxy)-5,11-dihydro-chromeno[4,3-c]chromen-5-yl]-phenoxy}-ethyl)-piperidine

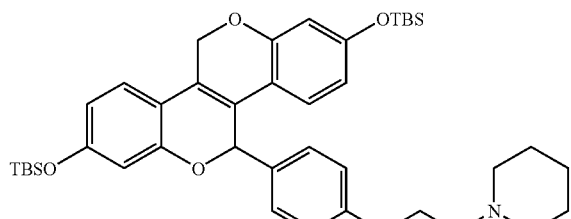

Method B:

1-[2-(4-Iodo-phenoxy)-ethyl]-piperidine(1.656, 5 mmol) was dissolved in THF and cooled to −78° C. To the reaction mixture, was then added n-butyl lithium (2M solution in pentane, 2.5 mL, 10 mmol), slowly over 5 min. The resulting solution was stirred for 1 h at −78° C. 2,8-Bis-(tert-butyl-dimethyl-silyloxy)-5,11-dihydro-chromeno[4,3-c]chromen-5-ol 1 g 1.953 mmol) was dissolved in THF (20 mL) and then added to the reaction mixture containing 1-[2-(4-Iodo-phenoxy)-ethyl]-piperidine and n-butyl lithium, slowly over 10 min. The reaction mixture was stirred for an additional hour. The reaction mixture was quenched with MeOH (1 mL) and then treated with a saturated solution of ammonium chloride (30 mL) and then diluted with diethyl ether (150 mL). The organic layer was separated and washed with brine (100 mL). The organic layer was dried over anhydrous $Na_2SO_4$, filtered and the solvent evaporated to yield a crude oil. The crude oil was diluted with toluene (150 mL) and HCl (37%, 6.0 mL) and stirred for 30 min at room temperature. The solution was diluted with EtOAc (300 mL), the organic layer washed twice with water (100 ml) and then with a saturated solution of $NaHCO_3$ (150 ml). The organic layer was separated and dried over anhydrous $Na_2SO_4$, filtered, and evaporated to yield the title compound as a foamy material.

MS(Cl) m/z 700 (M+H$^+$), 723 (M+Na$^+$) $^1$H NMR (300 MHz, CDCl$_3$) δ: 7.30 (2H, d, J=8.7 Hz), 6.87 (1H, d, J=8.30 Hz), 6.79 (2H, d, J=1.91, 6.82 Hz), 6.70 (1H, d, J=8.42 Hz), 6.39 (2H, m), 6.29 (2H, m), 6.14 (1H, s), 5.30 (1H, d, J=13.90 Hz), 5.10 (1H, d, d, J=1.654, 13.90 Hz), 4.04 (2H, t, J=5.97 Hz), 2.48 (2H, t, J=6.0 Hz), 2.48 (4H, m), 1.58 (4H, m), 1.43 (2H, m), 0.95 (9H, s), 0.93 (9H, s), 0.18 (6H, s), 0.16 (6H, s).

EXAMPLE 67

2,2-Dimethyl-propionic acid 8-(2,2-dimethyl-propionyloxy)-5S*-(+)-[4-(2-piperidin-1-yl-ethoxy)-phenyl]-5,11dihydro-chromeno[4,3-c]chromen-2-yl ester

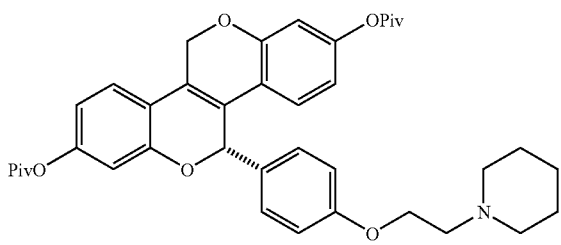

1 M TBAF (in THF, 17 mL, 17 mmol, 3 eq.) was added drop-wise into a solution of 1-(2-{4-[2,8-Bis-(tert-butyl-dimethyl-silyloxy)-5,11-dihydro-chromeno[4,3-c]chromen-5-yl]-phenoxy}-ethyl)-piperidine (4.0 g, 5.7 mmol) in THF (40 mL) at −10° C. The reaction mixture was stirred for 15 minutes. To the reaction mixture was then added 2,2-dimethylpropionic acid chloride (2.5 mL, 20 mmol, 3.5 eq). The reaction mixture was diluted with ethyl acetate and washed with 5% sodium bicarbonate and then with brine. The organic layer was dried over anhydrous $Na_2SO_4$, and concentrated to yield a 1:2 mixture of mono-pivalate:di-pivalate. To the crude product dissolved in $CH_2Cl_2$, was added 2,2-dimethylpropionic acid chloride (4.3 ml) and triethylamine (5 mL) and the reaction mixture was stirred for 30 min. The reaction mixture was diluted with ethyl acetate (300 mL) and then washed with brine. Flash chromatography on Biotage column eluted with 2% to 5% MeOH in $CH_2Cl_2$ yielded the title product as a racemic mixture of 2,2-dimethyl-propionic acid 8-(2,2-dimethyl-propionyloxy)-5[4-(2-piperidin-1-yl-ethoxy)-phenyl]-5,11-dihydro-chromeno[4,3-c]chromen-2-yl ester.

The racemic compound (2,2-dimethyl-propionic acid 8-(2,2-dimethyl-propionyloxy)-5[4-(2-piperidin-1-yl-ethoxy)-phenyl]-5,11-dihydro-chromeno[4,3-c]chromen-2-yl ester) (2.5 g) was loaded onto a ChiralPak AD chiral HPLC column (5 cm I.D.×50 cm L) and eluted with 20% MeOH in IPA at the 90 mL/min flow rate. The two peaks were removed under vacuum to yield: 2,2-dimethyl-propionic acid 8-(2,2-dimethyl-propionyloxy)-5R*-(−)-[4-(2-piperidin-1-yl-ethoxy)-phenyl]-5,11-dihydro-chromeno[4,3-c]chromen-2-yl ester as peak one and 2,2-dimethyl-propionic acid 8-(2,2-dimethyl-propionyloxy)-5S*-(+)-[4-(2-piperidin-1-yl-ethoxy)-phenyl]-5,11-dihydro-chromeno[4,3-c]chromen-2-yl ester as peak two.

MS m/z 640 (M+H$^+$), 663 (M+Na$^+$) $^1$H NMR (300 MHz, CDCl$_3$): δ 7.30 (2H, d, J=8.7 Hz), 7.01 (1H, d, J=8.4 Hz), 6.83-6.78 (3H, m), 6.64 (1H, d, d, J=2.3, 8.5 Hz), 6.63 (1H, d, J=2.3 Hz), 6.54-6.49 (2H, m), 6.21 (1H, s), 5.37 (1H, d, J=14 Hz), 5.16 (1H, d, J=14 Hz), 4.05 (2H, t, J=6.0 Hz), 2.74 (1H, t, J=6.0 Hz), 2.49 (4H, brs), 1.59 (4H, m), 1.37 (2H, m), 1.32 (9H, s), 1.30 (9H, s)

EXAMPLE 68

(1S)-(−)-camphanic acid-8-((1S)-(−)-camphanyl)-5S*-[4-(2-piperidin-1-yl-ethoxy)-phenyl]-5,1,1-dihydro-chromeno[4,3-c]chromen-2-yl ester Compound #49

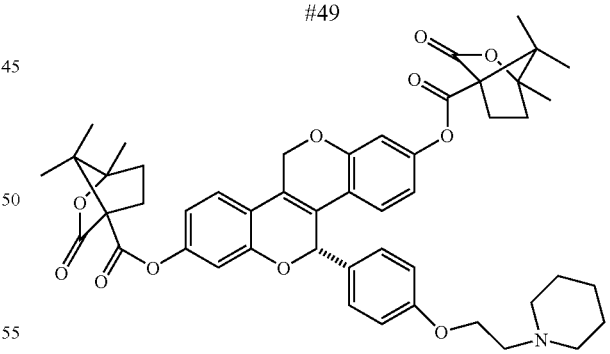

1 M TBAF (in THF, 8.5 mL, 8.5 mmol, 3 eq.) was added drop-wise into a solution of 1-(2-{4-[2,8-Bis-(tert-butyl-dimethyl-silyloxy)-5,11-dihydro-chromeno[4,3-c]chromen-5-yl]-phenoxy}-ethyl)-piperidine (2.00 g, 2.85 mmol) in THF (30 mL) at −10° C. and the reaction mixture stirred for 15 min. To the reaction mixture, was then added (1S)-(−)-camphanic chloride (1.69 g, 8.6 mmol, 3 eq). The reaction mixture was then diluted with ethyl acetate (300 mL) and washed with 5% sodium bicarbonate, then washed with brine. The organic layer was dried over anhydrous $Na_2SO_4$ and concentrated to yield a 1:3 mixture of the mono-camphane:di-camphane derivative.

To the crude product in CH$_2$Cl$_2$ (55 mL) was added (1S)-(−) camphanic chloride (1.5 g) and TEA (2.0 mL) and the reaction mixture was stirred for 30 minutes at room temperature. The reaction mixture was then diluted with ethyl acetate (250 mL) and then washed with brine. Flash chromatography on SiO$_2$ column eluted with 2% to 5% MeOH in CH$_2$Cl$_2$ yielded the title compound as a diastereomer mixture of (1S)-(−)-camphanic acid-8-((1S)-(−)-camphanyl)-5S*-[4-(2-piperidin-1-yl-ethoxy)-phenyl]-5,1,1-dihydro chromeno[4,3-c]chromen-2-yl ester and (1S)-(−)-camphanic acid-8-((1S)-(−)-camphanyl)-5R*-[4-(2-piperidin-1-yl-ethoxy)-phenyl]-5,1,1-dihydro chromeno[4,3-c]chromen-2-yl ester.

The mixture of diastereomers was suspended in hot ethanol (110 mL) in presence of (R)-(−)-10 camphorsulphonic acid (0.6 eq.) and stirred at 70° C. for 4 h until the solution became clear. The solution was filtered and cooled to room temperature. A solid was formed after 64 h, the solid was filtered and dried under vacuum to yield the title compound as a solid. (84% de)

MS m/z 832 (M+H$^+$); 854 (M+Na$^+$) $^1$H-NMR(CDCl$_3$, 300 MHz) δ(ppm): 7.3 (d, J=8.3 Hz, 2H), 7.1 (d, J=8.7 Hz, 2H), 7.7-7.8 (m, 3H), 6.7-6.5 (m, 4H), 6.21 (s, 1H), 5.4-5.2 (Abq, J=14.4 Hz, 2H), 4.1 (t, J=3 Hz, 2H), 2.75 (t, J=6 hz, 2H), 2.29-1.5 (m, 18H), 1.2-0.8 (m, 18H)

EXAMPLE 69

3-(2,4-Bis-methoxymethoxy-phenyl)-7-methoxymethoxy-4-methyl-chromen-2-one

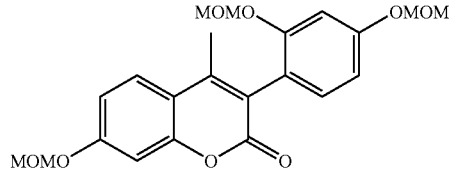

MOMCl (6.62 ml, 82.9 mmol) was added to the mixture of K$_2$CO$_3$ (18.6 g, about 367.1 mmol) and 3-(2,4-dihydroxyphenyl)-7-hydroxy-4-methyl-chromen-2-one (4.7 g, 16.5 mmol) in acetone (600 ml) at 0° C. under nitrogen for 1 hour. The reaction mixture was then stirred for 4 h, over which time the solution was allowed to warm to room temperature. The reaction mixture was then filtered and evaporated to yield a thick oil. The oil was purified by SiO$_2$ using 5-10 Ethyl acetate:hexane as solvent gradient to yield 3-(2,4-Bis-methoxymethoxy-phenyl)-7-methoxymethoxy-4-methyl-chromen-2-one as a solid.

MS m/e 417 (M+H$^+$) and 439 (M+Na$^+$) $^1$H-NMR(CDCl$_3$, 300 MHz) δ (ppm): 7.7 (d, 6.7 Hz, 1H), 7.1-6.6 (m, 5H), 5.3-5.1 (m, 6H), 3.411 (s, 3H), 3.41 (s, 3H), 3.3 (s, 3H), 2.2 (s, 3H)

EXAMPLE 70

[3-(2,4-Bis-methoxymethoxy-phenyl)-7-methoxymethoxy-2-oxo-2H-chromen-4-yl]-acetaldehyde

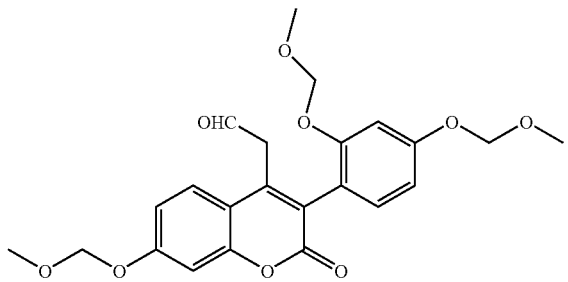

To a clean dry 200 ml flask purged with nitrogen was added diisopropylamine (2.7 ml, 19.5 mmol, 3 eq), dry THF (50 mL) and 3-(2,4-Bis-methoxymethoxy-phenyl)-7-methoxymethoxy-4-methyl-chromen-2-one (8.1 mL, 16.25 mmol, 2.5 eq.) at −78° C. After 30 minutes, to this solution was added drop-wise, a solution of 3-(2,4-bis-methoxymethoxy-phenyl)-7-methoxymethoxy-4-methyl-chromen-2-one (2.7 g, 6.5 mmol, 1 eq.) in dry THF (13 mL). The solution was warmed to −10° C. and stirred at this temperature for 30 minutes. Phenyl formate (3.6 ml, 33 mmol, 5 eq) was then added slowly into the reaction mixture. The reaction mixture was then stirred for 30 mins, quenched with saturated aqueous NH$_4$Cl, extracted with ethyl acetate and then concentrated to yield th title product as a crude solid which was purified by flash chromatography eluting with 30% ethyl acetate in hexane to yield the title product as a solid.

MS: 443.0, M−H; $^1$H-NMR (300 MHz, CDCl$_3$): δ (ppm) 9.7 (s, 1H), 6.8-7.4 (m, 6H), 5.25 (s, 2H), 5.2 (s, 2H), 5.1 (s, 2H), 3.7-3.9 (m, 2H), 3.49 (s, 3H), 3.5 (s, 3H), 3.4 (s, 3H).

EXAMPLE 71

3-(2,4-Bis-methoxymethoxy-phenyl)-4-(2-hydroxy-ethyl)-7-methoxymethoxy-chromen-2-one

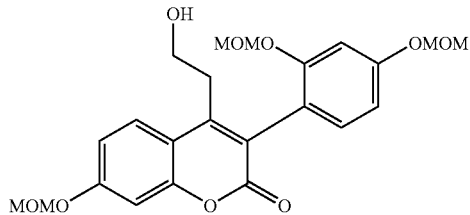

Sodium borohydride (17 mg, 0.45 mmol, 0.5 eq.) was dissolved in ethanol (5 mL), then added into the solution of [3-(2,4-Bis-methoxymethoxy-phenyl)-7-methoxymethoxy-2-oxo-2H-chromen-4-yl]-acetaldehyde (400 mg, 0.90 mmol, 1 eq.) ethanol (10 mL) at −10° C. and the reaction mixture was stirred for 30 minutes. The solvent was evaporated and the resulting residue was dissolved in ethyl acetate (100 mL) and washed twice with brine. The organic layer was dried over anhydrous sodium sulfate then concentrated to yield the crude product which was purified by flash chromatography eluted with 50% ethyl acetate to yield the title compound 3-(2,4-Bis-methoxymethoxy-phenyl)-4-(2-hydroxy-ethyl)-7-methoxymethoxy-chromen-2-one as a solid.

MS: 447.1, M+H; 469.1, M+Na; 445.1 M−H $^1$H-NMR (300 MHz, CDCl$_3$): δ (ppm) 6.8-7.7 (m, 6H), 5.3 (s, 2H), 5.25 (s, 2H), 5.2 (s, 2H), 3.8 (m, 2H), 3.51 (s, 3H), 3.50 (s, 3H), 3.4 (s, 3H), 3.0 (m, 2H), 1.75 (t, 1H).

EXAMPLE 72

3-(2,4-Dihydroxy-phenyl)-7-hydroxy-4-(2-hydroxy-ethyl)-chromen-2-on

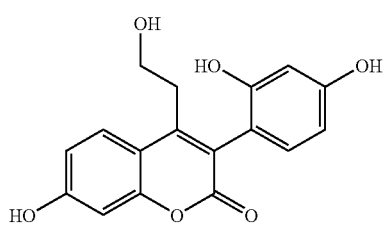

Into a flask purged with nitrogen was added 3-(2,4-Bis-methoxymethoxy-phenyl)-4-(2-hydroxy-ethyl)-7-methoxymethoxy-chromen-2-one (200 mg) and 1N HCl (10 mL) in 1:1 isopropanol:THF. The reaction mixture was stirred overnight, then diluted with ethyl acetate (200 mL) and washed three times with brine. The organic layer was dried over anhydrous sodium sulfate and then concentrated. The residue was purified by flash chromatography eluted with 10% methanol in dichloromethane to yield 3-(2,4-dihydroxy-phenyl)-7-hydroxy-4-(2-hydroxy-ethyl)-chromen-2-one as a solid.

MS: 313.0 M–H; 315.1 M+H, 337.0, mina; ¹H-NMR (300 MHz, CD₃OD): δ (ppm) 6.3-7.8 (m, 6H), 3.65 (m, 2H), 2.9 (m, 2H).

EXAMPLE 73

2,8-Dihydroxy-11,12-dihydro-6,13-dioxa-benzo[3,4]cyclohepta[1,2-a]naphthalen-5-one Compound #56

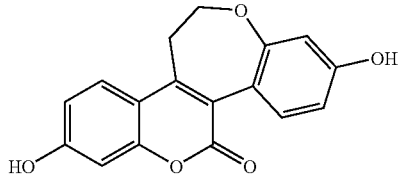

Into a dry clean flask purged with nitrogen was added 3-(2,4-Dihydroxy-phenyl)-7-hydroxy-4-(2-hydroxy-ethyl)-chromen-2-on (50 mg, 0.16 mmol, 1 eq.) triphenylphosphine (176 mg, 0.67 mmol, 4.2 eq.), 4 Å molecular sieve (50 mg) and dry THF (10 mL) and the reaction mixture was stirred for 30 minutes. To the reaction mixture was then added DEAD (0.11 mL, 0.67 mmol, 4.2 eq.) and the reaction stirred at room temperature for 1 hour. The insoluble material was filtered and the filtrate was concentrated. The residue was purified by flash chromatography eluted with 2% methanol in dichloromethane to yield the title product as a solid.

MS: 295.0 M–H; 297 M+H; 319 mina; ¹H-NMR (300 MHz, THF-d8): δ (ppm) 6.5-7.8 (m, 6H), 4.6 (t, 2H), 3.0 (t, 2H).

EXAMPLE 74

2,8-Dihydroxy-11,12-dihydro-6,13-dioxa-benzo[3,4]cyclohepta[1,2-a]naphthalen-5one

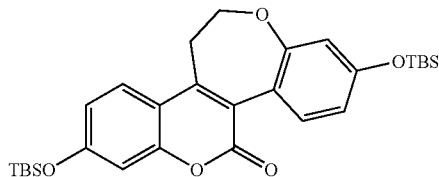

2,8-Dihydroxy-11,12-dihydro-6,13-dioxa-benzo[3,4]cyclohepta[1,2-a]naphthalen-5-one (30 mg) was dissolved in THF (1 mL). To the reaction mixture was then added triethylamine (0.2 mL) and 1 M TBSCl (0.2 mL) in dichloromethane and the reaction mixture stirred at room temperature for 30 minutes. The reaction was diluted with ethyl acetate (20 mL) and then washed twice with brine. The organic layer was dried over anhydrous sodium sulfate and concentrated. The crude product was purified by flash chromatography eluted with 100:10:2 hexane/dichloromethane/ethyl acetate, to yield 2,8-Bis-(tert-butyl-dimethyl-silyloxy)-11,12-dihydro-6,13-dioxa-benzo[3,4]cyclohepta[1,2-a]naphthalen-5-one as a solid.

MS m/z 525(M+H⁺), 547(M+Na⁺) ¹H NMR(CDCl₃, 300 MHz) δ(ppm): 6.6-7.8 (m, 6H), 4.6 (t, 2H), 3.0 (t, 2H). 1.1(2s, 18H), 10.2-0.1(2s, 12H)

EXAMPLE 75

2,8-Bis-(tert-butyl-dimethyl-silyloxy)-11,12-dihydro-5H-6,13-dioxa-benzo[3,4]cyclohepta[1,2-a]naphthalen-5-ol

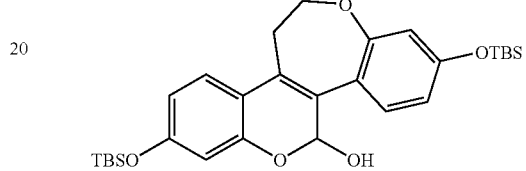

2,8-Bis-(tert-butyl-dimethyl-silyloxy)-11,12-dihydro-6,13-dioxa-benzo[3,4]cyclohepta[1,2-a]naphthalen-5-one (35 mg, 0.066 mmol) was dissolved in toluene (5 mL) and the resulting solution was cooled to −78° C. A solution of Dibal-H solution (70 μL, 1.5 M solution in toluene) was then added to above reaction mix at −78° C. The reaction mixture was stirred at −78° C. for 3 h. To the reaction mixture was then added methanol (0.5 mL), and then Rochelle solution (2 ml, 1M solution). The reaction mixture was gradually warmed to room temperature. The reaction mix was diluted with CH₂Cl₂ (30 mL), the organic layer was separated and dried over Na₂SO₄. The solution was filtered and evaporated to yield a crude product that was purified on SiO₂ to yield the title compound as a solid.

MS m/z 527(M+H+), 550(M+Na⁺) ¹H NMR (300 MHz, CDCl₃): δ 7.15 (1H, d, J=8.4 Hz), 6.96 (1H, J=8.4 Hz), 6.59 (1H, d, J=2.24 Hz), 6.54 (1H, d, d, J=2.31, 11.62 Hz), 6.46 (1H, d, d, J=2.31, 8.35 Hz), 6.41 (1H, d, J=2.31 Hz), 6.11 (1H, d, J=8.1 Hz), 4.6 (2H, m), 3.0 (2H, m) 0.98 (18H, s),). 0.22 (6H, s), 0.21 (6H, s)

EXAMPLE 76

1-(2-{4-[2,8-Bis-(tert-butyl-dimethyl-silyloxy)-11,12-dihydro-5H-6,13-dioxa-benzo[3,4]cyclohepta[1,2-a]naphthalen-5-yl]-phenoxy}-ethyl)-piperidine

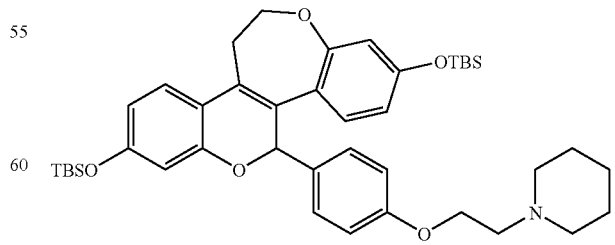

1-[2-(4-Iodo-phenoxy)-ethyl]-piperidine (150 mg, 0.453 mmol) was dissolved in THF and cooled to −78° C. To the reaction mixture was then added n-butyl lithium (2M solution in pentane, 226 μl), slowly over 5 min. The reaction mixture was stirred for 1 h at −78° C. In a separate flask, 2,8-bis-(tert-butyl-dimethyl-silyloxy)-11,12-dihydro-5H-6, 13-dioxa-benzo[3,4]cyclohepta[1,2-a]naphthalen-5-ol (28 mg, 0.053 mmol)) was dissolved in THF (1 mL) and added to the reaction mixture containing the 1-[2-(4-Iodo-phenoxy)-ethyl]-piperidine and n-butyl lithium, slowly over 5 min. The reaction mixture was stirred for additional 1 hr. The reaction mixture was quenched by MeOH (0.5 mL), treated with a saturated solution of ammonium chloride (30 mL) and then diluted with diethyl ether (25 mL). The organic layer was separated and washed with brine (15 mL). The organic layer was dried over anhydrous $Na_2SO_4$, filtered and the solvent evaporated to yield a crude oil. The crude oil was diluted with toluene (30 mL) and 1 N HCl (6.0 mL) and then stirred for 30 min at room temperature. The reaction mixture was diluted with EtOAc (20 mL) and the organic layer was washed twice with water (20 ml) and with a saturated solution of $NaHCO_3$ (10 ml). The organic layer was separated, dried over anhydrous $Na_2SO_4$, filtered and evaporated to yield 1-(2-{4-[2,8-Bis-(tert-butyl-dimethyl-silyloxy)-11,12-dihydro-5H-6,13-dioxa-benzo[3,4]cyclohepta[1,2-a]naphthalen-5-yl]-phenoxy}-ethyl)piperidine as an oil.

MS m/z 714(M+H$^+$) $^1$H NMR (300 MHz, CDCl$_3$) δ: 7.46 (2H, d, J=8.7 Hz), 6.87 (1H, d, J=8.30 Hz), 6.79 (2H, d, J=1.91, 6.82 Hz), 6.70 (1H, d, J=8.42 Hz), 6.39 (2H, m), 6.29 (2H, m), 6.14 (1H, s), 5.30 (1H, d, J=13.90 Hz), 5.10 (1H, d, d, J=b1.654, 13.90 Hz), 4.6 (m, 2H), 4.04 (2H, m), 3.0 (m, 2H), 2.48 (2H, t, J=6.0 Hz), 2.48 (4H, m), 1.58 (4H, m), 1.43 (2H, m), 0.95 (9H, s), 0.93 (9H, s), 0.18 (6H, s), 0.16 (6H, s).

EXAMPLE 77

5-[4-(2-Piperidin-1-yl-ethoxy)-phenyl]-11,12-dihydro-5H-6,13-dioxa-benzo[3,4]cyclohepta[1,2-a]naphthalene-2,8-diol Compound #55

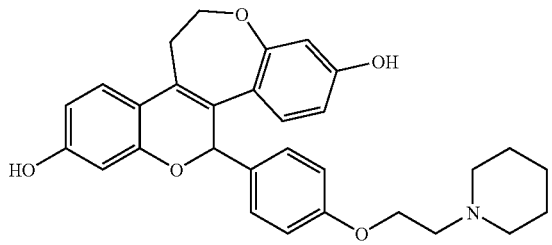

To the solution of 1-(2-{4-[2,8-Bis-(tert-butyl-dimethyl-silyloxy)-11,12-dihydro-5H-6,13-dioxa-benzo[3,4]cyclohepta[1,2-a]naphthalen-5-yl]-phenoxy}-ethyl)-piperidine (1.6 mg, 0.0022 mmol), prepared as in Example 76, in THF (0.1 mL) was added TBAF (10 μl, 1M solution in THF, 0.010 mmol) at −10° C. The solution changed to slight yellow. The solution was stirred at −10° C. for 30 mins. To the solution was then added saturated aqueous NH$_4$Cl (0.1 mL) to quench the reaction. The reaction mixture was extracted by ethyl acetate (100 ml), the organic solvent was dried over anhydrous Na$_2$SO$_4$, the organic solvent was filtered and concentrated in vacuum to yield an oil which was purified by reverse phase HPLC to yield the title compound.

$^1$HNMR (300 MHz, CD$_3$OD): 7.4(d, J=10 Hz, 2H), 7.15 (d, J=10 Hz, 1H), 7.0 (d, J=10 Hz, 1H), 6.85 (d, J=10 Hz, 2H), 6.5 (m, 2H), 6.35 (dd, 1H), 6.15 (d, J=3 Hz, 1H), 6.05 (s, 1H), 4.6 (m, 2H), 4.3 (t, J=5 Hz, 2H), 3.55 (d, J=12 Hz, 2H), 3.45 (t, J=5 Hz, 2H), 3.3 (m, 2H), 3.0 (m, 2H), 2.8 (m, 2H), 1.9 (m, 2H), 1.75 (m, 2H); MS(Cl) m/z: 485(M+H$^+$).

EXAMPLE 78

5R*-(−)-[4-(2-Piperidin-1-yl-ethoxy)-phenyl]-5,11-dihydro-chromeno[4,3-c]chromene-2,8-diol and 5S*-(+)-[4-(2-Piperidin-1-yl-ethoxy)-phenyl]-5,11-dihydro-chromeno[4,3-c]chromene-2,8-diol Compounds #14, #15

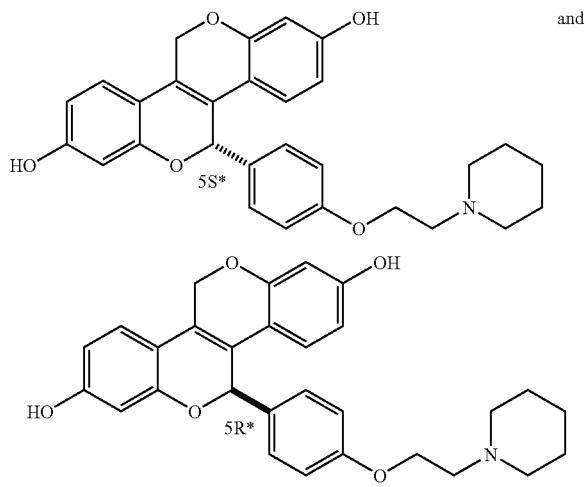

The racemic mixture of 5-[4-(2-Piperidin-1-yl-ethoxy)-phenyl]-5,11-dihydro-chromeno[4,3-c]chromene-2,8-diol (50 mg) was loaded onto a ChiralPak AD chiral HPLC column (21 mm I.D.×250 mm L) and eluted with 50% methanol in isopropyl alcohol at the 4 mL/min flow rate. Two peaks were collected separately and were removed under vacuum to yield: 5R*-(−)-[4-(2-Piperidin-1-yl-ethoxy)-phenyl]-5,11-dihydro-chromeno[4,3-c]chromene-2,8-diol as peak one.

MS(Cl) m/z 472(M+H$^+$)

and 5S*-(+)-[4-(2-Piperidin-1-yl-ethoxy)-phenyl]-5,11-dihydro-chromeno[4,3-c]chromene-2,8-diol as peak two.

MS(Cl) m/z 472(M+H$^+$)

EXAMPLE 79

2,2-Dimethyl-propionic acid 8-hydroxy-11-[4-(2-piperidin-1-yl-ethoxy)-phenyl]-5,11-dihydro-chromeno[4,3-c]chromen-2-yl ester and 2,2-Dimethyl-propionic acid 8-hydroxy-5-[4-(2-piperidin-1-yl-ethoxy)-phenyl]-5,11-dihydro-chromeno[4,3-c]chromen-2-yl ester Compouns #51, #52

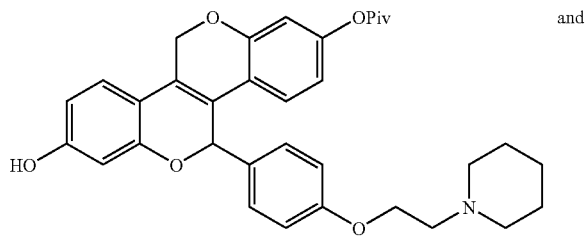

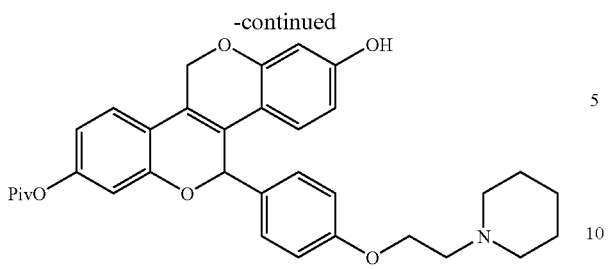

TBAF (1 M in THF, 850 μL, 0.85 mmol, 3 eq.) was added drop-wise into a solution of 1-(2-{4-[2,8-Bis-(tert-butyl-dimethyl-silyloxy)-5,11-dihydro-chromeno[4,3-c]chromen-5-yl]-phenoxy}-ethyl)-piperidine (200 mg, 0.285 mmol) in THF (10 mL) at −10° C. The reaction mixture was stirred for 15 minutes. To the reaction mixture was then added 2,2-dimethylpropionic acid chloride (714 μL, 0.285 mmol, 1 eq). The reaction mixture was diluted with ethyl acetate and washed with 5% sodium bicarbonate and then with brine. The organic layer, was dried over anhydrous Na$_2$SO$_4$, and concentrated to yield a crude oil, which was purified by HPLC (using Luna C18 column, 1% TFA in acetonitrile (ACN) and 1% TFA in H$_2$O as gradient solvent system). Two peak were collected separately and evaporated to dryness in vacuum to yield 2,2-Dimethyl-propionic acid 8-hydroxy-11-[4-(2-piperidin-1-yl-ethoxy)-phenyl]-5,11-dihydro-chromeno[4,3-c]chromen-2-yl ester as peak one MS(Cl) m/z: 556(M=H$^+$)

and 2,2-Dimethyl-propionic acid 8-hydroxy-5-[4-(2-piperidin-1-yl-ethoxy)-phenyl]-5,11-dihydro-chromeno[4,3-c]chromen-2-yl ester as peak two.

MS(Cl) m/z: 556(M=H$^+$) $^1$HNMR (300 MHz, CDCl$_3$): δ 7.42 (2H, d, J=8.7 Hz), 7.03 (1H, d, J=8.4 Hz), 6.83-6.79 (3H, m), 6.64 (1H, d, d, J=2.3, 8.5 Hz), 6.64 (1H, d, J=2.3 Hz), 6.54-6.49 (2H, m), 6.51 (1H, s), 5.47 (1H, d, J=14 Hz), 5.17 (1H, d, J=14 Hz), 4.05 (2H, t, J=6.0 Hz), 2.74-2.49 (5H, brs), 1.59 (4H, m), 1.37 (2H, m), 1.32 (9H, s)

EXAMPLE 80

3-[2,4-Bis-(2-trimethylsilanyl-ethoxymethoxy)-phenyl]-4-(3-chloro-2-oxo-propyl)-7-(2-trimethylsilanyl-ethoxymethoxy)-chromen-2-one

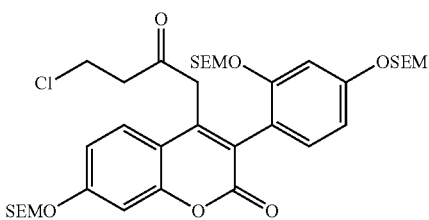

At room temperature, 3-[2,4-Bis-(2-trimethylsilanyl-ethoxymethoxy)-phenyl]-4-methyl-7-(2-trimethylsilanyl-ethoxymethoxy)-chromen-2-one (1.6 g, 2.37 mmol) in THF (10 mL) was added LiHMDS (2.9 mL, 2.84 mmol) slowly. The reaction mixture was stirred for 10 min and then added chloroacetyl chloride (0.28 mL, 1.5 equiv.) in THF (20 mL) at −20° C. The reaction mixture was maintained at −20° C. for 1 hour, then diluted with diethyl ether (200 mL), washed with aqueous NH$_4$Cl (100 ml), brine and organic layer was dried over anhydrous MgSO$_4$. The resulting product was then concentration by vacuum to dryness and purified by silica gel column chromatography to yield the title compound as a colorless oil.

$^1$H NMR (CDCl$_3$) δ −0.1~0.2 (m, 27H), 3.52~4.12 (m, 10H), 5.08 (s, 2H), 5.26 (s, 2H), 5.27 (s, 2H), 6.74 (m, 1H), 6.95~7.18 (m, 4H), 7.31 (m, 1H) MS (m/z): MNa$^+$ (773), MH$^-$ (749).

EXAMPLE 81

4-(3-Chloro-2-oxo-propyl)-3-(2,4-dihydroxy-phenyl)-7-hydroxy-chromen-2-one

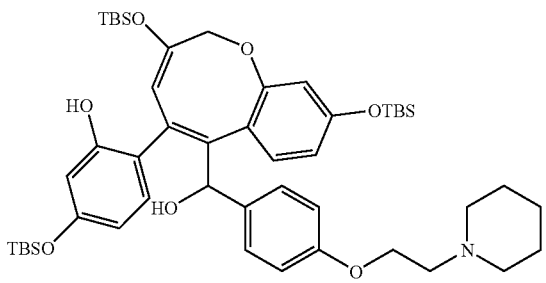

3-[2,4-Bis-(2-trimethylsilanyl-ethoxymethoxy)-phenyl]-4-(3-chloro-2-oxo-propyl)-7-(2-trimethylsilanyl-ethoxymethoxy)-chromen-2-one (0.846 g, 1.13 mmol) in HCl (1N, 40 mL 1:1 THF:iPrOH) was stirred overnight at 25° C. The reaction mixture was then diluted with ethyl acetate (10 mL) and washed with brine (2×30 mL). The aqueous layer was extracted with ethyl acetate (2×50 mL). The organic layers were combined, dried, concentrated and purified by silica gel column chromatograph (5% MeOH/DCM) to yield the title compound as white crystals.

$^1$H NMR (CDCl$_3$) δ 3.71 (d, 1H, J=15.0 Hz), 4.12 (d, 1H, J=15.0 Hz), 4.52 (m, 2H), 6.25 (m, 2H), 6.75 (m, 3H), 7.5 (m, 1H), 9.35 (s, 1H), 9.45 (s, 1H), 10.50 (s, 1H) MS (m/z): MH$^+$ (361), MNa$^+$ (383), MH$^-$ (359).

EXAMPLE 82

6,12-dihydroxy-[1]benzopyrano[4,3-e][1]benzoxocin-2,9(1H,3H-dione Compound #211

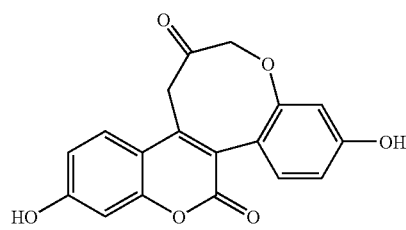

4-(3-Chloro-2-oxo-propyl)-3-(2,4-dihydroxy-phenyl)-7-hydroxy-chromen-2-one (356 mg, 0.86 mmol) was stirred with K$_2$CO$_3$ (356 mg, 2.57 mmol) in a mixture of acetone (40 mL) and MeOH (20 mL) for 2 h at 25° C. The color of the reaction mixture was observed to be yellow green. Aqueous HCl (2N, 20 mL) was added and the volatile organic solvents removed by evaporation. The residue was washed with water and filtered to yield the title compound as a slightly yellow powder.

$^1$H NMR (CDCl$_3$) δ 2.08 (m, 2H), 2.68~2.92 (m, 2H), 4.95 (m, H), 5.02 (m, 1H), 5.62 (d, 1H, J=9.8 Hz), 5.96 (d, 1H, J=9.8 Hz), 7.03 (s, 1H), 7.51 (s, 1H) MS (m/z): MH$^-$ (323).

EXAMPLE 83

6,12-bis[[(1,1-dimethylethyl)dimethylsilyl]oxy]-[1]benzopyrano[4,3-e][1]benzoxocin-2,9(1H,3H)-dione Compound #212 and 2,6,12-tris[[(1,1-dimethylethyl)dimethylsilyl]oxy]-2,3-dihydro-[1]benzopyrano[4,3-e][1]benzoxocin-9(1H)-one

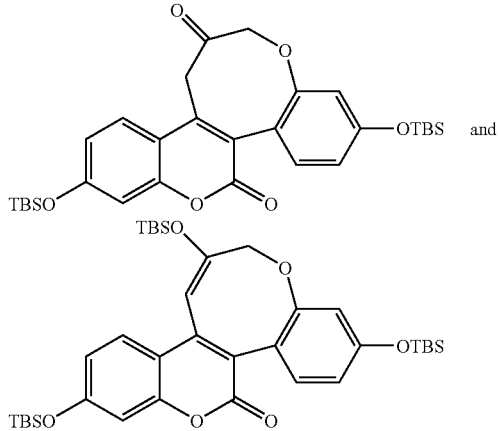

6,12-dihydroxy-[1]benzopyrano[4,3-e][1]benzoxocin-2,9(1H,3H)-dione (prepared as in Example 82 above) (283 mg, 0.87 mmol), TBSCl (1.0 M in DCM, 2.6 mL, 3 equiv.) and TEA (0.36 mL, 3 equiv.) in DCM (10 mL) were stirred at 25° C. for 30 min. LC-MS showed the presence of only the 2,8-di(OTBS) product. The reaction mixture was then stirred overnight at 25° C., after which time LC-MS showed the presence of the second 2,8,12-tri(OTBS) substituted product. The reaction mixture was then diluted with diethyl ether (50 mL), washed with water (50 mL), brine and dried over MgSO$_4$. The product was purified on silica gel to yield the title compounds as a yellow foam.

6,12-bis[[(1,1-dimethylethyl)dimethylsilyl]oxy]-[1]benzopyrano[4,3-e][1]benzoxocin-2,9(1H,3H)-dione:

$^1$H NMR (CDCl$_3$) δ 0.10~0.19 (m, 18H), 0.84, 0.92 (d, 27 H), 4.22 (d, 1H, J=13.2 Hz), 4.79 (d, 1H, J=13.2 Hz), 5.72 (s, 1H), 6.51 (s, 1H), 6.64 (m, 1H), 6.72 (m, 1H), 6.76 (m, 1H), 7.32 (d, 1H, J=10.5 Hz), 7.41 (d, 1H, J=10.5 Hz) MS (m/z): MH$^-$ (551)

EXAMPLE 84

2,6,12-tris[[(1,1-dimethylethyl)dimethylsilyl]oxy]-1,2,3,9-tetrahydro-[1]benzopyrano[4,3-e][1]benzoxocin-9-ol

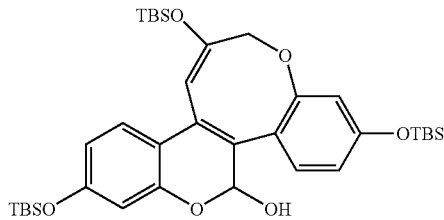

2,6,12-tris[[(1,1-dimethylethyl)dimethylsilyl]oxy]-2,3-dihydro-[1]benzopyrano[4,3-e][1]benzoxocin-9(1H)-one prepared as in Example 83 above (208 mg, 0.31 mmol) in toluene (5 mL) at −78° C. was reacted with DIBAL (0.21 mL, 1.5 M in toluene, 1 eq.). After 3 hours, another 1 eq. of DIBAL was added to the reaction mixture. The reaction mixture was then diluted with ethyl acetate (100 mL), washed with Rocelle solution three times and reverse extracted twice with ethyl acetate (25 mL). The organic layers were dried and concentrated. The residue was purified on silica gel (5% ethyl acetate in Hexane) to yield the title compound as a a yellow foam.

$^1$H NMR (CDCl$_3$) δ 0.10~0.23 (m, 18H), 0.86~1.25 (m, 27H), 3.16 (d, 1H, J=8.8 Hz), 4.25 (d, 1H, J=14.8 Hz), 5.01 (d, 1H, J=17.7 Hz), 5.57 (s, 1H), 6.02 (d, 1H, J=8.0 Hz), 6.53~6.70 (m, 4H), 7.15 (m, 1H), 7.23 (m, 1H) MS (m/z): MH$^-$ (667)

EXAMPLE 85

2-(3,9-Bis-(tert-butyl-dimethyl-silyloxy)-6-{hydroxy-[4-(2-piperidin-1-yl-ethoxy)-phenyl]-methyl}-2H-benzo[b]oxocin-5-yl)-5-(tert-butyl-dimethylsilyloxy)-phenol

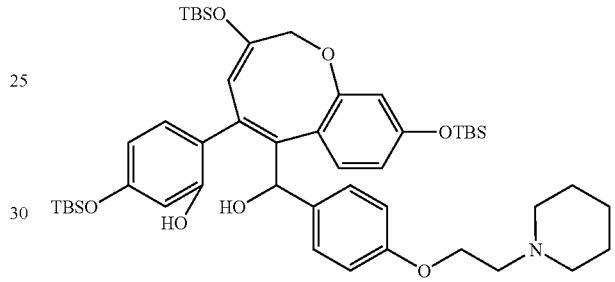

Iodide (634 mg, 1.91 mmol, 5 eq.) in THF (5 mL) at −78° C. was reacted with nBuLi (0.76 mL, 2.5 M in hexanes) for 15 min. The mixture was then added to a solution of 2,6,12-tris[[(1,1-dimethylethyl)dimethylsilyl]oxy]-1,2,3,9-tetrahydro-[1]benzopyrano[4,3-e][1]benzoxocin-9-ol, the compound prepared as in Example 84 above (256 mg, 0.38 mmol) in THF (5 mL) at −78° C. and the resulting reaction mixture stirred for 1 h. The reaction mixture was quenched with MeOH (0.1 mL) and then with aqueous NH$_4$Cl. The resulting mixture was extracted with ethyl acetate (200 mL). The organic layers were dried and concentrated and azeotropically distilled with benzene (50 mL) to yield the title product as a crude oil.

MS (m/z): MH$^+$ (874), MH$^-$ (872).

EXAMPLE 86

1-[2-[4-[2,6,12-tris[[(1,1-dimethylethyl)dimethylsilyl]oxy]-3,9-dihydro[1]benzopyrano[4,3-e][1]benzoxocin-9-yl]phenoxy]ethyl]-piperidine and 6,12-bis[[(1,1-dimethylethyl)dimethylsilyl]oxy]-1,9-dihydro-9-[4-[2-(1-piperidinyl)ethoxy]phenyl]-[1]benzopyrano[4,3-e][1]benzoxocin-2(3H)-one Compound #95

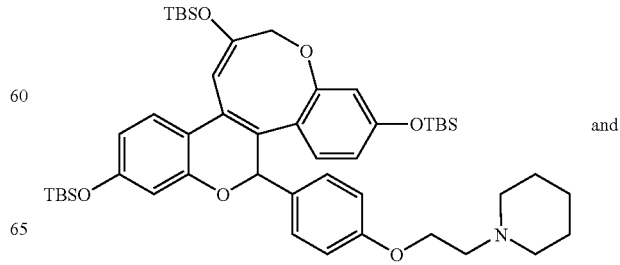

-continued

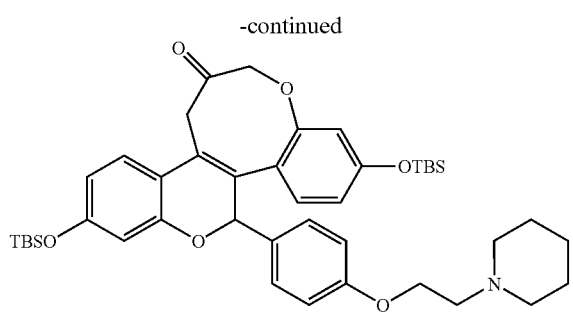

The crude 2-(3,9-Bis-(tert-butyl-dimethyl-silyloxy)-6-{hydroxy-[4-(2-piperidin-1-yl-ethoxy)-phenyl]-methyl}-2H-benzo[b]oxocin-5-yl)-5-(tert-butyl-dimethyl-silyloxy)-phenol, as in Example 85 (0.38 mmol) in DCM (10 mL) at −10° C. was mixed with $BF_3.Et_2O$ (0.32 mL, 2.47 mol, 6.5 equiv.) for 30 min. The resulting reaction mixture was quenched with water (5 mL) and stirred for 10 min. The reaction mixture was then diluted with ethyl acetate (100 mL), washed twice with 5% HCl twice and then twice with brine. The resulting residue was dried and concentrated to yield the title compounds as a mixture, as an oil.

The oil was separated into the following components by flash chromatography.

1-[2-[4-[2,6,12-tris[[(1,1-dimethylethyl)dimethylsilyl]oxy]-3,9-dihydro[1]benzopyrano[4,3-e][1]benzoxocin-9-yl]phenoxy]ethyl]-piperidine MS (m/z): MH$^+$ (856)

6,12-bis[[(1,1-dimethylethyl)dimethylsilyl]oxy]-1,9-dihydro-9-[4-[2-(1-piperidinyl)ethoxy]phenyl]-[1]benzopyrano[4,3-e][1]benzoxocin-2(3H)-one MS (m/z): MH$^-$ (740)

EXAMPLE 87

1,9-dihydro-6,12-dihydroxy-9-[4-[2-(1-piperidinyl)ethoxy]phenyl]-[1]benzopyrano[4,3-e][1]benzoxocin-2(3H)-one Compound #96

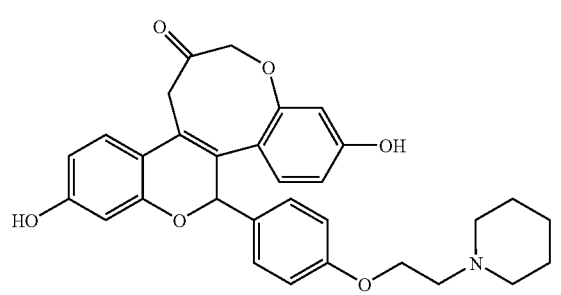

The crude product mixture, 1-[2-[4-[2,6,12-tris[[(1,1-dimethylethyl)dimethylsilyl]oxy]-3,9-dihydro[1]benzopyrano[4,3-e][1]benzoxocin-9-yl]phenoxy]ethyl]-piperidine and 6,12-bis[[(1,1-dimethylethyl)dimethylsilyl]oxy]-1,9-dihydro-9-[4-[2-(1-piperidinyl)ethoxy]phenyl]-[1]benzopyrano[4,3-e][1]benzoxocin-2(3H)-one, prepared as in Example 86 above (0.38 mmol), was dissolved in THF (4 mL). A pre-made solution of TBAF (1.50 mL, 1.5 mmol, 4.0 eq.) and acetic acid (0.043 mL, 0.76 mmol, 2.0 eq.) in THF was added (2.0 mL) and the reaction mixture was stirred for 14 hours. The reaction mixture was then diluted with ethyl acetate (10 mL) and washed with brine (2×30 mL). The aqueous layer was extracted with ethyl acetate (2×50 mL). The organic layers were combined, dried, concentrated and purified by silica gel column chromatograph (50-100% Hexanes/Ethyla acetate) to yield the title compound as white powder.

MS (m/z): MH$^+$ (514)

EXAMPLE 88

6,12-bis[[(1,1-dimethylethyl)dimethylsilyl]oxy]-2,3-dihydro-2-hydroxy-[1]benzopyrano[4,3-e][1]benzoxocin-9(1H)-one Compound #216

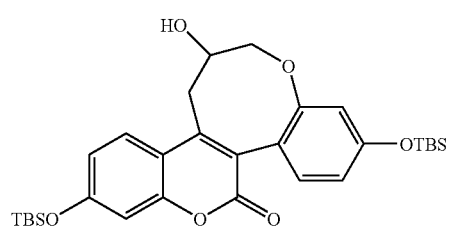

A solution of 6,12-bis[[(1,1-dimethylethyl)dimethylsilyl]oxy]-[1]benzopyrano[4,3-e][1]benzoxocin-2,9(1H,3H)-dione, prepared as in Example 83 (216 mg, 0.4 mmol) in ethanol (4 mL) and was added to $NaBH_4$ (7.4 mg, 0.5 eq.) at −10° C. The reaction mixture was maintained at this temperature, with stirring for 2 hours. At that time, additional $NaBH_4$ (12 mg) was added and the reaction mixture stirred for another hour. The reaction mixture was quenched with aqueous $NH_4Cl$ (5 mL) and then extracted with ethyl acetate (50 mL). The Organic ayers was separated and, dried over anhydrous $Na_2SO_4$, concentrated and purified on silica gel (15% Ethyl acetate in Hexane) to yield the title compound as a solid foam.

MS (m/z): MH$^+$ (554).

EXAMPLE 89

O-[6,12-bis[[(1,1-dimethylethyl)dimethylsilyl]oxy]-1,2,3,9-tetrahydro-9-oxo[1]benzopyrano[4,3-e][1]benzoxocin-2-yl] O-phenyl ester carbonothioic acid

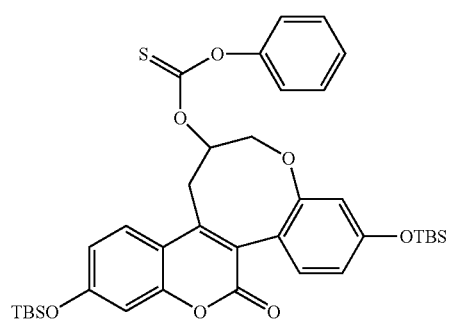

6,12-Bis[[(1,1-dimethylethyl)dimethylsilyl]oxy]-2,3-dihydro-2-hydroxy-[1]benzopyrano[4,3-e][1]benzoxocin-9(1H)-one, prepared as in Example 88 above (215 mg, 0.388 mmol) was mixed with thionyl chloride (80.081 mL, 0.582 mmol, 1.5 eq.), pyridine (0.082 mL, 1 mmol, 2.6 eq.) and DMAP (2.4 mg, 0.02 mmol, 5% eq.) in DCM (4 mL) and the reaction mixture stirred at room temperature overnight. The reaction mixture was then diluted with wthyl acetate (50 mL), washed twice with saturated CuSO$_4$ and then washed twice with brine. The organic layer was dried over anhydrous sodium sulphate and concentrated under reduced pressure. The resulting oil was purified by flash column (5% ethyl acetate/hexane) to yield the title compound as a colorless foam solid.

MS (m/z): MH$^+$ (691), MNa$^+$ (713).

EXAMPLE 90

6,12-bis[[(1,1-dimethylethyl)dimethylsilyl]oxy]-2,3-dihydro-[1]benzopyrano[4,3-e][1]benzoxocin-9(1H)-one Compound #214

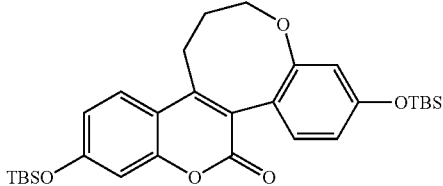

O-[6,12-bis[[(1,1-dimethylethyl)dimethylsilyl]oxy]-1,2,3,9-tetrahydro-9-oxo[1]benzopyrano[4,3-e][1]benzoxocin-2-yl] O-phenyl ester carbonothioic acid, prepared as in Example 89 above (236 mg, 0.34 mmol), AIBN (2.8 mg, 0.05 eq.) and nBu$_3$SnH (0.137 mL, 1.5 eq.) in toluene (4 mL) were degassed for 5 min by N$_2$, heated to 80° C. and stirred overnight. The reaction mixture was then diluted with ethyl acetate (50 mL) and washed with aqueous CuSO$_4$ and brine. The organic layer was concentration and purified by silica gel to yield the title compound as white crystals.

MS (m/z): MH$^+$ (539).

EXAMPLE 91

6,12-bis[[(1,1-dimethylethyl)dimethylsilyl]oxy]-1,2,3,9-tetrahydro-[1]benzopyrano[4,3-e][1]benzoxocin-9-ol Compound #94

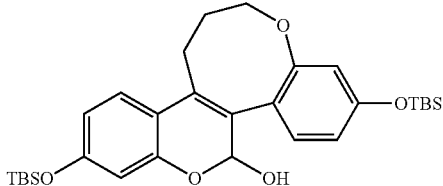

The compound prepared as in Example 90 above (227 mg, 0.42 mmol) was reduced according to the procedure described in Example 84, to yield the title compound as a white solid.

MS (m/z): MNa$^+$ (563), MH$^-$ (539).

EXAMPLE 92

5-(tert-Butyl-dimethyl-silyloxy)-2-(9-(tert-butyl-dimethyl-silyloxy)-6-{hydroxy-[4-(2-piperidin-1-yl-ethoxy)-phenyl]-methyl}-3,4-dihydro-2H-benzo[b]oxocin-5-yl)-phenol Compound #291

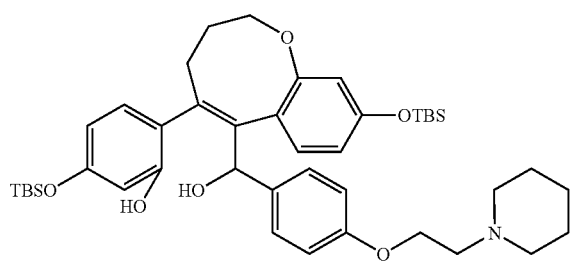

The title compound was prepared according to the procedure described in Example 85 above, substituting 6,12-bis[[(1,1-dimethylethyl)dimethylsilyl]oxy]-1,2,3,9-tetrahydro-[1]benzopyrano[4,3-e][1]benzoxocin-9-ol for 2,6,12-tris[[(1,1-dimethylethyl)dimethylsilyl]oxy]-1,2,3,9-tetrahydro-[1]benzopyrano[4,3-e][1]benzoxocin-9-ol to yield the title compound as a yellow oil.

MS (m/z): MH$^+$ (746).

EXAMPLE 93

1-[2-[4-[6,12-bis[[(1,1-dimethylethyl)dimethylsilyl]oxy]-1,2,3,9-tetrahydro[1]benzopyrano[4,3-e][1]benzoxocin-9-yl]phenoxy]ethyl]-piperidine Compound #282

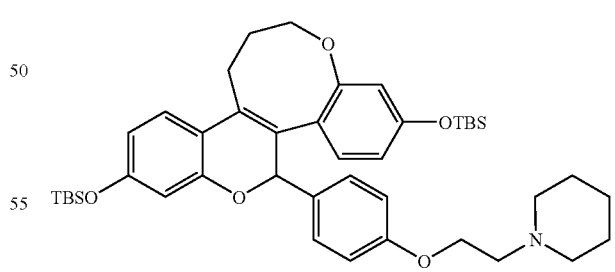

The title compound was prepared according to the procedure described in Example 86 above, substituting 5-(tert-Butyl-dimethyl-silyloxy)-2-(9-(tert-butyl-dimethyl-silyloxy)-6-{hydroxy-[4-(2-piperidin-1-yl-ethoxy)-phenyl]-methyl}-3,4-dihydro-2H-benzo[b]oxocin-5-yl)-phenol for 2-(3,9-Bis-(tert-butyl-dimethyl-silyloxy)-6-{hydroxy-[4-(2-piperidin-1-yl-ethoxy)-phenyl]-methyl}-2H-benzo[b]oxocin-5-yl)-5-(tert-butyl-dimethyl-silyloxy)-phenol, to yield the title compound as a foam.

MS (m/z): MH$^+$ (728).

EXAMPLE 94

1,2,3,9-tetrahydro-9-[4-[2-(1-piperidinyl)ethoxy]phenyl]-[1]benzopyrano[4,3-e][1]benzoxocin-6,12-diol Compound #97

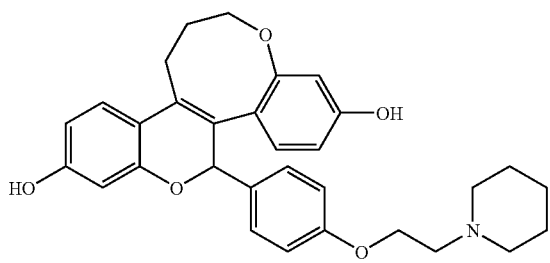

The title compound was prepared according to the procedure described in Example 87 above, substituting 1-[2-[4-[6,12-bis[[(1,1-dimethylethyl)dimethylsilyl]oxy]-1,2,3,9-tetrahydro[1]benzopyrano[4,3-e][1]benzoxocin-9-yl]phenoxy]ethyl]-piperidine for the crude product mixture to yield the title compound as a pink solid.

MS (m/z): MH+ (500).

The racemic 1,2,3,9-tetrahydro-9-[4-[2-(1-piperidinyl)ethoxy]phenyl]-[1]benzopyrano[4,3-e][1]benzoxocin-6,12-diol (1.0 g) was loaded onto a ChiralPak AS chiral HPLC column (5 cm I.D.×50 cm L) and eluted with 20% MeOH in IPA at the 90 mL/min flow rate. The two peaks were removed under vacuum to yield the two enantiomers as follows:

Peak 2: 1,2,3,9-tetrahydro-9-R*-(−)-[4-[2-(1-piperidinyl)ethoxy]phenyl]-[1]benzopyrano[4,3-e][1]benzoxocin-6,12-diol

[α]=−57°, (c=0.302, MeOH) $^1$H NMR (CD$_3$OD) δ 1.49 (broad s, 2H), 1.69 (broad s, 4H), 1.91 (broad m, 2H), 2.08 (broad m, 2H), 2.71 (broad m, 4H), 2.92 (broad m, 2H), 3.74 (broad s, 1H), 4.12 (broad m, 2H), 4.56 (broad s, 1H), 5.95 (s, 1H), 6.08~7.65 (m, 10H) MS (m/z): MH+ (500)

Peak 1: 1,2,3,9-tetrahydro-9-S*-(+)-[4-[2-(1-piperidinyl)ethoxy]phenyl]-[1]benzopyrano[4,3-e][1]benzoxocin-6,12-diol

[α]=+66°, (c=0.402, MeOH) $^1$H NMR (CD$_3$OD) δ 1.49 (broad s, 2H), 1.69 (broad s, 4H), 1.91 (broad m, 2H), 2.08 (broad m, 2H), 2.71 (broad m, 4H), 2.92 (broad m, 2H), 3.74 (broad s, 1H), 4.12 (broad m, 2H), 4.56 (broad s, 1H), 5.95 (s, 1H), 6.08~7.65 (m, 10H) MS (m/z): MH+ (500)

EXAMPLE 95

[2,8-Bis-(tert-butyl-dimethyl-silyloxy)-5,11-dihydro-chromeno[4,3-c]chromen-5-yl]-acetic acid Compound #98

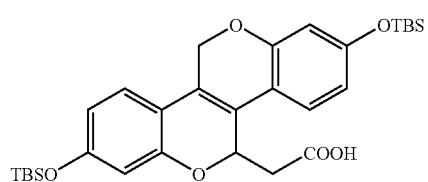

To a solution of 2,8-bis-(tert-butyl-dimethyl-silyloxy)-5,11-dihydro-chromeno[4,3-c]chromen-5-ol (prepared as in Example 24) (2.87 g, 5.6 mmol) in DCM (50 mL) was added BF$_3$.etherate (1.42 mL, 11.2 mmol). The reaction mixture was then stirred and observed to turn dark red. After 20 min, 1,1-bis-trimethylsilyloxy-ethene (2 mL, 8.4 mmol, 1.5 eq.) was added slowly. After 15 min another portion of 1,1-bis-trimethylsilyloxy-ethene (1 g) was added and the solution turned yellow in 10 min. The reaction mixture was diluted with ethyl acetate (200 mL) and then washed with aqueous NH$_4$Cl solution and brine. Flash chromatograph (20% Ethyl acetate/hexanes) yielded the title compound as a yellow solid.

$^1$H NMR (CDCl$_3$) 0.10 (s, 12H), 0.72 (s, 18H), 2.31 (d, 1H, J=11.7 Hz), 2.68 (m, 1H), 4.69 (d, 1H, J=13.6 Hz), 4.98 (d, 1H, J=13.6 Hz), 5.60 (d, 1H, J=11.8 Hz), 6.18~6.26 (m, 3H), 6.62 (d,1H, J=7.8 Hz), 6.72 (d,1H, J=7.8 Hz) MS (m/z): MH+ (555), MNa+ (577), MH− (553).

EXAMPLE 96

[2,8-Bis-(tert-butyl-dimethyl-silyloxy)-5,11-dihydro-chromeno[4,3-c]chromen-5-yl]-acetic acid methyl ester Compound #101

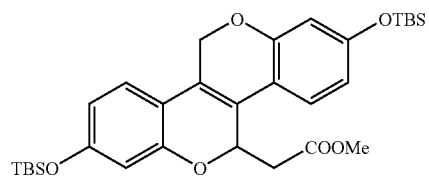

At room temperature, to a solution of [2,8-Bis-(tert-butyl-dimethyl-silyloxy)-5,11-dihydro-chromeno[4,3-c]chromen-5-yl]-acetic acid, the compound prepared as in Example 95 above (56 mg, 0.10 mmol) in benzene (0.7 mL) and MeOH (0.2 mL) was added to TMSCHN$_2$ (0.075 mL, 2.0 M in hexanes) and the reaction mixture stirred for 15 min. The solvent was removed and the residue purified by flash chromatograph yielded the title compound as a yellow oil.

$^1$H NMR (CDCl$_3$) δ 0.08 (s, 12H), 0.78 (s, 18H), 2.26 (d, 1H, J=15.5 Hz), 3.51 (s, 3H), 4.69 (d, 1H, J=13.8 Hz), 4.98 (d, 1H, J=13.8 Hz), 5.56 (d, 1H, J=10.5 Hz), 6.17~6.24 (m, 4H), 6.63 (d, 1H, J=6.6 Hz), 6.74 (d, 1H, J=6.6 Hz) MS (m/z): MH+ (569), MNa+ (591), MH− (567).

EXAMPLE 97

(2,8-Dihydroxy-5,11-dihydro-chromeno[4,3-c]chromen-5-yl)-acetic acid methyl ester Compound #102

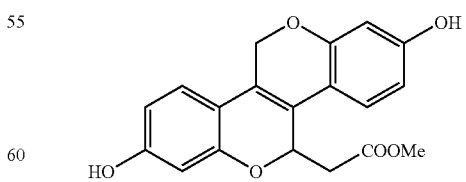

Following the same procedure as described in Example 87, [2,8-Bis-(tert-butyl-dimethyl-silyloxy)-5,11-dihydro-chromeno[4,3-c]chromen-5-yl]-acetic acid methyl ester, the compound prepared as in Example 96 was reacted with TBAF to yield the title compound, as a yellow solid.

$^1$H NMR (CDCl$_3$) δ 2.47 (m, 1H), 2.72 (m, 1H), 3.69 (s, 3H), 4.88 (d, 1H, J=14.5 Hz), 5.27 (d, 1H, J=14.5 Hz), 5.74 (d, 1H, J=10.5 Hz), 6.34 (m, 2H), 6.44 (m, 2H), 7.00 (m, 2H) MS (m/z): MNa$^+$ (363), MH$^-$ (339).

EXAMPLE 98

(2,8-Dihydroxy-5,11-dihydro-chromeno[4,3-c]chromen-5-yl)-acetic acid 2-dimethylamino-ethyl ester Compound #104

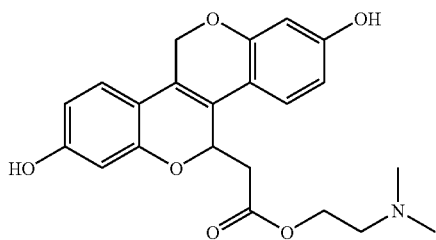

Step A:

A mixture of [2,8-Bis-(tert-butyl-dimethyl-silyloxy)-5,11-dihydro-chromeno[4,3-c]chromen-5-yl]-acetic acid, the compound prepared as in Example 95 above, (56 mg, 0.1 mmol), 2-dimethylamino-ethanol (30 μL, 27 mg, 3.0 eq.), DIC (14 mg, 18 μL) and DMAP (12 mg) in DCM (2 mL) was stirred for 13 hours. The reaction mixture was then concentrated to yield [2,8-Bis-(tert-butyl-dimethyl-silyloxy)-5,11-dihydro-chromeno[4,3-c]chromen-5-yl]-acetic acid 2-dimethylamino-ethyl ester as a crude foam.

Step B:

Following the procedure described in Example 87, crude [2,8-Bis-(tert-butyl-dimethyl-silyloxy)-5,11-dihydro-chromeno[4,3-c]chromen-5-yl]-acetic acid 2-dimethylamino-ethyl ester, the compound prepared in Step A above, was dissolved in THF (1 mL) at −10° C. and then treated TBAF to yield the title compound as a yellow solid.

MS (m/z): MH$^+$ (398), MNa$^+$ (420), MH$^-$ (396).

EXAMPLE 99

(2,8-Dihydroxy-5,11-dihydro-chromeno[4,3-c]chromen-5-yl)-acetic acid Compound #107

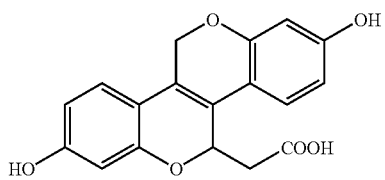

Following the procedure described in Example 87, [2,8-Bis-(tert-butyl-dimethyl-silyloxy)-5,11-dihydro-chromeno[4,3-c]chromen-5-yl]-acetic acid, the compound prepared as in Example 95 was (56 mg, 0.1 mmol) reacted with TBAF to yield the title compound as a yellow solid.

$^1$H NMR (acetone-d$_6$) δ 2.39 (m, 1H), 2.75 (m, 1H), 4.91 (m, 1H), 5.25 (m, 1H), 5.78 (m, 1H), 6.41 (m, 2H), 6.50 (m, 2H), 7.00 (m, 2H) MS (m/z): MH$^-$ (325), (M+OAc)$^-$ (385).

EXAMPLE 100

[2,8-Bis-(tert-butyl-dimethyl-silyloxy)-5,11-dihydro-chromeno[4,3-c]chromen-5-yl]-acetaldehyde

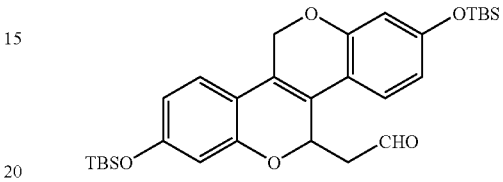

At −78° C., to a solution of [2,8-Bis-(tert-butyl-dimethyl-silyloxy)-5,11-dihydro-chromeno[4,3-c]chromen-5-yl]-acetic acid methyl ester, the compound prepared as in Example 96 (120 mg, 0.21 mmol) in toluene (2 mL) was added DIBAL (0.28 mL, 1.5 M in toluene, 2 eq.) at −78° C. and stirred for 6 hours at −78° C. The reaction mixture was then quenched at −78° C. with chilled MeOH. HPLC purification of the residue yielded the title compound as a thick oil.

$^1$H NMR (CDCl$_3$) δ 0.05 (s, 12H), 0.79 (s, 18H), 2.29 (m, 1H), 2.85 (m, 1H), 4.72 (d, 1H, J=13.7 Hz), 5.08 (d, 1H, J=13.7 Hz), 5.75 (d, 1H, J=10.0 Hz), 6.25 (m, 4H), 6.69 (d, 2H, J=9.6 Hz), 9.61 (s, 2H) MS (m/z): MH$^+$ (561), MNa$^+$ (593)

A side product, 2-[2,8-bis-(tert-butyl-dimethyl-silyloxy)-5,11-dihydro-chromeno[4,3-c]chromen-5-yl]-ethanol, was also isolated by HPLC as an oil.

$^1$H NMR (CDCl$_3$) δ 0.05 (s, 12H), 0.79 (s, 18H), 3.56 (m, 1H), 3.71 (m, 1H), 4.72 (d, 1H, J=13.7 Hz), 4.96 (d, 1H, J=13.7 Hz), 5.31 (d, 1H), 6.21~6.78 (m, 6H), 9.61 (s, 2H) MS (m/z): MH$^+$ (563).

EXAMPLE 101

5-(2-Hydroxy-ethyl)-5,11-dihydro-chromeno[4,3-c]chromene-2,8-diol Compound #122

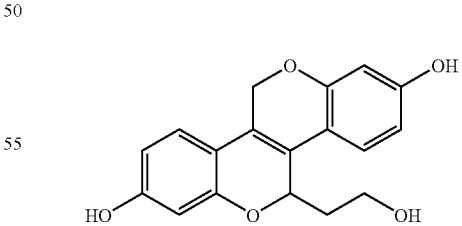

Following the procedure described in Example 87, 2-[2,8-bis-(tert-butyl-dimethyl-silyloxy)-5,11-dihydro-chromeno[4,3-c]chromen-5-yl]-ethanol was reacted with TBAF to yield the title compound as a yellow solid.

$^1$H NMR (CD$_3$OD) δ 0.05 (s, 12H), 0.79 (s, 18H), 3.56 (m, 1H), 3.71 (m, 1H), 4.72 (d, 1H, J=13.8 Hz), 4.96 (d, 1H, J=13.8 Hz), 5.31 (d, 1H, J=9.8 Hz), 6.21~6.78 (m, 6H), 9.61 (s, 2H) MS (m/z): MH$^+$ (313), MH$^-$ (311)

EXAMPLE 102

8-(tert-Butyl-dimethyl-silyloxy)-11,12-dihydro-6,13dioxa-benzo[3,4]cyclohepta[1,2-a]naphthalen-5-one Compound #220

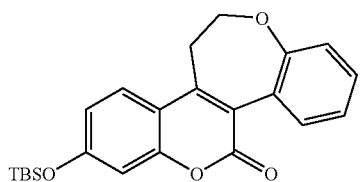

At room temperature, a mixture of 8-Hydroxy-11,12-dihydro-6,13-dioxa-benzo[3,4]cyclohepta[1,2-a]naphthalen-5-one, prepared as in Example 74, (2.0 g crude, 7.0 mmol) and TBSCl (5.34 g, 35 mmol), triethylamine (5 mL) in DCM (80 mL) was stirred overnight. The reaction mixture was then washed with water and brine. The organic layers were dried over anhydrous sodium sulphate and concentrated and purified by flash chromatography to yield the title compound as a white solid.

$^1$H NMR (CD$_3$OD) δ 0.19 (s, 6H), 0.95 (s, 9H), 2.85 (m, 2H), 4.59 (m, 2H), 6.76~7.72 (m, 6H) MS (m/z): MH$^+$ (395), MNa$^+$ (417), 2MNa$^+$ (811).

EXAMPLE 103

2-(tert-Butyl-dimethyl-silyloxy)-11,12-dihydro-6,13-dioxa-benzo[3,4]cyclohepta[1,2-a]naphthalen-5-one Compound #221

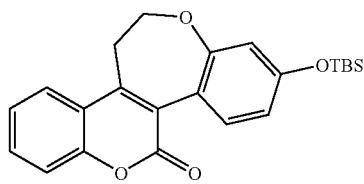

Following the procedure described in Example 102 above, 2-Hydroxy-11,12-dihydro-6,13-dioxa-benzo[3,4]cyclohepta[1,2-a]naphthalen-5-one, prepared as in Example 74 (11.2 g, 40 mmol) was reacted to yield the title compound as a white powder.

$^1$H NMR (CD$_3$OD) δ 0.19 (s, 6H), 0.95 (s, 9H), 2.85 (m, 2H), 4.60 (m, 2H), 6.55~7.55 (m, 6H) MS (m/z): MH$^+$ (395), MNa$^+$ (417), 2MNa$^+$ (811), MH$^-$ (393).

EXAMPLE 104

8-(tert-Butyl-dimethyl-silyloxy)-11,12-dihydro-5H-6,13-dioxa-benzo[3,4]cyclohepta[1,2-a]naphthalen-5-ol Compound #138

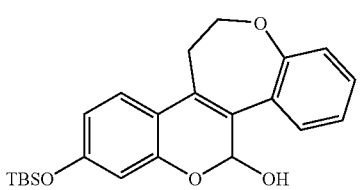

To a solution of 8-(tert-Butyl-dimethyl-silyloxy)-11,12-dihydro-6,13-dioxa-benzo[3,4]cyclohepta[1,2-a]naphthalen-5-one, the compound prepared as in Example 102 above (3.0 g, 7.56 mmol) at −78° C. was slowly added DIBAL (5.10 mL, 1.5 M in toluene, 1.0 eq). After 3 h, the reaction mixture was diluted with ethyl acetate (100 mL), washed with Rocelle solution three times and reverse extracted twice with ethyl acetate (25 mL). The organic layers were dried and concentrated. The residue was purified on silica gel (5% ethyl acetate in Hexane) to yield the title compound as a white solid.

$^1$H NMR (CD$_3$OD) δ 0.21 (s, 6H), 0.98 (s, 9H), 2.72~3.12 (m, 3H), 4.58 (m, 2H), 6.12 (m, 1H), 6.61 (m, 2H), 7.02~7.58 (m, 6H). MS (m/z): MNa$^+$ (419).

EXAMPLE 105

2-(tert-Butyl-dimethyl-silyloxy)-11,12-dihydro-5H-6,13-dioxa-benzo[3,4]cyclohepta[1,2-a]naphthalen-5-ol Compound #139

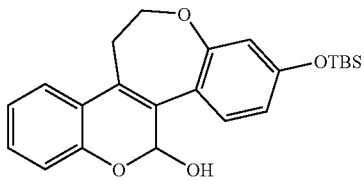

Following the procedure described in Example 104 above, 2-(tert-Butyl-dimethyl-silyloxy)-11,12-dihydro-6,13-dioxa-benzo[3,4]cyclohepta[1,2-a]naphthalen-5-one, the compound prepared as in Example 103 above, (4.0 g, 10.1 mmol) was reacted to yield the title compound as a white solid.

$^1$H NMR (CD$_3$OD) δ 0.26 (s, 6H), 1.05 (s, 9H), 2.85~3.48 (m, 3H), 4.58 (m, 2H), 6.12 (m, 1H), 6.61~6.73 (m, 2H), 7.05~7.42 (m, 6H) MS (m/z): MNa$^+$ (419), MH$^-$ (395).

EXAMPLE 106

5-[4-(2-Piperidin-1-yl-ethoxy)-phenyl]-11,12-dihydro-5H-6,13-dioxa-benzo[3,4]cyclohepta[1,2-a]naphthalen-2-ol Compound #140

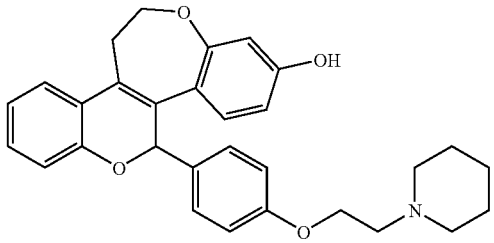

Following the procedure described in Examples 76, 2-(tert-Butyl-dimethyl-silyloxy)-11,12-dihydro-5H-6,13-dioxa-benzo[3,4]cyclohepta[1,2-a]naphthalen-5-ol, the compound prepared as in Example 105 above, was reacted with 1-[2-(4-Iodo-phenoxy)-ethyl]-piperidine to yield 2-(8-(tert-Butyl-dimethyl-silyloxy)-5-{hydroxy-(4-(2-piperidin-1-yl-ethoxy)-phenyl]-methyl}-2,3-dihydro-benzo[b]oxepin-4-yl)-phenol as a crude oil. The crude 2-(8-(tert-Butyl-dimethyl-silyloxy)-5-{hydroxy-[4-(2-piperidin-1-yl-ethoxy)-phenyl]-methyl}-2,3-dihydro-benzo[b]oxepin4-yl)-phenol was then further treated with HCl (12N, 4 eq., 0.67 mL) in toluene (100 mL) to generate yield 1-(2-{4-[2-(tert-Butyl-dimethyl-silyloxy)-11,12-dihydro-5H-6,13-dioxa-benzo[3,4]cyclohepta[1,2-a]naphthalen-5-yl]-phenoxy}-ethyl)-piperidine as a crude oil. The crude 1-(2-{4-[2-(tert-Butyl-dimethyl-silyloxy)-11,12-dihydro-5H-6,13-dioxa-benzo[3,4]cyclohepta[1,2-a]naphthalen-5-yl]-phenoxy}-ethyl)-piperidine was then further treated with HF•Pyridine (70% HF, 30% Pyridine, 0.5 mL) in CH$_3$CN (20 mL) at room temperature for 30 min. The reaction mixture was diluted with ethyl acetate:THF (1:1) and then washed with 5% NaHCO$_3$ and brine. The reaction mixture was dried, concentrated and purified by flash chromatograph eluted with 5% MeOH in DCM to yield the title compound as a slightly yellow solid.

$^1$H NMR (Acetone-d$_6$) δ 1.35 (m, 2H), 1.49 (m, 4H), 2.42 (br s, 4H), 2.64 (m, 2H), 2.71~2.98 (m, 3H), 3.91 (m, 2H), 4.59~4.74 (m, 2H), 6.21 (s, 1H), 6.55~7.45 (m, 11H) MS (m/z): MH$^+$ (470)

The racemic 5-[4-(2-piperidin-1-yl-ethoxy)-phenyl]-11,12-dihydro-5H-6,13-dioxa-benzo[3,4]cyclohepta[1,2-a]naphthalen-2-ol compound 800 mg) was loaded was loaded onto a ChiralPak AD chiral HPLC column (5 cm I.D,×50 cm L) and eluted with 100% IPA at the 150 mL/min flow rate. The two peaks were removed under vacuum to yield the enantiomers as follows:

Peak 1: 5R*-(+)-[4-(2-piperidin-1-yl-ethoxy)-phenyl]-11,12-dihydro-5H-6,13-dioxa-benzo[3,4]cyclohepta[1,2-a]naphthalen-2-ol $^1$H NMR (DMSO-d6) δ 1.36 (m, 6H), 2.28~2.59 (m, 6H), 2.65 (m, 1H), 2.89 (m, 1H), 3.91 (t, 2H, J=6.6 Hz), 4.59 (m, 2H), 6.16~7.38 (m, 12H), 9.65 (s, 1H). MS (m/z): MH$^+$ (470); [a]D=+39 (c=0.23, MeOH)

Peak 2: 5S*-(−)-[4-(2-piperidin-1-yl-ethoxy)-phenyl]-11,12-dihydro-5H-6,13-dioxa-benzo[3,4]cyclohepta[1,2-a]naphthalen-2-ol

[α]D=−37 (c=0.43, MeOH) MS (m/z): MH$^+$ (470)

EXAMPLE 107

5-[4-(2-Azepan-1-ylethoxy)-phenyl]-11,12-dihydro-5H-6,13-dioxa-benzo[3,4]cyclohepta[1,2-a]naphthalen-2-ol Compound #141

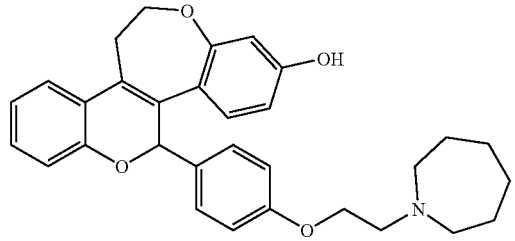

Following the procedure described in Example 106 above, 2-(tert-Butyl-dimethyl-silyloxy)-11,12-dihydro-5H-6,13-dioxa-benzo[3,4]cyclohepta[1,2-a]naphthalen-5-ol, the compound prepared as in Example 105 above, (0.8 g, 2.0 mmol) was reacted with 1-[2-(4-Iodo-phenoxy)-ethyl]-azepane to yield the title compound as a yellow solid.

$^1$H NMR (Acetone-d$_6$) δ1.54 (m, 8H), 2.58~2.95 (m, 8H), 3.95 (m, 2H), 4.59~4.74 (m, 2H), 6.21 (s, 1H), 6.51~7.45 (m, 11H) MS (m/z): MH$^+$ (484).

The racemic 5-[4-(2-Azepan-1-yl-ethoxy)-phenyl]-11,12-dihydro-5H-6,13-dioxa-benzo[3,4]cyclohepta[1,2-a]naphthalen-2-ol compound (950 mg) was loaded was loaded onto a ChiralPak AD chiral HPLC column (5 cm I.D.×50 cm L) and eluted with 100% IPA at the 150 mL/min flow rate. The two peaks were removed under vacuum to yield the enantiomers as follows:

Peak 2: 5S*-(−)-[4-(2-Azepan-1-yl-ethoxy)-phenyl]-11,12-dihydro-5H-6,13-dioxa-benzo[3,4]cyclohepta[1,2-a]naphthalen-2-ol

[α]$_D$=−28(c=0.12, MeOH) $^1$H NMR (DMSO-d$_6$) δ 1.51 (broad s, 8H), 2.45 (broad m, 4H), 2.70 (broad m, 2H), 3.22 (broad s, 2H), 3.91 (t, 2H, J=6.6 Hz), 4.56 (m, 2H), 6.15 (s, 1H), 6.39~7.36 (m, 11H), 9.67 (s, 1H) MS (m/z): MH$^+$ (484)

Peak 1: 5R*-(+)-[4-(2-Azepan-1-yl-ethoxy)-phenyl]-11,12-dihydro-5H-6,13-dioxa-benzo[3,4]cyclohepta[1,2-a]naphthalen-2-ol

[α]$_D$=+38(c=0.25, MeOH). MH$^+$ (484).

EXAMPLE 108

5-[4-(2-Dimethylamino-ethoxy)-phenyl]-11,12-dihydro-5H-6,13-dioxa-benzo[3,4]cyclohepta[1,2-a]naphthalen-2-ol Compound #142

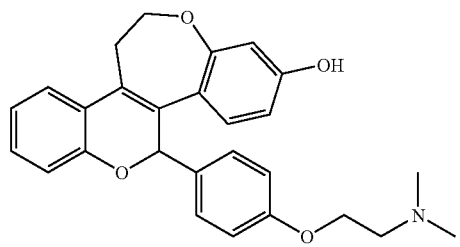

Following the procedure described in Example 106, 2-(tert-Butyl-dimethyl-silyloxy)-11,12-dihydro-5H-6,13-dioxa-benzo[3,4]cyclohepta[1,2-a]naphthalen-5-ol, the compound prepared as in Example 105 was reacted in sequence with [2-(4-Iodo-phenoxy)-ethyl]-dimethyl-amine, HCl and then HF•Pyridine to yield the title compound as a yellow solid.

$^1$H NMR (CDCl$_3$) δ 2.28 (s, 6H), 2.72 (m, 2H), 2.82 (m, 2H), 3.95 (m, 2H), 4.59 (m, 2H), 6.02 (s, 1H), 6.41~7.29 (m, 11H) MS (m/z): MH$^+$ (430)

The racemic 5-[4-(2-Dimethylamino-ethoxy)-phenyl]-11,12-dihydro-5H-6,13-dioxa-benzo[3,4]cyclohepta[1,2-a]naphthalen-2-ol compound (890 mg) was loaded onto a ChiralPak AD chiral HPLC column (5 cm I.D.×50 cm L) and eluted with 20% MeOH and 80% IPA at the 150 mL/min flow rate. The two peaks were removed under vacuum to yield the enantiomers as follows:

Peak 1: 5R*-(+)-[4-(2-Dimethylamino-ethoxy)-phenyl-11,12-dihydro-5H-6,13-dioxa-benzo[3,4]cyclohepta[1,2-a]naphthalen-2-ol

[α]$_D$=+38(C=0.3, MeOH) $^1$H NMR (DMSO-d6) δ 2.13 (s, 6H), 2.43~2.92 (m, 4H), 3.95 (t, 2H, J=6.6 Hz), 4.59 (m, 2H), 6.15 (s, 1H), 6.38~7.39 (m, 11H), 9.69 (s, 1H) MS (m/z): MH$^+$ (430)

Peak 2: 5S*-(−)-[4-(2-Dimethylamino-ethoxy)-phenyl]-11,12-dihydro-5H-6,13-dioxa-benzo[3,4]cyclohepta[1,2-a]naphthalen-2-ol [α]$_D$=−36(C=0.32, MeOH) MS (m/z): MH$^+$ (430)

EXAMPLE 109

5-[4-(2-Azepan-1-yl-ethoxy)-phenyl]-11,12-dihydro-5H-6,13-dioxa-benzo[3,4]cyclohepta[1,2-a]naphthalen-8-ol Compound #143

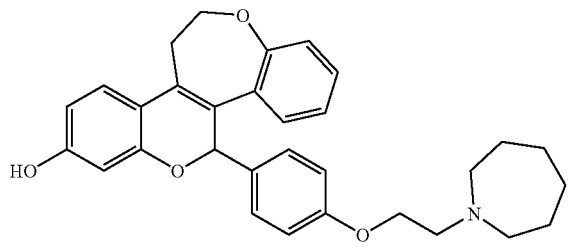

Following the procedure described in Example 106, 8-(tert-Butyl-dimethyl-silyloxy)-11,12-dihydro-5H-6,13-dioxa-benzo[3,4]cyclohepta[1,2-a]naphthalen-5-ol, the compound prepared as in Example 105, was reacted in sequence with 1-[2-(4-Iodo-phenoxy)-ethyl]-azepane, HCl and then HF•Pyridine to yield the title compound as a yellow solid.

$^1$H NMR (Acetone-d$_6$) δ δ1.54 (m, 8H), 2.68~2.95 (m, 8H), 3.98 (m, 2H), 4.74 (m, 2H), 6.18 (s, 1H), 6.21~7.39 (m, 11H) MS (m/z): MH$^+$ (484).

The racemic 5-[4-(2-Azepan-1-yl-ethoxy)-phenyl]-11,12-dihydro-5H-6,13-dioxa-benzo[3,4]cyclohepta[1,2-a]naphthalen-8-ol compound (840 mg) was loaded onto a ChiralPak AD chiral HPLC column (5 cm I.D.×50 cm L) and eluted with 40% MeOH and 60% IPA at the 100 mL/min flow rate. The two peaks were removed under vacuum to yield the two enantiomers:

Peak 1: 5R*-(+)-[4-(2-Azepan-1-yl-ethoxy)-phenyl]-11,12-dihydro-5H-6,13-dioxa-benzo[3,4]cyclohepta[1,2-a]naphthalen-8-ol

[α]D=+37(c=0.11, MeOH) $^1$H NMR (DMSO-d6) δ 1.55 (broad s, 8H), 2.68~2.92 (m, 8H), 3.92 (t, 2H, J=6.6 Hz), 4.61 (m, 2H), 6.14~7.38 (m, 12H). 9.56 (s, 1H) MS (m/z): MH$^+$ (484)

Peak 2: 5S*-(−)-[4-(2-Azepan-1-yl-ethoxy)-phenyl]-11,12-dihydro-5H-6,13-dioxa-benzo[3,4]cyclohepta[1,2-a]naphthalen-8-ol

[α]D=−39(c=0.51, MeOH) $^1$H NMR (DMSO-d6) δ 1.55 (broad s, 8H), 2.68~2.92 (m, 8H), 3.92 (t, 2H, J=6.6 Hz), 4.61 (m, 2H), 6.14~7.38 (m, 12H). 9.56 (s, 1H) MS (m/z): MH$^+$ (484)

EXAMPLE 110

5-[4-(2-Dimethylamino-ethoxy)-phenyl]-11,12-dihydro-5H-6,13-dioxa-benzo[3,4]cyclohepta[1,2-a]naphthalen-8-ol Compound #144

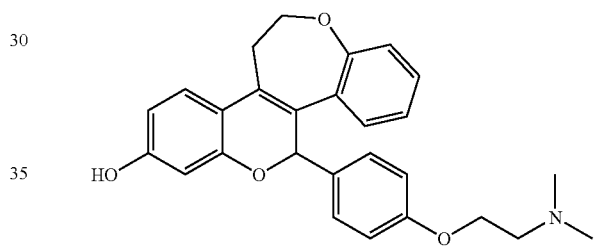

Following the procedure described in Example 106, 8-(tert-Butyl-dimethyl-silyloxy)-11,12-dihydro-5H-6,13-dioxa-benzo[3,4]cyclohepta[1,2-a]naphthalen-5-ol, the compound prepared as in Example 104 was reacted in sequence with [2-(4-Iodo-phenoxy)-ethyl]-dimethyl-amine, HCl and then HF•Pyridine to yield the title compound as a yellow solid.

MS (m/z): MH$^+$ (430)

The racemic 5-[4-(2-Dimethylamino-ethoxy)-phenyl]-11,12-dihydro-5H-6,13-dioxa-benzo[3,4]cyclohepta[1,2-a]naphthalen-8-ol compound (800 mg) was loaded onto a ChiralPak AD chiral HPLC column (5 cm I.D.×50 cm L) and eluted with 100% IPA at the 150 mUmin flow rate. The two peaks were removed under vacuum to yield the two enantiomers as follows:

Peak 1: 5R*-(+)-[4-(2-Dimethylamino-ethoxy)-phenyl]-11,12-dihydro-5H-6,13-dioxa benzo[3,4]cyclohepta[1,2-a]naphthalen-8-ol

[α]$_D$=+42(c=0.34, MeOH). $^1$H NMR (DMSO-d6) δ 2.12 (s, 6H), 2.49~2.90 (m, 4H), 3.95 (t, 2H, J=6.6 Hz), 4.61 (m, 2H), 6.09~7.23 (m, 11H), 9.54 (s, 1H) MS (m/z): MH$^+$ (430)

Peak 2: 5S*-(−)-[4-(2-Dimethylamino-ethoxy)-phenyl]-11,12-dihydro-5H-6,13-dioxa benzo[3,4]cyclohepta[1,2-a]naphthalen-8-ol

[α]$_D$=−42(c=0.34, MeOH) MS (m/z): MH$^+$ (430)

EXAMPLE 111

5-[4-(2-Azepan-1-yl-ethoxy)-phenyl]-11,12-dihydro-5H-6,13-dioxa-benzo[3,4]cyclohepta[1,2-a]naphthalene-2,8-diol Compound #159

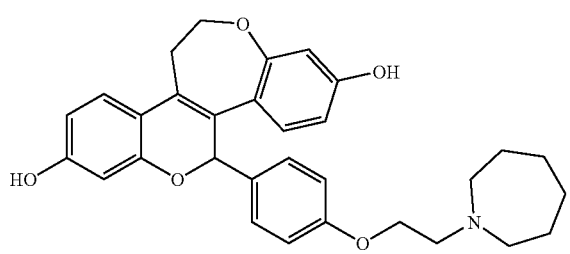

Following the procedure described in Example 106, 2,8-Bis-(tert-butyl-dimethyl-silyloxy)-11,12-dihydro-5H-6,13-dioxa-benzo[3,4]cyclohepta[1,2-a]naphthalen-5-ol, prepared as in Example 75 (1.5 g, 2.85 mmol) was reacted in sequence with 1-[2-(4-Iodo-phenoxy)-ethyl]-azepane, HCl and then HF•Pyridine to yield the title compound as a foam.

$^1$H NMR (CDOD$_3$) δ 1.65 (m, 4H), 1.84 (m, 4H), 2.78 (m, 2H), 3.35 (m, 4H), 3.48 (m, 2H), 4.18 (m, 2H), 4.61 (m, 2H), 6.02 (s, 1H), 6.18~7.35 (m, 10 H) MS (m/z): MH$^+$ (500), MH$^-$ (498).

The racemic 5-[4-(2-Azepan-1-yl-ethoxy)-phenyl]-11,12-dihydro-5H-6,13-dioxa-benzo[3,4]cyclohepta[1,2-a]naphthalene-2,8-diol compound (1.02 g) was loaded onto a ChiralPak AD chiral HPLC column (5 cm I.D.×50 cm L) and eluted with 100% IPA at the 150 mL/min flow rate. The two peaks were removed under vacuum to yield the two enantiomers as follows:

Peak 1: 5R*-(+)-[4-(2-Azepan-1-yl-ethoxy)-phenyl]-11,12-dihydro-5H-6,13-dioxa-benzo[3,4]cyclohepta[1,2-a]naphthalene-2,8-diol
[α]$_D$=+33(c=0.11, MeOH) MS (m/z): MH$^+$ (500), MH$^-$ (498)

Peak 2: 5S*-(−)-[4-(2-Azepan-1-yl-ethoxy)-phenyl]-11,12-dihydro-5H-6,13-dioxa-benzo[3,4]cyclohepta[1,2-a]naphthalene-2,8-diol
[α]$_D$=−39(c=0.51, MeOH) MS (m/z): MH$^+$ (500), MH$^-$ (498)

EXAMPLE 112

5-[4-(2-Diisopropylamino-ethoxy)-phenyl]-11,12-dihydro-5H-6,13-dioxa-benzo[3,4]cyclohepta[1,2-a]naphthalene-2,8-diol Compound #160

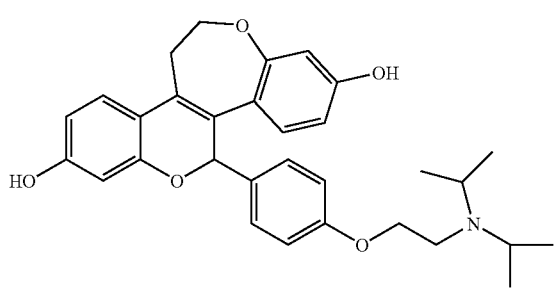

Following the procedure described in Example 106, 2,8-Bis-(tert-butyl-dimethyl-silyloxy)-11,12-dihydro-5H-6,13-dioxa-benzo[3,4]cyclohepta[1,2-a]naphthalen-5-ol, prepared as in Example 75 (1.5 g, 2.85 mmol) was reacted in sequence with [2-(4-Iodo-phenoxy)-ethyl]-diisopropyl-amine, HCl and then HF•Pyridine to yield the title compound as a pink solid.

$^1$H NMR (CDOD$_3$) δ 1.28 (d, 12H, J=5.3 Hz), 2.78 (m, 2H), 3.25 (m, 2H), 3.52 (m, 2H), 4.05 (m, 2H), 4.56 (m, 2H), 6.05~7.35 (m, 11H). MS (m/z): MH$^+$ (502), MH$^-$ (500).

The racemic 5-[4-(2-Diisopropylamino-ethoxy)-phenyl]-11,12-dihydro-5H-6,13-dioxa-benzo[3,4]cyclohepta[1,2-a]naphthalene-2,8-diol compound (1.4 g) was loaded onto a ChiralPak AD chiral HPLC column (5 cm I.D.×50 cm L) and eluted with 80% IPA and 20% Hexanes at the 150 mL/min flow rate. The two peaks were removed under vacuum to yield the tow enantiomers as follows:

Peak 1: 5R*-(+)-[4-(2-Diisopropylamino-ethoxy)-phenyl]-1,12-dihydro-5H-6,13-dioxa-benzo[3,4]cyclohepta[1,2-a]naphthalene-2,8-diol
[α]$_D$=+43(c=0.112, MeOH) MS (m/z): MH$^+$ (502), MH$^-$ (500)

Peak 2: 5S*-(−)-[4-(2-Diisopropylamino-ethoxy)-phenyl]-11,12-dihydro-5H-6,13-dioxa-benzo[3,4]cyclohepta[1,2-a]naphthalene-2,8-diol
[α]$_D$=−69(c=0.812, MeOH) MS (m/z): MH$^+$ (502), MH$^-$ (500)

EXAMPLE 113

5-[4-(2-Dimethylamino-ethoxy)-phenyl]-11,12-dihydro-5H-6,13-dioxa-benzo[3,4]cyclohepta[1,2-a]naphthalene-2,8-diol Compound #161

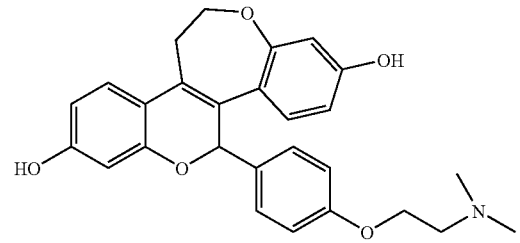

Following the procedure described in Example 106, 2,8-Bis-(tert-butyl-dimethyl-silyloxy)-11,12-dihydro-5H-6,13-dioxa-benzo[3,4]cyclohepta[1,2-a]naphthalen-5-ol, prepared as in Example 75 (2.8 g, 5.3 mmol) was reacted in sequence with [2-(4-Iodo-phenoxy)-ethyl]-dimethyl-amine, HCl and then HF•Pyridine to yield the title compound as a yellow solid.

$^1$H NMR (CDOD$_3$) δ 2.85 (s, 6H), 3.28 (m, 2H), 3.54 (m, 2H), 4.28 (m, 2H), 4.61 (m, 2H), 6.06 (s, 1H), 6.15~7.41 (m, 10H). MS (m/z): MH$^+$ (446), MH− (444).

The racemic 5-[4-(2-Dimethylamino-ethoxy)-phenyl]-11,12-dihydro-5H-6,13-dioxa-benzo[3,4]cyclohepta[1,2-a]naphthalene-2,8-diol compound (1.7 g) was loaded onto a ChiralPak AD chiral HPLC column (5 cm I.D.×50 cm L) and eluted with 80% IPA and 20% Hexanes at the 150 mL/min flow rate. The two peaks were removed under vacuum to yield the two enantiomers as follows:

Peak 1: R*-(+)-5-[4-(2-Dimethylamino-ethoxy)-phenyl]-11,12-dihydro-5H-6,13-dioxa-benzo[3,4]cyclohepta[1,2-a]naphthalene-2,8-diol.

[α]D=+39(c=0.14, MeOH) MS (m/z): MH⁺ (446), MH– (444)

Peak 2: S*-(–)-5-[4-(2-Dimethylamino-ethoxy)-phenyl]-11,12-dihydro-5H-6,13-dioxa-benzo[3,4]cyclohepta[1,2-a]naphthalene-2,8-diol

[α]D=–49(c=0.4, MeOH) MS (m/z): MH⁺ (446), MH– (444)

EXAMPLE 114

9-Methyl-5-[4-(2-piperidin-1-yl-ethoxy)-phenyl]-11,12-dihydro-5H-6,13-dioxa-benzo[3,4]cyclohepta[1,2-a]naphthalen-2-ol Compound #283

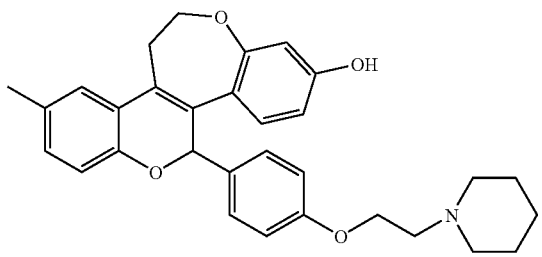

Following the procedure described in Example 106, 2-(tert-Butyl-dimethyl-silyloxy)-9-methyl-11,12-dihydro-5H-6,13-dioxa-benzo[3,4]cyclohepta[1,2-a]naphthalen-5-ol, prepared as in Example 106 (0.80 g, 1.95 mmol) was reacted in sequence with [2-(4-Iodo-phenoxy)-ethyl]-morpholine, HCl and then HF•Pyridine to yield the title compound as a yellow solid.

MS (m/z): MH⁺ (484).

EXAMPLE 115

2,2-Dimethyl-propionic acid 8-fluoro-5-[4-(2-piperidin-1-yl-ethoxy)-phenyl]-5,11-dihydro-chromeno[4,3-c]chromen-2-yl ester Compound #93

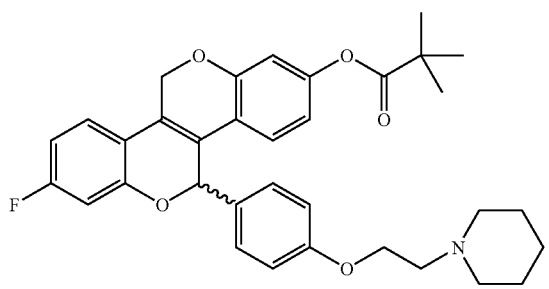

The title compound was prepared according to the procedure described in Example 54, substituting 5-[4-(2-Piperidin-1-yl-ethoxy)-phenyl]-5,11-dihydrochromeno[4,3-cd-chromene-2,8-diol with 8-Fluoro-5-[4-(2-piperidin-1-yl-ethoxy)-phenyl]-5,11-dihydro-chromeno[4,3c]chromen-2-ol, to yield a foam.

¹H NMR (CDCl₃) δ 1.18, 1.32 (9H, two s), 1.42 (2H, m), 1.63 (4H, m), 2.64 (4H, br s), 2.87 (2H, t, J=5.5 Hz), 4.11 (2H, t, J=5.5 Hz), 5.15 (1H, d, J=14.0 Hz), 5.38 (1H, d, J=14.0 Hz), 6.18 (1H, s), 6.48~7.31 (1OH, m). MS (m/z): MH⁺ (558).

The racemic 5-[4-(2-Dimethylamino-ethoxy)-phenyl]-11,12-dihydro-5H-6,13-dioxa-benzo[3,4]cyclohepta[1,2-a]naphthalene2,8-diol compound (1.7 g) was loaded onto a ChiralPak AD chiral HPLC column (5 cm I.D.×50 cm L) and eluted with 100% IPA at the 100 mL/min flow rate. The two peaks were removed under vacuum to yield the two enantiomers as follows:

Peak 2: 2,2-Dimethyl-propionic acid 8-fluoro-5-[4-(2-piperidin-1-yl-ethoxy)-phenyl]-5,11-dihydro-chromeno[4,3-c]chromen-2-yl ester m.p. 182~183° C. [α]=+160°(c=0.225, CHCl₃)

Peak 1: 2,2-Dimethyl-propionic acid 8-fluoro-5-[4-(2-piperidin-1-yl-ethoxy) phenyl]-5,11-dihydro-chromeno[4,3-c]chromen-2-yl ester m.p. 178~179° C. [α]=–173°(c=0.205, CHCl₃)

EXAMPLE 116

3-(2,4-Dimethoxy-phenyl)-4-methyl-chromen-2-one Compound #239

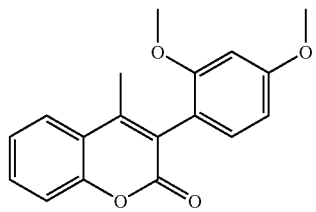

The title compound was prepared according to the procedure described in Example 1, substituting 2,4-dimethoxy acetophenone with 2-hydroxy acetophenone, to yield a yellow solid.

MS (m/z): MH⁺ (297), MNa⁺ (319), 2MNa⁺ (615). ¹H NMR (CDCl₃) δ 6.65~7.69 (m, 7H), 3.83 (s, 3H), 3.73 (s, 3H), 2.32 (s, 3H).

EXAMPLE 117

4-Bromomethyl-3-(2,4-dimethoxy-phenyl)-chroman-2-one Compound #240

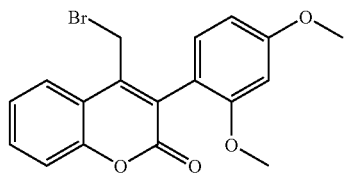

The title compound was prepared according to the procedure described in Example 63, substituting 3-(2,4-dihydroxyphenyl)-7-hydroxy-4-methyl-chromen-2-one with 3-(2,4-dimethoxy-phenyl)-4-methyl-chromen-2-one, and replacing bromine by NBS, to yield a yellow solid.

¹H NMR (CDCl₃) δ 7.08~7.61 (m, 5H), 6.41 (m, 2H), 4.39 (1H, d, J=10.1 Hz), 4.12 (1H, d, J=10.1 Hz). MS (m/z): MNa⁺ (399), 2MNa⁺ (773).

EXAMPLE 118

2-Hydroxy-11H-chromeno[4,3-c]chromen-5-one Compound #218

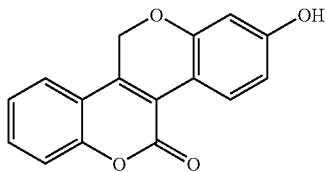

To a mixture of 4-bromomethyl-3-(2,4-dimethoxy-phenyl)-2H-chromene (25.8 g, 68.76 mmol) in CH$_2$Cl$_2$ (1.27 L) under nitrogen was slowly added BBr$_3$ (1.0 M in CH$_2$Cl$_2$, 310 mL, 4.5 eq.) at 25° C. After 16 h stirring, the reaction mixture was poured into a cold solution of saturated NaHCO$_3$ (700 mL) and water (700 mL). Aqueous NaOH solution (75 mL, 10 N) was then added to the reaction mixture. The aqueous layer was separated and then acidified with aqueous (10 N) to pH~1.0 resulting in the formation of a yellow solid that was filtered, washed with water and air-dried under vacuum overnight to yield title compound as yellow solid.

$^1$H NMR (CDCl$_3$) δ 9.95 (1H, s), 8.24 (d, 1H, J=8.7 Hz), 7.79 (1H, J=7.9 Hz), 7.62 (1H, t, J=7.2 Hz), 7.41 (m, 2H), 6.55~6.42 (2H, m), 5.42 (2H, s). MS (m/z): MH$^+$ (267), MNa$^+$ (289).

EXAMPLE 119

2-(tert-Butyl-dimethyl-silyloxy)-11H-chromeno[4,3-c]chromen-5-one Compound #219

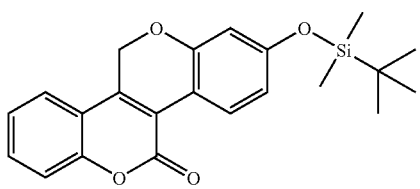

2-Hydroxy-11H-chromeno[4,3-c]chromen-5-one (0.5 g) prepared as in Example 118 was dissolved in THF (5 mL). To the reaction mixture was then added triethylamine (1.5 mL) and 1M TBSCl (2.0 mL) in dichloromethane and the reaction mixture stirred at room temperature for 1 h. The reaction mixture was diluted with ethyl acetate (100 mL) and then washed twice with brine. The organic layer was dried over anhydrous sodium sulfate and concentrated. The crude product was purified by flash chromatography eluted with 100:10:2 hexane/dichloromethane/ethyl acetate, to yield title compound as a solid.

$^1$H NMR (CDCl$_3$) δ 8.43 (1H, d, J=8.7 Hz), 7.58~7.28 (m, 4H), 6.59~6.43 (m, 2H), 5.31 (2H, s). MS (m/z): MH$^+$ (381), MNa$^+$ (403).

EXAMPLE 120

2-(tert-Butyl-dimethyl-silyloxy)-5,11-dihydro-chromeno[4,3-c]chromen-5-ol Compound #135

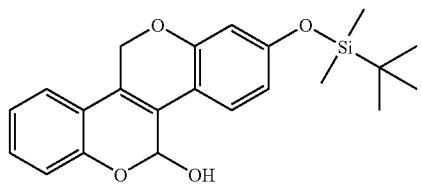

The title compound was prepared according to the procedure described in Example 24, replacing 2,8-bis-(tert-butyl-dimethyl-silyloxy)-11H-chromeno[4,3-c]chromen-5-one with 2-(tert-butyl-dimethyl-silyloxy)-11H-chromeno[4,3-c]chromen-5-one, to yield a solid.

$^1$H NMR (CDCl$_3$) δ 7.28~7.02 (m, 4H), 6.48~6.32 (m, 3H), 5.32~5.13 (m, 2H), 3.09 (1H, d, J=7.6 Hz), MS (m/z): MNa$^+$ (405).

EXAMPLE 121

3-(2,4-Dimethoxy-phenyl)-5,7-dimethoxy4-methyl-chromen-2-one Compound #284

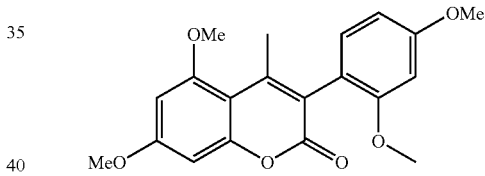

The title compound was prepared according to the procedure described in Example 1, replacing 2,4-dihydroxy acetophenone with 1-(2-Hydroxy-4,6-dimethoxy-phenyl)-ethanone, to yield a yellow solid.

$^1$H NMR (CDCl$_3$) δ 7.08~6.28 (m, 6H), 3.86 (6H, s), 3.84 (3H, s), 3.76 (3H, s), 2.34 (s, 3H). MS (m/z): MH$^+$ (357), MNa$^+$ (379).

EXAMPLE 122

3-Acetyl-5,7-dimethoxy-4-methyl-chromen-2-one

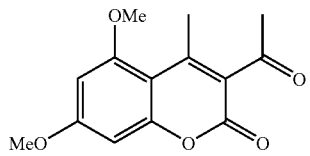

The title compound was isolated as a side product in the synthesis described in Example 123 above.

m.p. 166~167° C.

| | | |
|---|---|---|
| Anal. Calculated for $C_{14}H_{14}O_5$ | C, 64.12; | H, 5.38; |
| Measured | C, 64.20; | H, 5.43. |

$^1$H NMR (CDCl$_3$) δ 6.42 (1H, d, J=2.3 Hz), 6.37 (1H, d, J=2.3 Hz), 3.89 (s, 3H), 2.61 (s, 3H), 2.41 (s, 3H). MS (m/z): MH$^+$ (263), MNa$^+$ (285), 2MNa$^+$ (547).

EXAMPLE 123

2-(7-(tert-Butyl-dimethyl-silyloxy)-4-{hydroxy-[4-(2-piperidin-1-yl-ethoxy)-phenyl]-1-methyl}-2H-chromen-3-yl)-phenol

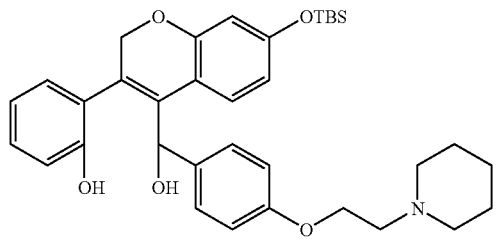

The title compound was prepared according to the procedure for described in Example 26, replacing 2,8-bis-(tert-Butyl-dimethyl-silanlyoxy)-5,11-dihydro-chromeno [4,3-c]-chromen-5-ol with 2-(tert-Butyl-dimethyl-silyloxy)-5,11-dihydro-chromeno[4,3-c]chromen-5-ol, to yield a oil.

$^1$H NMR (CDCl$_3$) δ 7.24~6.15 (m, 11H), 5.46 (s, 1H), 4.92 (m, 2H), 4.18 (br s, 2H). 3.02 (br s, 2H), 2.78 (br s, 4H). 1.78 (br s, 4H), 1.52 (br s, 2H), 0.92 (s, 9H), 0.14 (s, 6H) MS (m/z): MH$^+$ (588), MH$^-$(586).

EXAMPLE 124

1-(2-{4-[2-(tert-Butyl-dimethyl-silyloxy)-5,11-dihydro-chromeno[4,3-c]chromen-5-yl]-phenoxy}-ethyl)-piperidine Compound #158

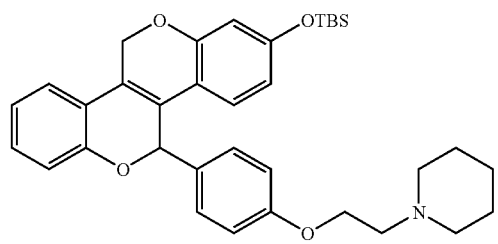

The title compound was prepared according to the procedure described in Example 35, replacing 5-(tert-butyl-dimethyl-silyloxy)-2-(7-(tert-butyl-dimethyl-silyloxy)-4-{hydroxy-[4-(2-piperidine-1-yl-ethoxy)-phenyl]-methyl}-2H-chromen-3-yl)-phenol with 1-(2-{4-[2-(tert-Butyl-dimethyl-silyloxy)-5,11-dihydro-chromeno[4,3-c]chromen-5-yl]-phenoxy}-ethyl)-piperidine, to yield a foam.

$^1$H NMR (CDCl$_3$) δ 7.16~6.12 (m, 11H), 6.05 (s, 1H), 5.15 (1H, d, J=14.1 Hz), 4.95 (1H, d J=14.1 Hz), 4.16 (2H, br s), 3.05 (br s, 2H), 2.81 (br s, 4H), 1.72 (br s, 4H), 1.38 (br s, 2H), 0.79 (s, 9H), 0.19 (s, 9H). MS (m/z): MH$^+$ (570).

EXAMPLE 125

5-[4-(2-Piperidin-1-yl-ethoxy)-phenyl]-5,11-dihydro-chromeno[4,3-c]chromen-2-ol Compound #133

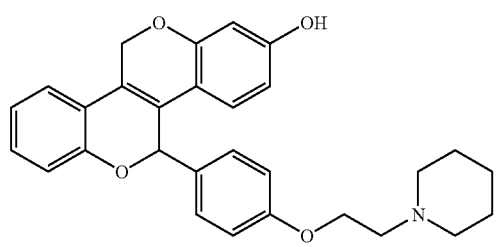

The title compound was prepared according to the procedure described in Example 44, replacing 1-(2-{4-[2,8-Bis-(tert-butyl-dimethyl-silyloxy)-5,11-dihydro-chromeno[4,3-c]-chromen-5-yl]-phenoxy}-ethyl)-piperidine with 1-(2-{4-[2-(tert-Butyl-dimethyl-silyloxy)-5,11-dihydro-chromeno [4,3-c]chromen-5-yl]-phenoxy}-ethyl)-piperidine, to yield a solid.

$^1$H NMR (CDCl$_3$) δ 7.39~6.31 (m, 12H), 5.45 (1H, d, J=14.2 Hz), 5.15 (1H, d, J=14.2 Hz), 4.02 (t, 2H, J=6.2 Hz), 2.65 (t, 2H, J=6.2 Hz), 2.45 (br s, 4H), 2.05 (br s, 4H), 1.51 (m, 2H). MS (m/z): MH$^+$ (456).

EXAMPLE 126

2,2-Dimethyl-propionic acid 5-[4-(2-piperidin-1-yl-ethoxy)-phenyl]-5,11-dihydro-chromeno[4,3-c]chromen-2-yl ester Compound 134

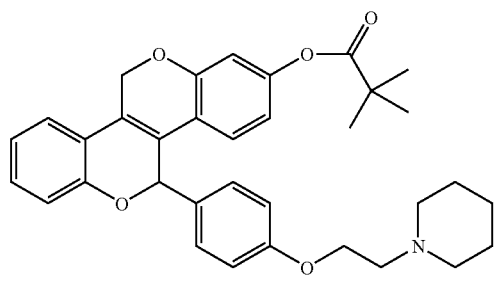

The title compound was prepared according to the procedure described in Example 54, replacing 5-[4-(2-Piperidin-1-yl-ethoxy)-phenyl]-5,11-dihydrochromeno[4,3-c]chromene-2,8-diol with 5-[4-(2-Piperidin-1-yl-ethoxy)-phenyl]-5,11-dihydro-chromeno[4,3-c]chromen-2-ol, prepared as in Example 127, to yield a solid.

$^1$H NMR (CDCl$_3$) δ 7.38~6.38 (m, 11H), 6.21 (s, 1H), 5.40 (1H, d, J=14.0 Hz), 5.18 (1H, d, J=14.0 Hz), 4.13 (2H, t, J=5.5 Hz), 2.95 (2H, t, J=5.4 Hz), 2.71 (br s, 4H), 1.68 (br m, 4H), 1.47 (m, 2H), 1.32 (s, 9H). MS (m/z): MH$^+$ (539).

EXAMPLE 127

7-Fluoro-3-(2-methoxy-phenyl)-4-methyl-chromen-2-one Compound #284

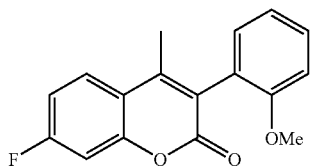

The title compound was prepared according to the procedure described in Example 1, replacing 2,4-dihydroxy acetophenone with fluoro-2-hydroxy-phenyl)-ethanone and replacing 2,4-dimethoxyphenyl acetic acid with 2-methoxy phenyl acetic acid. 1-(4-Fluoro-2-hydroxy-phenyl)-ethanone, to yield a solid.

$^1$H NMR (CDCl$_3$) δ 7.65~6.94 (m, 6H), 3.79 (s, 3H), 2.23 (s, 3H). MS (m/z): MH$^+$ (285), MNa$^+$ (307).

EXAMPLE 128

3-(2-Methoxy-phenyl)-4-methyl-chromen-2-one Compound #241

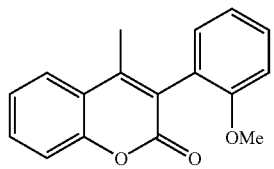

The title compound was prepared according to the procedure described in Example 1, replacing 2,4-dihydroxy-acetophenone by 1-(2-Hydroxy-phenyl)-ethanone and 2,4-dimethoxy-phenylacetic-acid with 2-methoxy-phenyl acetic acid, to yield a solid.

$^1$H NMR (CDCl$_3$) δ 7.68~6.96 (m, 8H), 3.79 (s, 3H), 2.25 (s, 3H). MS (m/z): MH$^+$ (267), MNa$^+$ (289).

EXAMPLE 129

4-Bromomethyl-3-(2,4-dimethoxy-phenyl)-5,7-dimethoxy-chromen-2-one Compound #242

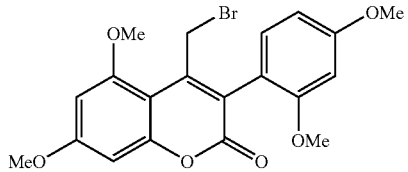

The title compound was prepared according to the procedure described in Example 63, replacing 3-[2,4-bis-(2-trimethylsilanyl-ethoxymethoxy)-phenyl]4-methyl-7-(2-trimethylsilanyl-ethoxymethoxy)-chromen-2-one with 3-(2,4-Dimethoxy-phenyl)-5,7-dimethoxy-4-methyl-chromen-2-one, and bromine with NBS (1.1 eq.), to yield a solid.

$^1$H NMR (CDCl$_3$) δ 7.28~6.38 (m, 5H), 4.49 (d, 1H, J=8.8 Hz), 4.31 (d, 1H, J=8.8 Hz), 3.94 (s, 3H), 3.87 (s, 3H), 3.85 (s, 3H), 3.75 (s, 3H). MS (m/z): MH$^+$ (436, 438), MNa$^+$ (457, 459).

EXAMPLE 130

4-Bromomethyl-3-(2-methoxy-phenyl)-chromen-2-one Compound #243

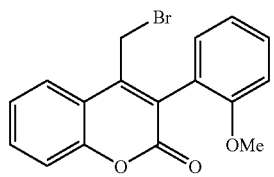

The title compound was prepared according to the procedure described in in Example 63, replacing 3-[2,4-bis-(2-trimethylsilanyl-ethoxymethoxy)-phenyl]-4-methyl-7-(2-trimethylsilanyl-ethoxymethoxy)-chromen-2-one with 3-(2-Methoxy-phenyl)-4-methyl-chromen-2-one, and replacing brominne with NBS (1.1 eq.) instead of Br$_2$, to yield a solid.

$^1$H NMR (CDCl$_3$) δ 7.82~7.01 (m, 8H), 4.44 (d, 1H, J=10.2 Hz), 4.25 (d, 1H, J=10.2 Hz). MS (m/z): MH$^+$ (347), MNa$^+$ (369).

EXAMPLE 131

4-Bromomethyl-3-(2-hydroxy-phenyl)-chromen-2-one Compound 244

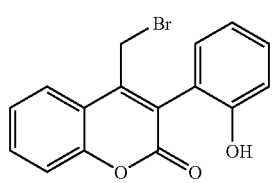

The title compound was prepared according to the same procedure described in Example 120, replacing 4-bromomethyl-3-(2,4-dimethoxy-phenyl)-2H-chromene with 4-bromomethyl-3-(2-methoxy-phenyl)-chromen-2-one, to yield a solid.

m.p. 213~215° C. $^1$H NMR (CDCl$_3$) δ 7.82~7.01 (m, 8H), 5.02 (s, 1H), 4.50 (1H, d, J=10.2 Hz), 4.30 (1H, d, J=10.2 Hz). MS (m/z): MH$^+$ (333), MNa$^+$ (355).

EXAMPLE 132

11H-Chromeno[4,3-c]chromen-5-one

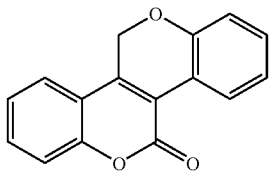

The title compound was prepared according to the procedure described in Example 61, starting from 4-bromomethyl-3-(2-hydroxy-phenyl)-chromen-2-one instead of 4-bromomethyl-3-(2,4-dibenzoyl-phenyl)-7-benzoyl-chromen-2-one, to yield a solid.

| Anal. Calculated for $C_{16}H_{11}BrO_3$ | C, 58.03; | H, 3.35. |
|---|---|---|
| Measured | C, 58.02; | H, 3.29. | m.p. 201.5~202.0° C. $^1$H NMR (CDCl$_3$) δ 8.61~7.01 (m, 8H), 5.34 (s, 2H). MS (m/z): MH$^+$ (333), MNa$^+$ (355).

EXAMPLE 133

5,11-Dihydro-chromeno[4,3-c]chromen-5-ol Compound 136

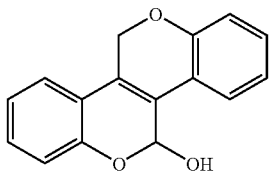

The title compound was prepared according to the procedure described in Example 24, starting from 11H-Chromeno[4,3-c]chromen-5-one instead 2,8-bis-(tert-butyl-dimethyl-silyloxy)-11H-chromeno[4,3-c]chromen-5-one, to yield a solid.

| Anal. Calculated for $C_{16}H_{12}O_3$ | C, 76.18; | H, 4.79. |
|---|---|---|
| Measured | C, 75.86; | H, 4.70. |

$^1$H NMR (CDCl$_3$) δ 7.34~6.86 (m, 8H), 6.41 (d,1H, J=6.3 Hz), 5.22 (m, 2H), 3.12 (d, 1H, J=7.8 Hz). MS (m/z): MH$^+$ (253), MNa$^+$ (275).

EXAMPLE 134

2-(4-{Hydroxy-[4-(2-piperidin-1-yl-ethoxy)-phenyl]-methyl}-2H-chromen-3-yl)-phenol Compound #246

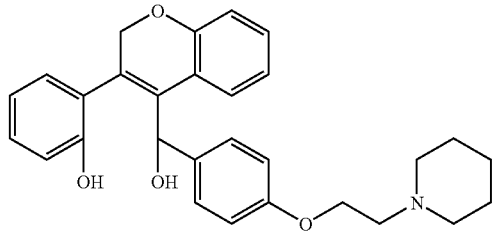

The title compound was prepared according to the procedure described in Example 26, starting from 2-(tert-Butyl-dimethyl-silyloxy)-5,11-dihydro-chromeno[4,3-c]chromen-5-ol replacing 2,8-bis-(tert-Butyl-dimethyl-silanlyoxy)-5,11-dihydro-chromeno [4,3-c]-chromen-5-ol to yield a solid.

| Anal. Calculated for $C_{29}H_{31}NO_4 \cdot 0.75\ H_2O$ | C, 73.94; | H, 6.95, | N, 2.97. |
|---|---|---|---|
| Measured | C, 73.98; | H, 6.92, | N, 2.97. |

$^1$H NMR (DMSO-d$_6$) δ 9.80 (s, 1H), 7.48~6.59 (m, 12H), 5.87 (br s, 1H), 5.58 (br s, 1H), 5.01 (br d, 1H), 4.64 (br d, 1H), 3.98 (br s, 2H), 2.58 (br s, 2H), 2.37 (br s, 4H), 1.42 (br s, 4H), 1.34 (br s, 2H). MS (m/z): MH$^+$ (458).

EXAMPLE 135

1-{2-[4-(5,11-Dihydro-chromeno[4,3-c]chromen-5-yl)-phenoxy]-ethyl}-piperidine Compound #137

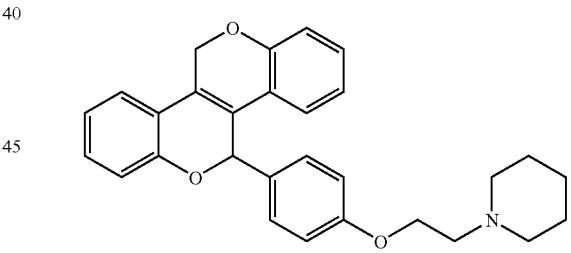

The title compound was prepared according to the procedure described in Example 35, starting from 2-(4-{Hydroxy-[4-(2-piperidin-1-yl-ethoxy)-phenyl]-methyl}-2H-chromen-3-yl)-phenol instead 5-(tert-butyl-dimethyl-silyloxy)-2-(7-(tert-butyl-dimethyl-silyloxy)-4-{hydroxy-[4-(2-piperidine-1-yl-ethoxy)-phenyl]-methyl}-2H-chromen-3-yl)-phenol, to yield a solid.

| Anal. Calculated for $C_{29}H_{29}NO_3$ | C, 79.24; | H, 6.65, | N, 3.19. |
|---|---|---|---|
| Measured | | C, 78.96; | H, 6.57, | N, 3.11. |

$^1$H NMR (CDCl$_3$) δ 7.38~6.71 (m, 12H), 6.22 (s, 1H), 5.38 (d, 1H, J=14.0 Hz), 5.15 (d, 1H, J=14.1 Hz), 4.03 (t, 2H, J=6.1 Hz), 2.71 (t, 2H, J=6.1 Hz), 2.45 (br s, 4H), 1.55 (br s, 4H), 1.45 (br m, 2H). MS (m/z): MH$^+$ (440).

EXAMPLE 136

1-(2-{4-[2,8-Bis-(tert-butyl-dimethyl-silyloxy)-11-methoxy-5,11-dihydro-chromeno[4,3-c]chromen-5-yl]-phenoxy}-ethyl)-piperidine Compound #162

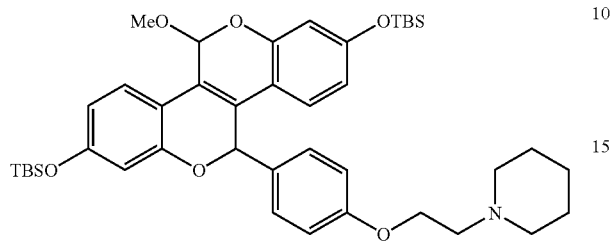

The title compound was isolated by flash chromatography, as a by-product of the reaction described in Example 35.

$^1$H NMR (CDCl$_3$) δ 7.38~6.10 (m, 11H), 5.91 (s, 1H), 4.41 (br s, 2H), 3.61 (s, 3H), 3.21 (br s, 2H), 3.15 (br m, 4H), 1.95 (br s, 4H), 1.54 (br s, 2H), 0.91 (m, 18H), 0.21 (m, 12H). MS (m/z): MH$^+$ (730).

EXAMPLE 137

2,2-Dimethyl-propionic acid 5R*-(−)-[4-(2-piperidin-1-yl-ethoxy)-phenyl]-5,11-dihydro-chromeno[4,3-c]chromen-2-yl ester Compound #172 and 2,2-Dimethyl-propionic acid 5S*-(+)-[4-(2-piperidin-1-yl-ethoxy)-phenyl]-5,11-dihydro-chromeno[4,3-c]chromen-2-yl ester Compound #171

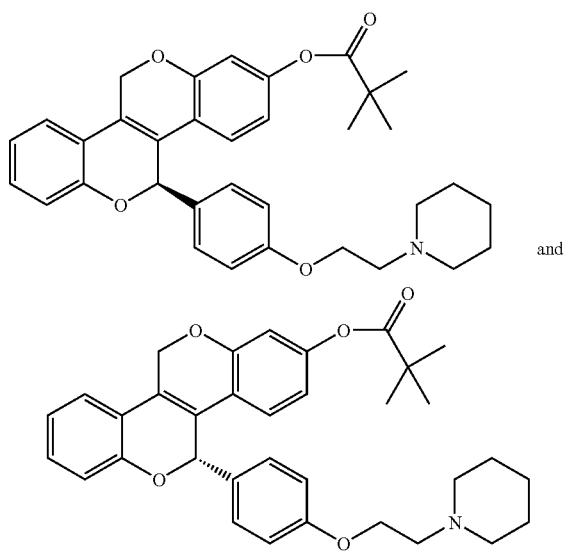

The racemic 2,2-Dimethyl-propionic acid 5S*-(+)-[4-(2-piperidin-1-yl-ethoxy)-phenyl]-5,11-dihydro-chromeno[4,3-c]chromen-2-yl ester compound, prepared as in Example 126, (400 mg) was loaded onto a ChiralPak AD chiral HPLC column (5 cm I.D.×50 cm L) and eluted with 80% IPA and 20% Hexanes at the 150 mL/min flow rate. The two peaks were removed under vacuum to yield the two enantiomers as follows:

Peak 1: 2,2-Dimethyl-propionic acid 5R*-(−)-[4-(2-piperidin-1-yl-ethoxy)-phenyl]-5,11-dihydro-chromeno[4,3-c]chromen-2-yl ester

[α]=−91° (c=0.21, CHCl$_3$).

Peak 2: 2,2-Dimethyl-propionic acid 5S*-(+)-[4-(2-piperidin-1-yl-ethoxy)-phenyl]-5,11-dihydro-chromeno[4,3-c]chromen-2-yl ester

[α]=+102° (c=0.31, CHCl$_3$).

EXAMPLE 138

5R*-(−)-1-{2-[4-(5,11-Dihydro-chromeno[4,3-c]chromen-5-yl)-phenoxy]-ethyl}-piperidine Compound #170 and 5S*-(+)-1-{2-[4-(5,11-Dihydro-chromeno[4,3-c]chromen-5-yl)-phenoxy]-ethyl}-piperidine Compound #169

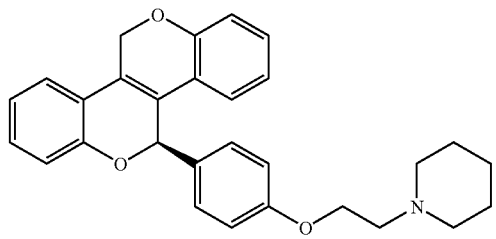

and

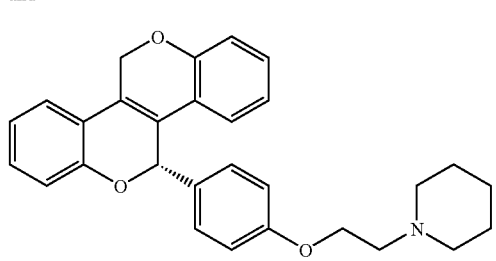

The racemic 2,2-Dimethyl-propionic acid 5S*-(+)-[4-(2-piperidin-1-yl-ethoxy)-phenyl]-5,11-dihydro-chromeno[4,3-c]chromen-2-yl ester compound, prepared as in Example 135, (900 mg) was loaded onto a ChiralPak AD chiral HPLC column (5 cm I.D.×50 cm L) and eluted with 50% IPA and 50% Hexanes at the 200 mL/min flow rate. The two peaks were removed under vacuum to yield the two enantiomers as follows:

Peak 1: 5R*-(−)-1-{2-[4-(5,11-Dihydro-chromeno[4,3-c]chromen-5-yl)-phenoxy]-ethyl}-piperidine

[α]=−135° (c=0.27, CHCl3).

Peak 2: 5S*-(+)-1-{2-[4-(5,11-Dihydro-chromeno[4,3-c]chromen-5-yl)-phenoxy]-ethyl}-piperidine

[α]=+146° (c=0.27, CHCl$_3$).

EXAMPLE 139

2-(tert-Butyl-dimethyl-silyloxy)-8-fluoro-11,12-dihydro-5H-6,13-dioxa-benzo[3,4]cyclohepta[1,2-a]naphthalen-5-ol Compound #286

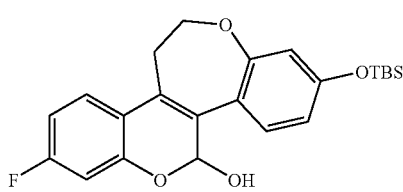

A solution of 2-(tert-Butyl-dimethyl-silyloxy)-8-fluoro-11,12-dihydro-6,13-dioxa-benzo[3,4]cyclohepta[1,2-a]naphthalen-5-one (1.56 g, 3.7 mmol) in toluene (40 mL) was treated with DIBAL (2.53 mL, 1.5 M in toluene, 1.0 eq.) at −78° C. for 3 hours. The reaction mixture was then quenched with chilled MeOH at −78° C. and the solvent was removed under reduced pressure. The residue was purified by flash chromatograph (10% EtOAc in hexanes) to yield the title compound as a white solid.

MS (m/z): MH+ (416).

EXAMPLE 140

5-[4-(2-Azepan-1-yl-ethoxy)-phenyl]-8-fluoro-11,12-dihydro-5H-6,13-dioxa-benzo[3,4]cyclohepta[1,2-a]naphthalen-2-ol Compound #174

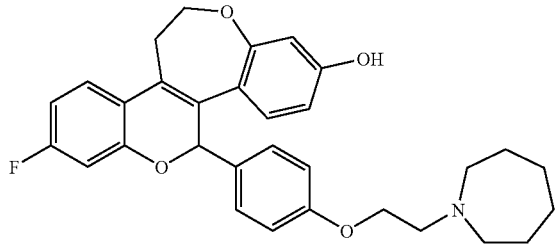

The title compound was prepared according to the procedure described in Example 106, substituting 2-(tert-Butyl-dimethyl-silyloxy)-8-fluoro-11,12-dihydro-5H-6,13-dioxa-benzo[3,4]cyclohepta[1,2-a]naphthalen-5-ol (1.1 g) for 2-(tert-Butyl-dimethyl-silyloxy)-11,12-dihydro-5H-6,13-dioxa-benzo[3,4]cyclohepta[1,2-a]naphthalen-5-ol to yield a yellow solid.

$^1$H NMR (CDCl$_3$) δ 1.61 (m, 8H), 2.71~2.99 (m, 8H), 3.92 (t, 2H, J=6.6 Hz), 4.66 (m, 2H), 6.08 (s,1H), 6.46~7.36 (m, 10H) MS (m/z): M+H=502

The racemic 5-[4-(2-Azepan-1-yl-ethoxy)-phenyl]-8-fluoro-11,12-dihydro-5H-6,13-dioxa-benzo[3,4]cyclohepta[1,2-a]naphthalen-2-ol compound (700 mg) was loaded onto a ChiralPak AD chiral HPLC column (5 cm I.D.×50 cm L) and eluted with 80% IPA and 20% Hexanes at the 150 mL/min flow rate. The two peaks were removed under vacuum to yield the two enantiomers as follows:

Peak 1: 5R*-(+)-[4-(2-Azepan-1-yl-ethoxy)-phenyl]-8-fluoro-11,12-dihydro-5H-6,13-dioxa-benzo[3,4]cyclohepta[1,2-a]naphthalen-2-ol
[α]D=+24.2(c=0.305, MeOH) MS (m/z): M+H=502

Peak 2: 5S*-(−)-[4-(2-Azepan-1-yl-ethoxy)-phenyl]-8-fluoro-11,12-dihydro-5H-6,13-dioxa-benzo[3,4]cyclohepta[1,2-a]naphthalen-2-ol
[α]D=−28.2(c=0.5, MeOH). MS (m/z): M+H=502

EXAMPLE 141

2,2-Dimethyl-propionic acid 8-hydroxy-11S*-(+)-[4-(2-piperidin-1-yl-ethoxy)-phenyl]-5,11-dihydro-chromeno[4,3-c]chromen-2-yl ester Compound #89 and 2,2-Dimethyl-propionic acid 8-hydroxy-5S*(+)-[4-(2-piperidin-1-yl-ethoxy)-phenyl]-5,11-dihydro-chromeno[4,3-c]chromen-2-yl ester Compound #90

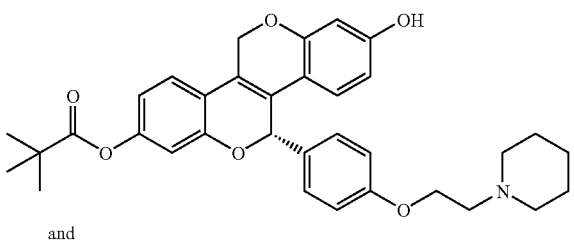

and

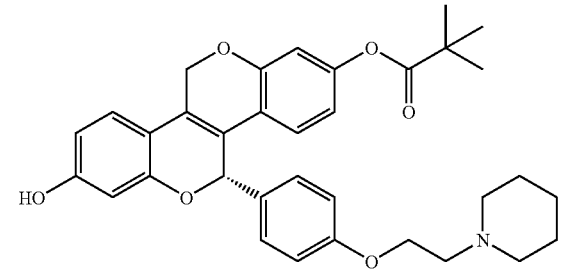

Dimethyl-propionic acid 8-(2,2-dimethyl-propionyloxy)-5S*-(+)-[4-(2-piperidin-1-yl-ethoxy)-phenyl]-5,11 dihydro-chromeno[4,3-c]chromen-2-yl ester, prepared as in Example 67, (10 g) was suspended in MeOH (200 mL) and 1.2 equivalents of diethylamine were added into a sealed tube. The resulting solution was heated to 150° C. for 3 h. The reaction mixture was concentrated on vacuum and purified on SiO$_2$ to yield a mixture of The mixture (3.1 g) was loaded onto a ChiralPak AD chiral HPLC column (5 cm I.D.×50 cm L) and eluted with 100% IPA at the 150 mL/min flow rate. The two peaks were removed under vacuum to yield the two regio-isomers as follow:

Peak 1: 2,2-Dimethyl-propionic acid 8-hydroxy-5S*(+)-[4-(2-piperidin-1-yl-ethoxy)-phenyl]-5,11-dihydro-chromeno[4,3-c]chromen-2-yl ester
$^1$H NMR (CDCl$_3$) δ 1.35 (s, 9H), 1.45 (broad s, 2H), 1.62 (broad s, 4H), 2.61 (broad s, 4H), 2.82 (broad s, 2H), 3.92 (t, 2H, J=6.0 Hz), 5.05 (d, 1H, J=14.7 Hz), 5.25 (d, 1H, J=14.7 Hz), 6.12~7.22 (m, 11H) MS (m/z): MH+ (556).

Peak 2: 2,2-Dimethyl-propionic acid 8-hydroxy-11S*-(+)-[4-(2-piperidin-1-yl-ethoxy)-phenyl]-5,11-dihydro-chromeno[4,3-c]chromen-2-yl ester
$^1$H NMR (CDCl$_3$) δ 1.19 (d, 9H, J=7.0 Hz), 1.42 (broad s, 2H), 1.61 (broad s, 4H), 2.59 (broad s, 4H), 2.72 (broad s, 2H), 4.06 (m, 2H), 5.05 (d, 1H, J=13.2 Hz), 5.24 (d, 1H, J=13.2 Hz), 6.16~7.23 (m, 11H) MS (m/z): MH+ (556).

EXAMPLE 142

8-Methoxy-5S*-[4-(2-piperidin-1-yl-ethoxy)-phenyl]-5,11-dihydro-chromeno[4,3-c]chromen-2-ol Compound #176

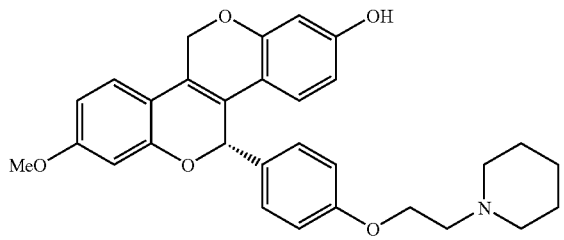

2,2-Dimethyl-propionic acid 8-hydroxy-5S*(+)-[4-(2-piperidin-1-yl-ethoxy)-phenyl]-5,11-dihydro-chromeno[4,3-c]chromen-2-yl ester (330 mg) the compound prepared as in Example 145 above, was dissolved in CH$_3$CN/MeOH (3:1) (8 mL). TMSCHN$_2$ (2M in hexane 3.3 mL) and was stirred over night. The reaction mixture was concentrated to dryness. The resulting crude oil was suspended in MeOH (5 mL) and TEA (0.800 mL) and heated in a sealed tube at 150° C. overnight. The reaction mixture was concentrated and purified on SiO$_2$ using 5-10% MeOH in CH$_2$Cl$_2$. to yield the title compound as a yellow foam.

$^1$H NMR (CDOD$_3$) δ 1.48 (m, 2H), 1.61 (m, 4H), 2.59 (broad s, 4H), 2.79 (t, 2H, J=5.6 Hz), 4.08 (t, 2H, J=5.6 Hz), 5.02 (d, 1H, J=13.8 Hz), 5.31 (d, 1H, J=13.6 Hz) MS (m/z): MH$^+$ (486).

EXAMPLE 143

8-Methoxy-11S*(−)-[4-(2-piperidin-1-yl-ethoxy)-phenyl]-5,11-dihydro-chromeno[4,3-c]chromen-2-ol Compound #181

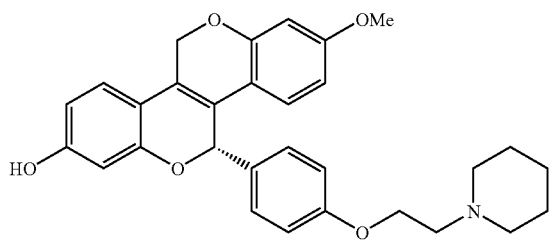

2,2-Dimethyl-propionic acid 8-hydroxy-11S*-(+)-[4-(2-piperidin-1-yl-ethoxy)-phenyl]-5,11-dihydro-chromeno[4,3-c]chromen-2-yl ester (300 mg), the compound prepared as in Example 145, was dissolved in CH$_3$CN/MeOH(3:1) (8 mL). TMSCHN$_2$ (2M in hexane, 3.3 mL) and was stirred overnight. The reaction mixture was concentrated to dryness. The resulting crude oil was suspended in MeOH (5 mL) and TEA (0.8 mL) and heated in a sealed tube at 150° C. overnight. The reaction mixture was concentrated and purified on SiO$_2$ using 5-10% MeOH in CH$_2$Cl$_2$. to yield the title compound as a yellow foam.

MS (m/z): MH$^+$ (486).

EXAMPLE 144

5S*-(+)-1-{2-[4-(2,8-Dimethoxy-5,11-dihydro-chromeno[4,3-]chromen-5-yl)-phenoxy]-ethyl}-piperidine Compound #173

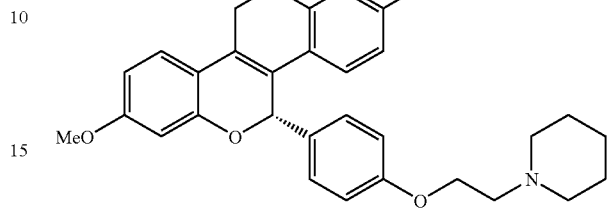

5S*-(+)-[4-(2-Piperidin-1-yl-ethoxy)-phenyl]-5,11-dihydro-chromeno[4,3-c]chromene-2,8-diol (290 mg), prepared as in Example 78, was dissolved in CH$_3$CN/MeOH (3:1) (5 mL). TMSCHN$_2$ (2M in hexane, 4 mL) and was stirred overnight. The reaction mixture was concentrated to dryness and purified over SiO$_2$ using 5% MeOH in CH$_2$Cl$_2$, to yield the title compound as a colorless oil.

$^1$H NMR (CDCl$_3$) δ 1.41 (broad s, 2H), 1.62 (broad s, 4H), 2.53 (broad s, 4H), 2.79 (s, 2H), 3.81 (s, 3H), 3.84 (s, 3H), 4.08 (t, 2H, J=5.5 Hz), 5.12 (d, 1H, J=13.6 Hz), 5.41 (d, 1H, J=13.6 Hz), 6.18 (s, 1H), 6.32~7.38 (m, 10 H). MS (m/z): MH+ (500).

EXAMPLE 145

5R*-(+)-[4-(2-Piperidin-1-yl-ethoxy)-phenyl]-11,12-dihydro-5H-6,13-dioxa-benzo[3,4]cyclohepta[1,2-a]naphthalene-2,8-diol Compound #99 and 5S*-(−)-[4-(2-Piperidin-1-yl-ethoxy)-phenyl]-11,12-dihydro-5H-6,13-dioxa-benzo[3,4]cyclohepta[1,2-a]naphthalene-2,8-diol Compound #100

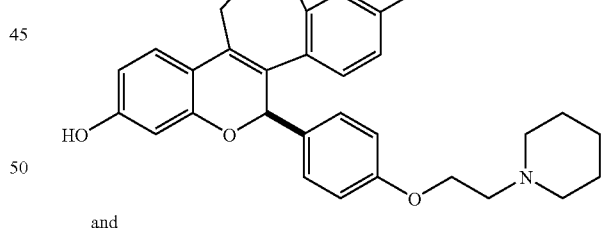

and

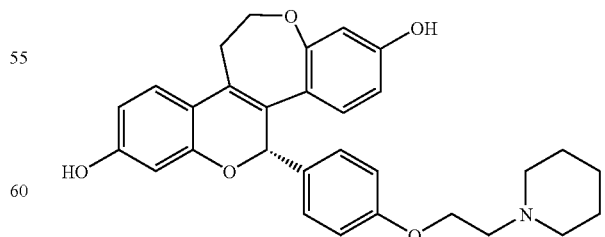

The racemic 5-[4-(2-Piperidin-1-yl-ethoxy)-phenyl]-11,12-dihydro-5H-6,13-dioxa-benzo[3,4]cyclohepta[1,2-a]naphthalene-2,8-diol compound, prepared as in Example 77, (1.18 g) was loaded onto a ChiralPak AD chiral HPLC column (5 cm I.D.×50 cm L) and eluted with 80% IPA and 20% MeOH at the 150 mL/min flow rate. The two peaks were removed under vacuum to yield the two enantiomers as follows:

Peak 1: 5R*-(+)-[4-(2-Piperidin-1-yl-ethoxy)-phenyl]-11,12-dihydro-5H-6,13-dioxa-benzo[3,4]cyclohepta[1,2-a]naphthalene-2,8-diol:

$^1$H NMR (CD$_3$OD) δ 1.46 (m, 2H), 1.59 (m, 4H), 2.55 (m, 4H), 2.72 (M, 2H), 2.81 (m, 2H), 4.02 (t, 2H, J=5.4 Hz). 4.60 (m, 2H), 6.05 (s, 1H), 6.14~7.34 (m, 10H). m.p. 147~149° C. [α]=+57°, (c=0.302, MeOH).

| Anal. Calculated for C$_{30}$H$_{31}$NO$_5$.0.95 H$_2$O | C, 71.68; | H, 6.60; | N, 2.79; |
|---|---|---|---|
| Found | C, 71.67; | H, 6.52; | N, 2.57. |

MS (m/z): MH+ (486).

Peak 2: 5S*-(-)-[4-(2-Piperidin-1-yl-ethoxy)-phenyl]-11,12-dihydro-5H-6,13-dioxa-benzo[3,4]cyclohepta[1,2-a]naphthalene-2,8-diol

[α]=-59°, (c=0.41, MeOH). MS (m/z): MH+ (486).

EXAMPLE 146

5S*-(-)-1-{2-[4-(2,8-Dimethoxy-11,12-dihydro-5H-6,13-dioxa-benzo[3,4]cyclohepta[1,2-a]naphthalen-5-yl)-phenoxy]-ethyl}-piperidine Compound #156

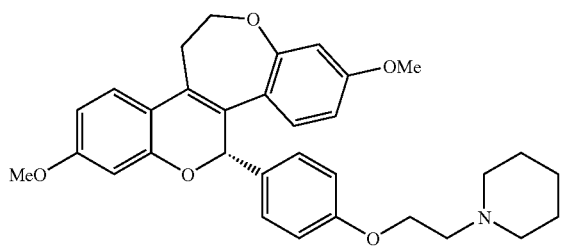

5S*-(-)-[4-(2-Piperidin-1-yl-ethoxy)-phenyl]-11,12-dihydro-5H-6,13-dioxa-benzo[3,4]cyclohepta[1,2-a]naphthalene-2,8-diol (1 g) prepared as in Example 145 was dissolved in CH$_3$CN/MeOH (3:1) (28 mL). TMSCHN$_2$ (2M in hexane, 3.3 mL) and was stirred overnight. The reaction mixture was concentrated to dryness and purified on SiO$_2$ using 5% MeOH in CH$_2$Cl$_2$ to yield the title compound as a yellow oil.

$^1$H NMR (CDCl$_3$) δ 1.40 (m, 2H), 1.59 (m, 4H), 2.49 (broad s, 4H), 2.72 (m, 2H), 2.91 (m, 2H), 3.71 (s, 3H), 3.78 (s, #H), 4.05 (m, 2H), 4.69 (m, 2H), 6.05 (s, 1H), 6.36~7.39 (m, 10H) MS (m/z): MH+ (514).

EXAMPLE 147

2-Methoxy-5S*-(-)-[4-(2-piperidin-1-yl-ethoxy)-phenyl]-11,12-dihydro-5H-6,13-dioxa-benzo[3,4]cyclohepta[1,2-a]naphthalen-8-ol Compound #196 and

8-Methoxy-5S*-(-)-[4-(2-piperidin-1-yl-ethoxy)-phenyl]-11,12-dihydro-5H-6,13-dioxa-benzo[3,4]cyclohepta[1,2-a]naphthalen-2-ol Compound #195

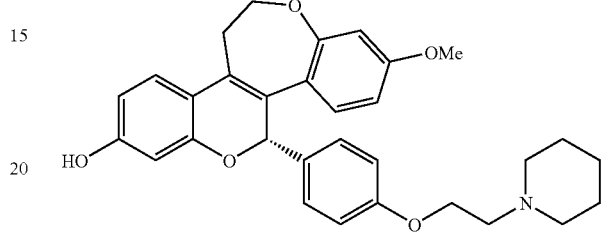

and

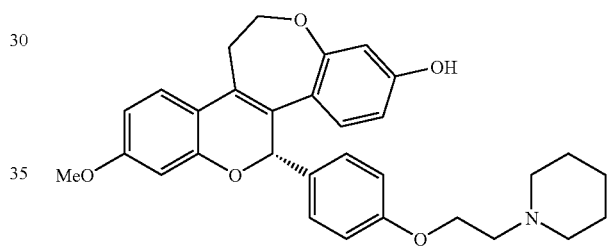

5S*-(-)-[4-(2-Piperidin-1-yl-ethoxy)-phenyl]-11,12-dihydro-5H-6,13-dioxa-benzo[3,4]cyclohepta[1,2-a]naphthalene-2,8-diol (10 g), prepared as in Example 145, was dissolved in CH$_3$CN/MeOH (3:1) (280 mL). 1.1 equivalent of TMSCHN$_2$ (2M in hexane, 10.2 mL) and was stirred overnight. The reaction mixture was concentrated to dryness and purified on SiO$_2$ using 5-10% MeOH in CH$_2$Cl$_2$. to yield a mixture of the title compounds as yellow foam.

The mixture of compounds (2.9 g) was loaded onto a ChiralPak AD chiral HPLC column 5 cm I.D.×50 cm L) and eluted with 100% IPA at the 150 mL/min flow rate. The two peaks were removed under vacuum to yield the two title compounds as follows:

Peak 1: 2-Methoxy-5S*-(-)-[4-(2-piperidin-1-y-ethoxy)-phenyl]-11,12-dihydro-5H-6,13-dioxa-benzo[3,4]cyclohepta[1,2-a]naphthalen-8-ol $^1$H NMR (DMSO-d6) δ 1.42 (s, 2H), 1.61 (s, 4H), 2.41~3.14 (m, 8H), 3.67 (s, 3H), 4.24 (s, 2H), 4.59 (m, 2H), 6.14~7.28 (m, 11H). MS (m/z): MH+ (500).

Peak 2: 8-Methoxy-5S*-(-)-[4-(2-piperidin-1-yl-ethoxy)-phenyl]-11,12-dihydro-5H-6,13-dioxa-benzo[3,4]cyclohepta[1,2-a]naphthalen-2-ol $^1$H NMR (CD$_3$OD) δ 1.41 (broad s, 2H), 1.59 (broad s, 4H), 2.50 (broad s, 4H0, 2.68 (m, 2H), 2.81 (m, 2H), 3.78 (m, 2H), 4.61 (t, 2H, J=6.0 Hz), 6.02 (s, 1H), 6.22~7.29 (m, 10H). MS (m/z): MH+ (500).

EXAMPLE 148

3-(2,4-Dimethoxy-phenyl)-7-methoxy-4-[2-(2-trimethylsilanyl-ethoxy)-ethyl]-chromen-2-one Compound #258

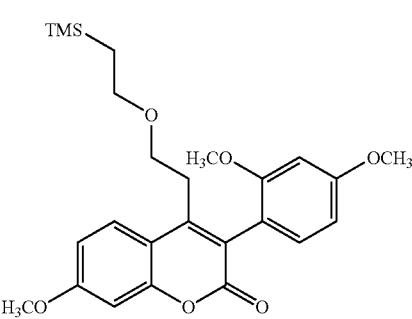

A 200 ml single neck flask was charged with lithium bis(trimethylsilyl)amide ((TMS)₂NLi, 16 mL 1M solution in THF). 3-(2,4-dimethoxy-phenyl)-7-methoxy-4-methyl-chromen-2-one (3.45 g) in anhydrous THF was added to the reaction mixture over a 10-min period and stirred at −20° C. for 45 min. (2-Chloromethoxy-ethyl)-trimethyl-silane (1.95 g) was added to the reaction mixture over a 10-min period and stirring was continued at −10° C. for 6 hours. The reaction mixture was quenched with saturated NH₄Cl (200 mL) and extracted with EtOAc (200 mL). The organic phase was condensed in vacuo at 60° C. to yield a crude product which was purified by flash chromatography to yield the title compound as a white solid.

MS (m/z): MH⁺ (457), MNa⁺ (479).

EXAMPLE 149

7-Methoxy-3-(2-methoxy-phenyl)-4-[2-(2-trimethyl-silanyl-ethoxy)-ethyl]-chromen-2-one Compound #262

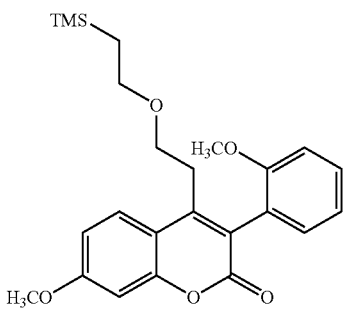

The title compound was prepared according to the procedure described in Example 148 above, substituting 3-(2,4-dimethoxy-phenyl)-7-methoxy-4-methyl-chromen-2-one with 7-methoxy-3-(2-methoxy-phenyl)-4-methyl-chromen-2-one, to yield a white solid.

MS (m/z): MH⁺ (427), MNa⁺ (449).

EXAMPLE 150

3-(2,4-Dimethoxy-phenyl)-4-[2-(2-trimethylsilanyl-ethoxy)-ethyl]-chromen-2-one Compound #259

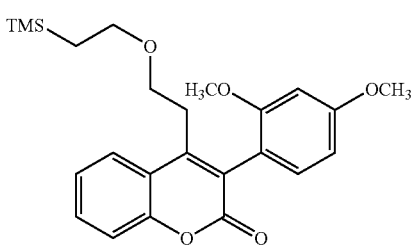

The title compound was prepared according to the procedure described in Example 148 above, substituting 3-(2,4-dimethoxy-phenyl)-7-methoxy-4-methyl-chromen-2-one with 3-(2,4-dimethoxy-phenyl)-4-methyl-chromen-2-one, to yield a white solid.

MS (m/z): MH⁺ (427), MNa⁺ (449).

EXAMPLE 151

3-(2,4-Dimethoxy-phenyl)-7-fluoro-4-[2-(2-trimethylsilanyl-ethoxy)-ethyl]-chromen-2-one Compound #264

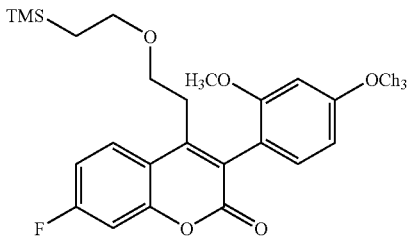

The title compound was prepared according to the procedure described in Example A above, substituting 3-(2,4-dimethoxy-phenyl)-7-methoxy-4-methyl-chromen-2-one with 3-(2,4-dimethoxy-phenyl)-7-fluoro-4-methyl-chromen-2-one, to yield a solid.

MS (m/z): MH⁺ (445), MNa⁺ (467).

EXAMPLE 152

3-(2,4-Dimethoxy-phenyl)-6-methyl-4-[2-(2-trimethylsilanyl-ethoxy)ethyl]-chromen-2one Compound #267

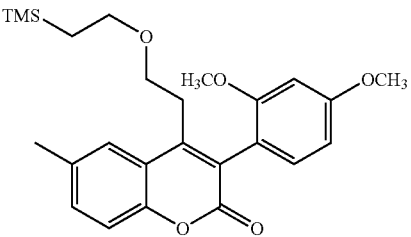

The title compound was prepared according to the procedure described in Example 148 above, substituting 3-(2, 4-dimethoxy-phenyl)-7-methoxy-4-methyl-chromen-2-one with 3-(2,4-dimethoxy-phenyl)-4,6-dimethyl-chromen-2-one, to yield a solid.

MS (m/z): MH$^+$ (441), MNa$^+$ (463).

EXAMPLE 153

3-(2,4-Dihydroxy-phenyl)-7-hydroxy-4-(2-hydroxy-ethyl)-chromen-2-one Compound #62

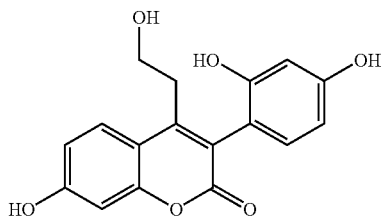

A 1 L flask was charged with CH$_2$Cl$_2$ (200 mL) and 3-(2,4-dimethoxy-phenyl)-7-methoxy-4-[2-(2-trimethylsilanyl-ethoxy)-ethyl]-chromen-2-one, prepared as in Example 148, (5 g) The solution was stirred at room temperature under N$_2$ and BBr$_3$ (8 mL) was added under N$_2$ pressure over a 20-min period. The reaction mixture was then stirred for 36 hours. The reaction mixture was cooled to 0° C., and the reaction mixture was poured in precooled 1N NaOH (200 ml, 5° C.). The resulting solution was neutralized by 1N HCl to pH 4 and was extracted by EtOAc (2 L). The organic layer was separated and concentrated on vacuum to dryness, then purified by flash chromatography to yield the title compound as a yellow solid.

MS (m/z): MH$^+$ (315), MNa$^+$ (337).

EXAMPLE 154

3-(2,4-Dihydroxy-phenyl)-4-(2-hydroxy-ethyl)-chromen-2-one Compound #269

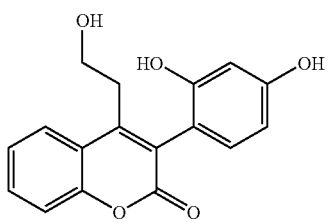

The title compound was prepared according to the procedure described in Example 153 above, substituting 3-(2,4-dimethoxy-phenyl)-7-methoxy-4-[2-(2-trimethylsilanyl-ethoxy)-ethyl]-chromen-2-one with 3-(2,4-Dimethoxy-phenyl)-4-[2-(2-trimethylsilanyl-ethoxy)-ethyl]-chromen-2-one, prepared as in Example 150, to yield a solid.

MS (m/z): MH$^+$ (299), MNa$^+$ (321).

EXAMPLE 155

7-Hydroxy-4-(2-hydroxy-ethyl)-3-(2-hydroxy-phenyl)-chromen-2-one Compound #271

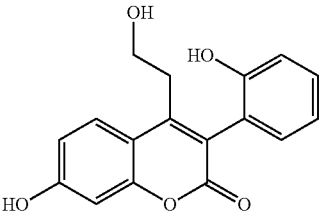

The title compound was prepared according to the procedure described in Example 153 above, substituting 3-(2,4-dimethoxy-phenyl)-7-methoxy-4-[2-(2-trimethylsilanyl-ethoxy)-ethyl]-chromen-2-one with 7-methoxy-3-(2-methoxy-phenyl)-4-[2-(2-trimethylsilanyl-ethoxy)-ethyl]-chromen-2-one, prepared as in Example 149, to yield a solid.

MS (m/z): MH$^+$ (299), MNa$^+$ (321).

EXAMPLE 156

3-(2,4-Dihydroxy-phenyl)-7-fluoro-4-(2-hydroxy-ethyl)-chromen-2-one Compound #270

The title compound was prepared according to the procedure described in Example 153 above, substituting 3-(2,4-dimethoxy-phenyl)-7-methoxy-4-[2-(2-trimethylsilanyl-ethoxy)-ethyl]-chromen-2-one with 3-(2,4-dimethoxy-phenyl)-7-fluoro-4-[2-(2-trimethylsilanyl-ethoxy)-ethyl]-chromen-2-one, prepared as in Example 151, to yield a solid.

MS (m/z): MH$^+$ (317), MNa$^+$ (339).

EXAMPLE 157

3-(2,4-Dihydroxy-phenyl)-4-(2-hydroxy-ethyl)-6-methyl-chromen-2-one Compound #268

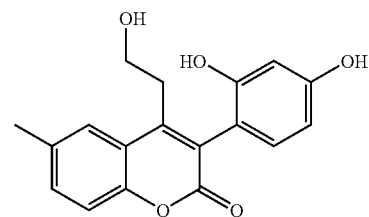

The title compound was prepared according to the procedure described in Example 153 above, substituting 3-(2,4-dimethoxy-phenyl)-7-methoxy-4-[2-(2-trimethylsilanyl-ethoxy)-ethyl]-chromen-2-one with 3-(2,4-dimethoxy-phenyl)-6-methyl-4-[2-(2-trimethylsilanyl-ethoxy)-ethyl]-chromen-2-one, prepared as in Example 152, to yield a solid.

MS (m/z): MH$^+$ (313), MNa$^+$ (335).

EXAMPLE 158

2,8-Dihydroxy-11,12-dihydro-6,13-dioxa-benzo[3,4]cyclohepta[1,2-a]naphthalen-5-one Compound #56

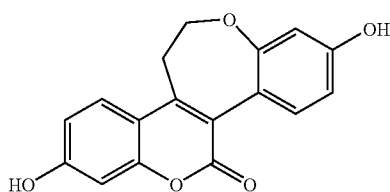

A suspension of 3-(2,4-Dihydroxy-phenyl)-7-hydroxy-4-(2-hydroxy-ethyl)-chromen-2-one, prepared as in Example 153, (2.5 g) and anhydrous THF (40 mL) was cooled to about −5 to 0° C. To the reaction mixture was then added diisopropyl azodicarboxylate (DIAD, 6.64.5 mL) over a 35-min period and the mixture stirred at −5° C. for 30 min. A solution of triphenylphosphine (8.41 g) in THF (160 ml) was then added over a 30-min period, the reaction was warmed to 20° C. and stirred for 18 hours. The solvent was condensed in vacuo at 60° C. and the resulting residue was dissolved in $CH_2Cl_2$ (300 mL) and washed with 2 N NaOH solutions three times (200, mL, 100 mL and 50 mL). The aqueous phases were combined and back-extracted with $CH_2Cl_2$ (50 ml). The aqueous phase was cooled to 0° C. and acidified to pH~1-2 with concentrated HCl solution (37%), and the resulting slurry was stirred at 10° C. for 1 hour. The solid was isolated by filtration and the filter cake was washed with $H_2O$ (50 mL). This solid was dried in a vacuum over to yield the title compound as a solid.

MS: 295.0 M−H; 297 M+H; 319 M+Na $^1$H-NMR (300 MHz, THF-d8): δ (ppm) 6.5-7.8 (m, 6H), 4.6 (t, 2H), 3.0 (t, 2H).

EXAMPLE 159

2-Hydroxy-11,12-dihydro-6,13-dioxa-benzo[3,4]cyclohepta[1,2-a]naphthalen-5-one Compound #225

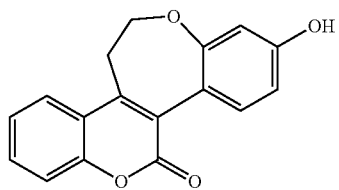

The title compound was prepared according to the procedure described in Example 153 above, substituting 3-(2,4-dihydroxy-phenyl)-7-hydroxy-4-(2-hydroxy-ethyl)-chromen-2-one, with 3-(2,4-Dihydroxy-phenyl)-4-(2-hydroxy-ethyl)-chromen-2-one, prepared as in Example 158, to yield a solid.

MS(m/z): M+H=281, M+Na=283

EXAMPLE 160

8-Hydroxy-11,12-dihydro-6,13-dioxa-benzo[3,4]cyclohepta[1,2-a]naphthalen-5-one Compound #223

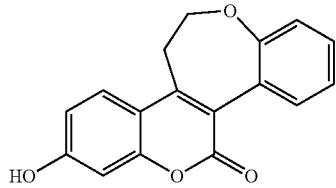

The title compound was prepared according to the procedure described in Example 153 above, substituting 3-(2,4-dihydroxy-phenyl)-7-hydroxy-4-(2-hydroxy-ethyl)-chromen-2-one, with 7-hydroxy-4-(2-hydroxy-ethyl)-3-(2-hydroxy-phenyl)-chromen-2-one, prepared as in Example 158, to yield a solid.

MS(m/z): M+H=281, M+Na=283.

EXAMPLE 161

8-Fluoro-2-hydroxy-11,12-dihydro-6,13-dioxa-benzo[3,4]cyclohepta[1,2-a]naphthalen-5-one Compound #226

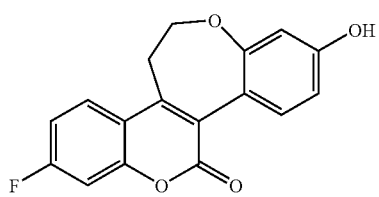

The title compound was prepared according to the procedure described in Example 153 above, substituting 3-(2,4-dihydroxy-phenyl)-7-hydroxy-4-(2-hydroxy-ethyl)-chromen-2-one, with 3-(2,4-Dihydroxy-phenyl)-7-fluoro-4-(2-hydroxy-ethyl)-chromen-2-one, prepared as in Example 158, to yield a solid.

MS(m/z): M+H=299, M+Na=321.

EXAMPLE 162

2-Hydroxy-9-methyl-11,12-dihydro-6,13-dioxa-benzo[3,4]cyclohepta[1,2-a]naphthalen-5-one Compound #287

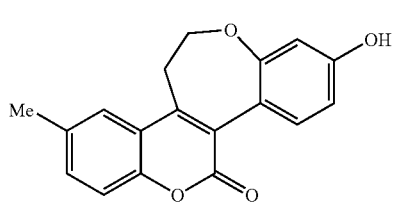

The title compound was prepared according to the procedure described in Example 153 above, substituting 3-(2,4-dihydroxy-phenyl)-7-hydroxy-4-(2-hydroxy-ethyl)-chromen-2-one, with 2-Hydroxy-9-methyl-11,12-dihydro-6,13-dioxa-benzo[3,4]cyclohepta[1,2-a]naphthalen-5-one, prepared as in Example 158, to yield a solid.

MS(m/z): M+H=295, M+Na=317.

EXAMPLE 163

2-(tert-Butyl-dimethyl-silyloxy)-9-methyl-11,12-dihydro-6,13-dioxa-benzo[3,4]cyclohepta[1,2-a]naphthalen-5-one Compound #228

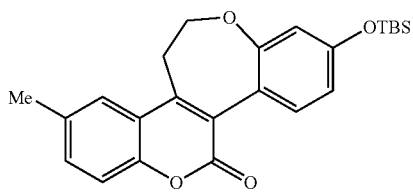

The title compound was prepared according to the procedure described in Example 22, substituting 2-hydroxy-9-methyl-11,12-dihydro-6,13-dioxa-benzo[3,4]cyclohepta[1,2-a]naphthalen-5-one for 2,8-dihydroxy-11H-chromeno[4,3-c]chromen-5-one, to yield a solid.

MS(m/z): M+H=409, M+Na=431

EXAMPLE 164

2-(tert-Butyl-dimethyl-silyloxy)-8-fluoro-11,12-dihydro-6,13-dioxa-benzo[3,4]cyclohepta[1,2-a]naphthalen-5-one Compound #288

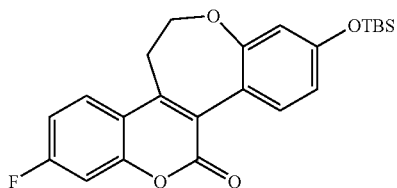

The title compound was prepared according to the procedure described in Example 22, substituting 8-fluoro-2-hydroxy-11,12-dihydro-6,13-dioxa-benzo[3,4]cyclohepta[1,2-a]naphthalen-5-one for 2,8-dihydroxy-11H-chromeno[4,3-c]chromen-5-one, to yield a solid.

MS(m/z): M+H=413, M+Na=435.

EXAMPLE 165

2-(tert-Butyl-dimethyl-silyloxy)-8-fluoro-11,12-dihydro-5H-6,13-dioxa-benzo[3,4]cyclohepta[1,2-a]naphthalen-5-ol Compound #205

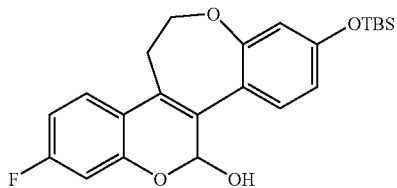

The title compound was prepared according to the procedure described in Example 84, substituting 2-(tert-butyl-dimethyl-silyloxy)-8-fluoro-11,12-dihydro-6,13-dioxa-benzo[3,4]cyclohepta[1,2-a] naphthalen-5-one for 2,6,12-tris[[(1,1-dimethylethyl)dimethylsilyl]oxy]-2,3-dihydro-[1]benzopyrano[4,3-e][1]benzoxocin-9(1H)-one, to yield a yellow solid.

MS(m/z): M+H=415, M+Na=437.

EXAMPLE 166

2-(tert-Butyl-dimethyl-silyloxy)-9-methyl-11,12-dihydro-5H-6,13-dioxa-benzo[3,4]cyclohepta[1,2-a]naphthalen-5-ol Compound #207

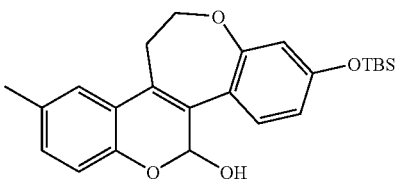

The title compound was prepared according to the procedure described in Example 84, substituting 2-(tert-butyl-dimethyl-silyloxy)-9-methyl-11,12-dihydro-6,13-dioxa-benzo[3,4]cyclohepta[1,2-a]-naphthalen-5-one for 2,6,12-tris[[(1,1-dimethylethyl)dimethylsilyl]oxy]-2,3-dihydro-[1]benzopyrano[4,3-e][1]benzoxocin-9(1H)-one, to yield a yellow solid.

MS(m/z): M+H=411, M+Na=433.

EXAMPLE 167

7-Methoxy-3-(2-methoxy-phenyl)-4-methyl-chromen-2-one Compound #289

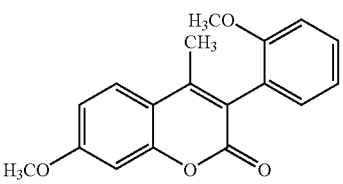

The title compound was prepared according to the procedure described in Example 1, substituting commercially available 2,4-dimethoxy acetophenone and 2-methoxy phenyl acetic acid for 2,4-dihydroxyacetophenone and 4-dimethoxy phenyl acetic acid, respectively, to yield a yellow solid.

MS(m/z): M+H=297, M+Na=319.

EXAMPLE 168

3-(2-Methoxy-phenyl)-4,6-dimethyl-chromen-2-one Compound #290

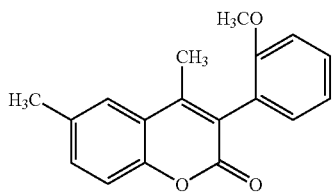

The title compound was prepared according to the procedure described in Example 1, substituting 4-methyl-2-hydroxy-acetophenone and 2-4-dimethoxy phenyl acetic acid for 2,4-dihydroxyacetophenone and 4-dimethoxy phenyl acetic acid, respectively, to yield a yellow solid.
MS(m/z): M+H=281, M+Na=303.

EXAMPLE 169

2-{4-[2,8-Bis-(tert-butyl-dimethyl-silyloxy)-11,12-dihydro-5H-6,13-dioxa-benzo[3,4]cyclohepta[1,2-a]naphthalen-5-yl]-phenoxy}-ethanol Compound #186

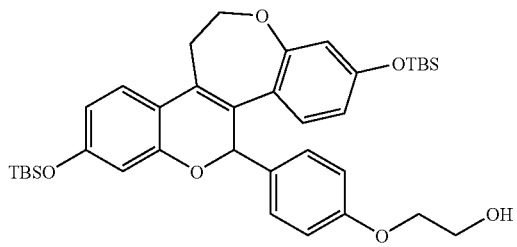

To a clear solution of 2-(4-iodo-phenoxy)-ethanol (400 mg, 5 eq.) in THF (10 mL) was added isopropyl magnesium bromide (3.0 mL, ~1.0 M, 10 eq.). After 10 min, 2,8-bis-(tert-butyl-dimethyl-silyloxy)-11,12-dihydro-5H-6,13-dioxa-benzo[3,4]cyclohepta[1,2-a]naphthalen-5-ol (example 75) (162 mg, 0.30 mmol) in THF (2 mL) was added at 25° C. and stirred for 30 min before the reaction mixture was quenched with NH$_4$Cl aqueous saturated solution. After quenching, EtOAc (200 mL) was added, the organic layer was separated and dried over anhydrous Na$_2$SO$_4$ and concentrated under reduced pressure yield a crude oil. The crude oil was dissolved in toluene (10 mL) and then treated with TFA (0.023 mL, 1 eq.) at 0° C. The reaction mixture was then diluted by EtOAc (200 mL) and washed with water (200 mL). The organic layer was separated and dried over Na$_2$SO$_4$, then concentrated under reduced pressure to yield a crude oil. This crude oil was purified by flash coloumn chromatography to yield the title compound as a foam.

$^1$H NMR (CDCl$_3$) δ 7.35-6.29 (m, 10H), 6.02 (s, 1H), 4.62 (t, 2H, J=6.5 Hz), 4.01-3.83 (m, 4H), 2.86 (m, 2H), 0.93 (d, 18H, J=13.7 Hz), 0.17 (d, 12H, J=15.2 Hz). MS (m/z): MH+ (647), MNa+ (669)

The racemic 2-{4-[2,8-Bis-(tert-butyl-dimethyl-silyloxy)-11,12-dihydro-5H-6,13-dioxa-benzo[3,4]cyclohepta[1,2-a]naphthalen-5-yl]-phenoxy}-ethanol product (950 mg) was loaded on to ChiralPak AD chiral HPLC column (5 cm I.D.×50 cm L) and eluted with 50% IPA and 50% Hexanes at the 150 mL/min flow rate. The two peaks were removed under vacuum to yield the two enantiomers as follows:

Peak 1: 5R*-(+)-2-{4-[2,8-Bis-(tert-butyl-dimethyl-silyloxy)-11,12-dihydro-5H-6,13-dioxa-benzo[3,4]cyclohepta[1,2-a]naphthalen-5-yl]-phenoxy}-ethanol
[α]$^{20}_D$=+33.5° (c 0.30, CHCl$_3$).

Peak 2: 5S*-(−)-2-{4-[2,8-Bis-(tert-butyl-dimethyl-silyloxy)-11,12-dihydro-5H-6,13-dioxa-benzo[3,4]cyclohepta[1,2-a]naphthalen-5-yl]-phenoxy}-ethanol
[α]$^{20}_D$=−33.5° (c 0.36, CHCl$_3$).

EXAMPLE 170

3-{4-[2,8-Bis-(tert-butyl-dimethyl-silyloxy)-11,12-dihydro-5H-6,13-dioxa-benzo[3,4]cyclohepta[1,2-a]naphthalen-5-yl]-phenoxy}-propan-1-ol Compound #191

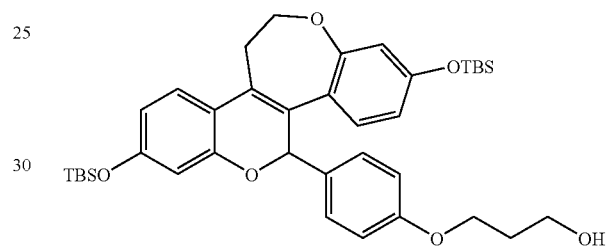

Following the same procedure described in Example 169, substituting 2-(4-iodo-phenoxy)-ethanol with 3-(4-Iodo-phenoxy)-propan-1-ol (2.78 g, 10 mmol, 5 eq.), to yield the title compound as a white solid.

| Anal. Calculated for C$_{38}$H$_{52}$O$_6$Si$_2$ | C, 69.05; | H, 7.93, | Si, 8.50. |
|---|---|---|---|
| Found | C, 68.68; | H, 8.00, | Si, 8.90. |

$^1$H NMR (CDCl$_3$) δ 7.19-6.35 (m, 10H), 5.63 (s, 1H), 4.49 (t, 2H, J=6.6 Hz), 3.99 (m, 2H), 3.66 (m, 2H), 2.42 (m, 2H), 1.93 (m, 2H), 0.94 (d, 18H, J=13.7 Hz), 0.16 (d, 12H, J=15.2 Hz). MS (m/z): MH+ (661).

The racemic 3-{4-[2,8-Bis-(tert-butyl-dimethyl-silyloxy)-11,12-dihydro-5H-6,13-dioxa-benzo[3,4]cyclohepta[1,2-a]naphthalen-5-yl]-phenoxy}-propan-1-ol product (850 mg) was loaded on to ChiralPak AD chiral HPLC column (5 cm I.D.×50 cm L) and eluted with 50% IPA and 50% Hexanes at the 150 mL/min flow rate. The two peaks were removed under vacuum to yield the two enantiomers as follows:

Peak 1: 5R*-(+)-3-{4-[2,8-Bis-(tert-butyl-dimethyl-silyloxy)-11,12-dihydro-5H-6,13-dioxa-benzo[3,4]cyclohepta[1,2-a]naphthalen-5yl]-phenoxy}-propan-1-ol
[α]$^{20}_D$=29.5° (c 0.36, CHCl$_3$).

Peak 2: 5S*-(−)-3-{4-[2,8-Bis-(tert-butyl-dimethyl-silyloxy)-11,12-dihydro-5H-6,13-dioxa-benzo[3,4]cyclohepta[1,2-a]naphthalen-5-yl]-phenoxy}-propan-1-ol
[α]$^{20}_D$=−29.5° (c 0.36, CHCl$_3$).

EXAMPLE 171

5S*-(+)-1-{2-[4-(2,8-Dihydroxy-11,12-dihydro-5H-6,13-dioxa-benzo[3,4]cyclohepta[1,2-a]naphthalen-5-yl)-phenoxy]-ethyl}-pyrrolidine-2,5-dione Compound #277

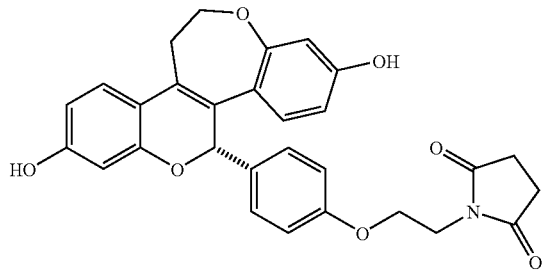

Step A:

To the solution of 5S*-(−)-2-{4-[2,8-Bis-(tert-butyl-dimethyl-silyloxy)-11,12-dihydro-5H-6,13-dioxa-benzo[3,4]cyclohepta[1,2-a]naphthalen-5-yl]-phenoxy}-ethanol (323 mg, 0.5 mm), prepared as in Example 169 and succinamide (49.5 mg) in $CH_2Cl_2$ (5 ml) was added triphenylphosphene (132 mg) and DEAD (0.8 ml) and the reaction mixture stirred for 12 hours. The reaction mixture was then quenched by adding 50 ml of water and diluted with ETOAc (100 ml). The organic layer was separated and dried over anhydrous $Na_2SO_4$. The compound was purified by flash chromatography to yield 1-(2-{4-[2,8-bis-(tert-butyl-dimethyl-silyloxy)-11,12-dihydro-5H-6,13-dioxa-benzo[3,4]cyclohepa[1,2-a]naphthalene-5-yl]-phenoxy}-ethyl)-pyrrolidine-2,5-dione as a solid.

MS (m/z): MH+ (729).): M−H (727) $[\alpha]^{20}_D=-35.5°$ (c 0.36, $CHCl_3$).

Step B:

1-(2-{4-[2,8-Bis-(tert-butyl-dimethyl-silyloxy)-11,12-dihydro-5H-6,13-dioxa-benzo[3,4]cyclohepta[1,2-a]naphthalen-5-yl]-phenoxy}-ethyl)-pyrrolidine-2,5-dione, prepared as in Step A above, (220 mg) was dissolved in acetonitrile: pyridine (10:1). HF•Pyridine (0.5 ml) was added and the reaction mixture was stirred for 12 hours room temprature. The reaction mixture was quenched by aqueous saturated solution of $NaHCO_3$ (100 mL) and then diluted by ethyl acetate (200 mL). The organic layer was separated and then concentrated under reduced pressure to yield a crude oil. The crude oil was purified by flash chromatography to yield the title compound as a solid.

MS (m/z): MH+ (500).): M−H (498).

Following the procedures described in the Schemes and Examples above, representative compounds of the present invention were prepared, as listed in Tables 1-3. For the stereo-configuration of the $R^2$ group, the R* and S* notations indicate that the exact orientation was not determined.

TABLE 1

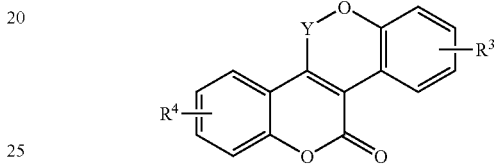

| ID No | Y | $R^3$ | $R^4$ | Calc. MW. |
|---|---|---|---|---|
| 1 | —$CH_2$— | 2-hydroxy | 8-hydroxy | 282.25 |
| 2 | —$CH_2$— | 2-methoxy | 8-methoxy | 310.30 |
| 3 | —$CH_2$— | 2-(t-butyl-dimethyl-silyloxy) | 8-(t-butyl-dimethyl-silyloxy) | 510.78 |
| 7 | C(O) | 2-methoxy | 8-methoxy | 324.29 |
| 37 | —$CH_2$— | 2-hydroxy | 8-fluoro | 284.24 |
| 84 | —$CH_2$— | 2-hydroxy | 7-hydroxy | 282.25 |
| 85 | —$CH_2$— | 2-(t-butyl dimethyl-silyloxy) | 8-fluoro | 398.50 |
| 88 | —$CH_2$— | — | 8-t-butyl-dimethyl-silyloxy | 380.52 |
| 272 | —$CH_2$— | 2-methoxy | 8-methoxy | 310.31 |

The symbol "—" indicates that no $R^3$ substituent was present.

TABLE 2

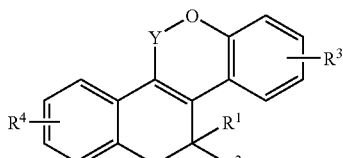

| ID No | Y | $R^1$ | $R^2$ | $R^3$ | $R^4$ | Calc. MW |
|---|---|---|---|---|---|---|
| 4 | —$CH_2$— | H | hydroxy | 2-(t-butyl-dimethyl-silyloxy) | 8-(t-butyl-dimethyl-silyloxy) | 512.79 |
| 5 | —$CH_2$— | H | phenyl | 2-(t-butyl-dimethyl-silyloxy) | 8-(t-butyl-dimethyl-silyloxy) | 572.89 |
| 6 | —$CH_2$— | H | phenyl | 2-hydroxy | 8-hydroxy | 344.36 |
| 8 | —$CH_2$— | H | 4-(1-piperidinyl-ethoxy)-phenyl | 2-(t-butyl-dimethyl-silyloxy) | 8-(t-butyl-dimethyl-silyloxy) | 700.08 |
| 9 | —$CH_2$— | H | 4-(1-piperidinyl-ethoxy)-phenyl | 2-hydroxy | 8-hydroxy | 471.55 |

TABLE 2-continued

| ID No | Y | R¹ | R² | R³ | R⁴ | Calc. MW |
|---|---|---|---|---|---|---|
| 10 | —CH₂— | H | 4-(1-pyrrolidinyl-ethoxy)-phenyl | 2-(t-butyl-dimethyl-silyloxy) | 8-(t-butyl-dimethyl-silyloxy) | 686.05 |
| 11 | —CH₂— | H | 4-(1-pyrrolidinyl-ethoxy)-phenyl | 2-hydroxy | 8-hydroxy | 457.52 |
| 12 | —CH₂— | H | 4-(4-morpholinyl-ethoxy)-phenyl | 2-(t-butyl-dimethyl-silyloxy) | 8-(t-butyl-dimethyl-silyloxy) | 702.05 |
| 13 | —CH₂— | H | 4-(4-morpholinyl-ethoxy)-phenyl | 2-hydroxy | 8-hydroxy | 473.52 |
| 14 | —CH₂— | H | R*-(−)-[4-(1-piperidinyl-ethoxy)-phenyl] | 2-hydroxy | 8-hydroxy | 471.55 |
| 15 | —CH₂— | H | S*-(+)-[4-(1-piperidinyl-ethoxy)-phenyl} | 2-hydroxy | 8-hydroxy | 471.55 |
| 16 | —CH₂— | H | 4-(1-azepanyl-ethoxy)-phenyl | 2-(t-butyl-dimethyl-silyloxy) | 8-(t-butyl-dimethyl-silyloxy) | 714.10 |
| 17 | —CH₂— | H | 4-(1-azepanyl-ethoxy)-phenyl | 2-hydroxy | 8-hydroxy | 485.58 |
| 18 | —CH₂— | H | 4-(diethylamino-ethoxy)-phenyl | 2-(t-butyl-dimethyl-silyloxy) | 8-(t-butyl-dimethyl-silyloxy) | 688.06 |
| 19 | —CH₂— | H | 4-(diethylamino-ethoxy)-phenyl | 2-hydroxy | 8-hydroxy | 459.54 |
| 20 | —CH₂— | H | 4-(dimethylamino-ethoxy)-phenyl | 2-(t-butyl-dimethyl-silyloxy) | 8-(t-butyl-dimethyl-silyloxy) | 660.01 |
| 21 | —CH₂— | H | 4-(dimethylamino-ethoxy)-phenyl | 2-hydroxy | 8-hydroxy | 431.49 |
| 22 | —CH₂— | H | 4-(1-piperidinyl-ethoxy)-phenyl | 2-t-butyl-C(O)O— | 8-t-butyl-C(O)O— | 639.78 |
| 23 | —CH₂— | H | 4-(dimethyl amino)-phenyl | 2-(t-butyl-dimethyl-silyloxy) | 8-(t-butyl-dimethyl-silyloxy) | 615.96 |
| 24 | —CH₂— | H | R*-(−)-[4-(1-piperidinyl-ethoxy)-phenyl] | 2-t-butyl-C(O)O— | 8-t-butyl-C(O)O— | 639.78 |
| 25 | —CH₂— | H | S*-(+)-[4-(1-piperidinyl-ethoxy)-phenyl] | 2-t-butyl-C(O)O— | 8-t-butyl-C(O)O— | 639.78 |
| 26 | —CH₂— | H | 4-(dimethyl amino)-phenyl | 2-hydroxy | 8-hydroxy | 387.43 |
| 27 | —CH(OCH₃)— | H | 4-(1-piperidinyl-ethoxy)-phenyl | 2-t-butyl-C(O)O— | 8-t-butyl-C(O)O— | 669.81 |
| 28 | —CH(OH)— | H | 4-(1-piperidinyl-ethoxy)-phenyl | 2-t-butyl-C(O)O— | 8-t-butyl-C(O)O— | 655.78 |
| 29 | —CH₂— | CH₃ | 4-(1-piperidinyl-ethoxy)-phenyl | 2-hydroxy | 8-hydroxy | 485.58 |
| 30 | —CH₂— | CH₃ | 4-(pyrrolidinyl-ethoxy)-phenyl | 2-t-butyl-C(O)O— | 8-t-butyl-C(O)O— | 639.78 |
| 31 | —CH₂— | CH₃ | 4-(pyrrolidinyl-ethoxy)-phenyl | 2-hydroxy | 8-hydroxy | 471.55 |
| 32 | —CH₂— | CH₃ | 4-(pyrrolidinyl-ethoxy)-phenyl | 2-t-butyl-dimethyl silyloxy | 8-t-butyl-dimethyl-silyloxy) | 700.08 |
| 33 | —CH₂— | CH₃ | 4-(azepanyl-ethoxy)-phenyl | 2-t-butyl-C(O)O— | 8-t-butyl-C(O)O— | 667.84 |
| 34 | —CH₂— | CH₃ | 4-(azepanyl-ethoxy)-phenyl | 2-hydroxy | 8-hydroxy | 499.60 |
| 35 | —CH₂— | CH₃ | 4-(azepanyl-ethoxy)-phenyl | 2-t-butyl-dimethyl silyloxy | 8-t-butyl-dimethyl-silyloxy) | 728.13 |

TABLE 2-continued

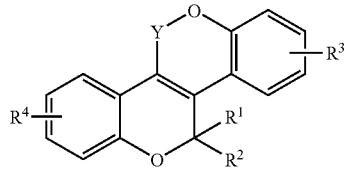

| ID No | Y | R$^1$ | R$^2$ | R$^3$ | R$^4$ | Calc. MW |
|---|---|---|---|---|---|---|
| 36 | —CH$_2$— | OH | 4-benzyloxy-phenyl | 2-t-butyl-dimethyl silyloxy | 8-(t-butyl-dimethyl-silyloxy) | 695.01 |
| 38 | —CH$_2$— | CH$_3$ | 3-(1-piperidinyl-n-ethoxy)-phenyl | 2-t-butyl-C(O)O— | 8-t-butyl-C(O)O— | 653.81 |
| 39 | —CH$_2$— | CH$_3$ | 3-(1-piperidinyl-n-ethoxy)-phenyl | 2-hydroxy | 8-hydroxy | 485.58 |
| 40 | —CH$_2$— | CH$_3$ | 3-(1-piperidinyl-n-ethoxy)-phenyl | 2-t-butyl-dimethyl silyloxy | 8-t-butyl-dimethyl silyloxy | 714.10 |
| 41 | —CH$_2$— | CH$_3$ | 4-(1-piperidinyl-n-ethoxy)-phenyl | 2-t-butyl-C(O)O— | 8-t-butyl-C(O)O— | 653.81 |
| 42 | —CH$_2$— | CH$_3$ | 4-(1-piperidinyl-n-ethoxy)-phenyl | 2-t-butyl-dimethyl silyloxy | 8-t-butyl-dimethyl silyloxy | 714.10 |
| 43 | —CH$_2$— | CH$_3$ | 4-(1-piperidinyl-n-ethoxy)-phenyl | 2-t-butyl-C(O)O— | 8-t-butyl-C(O)O— | 667.84 |
| 44 | —CH$_2$— | CH$_3$ | 4-(1-piperidinyl-n-propoxy)-phenyl | 2-hydroxy | 8-hydroxy | 499.60 |
| 45 | —CH$_2$— | CH$_3$ | 4-(1-piperidinyl-n-propoxy)-phenyl | 2-t-butyl-dimethyl silyloxy | 8-t-butyl-dimethyl silyloxy | 728.13 |
| 46 | —CH$_2$— | H | 4-(1-piperidinyl-n-ethoxy)-phenyl | 2-hydroxy | 8-fluoro | 473.54 |
| 47 | —CH-(iso-propyl)- | H | 4-(1-piperidinyl-n-ethoxy)-phenyl | 2-hydroxy | 8-fluoro | 515.62 |
| 48 | —CH$_2$— | H | 4-(1-piperidinyl-ethoxy)-phenyl | 2-OC(O)CH-(phenyl)-OC(O)CH$_3$ | 8-OC(O)-CH-(phenyl)-OC(O)CH$_3$ | 823.3 |
| 49 | —CH$_2$— | H | S*-4-(1-piperidinyl-ethoxy)-phenyl | 2-OC(O)-1,7,7-trimethyl-2-oxabi-cyclo [2.2.1] heptan-3-one | 8-OC(O)-1,7,7-trimethyl-2-oxabicyclo [2.2.1] heptan-3-one | 831.36 |
| 50 | —CH$_2$— | H | 4-(1-piperidinyl-ethoxy)-phenyl | 2-OC(O)-C(CH$_3$)(CF$_3$)-phenyl) | 8-OC(O)-C(CH$_3$)(CF$_3$)-phenyl) | 903.28 |
| 51 | —CH$_2$— | H | 4-(1-piperidinyl-ethoxy)-phenyl | 2-OC(O)-t-butyl) | 8-hydroxy | 55.26 |
| 52 | —CH$_2$— | H | 4-(1-piperidinyl-ethoxy)-phenyl | 2-hydroxy | 8-OC(O)-t-butyl | 555.26 |
| 53 | —CH$_2$CH$_2$— | H | hydroxy | 2-(t-butyl-dimethyl-silyloxy) | 8-(t-butyl-dimethyl-silyloxy) | 526.26 |
| 54 | —CH$_2$CH$_2$— | H | 4-(1-piperidinyl-ethoxy)-phenyl | 2-(t-butyl-dimethyl-silyloxy) | 8-(t-butyl-dimethyl-silyloxy) | 713.39 |
| 55 | —CH$_2$CH$_2$— | H | 4-(1-piperidinyl-ethoxy)-phenyl | 2-hydroxy | 8-hydroxy | 485.22 |
| 86 | —CH$_2$— | H | hydroxy | 2-(t-butyl-dimethyl-silyloxy) | 8-fluoro | 400.52 |
| 87 | —CH$_2$— | H | 4-(1-piperidinyl-ethoxy)-phenyl | 2-(t-butyl-dimethyl-silyloxy) | 8-fluoro | |

TABLE 2-continued

| ID No | Y | R¹ | R² | R³ | R⁴ | Calc. MW |
|---|---|---|---|---|---|---|
| 89 | —CH₂— | H | S*-4-(piperidinyl-ethoxy-phenyl | 2-t-butyl carbonyl-oxy | 8-hydroxy | 555.68 |
| 90 | —CH₂— | H | S*-4-(piperidinyl-ethoxy)-phenyl | 2-hydroxy | 8-t-butyl carbonyl-oxy | 555.68 |
| 91 | —CH₂— | H | R*-4-(piperidinyl-ethoxy)-phenyl | 2-t-butyl carbonyl-oxy | 8-hydroxy | 555.68 |
| 92 | —CH₂— | H | R*-4-(piperidinyl-ethoxy)-phenyl | 2-hydroxy | 8-t-butyl-carbonyloxy | 557.67 |
| 93 | —CH₂— | H | S*-4-(piperidinyl-ethoxy)-phenyl | 2-t-butyl carbonyl-oxy | 8-fluoro | 557.67 |
| 94 | —CH₂—CH₂—CH₂— | H | hydroxy | 2-(t-butyl-dimethyl-silyloxy) | 8-(t-butyl-dimethyl-silyloxy) | 540.85 |
| 95 | —CH₂—C(O)—CH₂— | H | 4-(piperidinyl-ethoxy)-phenyl | 2-(t-butyl-dimethyl-silyloxy) | 8-(t-butyl-dimethyl-silyloxy) | 742.12 |
| 96 | —CH₂—C(O)—CH₂— | H | 4-(piperidinyl-ethoxy)-phenyl | 2-hydroxy | 8-hydroxy | 513.6 |
| 97 | —CH₂—CH₂—CH₂— | H | 4-(piperidinyl-ethoxy)-phenyl | 2-hydroxy | 8-hydroxy | 499.61 |
| 98 | —CH₂— | H | carboxymethyl | 2-(t-butyl-dimethyl-silyloxy) | 8-(t-butyl-dimethyl-silyloxy) | 554.84 |
| 99 | —CH₂CH₂— | H | R*-4-(piperidinyl-ethoxy)-phenyl | 2-hydroxy | 8-hydroxy | 485.59 |
| 100 | —CH₂CH₂— | H | S*-4-(piperidinyl-ethoxy)-phenyl | 2-hydroxy | 8-hydroxy | 485.59 |
| 101 | —CH₂— | H | methoxy-carbonyl-methyl | 2-(t-butyl-dimethyl-silyloxy) | 8-(t-butyl-dimethyl-silyloxy) | 568.86 |
| 102 | —CH₂— | H | methoxy-carbonyl-methyl | 2-hydroxy | 8-hydroxy | 340.34 |
| 103 | —CH₂— | H | dimethylamino-n-propoxy-carbonyl-methyl | 2-hydroxy | 8-hydroxy | 411.46 |
| 104 | —CH₂— | H | dimethylamino-ethoxy-carbonyl-methyl | 2-hydroxy | 8-hydroxy | 397.43 |
| 105 | —CH₂— | H | pyrrolidinyl-ethoxy-carbonyl-methyl | 2-hydroxy | 8-hydroxy | 423.47 |
| 106 | —CH₂— | H | piperidinyl-ethoxy-carbonyl-methyl | 2-hydroxy | 8-hydroxy | 437.5 |
| 107 | —CH₂— | H | carboxy-methyl | 2-hydroxy | 8-hydroxy | 326.31 |
| 108 | —CH₂— | H | morpholinyl-ethyl-amino-carbonyl-methyl | 2-hydroxy | 8-hydroxy | 438.48 |
| 109 | —CH₂— | H | morpholinyl-ethoxy-carbonyl-methyl | 2-hydroxy | 8-hydroxy | 439.47 |
| 110 | —CH₂— | H | morpholinyl-n-propyl-amino-carbonyl-methyl | 2-hydroxy | 8-hydroxy | 452.51 |
| 111 | —CH₂— | H | pyrrolidinyl-ethyl-amino-carbonyl-methyl | 2-hydroxy | 8-hydroxy | 422.49 |
| 112 | —CH₂— | H | allyl | 2-hydroxy | 8-hydroxy | 308.34 |
| 113 | —CH₂— | H | 3-hydroxy-n-propyl | 2-hydroxy | 8-hydroxy | 326.35 |
| 114 | —CH₂— | H | allyl | 2-(t-butyl-dimethyl-silyloxy) | 8-(t-butyl-dimethyl-silyloxy) | 536.87 |

TABLE 2-continued

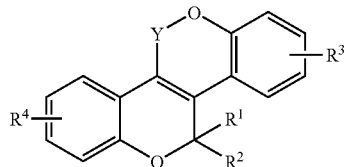

| ID No | Y | R¹ | R² | R³ | R⁴ | Calc. MW |
|---|---|---|---|---|---|---|
| 115 | —CH₂— | H | (4-(4-fluorophenyl)-piperazinyl)-carbonyl-methyl | 2-hydroxy | 8-hydroxy | 488.52 |
| 116 | —CH₂— | H | (4-(2-pyridyl)-piperazinyl)-carbonyl-methyl | 2-hydroxy | 8-hydroxy | 471.52 |
| 117 | —CH₂— | H | 4-(piperidinyl-ethoxy)-phenyl-carbonyl | 2-hydroxy | 8-hydroxy | 499.57 |
| 119 | —CH₂— | H | 3-hydroxy-n-propyl | 2-(t-butyl-dimethyl-silyloxy) | 8-(t-butyl-dimethyl-silyloxy) | 554.88 |
| 120 | —CH₂— | H | carboxy-methyl | 2-(t-butyl-dimethyl-silyloxy) | 8-(t-butyl-dimethyl-silyloxy) | 554.84 |
| 121 | —CH₂— | H | isopropoxy-carbonyl-methyl | 2-hydroxy | 8-hydroxy | 368.39 |
| 122 | —CH₂— | H | 2-hydroxy-ethyl | 2-hydroxy | 8-hydroxy | 312.33 |
| 123 | —CH₂— | H | 2-hydroxy-2-(4-piperidinyl-ethoxy-phenyl)-ethyl | 2-hydroxy | 8-hydroxy | 515.61 |
| 124 | —CH₂— | H | 4-(piperidinyl-ethoxy)-phenyl | — | 8-hydroxy | 455.56 |
| 125 | —CH₂—CH₂—CH₂— | H | R*-4-(piperidinyl-ethoxy)-phenyl | 2-hydroxy | 8-hydroxy | 499.61 |
| 126 | —CH₂—CH₂—CH₂— | H | S*-4-(piperidinyl-ethoxy)-phenyl | 2-hydroxy | 8-hydroxy | 499.61 |
| 127 | —CH₂— | H | R*-4-(piperidinyl-ethoxy)-phenyl | — | 8-hydroxy | 455.56 |
| 128 | —CH₂— | H | S*-4-(piperidinyl-ethoxy)-phenyl | — | 8-hydroxy | 455.56 |
| 129 | —CH₂CH₂— | H | R*-4-(piperidinyl-ethoxy)-phenyl | 2-hydroxy | 8-fluoro | 487.58 |
| 130 | —CH₂CH₂— | H | S*-4-(piperidinyl-ethoxy)-phenyl | 2-hydroxy | 8-fluoro | 487.58 |
| 131 | —CH₂CH₂— | H | R*-4-(piperidinyl-ethoxy)-phenyl | — | 8-hydroxy | 469.59 |
| 132 | —CH₂CH₂— | H | S*-4-(piperidinyl-ethoxy)-phenyl | — | 8-hydroxy | 469.59 |
| 133 | —CH₂— | H | 4-(piperidinyl-ethoxy)-phenyl | 2-hydroxy | — | 455.56 |
| 134 | —CH₂— | H | 4-(piperidinyl-ethoxy)-phenyl | 2-t-butyl-carbonyl-oxy | — | 539.68 |
| 135 | —CH₂— | H | hydroxy | 2-(t-butyl-dimethyl-silyloxy) | — | 382.54 |
| 136 | —CH₂— | H | hydroxy | — | — | 252.27 |
| 137 | —CH₂— | H | 4-(piperidinyl-ethoxy)-phenyl | — | — | 439.56 |
| 138 | —CH₂CH₂— | H | hydroxy | — | 8-(t-butyl-dimethyl-silyloxy) | 396.56 |
| 139 | —CH₂CH₂— | H | hydroxy | 2-(t-butyl-dimethyl-silyloxy) | — | 396.56 |
| 140 | —CH₂CH₂— | H | 4-(piperidinyl-ethoxy)-phenyl | 2-hydroxy | — | 469.59 |
| 141 | —CH₂CH₂— | H | 4-(azepanyl-ethoxy-phenyl) | 2-hydroxy | — | 483.61 |
| 142 | —CH₂CH₂— | H | 4-(dimethyl-amino-ethoxy-phenyl) | 2-hydroxy | — | 429.52 |
| 143 | —CH₂CH₂— | H | 4-(azepanyl-ethoxy-phenyl) | — | 8-hydroxy | 483.61 |

TABLE 2-continued

| ID No | Y | R¹ | R² | R³ | R⁴ | Calc. MW |
|---|---|---|---|---|---|---|
| 144 | —CH₂CH₂— | H | 4-(dimethyl-amino-ethoxy-phenyl) | — | 8-hydroxy | 429.52 |
| 145 | —CH₂— | H | R*-4-(dimethyl-amino-ethoxy-phenyl) | — | 8-hydroxy | 415.49 |
| 146 | —CH₂CH₂— | H | S*-4-(piperidinyl-ethoxy)-phenyl | — | — | 469.59 |
| 147 | —CH₂CH₂— | H | R*-4-(dimethyl-amino-ethoxy-phenyl) | — | 8-hydroxy | 429.52 |
| 148 | —CH₂CH₂— | H | R*-4-(piperidinyl-ethoxy)-phenyl | — | — | 469.59 |
| 149 | —CH₂CH₂— | H | S*-4-(dimethyl-amino-ethoxy-phenyl) | — | 8-hydroxy | 429.52 |
| 150 | —CH₂CH₂— | H | S*-4-(dimethyl-amino-ethoxy-phenyl) | 2-hydroxy | — | 429.52 |
| 151 | —CH₂CH₂— | H | R*-4-(dimethyl-amino-ethoxy-phenyl) | 2-hydroxy | — | 429.52 |
| 152 | —CH₂CH₂— | H | S*-4-(azepanyl-ethoxy-phenyl) | 2-hydroxy | — | 483.61 |
| 153 | —CH₂CH₂— | H | R*-4-(azepanyl-ethoxy-phenyl) | 2-hydroxy | — | 483.61 |
| 154 | —CH₂CH₂— | H | S*-4-(azepanyl-ethoxy-phenyl) | — | 8-hydroxy | 483.61 |
| 155 | —CH₂CH₂— | H | R*-4-(azepanyl-ethoxy-phenyl) | — | 8-hydroxy | 483.61 |
| 156 | —CH₂CH₂— | H | S*-4-(piperidinyl-ethoxy)-phenyl | 2-methoxy | 8-methoxy | 513.64 |
| 157 | —CH₂CH₂— | H | R*-4-(piperidinyl-ethoxy)-phenyl | 2-methoxy | 8-methoxy | 513.64 |
| 158 | —CH₂— | H | 4-(piperidinyl-ethoxy)-phenyl | 2-(t-butyl-dimethyl-silyloxy) | — | 569.82 |
| 159 | —CH₂CH₂— | H | 4-(azepanyl-ethoxy-phenyl) | 2-hydroxy | 8-hydroxy | 499.61 |
| 160 | —CH₂CH₂— | H | 4-(diisopropyl-amino-ethoxy-phenyl) | 2-hydroxy | 8-hydroxy | 501.63 |
| 161 | —CH₂CH₂— | H | 4-(dimethyl-amino-ethoxy-phenyl) | 2-hydroxy | 8-hydroxy | 445.52 |
| 162 | —CH(OCH₃)— | H | 4-(piperidinyl-ethoxy)-phenyl | 2-(t-butyl-dimethyl-silyloxy) | 8-(t-butyl-dimethyl-silyloxy) | 730.11 |
| 163 | —CH₂CH₂— | H | R*-4-(dimethyl-amino-ethoxy-phenyl) | 2-hydroxy | 8-hydroxy | 445.52 |
| 164 | —CH₂CH₂— | H | S*-4-(dimethyl-amino-ethoxy-phenyl) | 2-hydroxy | 8-hydroxy | 445.52 |
| 165 | —CH₂CH₂— | H | R*-4-(azepanyl-ethoxy-phenyl) | 2-hydroxy | 8-hydroxy | 499.61 |
| 166 | —CH₂CH₂— | H | S*-4-(azepanyl-ethoxy-phenyl) | 2-hydroxy | 8-hydroxy | 499.61 |
| 167 | —CH₂CH₂— | H | R*-4-(diisopropyl-amino-ethoxy-phenyl) | 2-hydroxy | 8-hydroxy | 501.63 |
| 168 | —CH₂CH₂— | H | S*-4-(diisopropyl-amino-ethoxy-phenyl) | 2-hydroxy | 8-hydroxy | 501.63 |

TABLE 2-continued

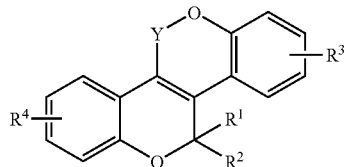

| ID No | Y | R¹ | R² | R³ | R⁴ | Calc. MW |
|---|---|---|---|---|---|---|
| 169 | —CH₂— | H | S*-4-(piperidinyl-ethoxy)-phenyl | — | — | 439.56 |
| 170 | —CH₂— | H | R*-4-(piperidinyl-ethoxy)-phenyl | — | — | 439.56 |
| 171 | —CH₂— | H | S*-4-(piperidinyl-ethoxy)-phenyl | 2-t-butyl carbonyl-oxy | — | 539.68 |
| 172 | —CH₂— | H | R*-4-(piperidinyl-ethoxy)-phenyl | 2-t-butyl carbonyl-oxy | — | 539.68 |
| 173 | —CH₂— | H | R*-4-(piperidinyl-ethoxy)-phenyl | 2-methoxy | 8-methoxy | 499.61 |
| 174 | —CH₂CH₂— | H | 4-(azepanyl-ethoxy-phenyl) | 2-hydroxy | 8-fluoro | 501.6 |
| 175 | —CH₂— | H | R*-4-(piperidinyl-ethoxy)-phenyll | 2-methoxy | 8-t-butyl carbonyl-oxy | 569.7 |
| 176 | —CH₂— | H | R*-4-(piperidinyl-ethoxy)-phenyl | 2-methoxy | 8-hydroxy | 485.59 |
| 177 | —CH₂CH₂— | H | S*-4-(azepanyl-ethoxy-phenyl) | 2-hydroxy | 8-fluoro | 501.6 |
| 178 | —CH₂CH₂— | H | R*-4-(azepanyl-ethoxy-phenyl) | 2-hydroxy | 8-fluoro | 501.6 |
| 179 | —CH₂CH₂— | H | R*-4-(piperidinyl-ethoxy)-phenyl | 2-t-butyl carbonyl-oxy | 8-t-butyl carbonyl-oxy | 653.82 |
| 180 | —CH₂CH₂— | H | S*-4-(piperidinyl-ethoxy)-phenyl | 2-t-butyl carbonyl-oxy | 8-t-butyl carbonyl-oxy | 653.82 |
| 181 | —CH₂— | H | R*-4-(piperidinyl-ethoxy)-phenyl | 8-hydroxy | 8-methoxy | 485.59 |
| 182 | —CH₂CH₂— | H | 4-(t-butyl-dimethyl-silyloxy-ethoxy)-phenyl | 2-t-butyl-dimethyl-silyloxy | 8-t-butyl-dimethyl-silyloxy | 775.27 |
| 183 | —CH₂CH₂— | H | 4-(3-hydroxy-n-propoxy)-phenyl | 2-hydroxy | 8-hydroxy | 432.48 |
| 184 | —CH₂CH₂— | H | 4-(2-hydrox-ethoxy)-phenyl | 2-hydroxy | 8-hydroxy | 418.45 |
| 185 | —CH₂CH₂— | H | hydroxy | 2-t-butyl-dimethyl-silyloxy | 9-methyl | 410.59 |
| 186 | —CH₂CH₂— | H | 4-(2-hydroxy-ethoxy)-phenyl | 2-t-butyl-dimethyl-silyloxy | 8-t-butyl-dimethyl-silyloxy | 646.98 |
| 187 | —CH₂CH₂— | H | 4-(formyl-methoxy)-phenyl | 2-t-butyl-dimethyl-silyloxy | 8-t-butyl-dimethyl-silyloxy | 644.96 |
| 188 | —CH₂CH₂— | H | 4-(carboxy-methoxy)-phenyl | 2-t-butyl-dimethyl-silyloxy | 8-t-butyl-dimethyl-silyloxy | 660.96 |
| 189 | —CH₂CH₂— | H | 4-(methoxy-carbonyl-methoxy)- | 2-t-butyl-dimethyl-silyloxy | 8-t-butyl-dimethyl-silyloxy | 674.99 |
| 190 | —CH₂CH₂— | H | 4-(methoxy-carbonyl-methoxy)-phenyl | 2-hydroxy | 8-hydroxy | 446.46 |
| 191 | —CH₂CH₂— | H | 4-(3-hydrox-n-propoxy)-phenyl | 2-(t-butyl-dimethyl-silyloxy) | 8-(t-butyl-dimethyl-silyloxy) | 661.01 |
| 192 | —CH₂— | H | 4-(piperidinyl-ethoxy)-phenyl | 2-methoxy | 8-methoxy | 499.61 |
| 193 | —CH₂CH₂— | H | 4-(formyl-methoxy)-phenyl | 2-t-butyl-dimethyl-silyloxy | 8-t-butyl-dimethyl-silyloxy | 658.99 |

TABLE 2-continued

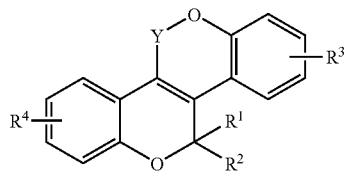

| ID No | Y | R¹ | R² | R³ | R⁴ | Calc. MW |
|---|---|---|---|---|---|---|
| 194 | —CH₂CH₂— | H | 4-(2-carboxy-ethoxy)-phenyl | 2-t-butyl-dimethyl-silyloxy | 8-t-butyl-dimethyl-silyloxy | 674.99 |
| 195 | —CH₂CH₂— | H | R-4-(piperidinyl-ethoxy)-phenyl | 2-methoxy | 8-hydroxy | 499.61 |
| 196 | —CH₂CH₂— | H | R-4-(piperidinyl-ethoxy)-phenyl | 2-hydroxy | 8-methoxy | 499.61 |
| 197 | —CH₂CH₂— | H | 4-(2-methoxy-carbonyl-ethoxy)-phenyl | 2-t-butyl-dimethyl-silyloxy | 8-t-butyl-dimethyl-silyloxy | 689.02 |
| 198 | —CH₂CH₂— | H | 4-(2-carboxy-ethoxy)-phenyl | 2-hydroxy | 8-hydroxy | 446.46 |
| 199 | —CH₂CH₂— | H | 4-(2-methoxy-carbonyl-ethoxy)-phenyl | 2-hydroxy | 8-hydroxy | 460.49 |
| 200 | —CH₂CH₂— | H | S*-4-(2-hydroxy-ethoxy)-phenyl | 2-t-butyl-dimethyl-silyloxy | 8-t-butyl-dimethyl-silyloxy | 646.98 |
| 201 | —CH₂CH₂— | H | R*-4-(2-hydroxy-ethoxy)-phenyl | 2-t-butyl-dimethyl-silyloxy | 8-t-butyl-dimethyl-silyloxy | 646.98 |
| 202 | —CH₂CH₂— | H | S*-4-(3-hydroxy-n-propoxy)-phenyl | 2-t-butyl-dimethyl-silyloxy | 8-t-butyl-dimethyl-silyloxy | 661.01 |
| 203 | —CH₂CH₂— | H | R*-4-(3-hydroxy-n-propoxy)-phenyl | 2-t-butyl-dimethyl-silyloxy | 8-t-butyl-dimethyl-silyloxy | 661.01 |
| 204 | —CH₂CH₂— | H | R*-4-(piperidinyl-2,6-dione-ethoxy)-phenyl | 2-t-butyl-dimethyl-silyloxy | 8-t-butyl-dimethyl-silyloxy | 742.08 |
| 205 | —CH₂CH₂— | H | hydroxy | 2-t-butyl-dimethyl-silyloxy | 8-fluoro | 414.55 |
| 206 | —CH₂CH₂— | H | hydroxy | 2-t-butyl-dimethyl-silyloxy | — | 396.56 |
| 207 | —CH₂CH₂— | H | hydroxy | 2-t-butyl-dimethyl-silyloxy | 9-methyl | 410.59 |
| 208 | —CH₂CH₂— | H | hydroxy | — | 8-t-butyl-dimethyl-silyloxy | 396.56 |
| 209 | —CH₂— | H | hydroxy | — | 8-t-butyl-dimethyl-silyloxy | 382.54 |
| 276 | —CH₂CH₂— | H | 4-(piperidinyl-ethoxy)-phenyl | 2-hydroxy | 8-hydroxy | 483.61 |
| 277 | —CH₂CH₂— | H | S*-4-(pyrrolidinyl-2,5-dione-ethoxy)-phenyl | 2-hydroxy | 8-hydroxy | 499.53 |
| 278 | —CH₂CH₂— | H | R*-4-(pyrrolidinyl-2,5-dione-ethoxy)-phenyl | 2-hydroxy | 8-hydroxy | 499.53 |
| 279 | —CH₂CH₂— | H | R*-4-(pyrrolidinyl-2,5-dione-n-propoxy)-phenyl | 2-hydroxy | 8-hydroxy | 513.55 |
| 280 | —CH₂CH₂— | H | S*-4-(pyrrolidinyl-2,5-dione-n-propoxy)-phenyl | 2-hydroxy | 8-hydroxy | 513.55 |
| 281 | —CH₂CH₂— | H | R*-4-(methoxy-ethoxy)-phenyl | 2-hydroxy | 8-hydroxy | 432.48 |
| 282 | —CH₂CH₂CH₂— | H | 4-(piperidinyl-ethoxy)-phenyl | 2-(t-butyl-dimethyl-silyloxy) | 8-(t-butyl-dimethyl-silyloxy) | |

TABLE 2-continued

| ID No | Y | R¹ | R² | R³ | R⁴ | Calc. MW |
|---|---|---|---|---|---|---|
| 283 | —CH₂CH₂— | H | 4-(piperidinyl-ethoxy)-phenyl | 2-hydroxy | 9-methyl | |
| 286 | —CH₂CH₂— | H | hydroxy | 2-(t-butyl-dimethyl-silyloxy) | 8-fluoro | |

The symbol "—" indicates that no R³ or R⁴ substituent was present.

TABLE 3

| ID No | Y(*) | R³ | R⁴ | Calc MW |
|---|---|---|---|---|
| 56 | —CH₂CH₂— | 2-hydroxy | 8-hydroxy | 296.27 |
| 57 | —CH₂CH₂— | 2-(t-butyl-dimethyl-silyloxy) | 8-(t-butyl-dimethyl-silyloxy) | 524.24 |
| 58 | —CH₂—C(O)— | 2-hydroxy | 8-hydroxy | 310.26 |
| 59 | —CH₂—C(O)— | 2-(t-butyl-dimethyl-silyloxy) | 8-(t-butyl-dimethyl-silyloxy) | 538.78 |
| 211 | —CH₂—C(O)—CH₂— | 2-hydroxy | 8-hydroxy | 324.29 |
| 212 | —CH₂—C(O)—CH₂— | 2-(t-butyl-dimethyl-silyloxy) | 8-(t-butyl-dimethyl-silyloxy) | 552.82 |
| 214 | —CH₂CH₂CH₂— | 2-(t-butyl-dimethyl-silyloxy) | 8-(t-butyl-dimethyl-silyloxy) | 538.84 |
| 215 | —CH₂CH₂CH₂— | 2-hydroxy | 8-hydroxy | 310.31 |
| 216 | —CH₂—CH(OH)—CH₂— | 2-(t-butyl-dimethyl-silyloxy) | 8-(t-butyl-dimethyl-silyloxy) | 554.84 |
| 218 | —CH₂— | 2-hydroxy | — | 266.26 |
| 219 | —CH₂— | 2-(t-butyl-dimethyl-silyloxy) | — | 380.52 |
| 220 | —CH₂CH₂— | — | 8-(t-butyl-dimethyl-silyloxy) | 394.55 |
| 221 | —CH₂CH₂— | 2-(t-butyl-dimethyl-silyloxy) | — | 394.55 |
| 222 | —CH₂— | 2-methyl-carbonyl-oxy | 8-methyl-carbonyl-oxy | 366.33 |
| 223 | —CH₂CH₂— | — | 8-hydroxy | 280.28 |
| 224 | —CH₂CH₂— | 2-hydroxy | 9-methyl | 294.31 |
| 225 | —CH₂CH₂— | 2-hydroxy | — | 280.28 |
| 226 | —CH₂CH₂— | 2-hydroxy | 8-fluoro | 298.27 |
| 227 | —CH₂CH₂— | 2-t-butyl-dimethyl-silyloxy | 8-fluoro | 412.54 |
| 228 | —CH₂CH₂— | 2-t-butyl-dimethyl-silyloxy | 9-methyl | 408.57 |
| 287 | —CH₂CH₂— | 2-hydroxy | 9-methyl | |
| 288 | —CH₂CH₂— | 2-(t-butyl-dimethyl-silyloxy) | 8-fluoro | |

(*)Within the table, the Y group is defined as it fits into the structure. Thus when Y is —CH₂—C(O)— the —CH₂ is bound to the B ring and the C(O)— is bound to the O.
The symbol "—" indicates that no R³ or R⁴ substituent was present.

Representative examples of intermediates in the preparation of the compounds of formula (I) are as listed in Table 4 and 5, below.

TABLE 4

| ID No | R12 | (R13)n | D | R11 | Calc MW |
|---|---|---|---|---|---|
| 60 | 8-Benzyloxy | 2-Benzyloxy | Benzoyl | —CH(OH)-phenyl | 702.71 |
| 61 | 8-hydroxy | 2-hydroxy | H | —CH(OH)-phenyl | 390.38 |
| 62 | 8-hydroxy | 2-hydroxy | H | —CH$_2$OH | 314.29 |
| 63 | 8-(2-SEMoxy) | 2-(2-SEMoxy) | SEM | —CH(OH)-phenyl | 781.17 |
| 64 | 8-(2-SEMoxy) | 2-(2-SEMoxy) | SEM | —CH(OH)-CH$_2$CH$_2$CH$_3$ | 747.16 |
| 65 | 8-Benzoyl-oxy | 2-Benzyloxy | Benzoyl | —C(O)-phenyl | 596.58 |
| 66 | 8-(2-SEMoxy) | 2-(2-SEMoxy) | SEM | —CH$_2$OH | 705.07 |
| 67 | 8-MOMoxy | 2-MOMoxy | MOM | —CHO | 444.43 |
| 68 | 8-MOMoxy | 2-MOMoxy | MOM | —CH$_2$OH | 446.44 |
| 69 | 8-(2-SEMoxy) | 2-(2-SEMoxy) | SEM | —C(O)OCH$_3$ | 733.08 |
| 70 | 8-(2-SEMoxy) | 2-(2-SEMoxy) | SEM | —C(O)O-phenyl | 796.15 |
| 71 | 8-hydroxy | 2-hydroxy | H | —C(O)O-phenyl | 404.37 |
| 72 | 8-(2-SEMoxy) | 2-(2-SEMoxy) | SEM | —CHO | 703.06 |
| 73 | 8-Methoxy | 2-Methoxy | methyl | H | 326.34 |
| 74 | 8-Methoxy | 2-Methoxy | methyl | Br | 405.24 |
| 75 | 8-(2-SEMoxy) | 2-(2-SEMoxy) | SEM | H | 675.05 |
| 76 | 8-(2-SEMoxy) | 2-(2-SEMoxy) | SEM | Br | 753.94 |
| 77 | 8-hydroxy | 2-hydroxy | H | Br | 363.16 |
| 78 | 8-MOMoxy | 2-MOMoxy | MOM | H | 416.42 |
| 79 | 8-MOMoxy | 2-MOMoxy | MOM | Br | 495.32 |
| 80 | 8-Benzyloxy | 2-Benzyloxy | Benzoyl | H | 596.58 |
| 81 | 8-Pivaloyloxy | 2-Pivaloyloxy | Pivaloyl | H | 536.61 |
| 82 | 8-hydroxy | 2-hydroxy | H | H | 284.07 |
| 83 | 8-Benzyloxy | 2-Benzyloxy | Benzyl | Br | 674.06 |
| 229 | 2-trimethylsilyl-ethoxy-methoxy | 8-trimethylsilyl-ethoxy-methoxy | trimethylsilyl-ethoxy-methyl | iodomethyl | 814.99 |
| 230 | 2-trimethylsilyl-ethoxy-methoxy | 8-trimethylsilyl-ethoxy-methoxy | trimethylsilyl-ethoxy-methyl | chloromethyl | 723.53 |
| 231 | 2-hydroxy | 8-hydroxy | H | chloromethyl | 332.74 |
| 232 | 2-hydroxy | 8-hydroxy | H | iodomethyl | 424.19 |
| 233 | 2-trimethylsilyl-ethoxy-methoxy | 8-trimethylsilyl-ethoxy-methoxy | trimethylsilyl-ethoxy-methyl | phenoxy-carbonyl | 797.19 |
| 234 | 2-hydroxy | 8-hydroxy | H | chloromethyl-carbonyl | 360.75 |
| 236 | 2-hydroxy | 8-hydroxy | H | 1-phenyl-1-hydroxy-methyl | 392.41 |
| 237 | 2-methoxy-methoxy | 8-methoxy-methoxy | methoxy-methyl | chloromethyl-carbonyl | 492.91 |
| 238 | 2-trimethylsilyl-ethoxy-methoxy | 8-trimethylsilyl-ethoxy-methoxy | trimethylsilyl-ethoxy-methyl | chloromethyl-carbonyl | 751.55 |
| 239 | 2-methoxy | — | methyl | H | 296.33 |
| 240 | 2-methoxy | — | methyl | bromo | 375.22 |
| 241 | — | — | methyl | H | 266.3 |
| 242 | 2-methoxy | 8,10-dimethoxy | methyl | bromo | 435.27 |
| 243 | — | — | methyl | bromo | 345.2 |
| 244 | — | — | H | bromo | 331.17 |
| 247 | 2-methoxy | 7-methoxy | methyl | H | 326.35 |
| 248 | 2-methoxy | 8-methoxy | methyl | chloromethyl-carbonyl | 402.83 |
| 251 | — | — | methyl | 4-methoxy-phenyl | 372.42 |

TABLE 4-continued

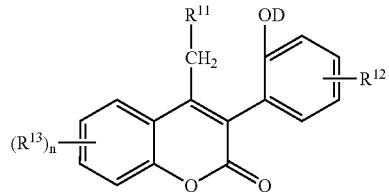

| ID No | $R^{12}$ | $(R^{13})_n$ | D | $R^{11}$ | Calc MW |
|---|---|---|---|---|---|
| 252 | — | — | H | 4-hydroxy-phenyl | 344.37 |
| 254 | — | — | methyl-carbonyl | bromo and 4-methoxy-carbonyl-phenyl | 507.34 |
| 255 | 2-methoxy | 8-methoxy | methyl | methoxy-methyl-carbonyl | 398.42 |
| 256 | 2-trimethylsilyl-ethoxy-methoxy | 8-trimethylsilyl-ethoxy-methoxy | trimethylsilyl-ethoxy-methyl | trimethylsilyl-ethoxy-methyl | 805.33 |
| 257 | 2-methoxy-methoxy | 8-methoxy-methoxy | methoxy-methyl | trimethylsilyl-ethoxy-methyl | 546.7 |
| 258 | 2-methoxy | 8-methoxy | methyl | trimethylsilyl-ethoxy-methyl | 456.62 |
| 259 | 2-methoxy | — | methyl | trimethylsilyl-ethoxy-methyl | 426.59 |
| 260 | 2-methoxy | — | methyl | methoxy-methyl | 340.38 |
| 261 | — | 8-methoxy | methyl | methoxy-methyl | 340.38 |
| 262 | — | 8-methoxy | methyl | trimethylsilyl-ethoxy-methyl | 426.59 |
| 263 | — | 8-fluoro | methyl | trimethylsilyl-ethoxy-methyl | 414.55 |
| 264 | 2-methoxy | 8-fluoro | methyl | trimethylsilyl-ethoxy-methyl | 444.58 |
| 265 | 2-methoxy | 8-fluoro | methyl | methoxy-methyl | 358.37 |
| 266 | 2-methoxy | 9-methyl | methyl | methoxy-methyl | 354.41 |
| 267 | 2-methoxy | 9-methyl | methyl | trimethylsilyl-ethoxy-methyl | 440.62 |
| 268 | 2-hydroxy | 9-methyl | H | hydroxy-methyl | 312.33 |
| 269 | 2-hydroxy | — | H | hydroxy-methyl | 298.3 |
| 270 | 2-hydroxy | 8-fluoro | H | hydroxy-methyl | 316.29 |
| 271 | — | 8-hydroxy | H | hydroxy-methyl | 298.3 |
| 284 | — | 8-fluoro | methyl | H | |
| 285 | 2-methoxy | 8,10-dimethoxy | H | H | |
| 289 | — | 8-methoxy | methyl | H | |
| 290 | — | 9-methyl | methyl | H | |

The symbol "—" indicates that no $R^{12}$ or $R^{13}$ substituent was present.

TABLE 5

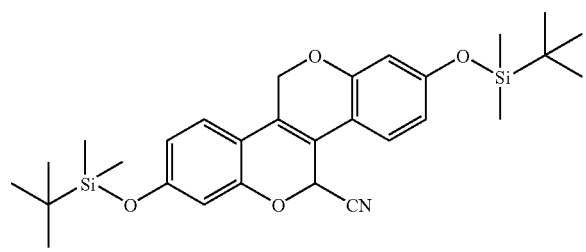

| ID No | R³ | R⁴ | Y | T | Calc MW |
|---|---|---|---|---|---|
| 249 | 2-(t-butyl-dimethyl-silyloxy) | 8-(t-butyl-dimethyl-silyloxy) | —CH₂CH₂— | 4-(hydroxy-n-propoxy)-phenyl | 679.02 |
| 245 | 2-(t-butyl-dimethyl-silyloxy) | 8-(t-butyl-dimethyl-silyloxy) | —CH₂CH₂— | 4-(piperidinyl-ethoxy)-phenyl | 587.84 |
| 246 | — | — | —CH₂— | 4-(piperidinyl-ethoxy)-phenyl | 457.57 |
| 235 | 2-(t-butyl-dimethyl-silyloxy) | 8-(t-butyl-dimethyl-silyloxy) | —CH₂CH₂— | 4-(piperidinyl-ethoxy)-phenyl | 732.13 |
| 291 | 2-(t-butyl-dimethyl-silyloxy) | 8-(t-butyl-dimethyl-silyloxy) | —CH₂CH₂CH₂— | 4-(piperidinyl-ethoxy)-phenyl | |

The symbol "—" indicates that no R³ or R⁴ substituent was present.

Additional compounds prepared as intermediates in the synthesis of the compounds of the present invention, include the following:

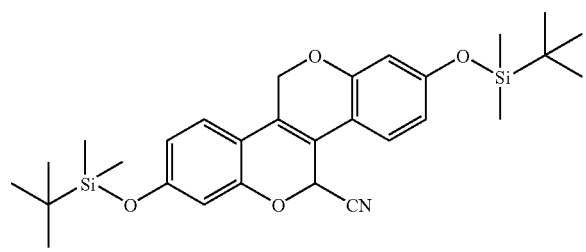

also known as 2,8-bis-(tert-butyl-dimethyl-silyloxy)-5,11-dihydro-chromeno[4,3-c]chromene-5-carbonitrile;

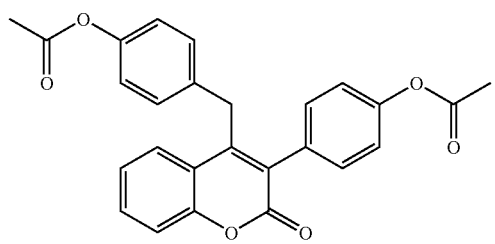

also known as acetic acid 4-[4-(4-acetoxy-benzyl)-2-oxo-2H-chromen-3-yl]-phenyl ester;

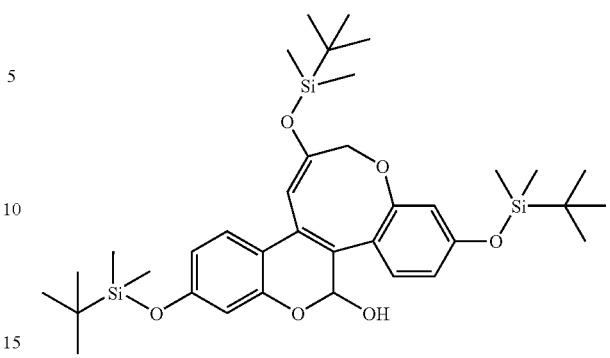

also known as 2,6,12-tris[[(1,1-dimethylethyl)dimethylsilyl]oxy]-3,9-dihydro-[1]benzopyrano[4,3-e][1]benzoxocin-9-ol;

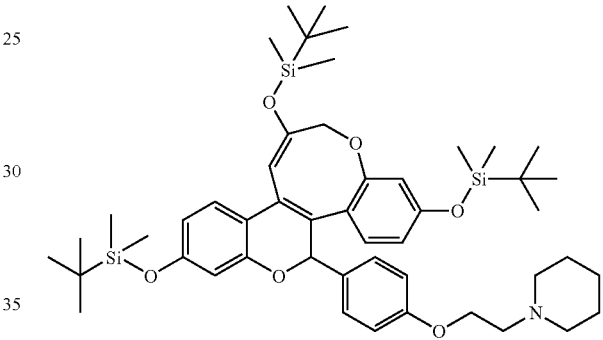

also known as 1-[2-[4-[2,6,12-tris[[(1,1-dimethylethyl)dimethylsilyl]oxy]-3,9-dihydro[1]benzopyrano[4,3-e][1]benzoxocin-9-yl]phenoxy]ethyl]-piperidine; tetrahydro-9-oxo[1]benzopyrano[4,3-e][1 benzoxocin-2-yl] 0-phenyl ester

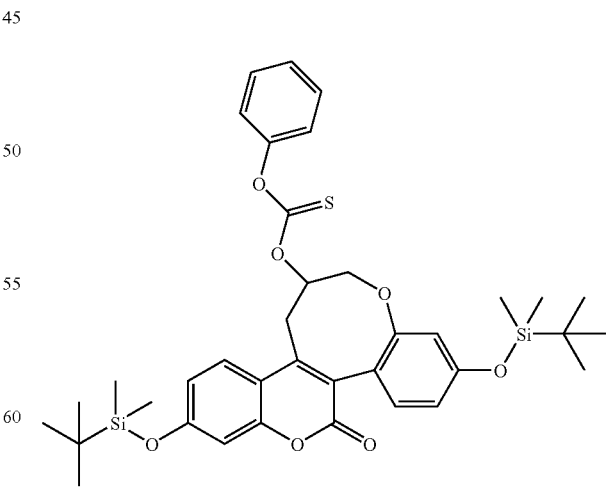

also known as O-[6,12-bis[[(1,1-dimethylethyl)dimethyl-silyl]oxy]-1,2,3,9-tetrahydro-9-oxo[1]benzopyrano[4,3-e][1]benzoxocin-2-yl] O-phenyl ester carbonothioic acid;

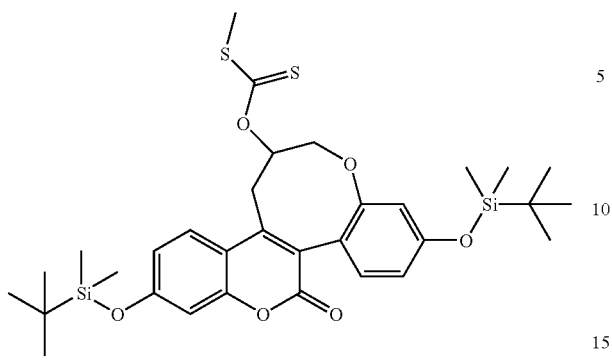

also known as O-[6,12-bis[[(1,1-dimethylethyl)dimethyl-silylloxy]-1,2,3,9-tetrahydro-9-oxo[1]benzopyrano[4,3-e][1]benzoxocin-2-yl] S-methyl ester carbonodithioic acid;

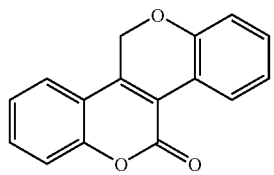

also known as 11H-chromeno[4,3-c]chromen-5-one; and

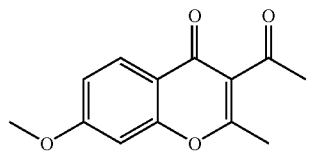

also known as 3-acetyl-7-methoxy-2-methyl-chromen-4-one.

EXAMPLE 172

Estrogen Receptor α Flash Plate Assay

This assay monitors binding of radiolabeled estrogen to the estrogen receptor. It is performed on a BioMek 2000 (Beckman). Plates are read in a scintillation counter (Packard TopCount), with decreased counts an indication of binding of a compound to the receptor. The assay was run according to the procedure described by Allan, et al., *Anal. Biochem.* (1999), 275(2), 243-247.

On day one, 100 µL of Estrogen Screening Buffer (ESB, Panvera) containing 5 mM dithiothreitol (DTT, Panvera), 0.5 µg mouse anti-estrogen receptor monoclonal antibody (SRA-1010, Stressgen) and 50 ng purified human estrogen receptor α (Panvera) were added to each well of a 96 well FlashPlate Plus plate crosslinked with goat anti-mouse antibodies (NEN Life Sciences). The plate was sealed and incubated at 40° C. overnight.

On day two, each well was washed three times with 200 µL PBS, pH 7.2, at room temperature. To each well was then added 98 µL radiolabeled estrogen (0.5 nM, which equals 6 nCi for a 120 Ci/mmol batch, Amersham), diluted in ESB and 5 mM dithiothreitol (DTT). To individual wells were then added 2.5 µL test compound diluted in 30% (v/v) dimethyl sulfoxide/50 mM HEPES, pH 7.5. The wells were mixed three times by aspiration, the plate sealed and incubated at room temperature for one hour. The wells were then counted for 1 min in a TopCount scintillation counter (Packard).

EXAMPLE 173

Estrogen Receptor β Fluorescence Polarization Assay

This assay monitors binding of a fluorescent analog of estrogen (Fluormone ES2, Panvera) to the estrogen receptor. Plates are read in a fluorometer that can be set to polarization mode. A decrease in fluorescence relative to vehicle control is an indication of binding of a compound to the receptor.

It is crucial to avoid introduction of air bubbles into the reaction in each well of the 96 well plate throughout this procedure. (Bubbles on the surface of the reaction disrupt light flow, affecting the polarization reading.) However, it is also crucial to effectively mix the reaction components upon addition to the well.

On ice, a 2× standard mixture of Assay Buffer (Panvera), 10 nM DTT and 40 nM ES2 was prepared. On ice, a 2× reaction mixture of Assay Buffer (Panvera), and 20 nM hER-β (Panvera) and 40 nM ES2 was also prepared.

Dilutions of test compound were prepared in 30% (v/v) dimethyl sulfoxide/50 mM HEPES, pH 7.5. At this point, the dilutions were 40× the final required concentration.

The standard mixture at 50 µL was then added to each well. The reaction mixture at 48 µL was added to all wells. The compound dilution at 2.5 µL was added to the appropriate wells. The reaction mixtures were mixed using a manual pipette, a roll of aluminum foil adhesive cover was placed on the plate and the plate incubated at room temperature for 1 hour.

Each well on the plate was then read in an LjL Analyst with an excitation wavelength of 265 nm and an emission wavelength of 538.

Representative compound of the present invention were tested according to the procedure described above for binding to the Estrogen Receptor α and Estrogen Receptor β, with results as listed in Table 6.

TABLE 6

| ID No | Estrogen Receptor α in µM (No.) | Estrogen Receptor β in µM (No.) |
|---|---|---|
| 1 | 0.505 (4) | 0.061 |
| 2 | >10K (4) | >10K (4) |
| 6 | 0.013 (2) | 0.016 (4) |
| 9 | .0023 (2) | 0.084 (2) |
| 11 | 0.009 (2) | 0.7 (6) |
| 13 | 0.006 (2) | 0.026 (2) |
| 14 | 0.0074 (4) | 0.15 (4) |
| 15 | 0.017 (4), 0.0064 | 0.017 (4), 0.028 |
| 17 | 0.0014 (2) | 0.031 (2) |
| 19 | 0.0019 (2) | 0.099 (2) |
| 21 | 0.015 (2) | 0.011 (2) |
| 22 | 3.45 (2) | >10K (2) |
| 24 | 5.95 (4) | >10K (2) |
| 25 | 1.2 (2) | >10K (2) |
| 26 | 0.014 (5) | 0.02 (4) |
| 27 | 0.69 (2) | >10K (2) |
| 28 | 0.14 (2) | 6.25 (2) |
| 29 | 0.004 (4) | 0.017 (4) |
| 30 | >10K (4) | >10K (4) |
| 33 | NA | NA |
| 41 | 1.9 (2) | >10K (2) |

TABLE 6-continued

| ID No | Estrogen Receptor α in μM (No.) | Estrogen Receptor β in μM (No.) |
|---|---|---|
| 43 | 0.62 (2) | 0.165 (2) |
| 89 | >1.00 | >1000 |
| 90 | 0.0066 | 90 |
| 99 | 0.0039 | 10 |
| 100 | 0.0026 | 20 |
| 125 | 0.079 | 28 |
| 126 | 0.0042 | 30 |
| 131 | 0.061 | 220 |
| 132 | 0.0048 | 66 |
| 146 | 0.0062 | 99 |
| 147 | 0.180 | 190 |
| 148 | 0.0036 | 26 |
| 149 | 0.015 | 34 |
| 150 | 0.019 | 110 |
| 151 | 0.014 | 25 |
| 152 | 0.0086 | 110 |
| 153 | 0.0066 | 23 |
| 154 | 0.0042 | 35 |
| 155 | 0.088 | 140 |
| 163 | 0.013 | 12 |
| 164 | 0.0028 | 24 |
| 165 | 0.0016 | 11 |
| 166 | 0.0018 | 20 |
| 167 | 0.0070 | 13 |
| 168 | 0.0042 | 28 |
| 169 | 0.072 | 1000 |
| 170 | 0.160 | 460 |
| 171 | 0.140 | 1000 |
| 172 | 0.260 | 1000 |
| 173 | 0.170 | 1000 |
| 174 | 0.0015, 0.0013 | 29, 18 |
| 175 | 0.660 | 1000 |
| 176 | 0.024 | 1000 |
| 177 | 0.040 | 330 |
| 178 | 0.0064, 0.0076 | 181.5, 360 |
| 179 | 1.00 | 1000 |
| 180 | 1.00 | 1000 |
| 181 | 0.0011 | 10 |
| 183 | 0.014 | 9.1 |
| 190 | 0.0089 | 16 |
| 195 | 0.125 | 200 |
| 196 | 0.055 | 595 |
| 276 | 0.024 | 260 |

NA indicates no detected activity at test concentration;

EXAMPLE 174

MCF-7 Cell Proliferation Assay

This assay was run according to the procedure described by Welshons, et al., (*Breast Cancer Res. Treat.*, 1987, 10(2), 169-75), with minor modification.

Briefly, MCF-7 cells (from Dr. C. Jordan, Northwestern University) were maintained in RPMI 1640 phenol red free medium (Gibco) in 10% FBS (Hyclone), supplemented with bovine insulin and non-essential amino acid (Sigma). The cells were initially treated with 4-hydoxyltamoxifen ($10^{-8}$ M) and let stand at 37° C. for 24 hours. Following this incubation with tamoxifen, the cells were treated with compounds at various concentrations.

Compounds to be tested in the agonist mode were added to the culture media at varying concentrations. Compounds to be treated in the antagonist mode were prepared similarly, and 10 nM 17β-estradiol was also added to the culture media. The cells were incubated for 24 hours at 37° C. Following this incubation, 0.1 μCi of $^{14}$C-thymidine (56 mCi/mmol, Amersham) was added to the culture media and the cells were incubated for an additional 24 hours at 37° C. The cells were then washed twice with Hank's buffered salt solution (HBSS) (Gibco) and counted with a scintillation counter. The increase in the $^{14}$C-thymidine in the compound treated cells relative to the vehicle control cells were reported as percent increase in cell proliferation.

Representative compound of the present invention were tested according to the procedure described above, with results as listed in Table. 7.

TABLE 7

| ID No | Agonist (No.) (nM) | Antagonist (No.) (nM) |
|---|---|---|
| 1 | 1200 (1) | >10K (1) |
| 2 | >10K (1) | >10K (1) |
| 6 | 97 (1) | >10K (1) |
| 9 | >10K (12) | 777 (6) |
| 11 | >10K (1) | 246 (3) |
| 13 | >10K (1) | 1400 (1) |
| 14 | >10K (7) | 5600 (2) |
| 15 | >10K (7) | 6.25 (2) |
| 17 | >10K (1) | 3580 (1) |
| 19 | >10K (6) | 713 (4) |
| 21 | >10K (4) | 970 (4) |
| 22 | >10K (8) | 662 (7) |
| 24 | >10K (6) | 672 (6) |
| 25 | >10K (10) | 1393 (6) |
| 26 | 64.3 (3) | >10K (3) |
| 27 | NA | NA |
| 28 | NA | NA |
| 29 | NA | NA |
| 30 | >10K (1) | 2200 (1) |
| 33 | >10K (1) | 4800 (1) |
| 41 | >10K (1) | >10K (1) |
| 43 | >10K (1) | >1K (1) |
| 89 | | 845 |
| 90 | | 1670 |
| 99 | | 182 |
| 100 | | 75 |
| 125 | | 4700 |
| 126 | | 245 |
| 131 | | >10000 |
| 132 | | 1280 |
| 146 | | 1123 |
| 147 | | >10000 |
| 148 | | 997 |
| 149 | | 1360 |
| 150 | | 2940 |
| 151 | | 2760 |
| 152 | | 2612 |
| 153 | | 1274 |
| 154 | | 1437 |
| 155 | | >10000 |
| 163 | | 687 |
| 164 | | 293 |
| 165 | | 401 |
| 166 | | 217 |
| 167 | | 424 |
| 168 | | 220 |
| 169 | | 10000 |
| 170 | | 10000 |
| 171 | | 5100 |
| 172 | | 2280 |
| 173 | | >10000 |
| 174 | | 1744 |
| 175 | | 5000 |
| 176 | | >10000, 4000 |
| 177 | | 3000 |
| 178 | | 1476 |
| 179 | | 1866 |
| 180 | | 655 |
| 181 | | 1335 |
| 183 | | 10000 |
| 190 | | >10000 |
| 195 | | >1000 |
| 196 | | >1000 |
| 276 | | 4680 |

NA indicates no detected activity at test concentration;

EXAMPLE 175

Alkaline Phosphatase Assay in Human Endometrial Ishikawa Cells

This assay was run according to the procedure described by Albert et a., Cancer Res, (9910) 50(11), 330-6-10, with minor modification.

Ishikawa cells (from ATCC) were maintained in DMEM/F12 (1:1) phenol red free medium (Gibco) supplemented with 10% calf serum (Hyclone). 24 hours prior to testing, the medium was changed to DMEM/F12 (1:1) phenol red free containing 2% calf serum.

Compound to be tested in the agonist mode were added to the culture media at varying concentrations. Compounds to be treated in the antagonist mode were prepared similarly, and 10 nM 17β-estradiol was also added to the culture media. The cells were then incubated at 37° C. for 3 days. On the fourth day, the media was remove, 1 volume of 1× Dilution Buffer (Clontech) was added to the well followed by addition of 1 volume of Assay Buffer (Clontech). The cells were then incubated at room temperature for 5 minutes. 1 volume of freshly prepared Chemiluminescence Buffer (1 volume of chemiluminescent substrate (CSPD) in 19 volume Chemiluminescent Enhancer with final concentration of CSPD at 1.25 mM; Sigma Chemical Co.) was added. The cells were incubated at room temperature for 10 minutes and then quantified on a luminometer. The increase of chemiluminescence over vehicle control was used to calculate the increase in alkaline phosphatase activity.

Representative compound of the present invention were tested according to the procedure described above, with results as listed in Table 8.

TABLE 8

| ID No | Agonist (No.) (nM) | Antagonist (No.) (nM) |
| --- | --- | --- |
| 1 | 130 (1) | >10 K (1) |
| 2 | >10 K (1) | >10 K (1) |
| 6 | 33 (2) | >10 K (1) |
| 9 | >10 K (12) | 110 (7) |
| 11 |  | 80 (1) |
| 13 | >10 K (2) | 228 (2) |
| 14 | >10 K (11) | 149 (6) |
| 15 | >10 K (11) | 112 (7) |
| 17 | >10 K (6) | 513 (5) |
| 19 | >10 K (1) | 250 (1) |
| 21 | >10 K (9) | 830 (8) |
| 22 | >10 K (11) | 53.5 (11) |
| 24 | >10 K (9) | 66 (10) |
| 25 | >10 K (11) | 235 (10) |
| 26 | >10 K (5) | 180 (1) |
| 27 | NA | NA |
| 28 | NA | NA |
| 29 | NA | NA |
| 30 | >10 K (1) | 630 (1) |
| 33 | >10 K (1) | 1000 (1) |
| 41 | >10 K (1) | 550 (1) |
| 43 | >10 K (1) | 1600 (1) |
| 89 |  | 10 |
| 90 |  | 57 |
| 99 |  | 130 |
| 100 |  | 19 |
| 125 |  | 1620 |
| 126 |  | 78 |
| 131 |  | 4940 |
| 132 |  | 548 |
| 146 |  | 154 |
| 147 |  | >10000 |
| 148 |  | 138 |
| 149 |  | 1020 |
| 150 |  | 850 |
| 151 |  | 605 |
| 152 |  | 324 |
| 153 |  | 509 |
| 154 |  | 167 |
| 155 |  | 3770 |
| 163 |  | 405 |
| 164 |  | 61 |
| 165 |  | 128 |
| 166 |  | 41 |
| 167 |  | 35 |
| 168 |  | 287 |
| 169 |  | 830 |
| 170 |  | 2664 |
| 171 |  | 56.7 |
| 172 |  | 68.4 |
| 173 |  | >10000 |
| 174 |  | 135 |
| 175 |  | 300 |
| 176 |  | >10000, 793 |
| 177 |  | 259 |
| 178 |  | 125 |
| 179 |  | 9 |
| 180 |  | 0.9 |
| 181 |  | 34 |
| 183 |  | 3000 |
| 190 |  | >10000 |
| 195 |  | 739 |
| 196 |  | 229 |
| 276 |  | 481 |

NA indicates no detected activity at test concentration;

EXAMPLE 176

As a specific embodiment of an oral composition, 100 mg of the compound #22, prepared as in Example 54 is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A compound of formula (I)

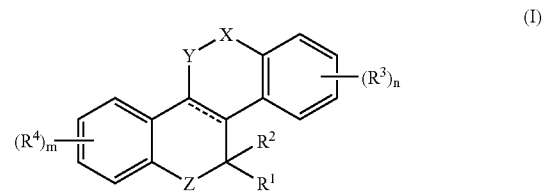

wherein

---represents a single or double bond,

X is selected from the group consisting of O and S and Y is selected from the group consisting of $CR^A R^B$, $CR^A R^B (CR^A R^B)_{1-2}$, $CR^A R^B C(O)$, $CR^A R^B C(O) CR^A R^B$ and $C(O)$; alternatively Y is selected from the group consisting of O and S and X is selected from the group consisting of $CR^A R^B$ and $C(O)$;

provided that when X is S, then Y is selected from the group consisting of $CR^A R^B$, $CR^A R^B (CR^A R^B)_{1-2}$ and $CH_2C(O)CH_2$; provided further that when Y is S, then X is selected from the group consisting of $CR^AR^B$;

wherein each $R^A$ and $R^B$ is independently selected from hydrogen, hydroxy, alkyl or alkoxy; provided that $R^A$ and $R^B$ are not each hydroxy;

Z is selected from the group consisting of O and S;

$R^1$ is selected from the group consisting of hydrogen, alkyl, alkenyl, cycloalkyl, aryl, —C(O)-aryl, aralkyl, heteroaryl and heteroaryl-alkyl; wherein the alkyl, cycloalkyl, aryl, aralkyl, heteroaryl or heteroaryl-alkyl group is optionally substituted with one or more substituents independently selected from halogen, hydroxy, alkyl, alkoxy, —SH, —S(alkyl), —NO$_2$, CN, CO$_2$H, $R^C$, —OR$^C$, —C(O)—OR$^C$, —C(O)O-(alkyl)-NR$^D$R$^E$, —C(O)—NR$^D$-(alkyl)-NR$^D$R$^E$, —C(O)-(heterocycloalkyl)-NR$^D$R$^E$, —C(O)-(heterocycloalkyl)-R$^F$, —SO$_2$—NR$^D$R$^E$, —NR$^D$R$^E$, NR$^D$—SO$_2$—R$^F$, -(alkyl)$_{0-4}$-C(O)NR$^D$R$^E$, (alkyl)$_{0-4}$-NR$^D$—C(O)—R$^F$, -(alkyl)$_{0-4}$-(Q)$_{0-1}$-(alkyl)$_{0-4}$-NR$^D$R$^E$, -(alkyl)$_{0-4}$-(Q)$_{0-1}$-(alkyl)$_{0-4}$-C(O)—OR$^F$, -(alkyl)$_{0-4}$-(Q)$_{0-1}$-(alkyl)$_{0-4}$-C(O)—NR$^D$R$^E$, -(alkyl)$_{0-4}$-C(O)-(alkyl)$_{0-4}$-C(O)—OR$^F$, —O-(alkyl)-OSi(alkyl)$_3$, —O-(alkyl)-OR$^D$ or —O-(alkyl)-formyl;

wherein $R^C$ is selected from the group consisting of alkyl, cycloalkyl, cycloalkyl-alkyl, aryl, aralkyl, heteroaryl, heteroaryl-alkyl, heterocycloalkyl and heterocycloalkyl-alkyl; wherein the cycloalkyl, cycloalkyl-alkyl, aryl, aralkyl, heteroaryl, heteroaryl-alkyl, heterocycloalkyl or heterocycloalkyl-alkyl group is optionally substituted with one or more substituents independently selected from halogen, hydroxy, alkyl, alkoxy, —SH, —S(alkyl), NO$_2$, CN, CO$_2$H, —SO$_2$—NR$^D$R$^E$, NR$^D$R$^E$, NR$^D$—SO$_2$—R$^F$, -(alkyl)$_{0-4}$-C(O)—NR$^D$R$^E$, (alkyl)$_{0-4}$NR$^D$—C(O)—R$^F$, -(alkyl)$_{0-4}$-(Q)$_{0-1}$-(alkyl)$_{0-4}$-NR$^D$R$^E$, -(alkyl)$_{0-4}$-(Q)$_{0-1}$-(alkyl)$_{0-4}$-C(O)—OR$^F$, -(alkyl)$_{0-4}$-(Q)$_{0-1}$-(alkyl)$_{0-4}$-C(O)—NR$^D$R$^E$ or -(alkyl)$_{0-4}$-C(O)-(alkyl)$_{0-4}$-C(O)—OR$^F$;

wherein Q is selected from the group consisting of O, S, NH, N(alkyl) and —CH═CH—;

wherein $R^D$ and $R^E$ are each independently selected from the group consisting of hydrogen and alkyl; alternatively $R^D$ and $R^E$ are taken together with the nitrogen atom to which they are bound to form a 3 to 10 membered ring selected from the group consisting of heteroaryl or heterocycloalkyl; wherein the heteroaryl or heterocycloalkyl group is optionally substituted with one or more substituents independently selected from halogen, hydroxy, oxo, alkyl, alkoxy, carboxy, amino, alkylamino, dialkylamino, nitro or cyano;

wherein $R^F$ is selected from the group consisting of hydrogen, alkyl, cycloalkyl, cycloalkyl-alkyl, aryl, aralkyl, heteroaryl, heteroaryl-alkyl, heterocycloalkyl and heterocycloalkyl-alkyl; wherein the cycloalkyl, aryl, heteroaryl, heteroaryl-alkyl, heterocycloalkyl or heterocycloalkyl-alkyl group is optionally substituted with one or more substituents independently selected from halogen, hydroxy, alkyl, alkoxy, carboxy, amino, alkylamino, dialkylamino, nitro or cyano;

$R^2$ is selected from the group consisting of hydroxy, alkyl, alkenyl, cycloalkyl, aryl, —C(O)-aryl, aralkyl, heteroaryl and heteroaryl-alkyl; wherein the alkyl, cycloalkyl, aryl, aralkyl, heteroaryl or heteroaryl-alkyl group is optionally substituted with one or more substituents independently selected from halogen, hydroxy, alkyl, alkoxy, —SH, —S(alkyl), NO$_2$, CN, CO$_2$H, $R^C$, —OR$^C$, —C(O)—R$^C$, —C(O)O-(alky)-NR$^D$R$^E$, —C(O)—NR$^D$-(alkyl)-NR$^D$R$^E$, —C(O)-(heterocycloalkyl)-NR$^D$R$^E$, —C(O)-(heterocycloalkyl)-R$^F$, —SO$_2$—NR$^D$R$^E$, —NR$^D$R$^E$, NR$^D$—SO$_2$—R$^F$, -(alkyl)$_{0-4}$-C(O)NR$^D$R$^E$, (alkyl)$_{0-4}$-NR$^D$—C(O)—R$^F$, -(alkyl)$_{0-4}$-(Q)$_{0-1}$-(alkyl)$_{0-4}$-NR$^D$R$^E$, -(alkyl)$_{0-4}$-(Q)$_{0-1}$-(alkyl)$_{0-4}$-C(O)—OR$^F$, -(alkyl)$_{0-4}$-(Q)$_{0-1}$-(alkyl)$_{0-4}$-C(O)—NR$^D$R$^E$, -(alkyl)$_{0-4}$-C(O)-(alkyl)$_{0-4}$-C(O)—OR$^F$, —O-(alkyl)-OSi(alkyl)$_3$, —O-(alkyl)-OR$^D$ or —O-(alkyl)-formyl;

alternatively, $R^1$ and $R^2$ are taken together with the carbon atom to which they are bound to form C(O);

provided that when $R^1$ and $R^2$ are taken together with the carbon atom to which they are bound to form C(O) and X is selected from the group consisting of O and S, then Y is selected from the group consisting of $CR^AR^B$, $CR^AR^B(CR^AR^B)_{1-2}$, $CR^AR^BC(O)$ and $CH_2C(O)CH_2$;

provided that when $R^1$ and $R^2$ are taken together with the carbon atom to which they are bound to form C(O) and Y is selected from the group consisting of O and S, then X is selected from the group consisting of $CR^AR^B$;

n is an integer selected from 0 to 4;

each $R^3$ is independently selected from the group consisting of halogen, hydroxy, $R^C$, amino, alkylamino, dialkylamino, nitro, cyano, —C(O)R$^G$, —C(O)OR$^G$, —OC(O)R$^G$, —OC(O)OR$^G$, —OC(O)N(R$^G$)$_2$, —N(R$^G$)C(O)R$^G$, —OSi(R$^G$)$_3$, —OR$^G$, —SO$_2$N(R$^G$)$_2$, —O-(alkyl)$_{1-4}$-C(O)R$^G$ and —O-(alkyl)$_{1-4}$-C(O)OR$^G$;

wherein each $R^G$ is independently selected from hydrogen, alkyl, aryl, aralkyl and 1,7,7-trimethyl-2-oxabicyclo[2.2.1]heptan-3-one; wherein the alkyl, aryl or aralkyl group is optionally substituted with one or more substituents independently selected from alkyl, halogenated alkyl, alkoxy, halogen, hydroxy, nitro, cyano, —OC(O)-alkyl or —C(O)O-alkyl;

alternatively two $R^G$ groups are taken together with the nitrogen atom to which they are bound to form a heterocycloalkyl group; wherein the heterocycloalkyl group is optionally substituted with one or more substituents independently selected from halogen, hydroxy, alkyl, alkoxy, carboxy, amino, alkylamino, dialkylamino, nitro or cyano;

m is an integer selected from 0 to 4;

each $R^4$ is independently selected from the group consisting of halogen, hydroxy, $R^C$, amino, alkylamino, dialkylamino, nitro, cyano, —C(O)R$^G$, —C(O)OR$^G$, —OC(O)R$^G$, —OC(O)OR$^G$, —OC(O)N(R$^G$)$_2$, —N(R$^G$)C(O)R$^G$, —OSi(R$^G$)$_3$, —OR$^G$, —SO$_2$N(alkyl)$_2$, —O-(alkyl)$_{1-4}$-C(O)R$^G$ and —O-(alkyl)$_{1-4}$-C(O)OR$^G$;

provided that when ---- is a double bond, X is $CH_2$, Y is O, Z is O and $R^1$ and $R^2$ are taken together with the carbon atom to which they are bound to form C(O), then at least one of n or m is an integer selected from 1 to 4;

provided further that when ---- is a single bond, X is O, Y is CH(alkyl), Z is O, $R^1$ is hydrogen and $R^2$ is alkyl, then at least one of n or m is an integer selected from 1 to 4;

provided further that when ---- is a single bond, X is O, Y is CH(alkyl), Z is O, $R^1$ is hydrogen, $R^2$ is alkyl, n is 1 and m is 1, then $R^3$ and $R^4$ are other than methoxy or ethoxy;

provided further that when ---- is a double bond, X is O, Y is $CH_2$, Z is O, $R^1$ and $R^2$ are taken together with the carbon atom to which they are bound to form C(O), n is 0 and m is 2, then each $R^4$ is not hydroxy or alkoxy;

provided further that when ---- is a double bond, X is $CH_2$; Y is O; Z is O; $R^1$ and $R^2$ are taken together with the carbon atom to which they are bound to form C(O), and m is 2 then $R^4$ is other than methoxy;

provided further that when ---- is a double bond, X is O; Y is $CH_2$; Z is O; $R^1$ and $R^2$ are taken together with the carbon atom to which they are bound to form C(O); n is 0 or 2, $R^3$ is methoxy and m is 1 or 2; then $R^4$ is other than hydroxy or methoxy;

or a pharmaceutically acceptable salt thereof.

2. A compound as in claim 1 wherein

---- represents a single bond or a double bond,

X is selected from the group consisting of O and S;

Y is selected from the group consisting of $CR^A R^B$, $CR^A R^B (CH_2)_{1-2}$, $CR^A R^B C(O)$, $CH_2 C(O) CH_2$, $C(O)$ and $CH_2 CR^A R^B CH_2$;

provided that when X is S, then Y is selected from the group consisting of $CR^A R^B$, $CR^A R^B (CH_2)_{1-2}$, $CH_2 C(O) CH_2$ and $CH_2 CR^A R^B CH_2$;

wherein each $R^A$ and $R^B$ is independently selected from hydrogen, hydroxy, lower alkyl or lower alkoxy; provided that both $R^A$ and $R^B$ are not hydroxy;

Z is selected from the group consisting of O and S;

$R^1$ is selected from the group consisting of hydrogen, lower alkyl, lower alkenyl, aryl, —C(O)-aryl, aralkyl, heteroaryl and heteroaryl-(lower alkyl); wherein the lower alkyl, aryl, aralkyl, heteroaryl or heteroaryl-(lower alkyl) group is optionally substituted with one to two substituents independently selected from halogen, hydroxy, lower alkyl, lower alkoxy, —SH, —S(lower alkyl), $NO_2$, CN, $CO_2H$, $R^C$, —$SO_2$—$NR^D R^E$, —$NR^D R^E$, $NR^D$—$SO_2$—$R^F$, -(alkyl)$_{0-4}$-C(O)$NR^D R^E$, —C(O)O-(lower alkyl)-$NR^D R^E$, —C(O)—NH-(lower alkyl)-$NR^D R^E$, —C(O)—(N containing heterocycloalkyl (wherein said N containing heterocycloalkyl is bound through the N atom))-$NR^D R^E$, —C(O)—(N containing heterocycloalkyl (wherein said N containing heterocycloalkyl is bound through the N atom))-$R^F$, -(alkyl)$_{0-4}$-$NR^D$—C(O)—$R^F$, -(alkyl)$_{0-4}$-(Q)$_{0-1}$-(alkyl)$_{0-4}$-$NR^D R^E$, -(alkyl)$_{0-4}$-(Q)$_{0-1}$-(alkyl)$_{0-4}$-C(O)—$OR^F$, -(alkyl)$_{0-4}$-(Q)$_{0-1}$-(alkyl)$_{0-4}$-C(O)—$NR^D R^E$, -(alkyl)$_{0-4}$-C(O)-(alkyl)$_{0-4}$-C(O)—$OR^F$, —O-(lower alkyl)-OSi(lower alkyl)$_3$, —O-(lower alkyl)-$OR^D$ or —O-(lower alkyl)-formyl;

wherein $R^C$ is selected from the group consisting of lower alkyl, aryl, aralkyl, heteroaryl, heteroaryl-(lower alkyl), heterocycloalkyl and heterocycloalkyl-(lower alkyl); wherein the aryl, aralkyl, heteroaryl, heteroaryl-(lower alkyl), heterocycloalkyl or heterocycloalkyl-(lower alkyl) group is optionally substituted with one to two substituents independently selected from halogen, hydroxy, lower alkyl, lower alkoxy, —SH, —S(alkyl), $NO_2$, CN, $CO_2H$, —$SO_2$—$NR^D R^E$, $NR^D R^E$, $NR^D$—$SO_2$—$R^F$, -(alkyl)$_{0-4}$-C(O)—$NR^D R^E$, -(alkyl)$_{0-4}$-$NR^D$—C(O)—$R^F$, -(alkyl)$_{0-4}$-(Q)$_{0-1}$-(alkyl)$_{0-4}$-$NR^D R^E$, -(alkyl)$_{0-4}$-(Q)$_{0-1}$-(alkyl)$_{0-4}$-C(O)—$OR^F$, -(alkyl)$_{0-4}$-(Q)$_{0-1}$-(alkyl)$_{0-4}$-C(O)—$NR^D R^E$ or -(alkyl)$_{0-4}$-C(O)-(alkyl)$_{0-4}$-C(O)—$OR^F$;

wherein Q is selected from the group consisting of O, S, NH, N(lower alkyl) and —CH=CH—;

wherein $R^D$ and $R^E$ are each independently selected from the group consisting of hydrogen and lower alkyl; alternatively $R^D$ and $R^E$ are taken together with the nitrogen atom to which they are bound to form a 5 to 6 membered ring selected from the group consisting of heteroaryl or heterocycloalkyl; wherein the heteroaryl or heterocycloalkyl group is optionally substituted with one to two substituents independently selected from halogen, hydroxy, oxo, lower alkyl, lower alkoxy, carboxy, amino, (lower alkyl)-amino, di(lower alkyl) amino, nitro or cyano;

wherein $R^F$ is selected from the group consisting of hydrogen, lower alkyl, aryl, aralkyl, heteroaryl, heteroaryl-(lower alkyl), heterocycloalkyl and heterocycloalkyl-(lower alkyl); wherein the aryl, heteroaryl, heteroaryl-(lower alkyl), heterocycloalkyl or heterocycloalkyl-(lower alkyl) group is optionally substituted with one to two substituents independently selected from halogen, hydroxy, lower alkyl, lower alkoxy, carboxy, amino, (lower alkyl)-amino, di(lower alkyl) amino, nitro or cyano;

$R^2$ is selected from the group consisting of hydroxy, lower alkyl, lower alkenyl, aryl, —C(O)-aryl, aralkyl, heteroaryl and heteroaryl-(lower alkyl); wherein the alkyl, aryl, aralkyl, heteroaryl or heteroaryl-(lower alkyl) group is optionally substituted with one to two substituents independently selected from halogen, hydroxy, lower alkyl, lower alkoxy, —SH, —S(lower alkyl), $NO_2$, CN, $CO_2H$, $R^C$, —$OR^C$, —$SO_2$—$NR^D R^E$, —$NR^D R^E$, -(alkyl)$_{0-4}$—C(O)$NR^D R^E$, —C(O)O-(lower alkyl)-$NR^D R^E$, —C(O)—NH-(lower alkyl)-$NR^D R^E$, —C(O)—(N containing heterocycloalkyl (wherein said N containing heterocycloalkyl is bound through the N atom))-$NR^D R^E$, —C(O)—(N containing heterocycloalkyl, bound through the N atom)-$R^F$, -(alkyl)$_{0-4}$-$NR^D$—C(O)—$R^F$, -(alkyl)$_{0-4}$-(Q)$_{0-1}$-(alkyl)$_{0-4}$-$NR^D R^E$, -(alkyl)$_{0-4}$-(Q)$_{0-1}$-(alkyl)$_{0-4}$-C(O)—$OR^F$, -(alkyl)$_{0-4}$-(Q)$_{0-1}$-(alkyl)$_{0-4}$-C(O)—$NR^D R^E$, -(alkyl)$_{0-4}$-C(O)-(alkyl)$_{0-4}$-C(O)—$OR^F$, —O-(lower alkyl)-OSi(lower alkyl)$_3$, —O-(lower alkyl)-$OR^D$ or —O-(lower alkyl)-formyl;

alternatively, $R^1$ and $R^2$ are taken together with the carbon atom to which they are bound to form C(O);

provided that when $R^1$ and $R^2$ are taken together with the carbon atom to which they are bound to form C(O) and X is selected from the group consisting of O and S, then Y is selected from the group consisting of $CR^A R^B$, $CR^A R^B (CH_2)_{1-2}$, $CR^A R^B C(O)$, $CH_2 C(O) CH_2$ and $CH_2 CR^A R^B CH_2$;

n is an integer selected from 0 to 2;

each $R^3$ is independently selected from the group consisting of halogen, hydroxy, $R^C$, amino, (lower alkyl)-amino, di(lower alkyl)amino, nitro, cyano, —OC(O)$R^G$, —OC(O)$OR^G$, —OC(O)N($R^G$)$_2$, —OSi($R^G$)$_3$, —$OR^G$, —O-(alkyl)$_{1-4}$-C(O)$R^G$ and —O-(alkyl)$_{1-4}$-C(O)$OR^G$;

wherein each $R^G$ is independently selected from hydrogen, alkyl, aryl, aralkyl and 1,7,7-trimethyl-2-oxabicyclo[2.2.1]heptan-3-one; wherein the alkyl, aryl or aralkyl group is optionally substituted with one to two substituents independently selected from lower alkyl, halogenated lower alkyl, lower alkoxy, halogen, hydroxy, nitro, cyano, —OC(O)-(lower alkyl) or —C(O)O-(lower alkyl);

alternatively two $R^G$ groups are taken together with the nitrogen atom to which they are bound to form a heterocycloalkyl group; wherein the heterocycloalkyl group is optionally substituted with one to two substituents independently selected from halogen, hydroxy, lower alkyl, lower alkoxy, carboxy, amino, (lower alkyl)-amino, di(lower alkyl)amino, nitro or cyano;

m is an integer selected from 0 to 2;

each $R^4$ is independently selected from the group consisting of halogen, hydroxy, $R^C$, amino, (lower alkyl)- amino, di(lower alkyl)amino, nitro, cyano, —OC(O)$R^G$, —OC(O)O$R^G$, —OC(O)N($R^G$)$_2$, —OSi($R^G$)$_3$, —O$R^G$, —O-(alkyl)$_{1-4}$-C(O)$R^G$ and —O-(alkyl)$_{1-4}$-C(O)O$R^G$;

provided that when ---- is a single bond, X is O, Y is CH(lower alkyl), Z is O, $R^1$ is hydrogen and $R^2$ is lower alkyl, then at least one of n or m is an integer selected from 1 to 4;

provided further that when ---- is a single bond, X is O, Y is CH(lower alkyl), Z is O, $R^1$ is hydrogen, $R^2$ is alkyl, n is 1 and m is 1, then $R^3$ and $R^4$ are other than methoxy or ethoxy;

provided further that when ---- is a double bond, X is O, Y is $CH_2$, Z is O, $R^1$ and $R^2$ are taken together with the carbon atom to which they are bound to form C(O), n is 0 and m is 2, then each $R^4$ is not hydroxy or alkoxy;

provided further that when ---- is a double bond, X is O; Y is $CH_2$; Z is O; $R^1$ and $R^2$ are taken together with the carbon atom to which they are bound to form C(O); n is 0 or 2; $R^3$ is methoxy and m is 1 or 2; then $R^4$ is other than hydroxy or methoxy;

or a pharmaceutically acceptable salt thereof.

3. A compound as in claim 1 wherein
---- represents a single bond or a double bond, X is selected from the group consisting of $CR^AR^B$ and C(O);

Y is selected from the group consisting of O and S;

provided that when Y is S, then X is selected from the group consisting of $CR^AR^B$;

wherein each $R^A$ and $R^B$ is independently selected from hydrogen, hydroxy, lower alkyl or lower alkoxy; provided that both $R^A$ and $R^B$ are not hydroxy;

Z is selected from the group consisting of O and S;

$R^1$ is selected from the group consisting of hydrogen, lower alkyl, lower alkenyl, aryl, —C(O)-aryl, aralkyl, heteroaryl and heteroaryl-(lower alkyl); wherein the lower alkyl, aryl, aralkyl, heteroaryl or heteroaryl-(lower alkyl) group is optionally substituted with one to two substituents independently selected from halogen, hydroxy, lower alkyl, lower alkoxy, —SH, —S(lower alkyl), $NO_2$, CN, $CO_2H$, $R^C$, —O$R^C$, —$SO_2$—$NR^DR^E$, —$NR^DR^E$, $NR^D$—$SO_2$—$R^F$, -(alkyl)$_{0-4}$-C(O)$NR^DR^E$, —C(O)O-(lower alkyl)-$NR^DR^E$, —C(O)—NH-(lower alkyl)-$NR^DR^E$, —C(O)—(N containing heterocycloalkyl (wherein said N containing heterocycloalkyl is bound through the N atom))-$NR^DR^E$, —C(O)—(N containing heterocycloalkyl (wherein said N containing heterocycloalkyl is bound through the N atom))-$R^F$, -(alkyl)$_{0-4}$-$NR^D$—C(O)—$R^F$, -(alkyl)$_{0-4}$-(Q)$_{0-1}$-(alkyl)$_{0-4}$-$NR^DR^E$, -(alkyl)$_{0-4}$-(Q)$_{0-1}$-(alkyl)$_{0-4}$-C(O)—O$R^F$, -(alkyl)$_{0-4}$-(Q)$_{0-1}$-(alkyl)$_{0-4}$-C(O)—$NR^DR^E$, -(alkyl)$_{0-4}$-C(O)-(alkyl)$_{0-4}$-C(O)—O$R^F$, —O-(lower alkyl)-OSi(lower alkyl)$_3$, —O-(lower alkyl)-O$R^D$ or —O-(lower alkyl)-formyl;

wherein $R^C$ is selected from the group consisting of lower alkyl, aryl, aralkyl, heteroaryl, heteroaryl-(lower alkyl), heterocycloalkyl and heterocycloalkyl-(lower alkyl); wherein the aryl, aralkyl, heteroaryl, heteroaryl-(lower alkyl), heterocycloalkyl or heterocycloalkyl-(lower alkyl) group is optionally substituted with one to two substituents independently selected from halogen, hydroxy, lower alkyl, lower alkoxy, —SH, —S(alkyl), $NO_2$, CN, $CO_2H$, —$SO_2$—$NR^DR^E$, $NR^DR^E$, $NR^D$—$SO_2$—$R^F$, -(alkyl)$_{0-4}$—C(O)—$NR^DR^E$, -(alkyl)$_{0-4}$-$NR^D$—C(O)—$R^F$, -(alkyl)$_{0-4}$-(Q)$_{0-1}$-(alkyl)$_{0-4}$-$NR^DR^E$, -(alkyl)$_{0-4}$-(Q)$_{0-1}$-(alkyl)$_{0-4}$-C(O)—O$R^F$, -(alkyl)$_{0-4}$-(Q)$_{0-1}$-(alkyl)$_{0-4}$-C(O)—$NR^DR^E$ or -(alkyl)$_{0-4}$-C(O)-(alkyl)$_{0-4}$-C(O)—O$R^F$;

wherein Q is selected from the group consisting of O, S, NH, N(lower alkyl) and —CH=CH—;

wherein $R^D$ and $R^E$ are each independently selected from the group consisting of hydrogen and lower alkyl; alternatively $R^D$ and $R^E$ are taken together with the nitrogen atom to which they are bound to form a 5 to 6 membered ring selected from the group consisting of heteroaryl or heterocycloalkyl; wherein the heteroaryl or heterocycloalkyl group is optionally substituted with one to two substituents independently selected from halogen, hydroxy, oxo, lower alkyl, lower alkoxy, carboxy, amino, (lower alkyl)-amino, di(lower alkyl) amino, nitro or cyano;

wherein $R^F$ is selected from the group consisting of hydrogen, lower alkyl, aryl, aralkyl, heteroaryl, heteroaryl-(lower alkyl), heterocycloalkyl and heterocycloalkyl-(lower alkyl); wherein the aryl, heteroaryl, heteroaryl-(lower alkyl), heterocycloalkyl or heterocycloalkyl-(lower alkyl) group is optionally substituted with one to two substituents independently selected from halogen, hydroxy, lower alkyl, lower alkoxy, carboxy, amino, (lower alkyl)-amino, di(lower alkyl) amino, nitro or cyano;

$R^2$ is selected from the group consisting of hydroxy, lower alkyl, lower alkenyl, aryl, —C(O)-aryl, aralkyl, heteroaryl and heteroaryl-(lower alkyl); wherein the lower alkyl, aryl, aralkyl, heteroaryl or heteroaryl-(lower alkyl) group is optionally substituted with one to two substituents independently selected from halogen, hydroxy, lower alkyl, lower alkoxy, —SH, —S(lower alkyl), $NO_2$, CN, $CO_2H$, $R^C$, —O$R^C$, —$SO_2$—$NR^DR^E$, —$NR^DR^E$, -(alkyl)$_{0-4}$-C(O)$NR^DR^E$, —C(O)O-(lower alkyl)-$NR^DR^E$, —C(O)—NH-(lower alkyl)-$NR^DR^E$, —C(O)—(N containing heterocycloalkyl (wherein said N containing heterocycloalkyl is bound through the N atom))-$NR^DR^E$, —C(O)—(N containing heterocycloalkyl (wherein said N containing heterocycloalkyl is bound through the N atom))-$R^F$, -(alkyl)$_{0-4}$-$NR^D$—C(O)—$R^F$, -(alkyl)$_{0-4}$-(Q)$_{0-1}$-(alkyl)$_{0-4}$-$NR^DR^E$, -(alkyl)$_{0-4}$-(Q)$_{0-1}$-(alkyl)$_{0-4}$-C(O)—O$R^F$, -(alkyl)$_{0-4}$-(Q)$_{0-1}$-(alkyl)$_{0-4}$-C(O)—$NR^DR^E$, -(alkyl)$_{0-4}$-C(O)-(alkyl)$_{0-4}$-C(O)—O$R^F$, —O-(lower alkyl)-OSi(lower alkyl)$_3$, —O-(lower alkyl)-O$R^D$ or —O-(lower alkyl)-formyl;

alternatively, $R^1$ and $R^2$ are taken together with the carbon atom to which they are bound to form C(O);

provided that when $R^1$ and $R^2$ are taken together with the carbon atom to which they are bound to form C(O) and Y is selected from the group consisting of O and S, then X is selected from the group consisting of $CR^AR^B$;

n is an integer selected from 0 to 2;

each $R^3$ is independently selected from the group consisting of halogen, hydroxy, $R^C$, amino, (lower alkyl)-amino, di(lower alkyl)amino, nitro, cyano, —OC(O)$R^G$, —OC(O)O$R^G$, —OC(O)N($R^G$)$_2$, —OSi($R^G$)$_3$, —O$R^G$, —O-(alkyl)$_{1-4}$-C(O)$R^G$ and —O-(alkyl)$_{1-4}$-C(O)O$R^G$;

wherein each $R^G$ is independently selected from hydrogen, lower alkyl, aryl, aralkyl and 1,7,7-trimethyl-2-oxabicyclo[2.2.1]heptan-3-one; wherein the lower alkyl, aryl or aralkyl group is optionally substituted with one to two substituents independently selected from lower alkyl, halogenated lower alkyl, lower alkoxy, halogen, hydroxy, nitro, cyano, —OC(O)-(lower alkyl) or —C(O)O-(lower alkyl);

alternatively two $R^G$ groups are taken together with the nitrogen atom to which they are bound to form a heterocycloalkyl group; wherein the heterocycloalkyl group is optionally substituted with one to two substituents independently selected from halogen, hydroxy, lower alkyl, lower alkoxy, carboxy, amino, (lower alkyl)-amino, di(lower alkyl)amino, nitro or cyano;

m is an integer selected from 0 to 2;

each $R^4$ is independently selected from the group consisting of halogen, hydroxy, $R^C$, amino, (lower alkyl)-amino, di(lower alkyl)amino, nitro, cyano, —OC(O)$R^G$, —OC(O)O$R^G$, —OC(O)N($R^G$)$_2$, —OSi($R^G$)$_3$, —O$R^G$, —O-(alkyl)$_{1-4}$-C(O)$R^G$ and —O-(alkyl)$_{1-4}$-C(O)O$R^G$;

provided that when ----is a double bond, X is CH$_2$, Y is O, Z is O and $R^1$ and $R^2$ are taken together with the carbon atom to which they are bound to form C(O), then at least one of n or m is an integer selected from 1 to 2;

provided further that when ----is a double bond, X is CH$_2$; Y is O; Z is O; $R^1$ and $R^2$ are taken together with the carbon atom to which they are bound to form C(O), and m is 2 then $R^4$ is other than methoxy;

or a pharmaceutically acceptable salt thereof.

4. A compound as in claim 2 wherein

----represents a double bond,

X is O;

Y is selected from the group consisting of —CH$_2$—, —CH$_2$CH$_2$—, —CH$_2$CH$_2$CH$_2$—, —CH(lower alkoxy)-, —CH(OH)—, —CH$_2$CH(OH)CH$_2$—, —CH(lower alkyl)-, —CH$_2$C(O)— and —CH$_2$C(O)CH$_2$—;

Z is O;

$R^1$ is selected from the group consisting of hydrogen and lower alkyl;

$R^2$ is selected from the group consisting of hydroxy, lower alkenyl, carboxy-lower alkyl, hydroxy-lower alkyl, aryl, 4-(1-N containing heterocycloalkyl (wherein said N containing heterocycloalkyl is bound through the N atom)-alkoxy)-phenyl, 4-(di(lower alkyl)amino-alkoxy)-phenyl, 4-(di(lower alkyl)amino)-phenyl, 4-aralkyloxy-phenyl, lower alkoxy-carbonyl-lower alkyl, 4-(lower alkoxy-lower alkoxy)-phenyl, di(lower alkyl)amino-(lower alkoxy)-carbonyl-(lower alkyl), (N containing heterocycloalkyl (wherein said N containing heterocycloalkyl is bound through the N atom))-(lower alkoxy)-carbonyl-(lower alkyl), (N containing heterocyloalkyl (wherein said N containing heterocycloalkyl is bound through the N atom))-(lower alkyl)-amino-carbonyl-(lower alkyl), (N containing heteroaryl)-(N containing heterocycloalkyl (wherein said N containing heterocycloalkyl is bound through the N atom))-C(O)-(lower alkyl), (halo-substituted aryl)-(N containing heterocycloalkyl (wherein said N containing heterocycloalkyl is bound through the N atom))-carbonyl-(lower alkyl), 4-((N containing heterocycloalkyl)-(lower alkoxy))-phenyl-carbonyl, 2-hydroxy-2-(4-N containing heterocycloalkyl-lower alkoxy)-phenyl)-ethyl, 4-(tri(lower alkyl)silyloxy-(lower alkoxy)-phenyl, 4-(hydroxy-lower alkoxy)-phenyl, 4-(formyl-lower alkoxy)-phenyl, 4-(carboxy-lower alkoxy)-phenyl, 4-(lower alkoxy-carbonyl-lower alkoxy)-phenyl, 4-(piperidinyl-2,6-dione-lower alkoxy)-phenyl, 4-(pyrrolidinyl-2,5-dione-(lower alkyl)-phenyl, R*-4-(pyrrolidinyl-2,5-dione-(lower alkoxy)-phenyl and S*-4-(pyrrolidinyl-2,5-dione-(lower alkoxy)-phenyl;

alternatively $R^1$ and $R^2$ are taken together with the carbon atom to which they are bound to form C(O);

n is an integer from 0 to 1;

$R^3$ is selected from the group consisting of halogen, hydroxy, lower alkoxy, tri(lower alkyl)-silyloxy, —OC(O)-(lower alkyl), —OC(O)-C(phenyl)-OC(O)-(lower alkyl), —OC(O)-(1,7,7-trimethyl-2-oxabicyclo[2.2.1]heptan-3-one) and —OC(O)—C(CH$_3$)(CF$_3$)-phenyl;

m is is an integer from 0 to 1;

$R^4$ is selected from the group consisting of halogen, hydroxy, lower alkyl, lower alkoxy, tri(lower alkyl)-silyloxy, —OC(O)-(lower alkyl), —OC(O)—CH(phenyl)-OC(O)-(lower alkyl), —OC(O)-(1,7,7-trimethyl-2-oxabicyclo[2.2.1]heptan-3-one) and —OC(O)—C(CH$_3$)(CF$_3$)-phenyl;

provided further that when ----is a double bond; X is O; Y is CH$_2$; Z is O; $R^1$ and $R^2$ are taken together with the carbon atom to which they are bound to form C(O); n is 0; $R^3$ is methoxy and m is 1; then $R^4$ is other than hydroxy or methoxy;

or a pharmaceutically acceptable salt thereof.

5. A compound as in claim 4 wherein

Y is selected from the group consisting of —CH$_2$—, —CH$_2$CH$_2$—, —CH$_2$CH$_2$CH$_2$—, —CH(OCH$_3$)—, —CH(OH)—, —CH$_2$CH(OH)CH$_2$—, —CH(CH(CH$_3$)$_2$)—, —CH$_2$C(O)— and —CH$_2$C(O)CH$_2$—;

$R^1$ is selected from the group consisting of hydrogen and methyl;

$R^2$ is selected from the group consisting of hydroxy, allyl, carboxymethyl, hydroxy-ethyl, 3-hydroxy-n-propyl, phenyl, 4-(1-piperidinyl-ethoxy)-phenyl, S*-4-(piperidinyl-ethoxy)-phenyl, R*-4-(piperidinyl-ethoxy)-phenyl, 4-(1-pyrrolidinyl-ethoxy)-phenyl, 4-(4-morpholinyl-ethoxy)-phenyl, 4-(1-azepanyl-ethoxy)-phenyl, R*-4-(1-azepanyl-ethoxy)-phenyl, S*-4-(1-azepanyl-ethoxy)-phenyl, 4-(diethylamino-ethoxy)-phenyl, 4-(dimethylamino-ethoxy)-phenyl, R*-4-(dimethylamino-ethoxy)-phenyl, S*-4-(dimethylamino-ethoxy)-phenyl, 4-(diisopropylamino-ethoxy)-phenyl, R*-4-(diisopropylamino-ethoxy)-phenyl, S*-4-(diisopropylamino-ethoxy)-phenyl, 4-(dimethylamino)-phenyl, 4-benzyloxy-phenyl, 4-(1-piperidinyl-n-propoxy)-phenyl, 4-(t-butyl-dimethyl-silyloxy-ethoxy)-phenyl, 4-(methoxy-ethoxy)-phenyl, methoxy-carbonyl-methyl, isopropoxy-carbonyl-methyl, dimethylamino-ethoxy-carbonyl-methyl, piperidinyl-ethoxy-carbonyl-methyl, pyrrolidinyl-ethoxy-carbonyl-methyl, morpholinyl-ethoxy-carbonyl-methyl, dimethylamino-n-propoxy-carbonyl-methyl, morpholinyl-ethyl-amino-carbonyl-methyl, morpholinyl-n-propyl-amino-carbonyl-methyl, pyrrolidinyl-ethyl-amino-carbonyl-methyl, 4-(2-pyridyl)-piperazinyl-carbonyl-methyl, 4-(4-fluorophenyl)-piperazinyl carboxy-methyl, 4-(piperidinyl-ethoxy)-phenyl-carbonyl, 2-hydroxy-2-(4-(piperidinyl-ethoxy)-phenyl)-ethyl, 4-(2-hydroxy-ethoxy)-phenyl, R*-4-(2-hydroxy-ethoxy)-phenyl, S*-4-(hydroxy-ethoxy)-phenyl, 4-(3-hydroxy-n-propoxy)-phenyl, R*-4-(3-hyd roxy-n-propoxy)-phenyl, S*-4-(3-hydroxy-n-propoxy)-phenyl, 4-(formyl-methoxy)-phenyl, 4-(carboxy-methoxy)-phenyl, 4-carboxy-ethoxy)-phenyl, 4-(methoxy-carbonyl-methoxy)-phenyl, 4-(methoxy-carbonyl-ethoxy)-phenyl, R*-4-(piperidinyl-2,6-dione-ethoxy)-phenyl, R*-4-(pyrrolidinyl-2,5-dione-ethoxy)-phenyl, S*-4-(pyrrolidinyl-2,5-dione-ethoxy)-phenyl, R*-4-(pyrrolidinyl-2,5-dione-n-propoxy)-phenyl and S*-4-(pyrrolidinyl-2,5-dione-n-propoxy)-phenyl;

alternatively $R^1$ and $R^2$ are taken together with the carbon atom to which they are bound to form C(O);

$R^3$ is selected from the group consisting of fluoro, hydroxy, methoxy, t-butyl-dimethyl-silyloxy, —OC(O)-methyl, —OC(O)-t-butyl, —OC(O)—CH(phenyl)-OC(O)CH$_3$, —OC(O)-(1,7,7-trimethyl-2-oxabicyclo[.2.1]heptan-3-one), and —OC(O)—C(CH$_3$)(CF$_3$)-phenyl;

$R^4$ is selected from the group consisting of fluoro, hydroxy, methyl, methoxy, t-butyl-dimethyl-silyloxy, —OC(O)-methyl, —OC(O)-t-butyl, —OC(O)—CH(phenyl)-OC(O)CH$_3$, —OC(O)-(1,7,7-trimethyl-2-oxabicyclo[.2.1]heptan-3-one) and —OC(O)—C(CH$_3$)(CF$_3$)-phenyl;

provided further that when ---- is a double bond; X is O; Y is CH$_2$; Z is O; $R^1$ and $R^2$ are taken together with the carbon atom to which they are bound to form C(O); n is 0; $R^3$ is methoxy and m is 1; then $R^4$ is other than hydroxy or methoxy;

or a pharmaceutically acceptable salt thereof.

6. A compound as in claim 5 wherein

Y is selected from the group consisting of —CH$_2$—, —CH$_2$CH$_2$—, —CH$_2$CH$_2$CH$_2$—, —CH(OCH$_3$)— and —CH(OH)—;

$R^2$ is selected from the group consisting of phenyl, 4-(1-piperidinyl-ethoxy)-phenyl, R*-4(piperidinyl-ethoxy)-phenyl, S*-4-(piperidinyl-ethoxy)-phenyl, 4-(1-pyrrolidinyl-ethoxy)-phenyl, 4-(4-morpholinyl-ethoxy)-phenyl, 4-(1-azepanyl-ethoxy)-phenyl, R*-4-(azepanyl-ethoxy)-ohenyl, S*-4-(1-azepanyl-ethoxy)-phenyl, 4-(diethylamino-ethoxy)-phenyl, 4-(dimethylamino-ethoxy)-phenyl, R*-4-(dimethylamino-ethoxy)-phenyl, S*-4-(dimethylamino-ethoxy)-phenyl, R*-4-(diisopropylamino-ethoxy)-phenyl, S*-4-(diisopropylamino-ethoxy)-phenyl, 4-(dimethylamino)-phenyl, 4-(3-hydroxy-n-propoxy)-phenyl;

alternatively $R^1$ and $R^2$ are taken together with the carbon atom to which they are bound to form C(O);

$R^3$ is selected from the group consisting of hydroxy, methoxy and —OC(O)-t-butyl;

$R^4$ is selected from the group consisting of fluoro, hydroxy, methoxy and —OC(O)-t-butyl;

provided further that when ---- is a double bond; X is O; Y is CH$_2$; Z is O; $R^1$ and $R^2$ are taken together with the carbon atom to which they are bound to form C(O); n is 0; $R^3$ is methoxy and m is 1; then $R^4$ is other than hydroxy or methoxy;

or a pharmaceutically acceptable salt thereof.

7. A compound as in claim 6 wherein

Y is selected from the group consisting of —CH$_2$—, —CH$_2$CH$_2$—, —CH$_2$CH$_2$CH$_2$— and —CH(OH)—;

$R^2$ is selected from the group consisting of phenyl, 4-(1-piperidinyl-ethoxy)-phenyl, R*-4-(piperidinyl-ethoxy)-phenyl, S*-4-(piperidinyl-ethoxy)-phenyl, 4-(1-pyrrolidinyl-ethoxy)-phenyl, 4-(4-morpholinyl-ethoxy)-phenyl, 4-(1-azepanyl-ethoxy)-phenyl, R*-4-(azepanyl-ethoxy)-phenyl, S*-4-(1-azepanyl-ethoxy)-phenyl, 4-(diethylamino-ethoxy)-phenyl, 4-(dimethylamino-ethoxy)-phenyl, R*-4-(dimethylamino-ethoxy)-phenyl, S*-4-(dimethylamino-ethoxy)-phenyl, R*-4-(diisopropylamino-ethoxy)-phenyl, S*-4-(diisopropylamino-ethoxy)-phenyl, 4-(dimethylamino)-phenyl, 4-(3-hydroxy-n-propoxy)-phenyl;

or a pharmaceutically acceptable salt thereof.

8. A compound as in claim 7 wherein $R^1$ is selected from the group consisting of hydrogen and methyl;

$R^2$ is selected from the group consisting of phenyl, 4-(1-piperidinyl-ethoxy)-phenyl, R*-4-(piperidinyl-ethoxy)-phenyl, S*-4-(piperidinyl-ethoxy)-phenyl, 4-(1-pyrrolidinyl-ethoxy)-phenyl, 4-(4-morpholinyl-ethoxy)-phenyl, 4-(1-azepanyl-ethoxy)-phenyl, R*-4-(1-azepanyl-ethoxy)-phenyl, S*-4-(azepanyl-ethoxy)-phenyl, 4-(dimethylamino-ethoxy)-phenyl, R*-4-(dimethylamino-ethoxy)-phenyl, S*-4-(dimethylamino-ethoxy)-phenyl, R*-4-(diisopropylamino-ethoxy)-phenyl, S*-4-(diisopropylamino-ethoxy)-phenyl, 4-(dimethylamino)-phenyl, 4-(3-hydroxy-n-propoxy)-phenyl;

$R^3$ is selected from the group consisting of hydroxy and —OC(O)-t-butyl;

or a pharmaceutically acceptable salt thereof.

9. A compound as in claim 5 wherein the compound of formula (I) is selected from the group consisting of 8-(2,2-dimethyl-propionyloxy)-5-[4-(2-piperidin-1-yl-ethoxy)-phenyl]-5,11-dihydro-chromeno[4,3-c]chromen-2-yl ester 2,2-dimethyl propionic acid;

8-(2,2-dimethyl-propionyloxy)-5R-[4-(2-piperidin-1-yl-ethoxy)-phenyl]-5,11-dihydro-chromeno[4,3-c]chromen-2-yl ester 2,2-dimethyl propionic acid;

8-(2,2-dimethyl-propionyloxy)-5S-[4-(2-piperidin-1-yl-ethoxy)-phenyl]-5,11-dihydro-chromeno[4,3-c]chromen-2-yl ester 2,2-dimethyl propionic acid;

8-fluoro-5-[4-(2-piperidin-1-yl-ethoxy)-phenyl]-5,11-dihydro-chromeno[4,3-c]chromenen-2-ol;

8-(2,2,-dimethyl-propionyloxy)-5-hydroxy-5H-6,13-dioxa-benzo[3,4]cyclohepta[1,2-a]naphthalen-2-yl ester 2,2-dimethyl-propionic acid;

5-[4-(2-Piperidin-1-yl-ethoxy)-phenyl]-5,11-dihydro-chromeno[4,3-c]chromene-2,8-diol;

5R*-[4-(2-Piperidin-1-yl-ethoxy)-phenyl]-5,11-dihydro-chromeno[4,3-c]chromene-2,8-diol;

5S*-[4-(2-Piperidin-1-yl-ethoxy)-phenyl]-5,11-dihydro-chromeno[4,3-c]chromene-2,8-diol;

2,2-Dimethyl propionic acid, 8-hydroxy-5-[4-(2-piperidin-1-yl-ethoxy)-phenyl]-5,11-dihydro-chromeno[4,3-c]chromen-2-yl ester;

2,2-Dimethyl propionic acid, 8-hydroxy-11-[4-(2-piperidin-1-yl-ethoxy)-phenyl]-5,11-dihydro-chromeno[4,3-c]chromen-2-yl ester;

5-[4-(2-Azepan-1-yl-ethoxy)-phenyl]-11,12-dihydro-5H-6,13-dioxa-benzo[3,4]cyclohepta[1,2-a]naphthalen-2-ol;

5S*-(−)-[4-(2-Azepan-1-yl-ethoxy)-phenyl]-11,12-dihydro-5H-6,13-dioxa-benzo[3,4]cyclohepta[1,2-a]naphthalen-2-ol;

5R*-(+)-[4-(2-Azepan-1-yl-ethoxy)-phenyl]-11,12-dihydro-5H-6,13-dioxa-benzo[3,4]cyclohepta[1,2-a]naphthalen-2-ol;

5-[4-(2-Dimethylamino-ethoxy)-phenyl]-11,12-dihydro-5H-6,13-dioxa-benzo[3,4]cyclohepta[1,2-a]naphthalen-2-ol;

5R*-(+)-[4-(2-Dimethylamino-ethoxy)-phenyl]-11,12-dihydro-5H-6,13-dioxa-benzo[3,4]cyclohepta[1,2-a]naphthalen-2-ol;

5S*-(−)-[4-(2-Dimethylamino-ethoxy)-phenyl]-11,12-dihydro-5H-6,13-dioxa-benzo[3,4]cyclohepta[1,2-a]naphthalen-2-ol;

5-[4-(2-Azepan-1-yl-ethoxy)-phenyl]-8-fluoro-11,12-dihydro-5H-6,13-dioxa-benzo[3,4]cyclohepta[1,2-a]naphthalen-2-ol;

5R*-(+)-[4-(2-Azepan-1-yl-ethoxy)-phenyl]-8-fluoro-11,12-dihydro-5H-6,13-dioxa-benzo[3,4]cyclohepta[1,2-a]naphthalen-2-ol;
5S*-(−)-[4-(2-Azepan-1-yl-ethoxy)-phenyl]-8-fluoro-11,12-dihydro-5H-6,13-dioxa-benzo[3,4]cyclohepta[1,2-a]naphthalen-2-ol;
2-Methoxy-5S*-(−)-[4-(2-piperidin-1-yl-ethoxy)-phenyl]-11,12-dihydro-5H-6,13-dioxa-benzo[3,4]cyclohepta[1,2-a]naphthalen-8-ol;
8-Methoxy-5S*-(−)-[4-(2-piperidin-1-yl-ethoxy)-phenyl]-11,12-dihydro-5H-6,13-dioxa-benzo[3,4]cyclohepta[1,2-a]naphthalen-2-ol;
and pharmaceutically acceptable salt thereof.

10. A compound of formula (I)

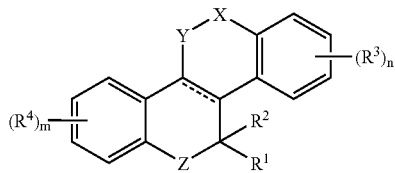

wherein
----represents a single or double bond,
X is selected from the group consisting of O and S and Y is selected from the group consisting of $CR^AR^B$, $CR^AR^B(CH_2)_{1-2}$, $CR^AR^BC(O)$ and $C(O)$; alternatively Y is selected from the group consisting of O and S and X is selected from the group consisting of $CR^AR^B$ and $C(O)$;
provided that when X is S, then Y is selected from the group consisting of $CR^AR^B$ and $CR^AR^B(CH_2)_{1-2}$; provided further that when Y is S, then X is selected from the group consisting of $CR^AR^B$;
wherein each $R^A$ and $R^B$ is independently selected from hydrogen, hydroxy, alkyl or alkoxy; provided that $R^A$ and $R^B$ are not each hydroxy;
Z is selected from the group consisting of O and S;
$R^1$ is selected from the group consisting of hydrogen, alkyl, cycloalkyl, aryl, aralkyl, heteroaryl and heteroaryl-alkyl; wherein the cycloalkyl, aryl, aralkyl, heteroaryl or heteroaryl-alkyl group is optionally substituted with one or more substituents independently selected from halogen, hydroxy, alkyl, alkoxy, —SH, —S(alkyl), $NO_2$, CN, $CO_2H$, $R^C$, —$OR^C$, —$SO_2$—$NR^DR^E$, —$NR^DR^E$, $NR^D$—$SO_2$—$R^F$, -(alkyl)$_{0-4}$-C(O)NR$^D$R$^E$, (alkyl)$_{0-4}$-NR$^D$—C(O)—R$^F$, -(alkyl)$_{0-4}$-(Q)$_{0-1}$-(alkyl)$_{0-4-NR}$$^D$R$^E$, -(alkyl)$_{0-4}$-(Q)$_{0-1}$-(alkyl)$_{0-4}$-C(O)—OR$^F$, -(alkyl)$^{0-4}$-(Q)$_{0-1}$-(alkyl)$_{0-4}$-C(O)—NR$^D$R$^E$ or -(alkyl)$_{0-4}$-C(O)-(alkyl)$_{0-4}$-C(O)—OR$^F$;
wherein $R^C$ is selected from the group consisting of alkyl, cycloalkyl, cycloalkyl-alkyl, aryl, aralkyl, heteroaryl, heteroaryl-alkyl, heterocycloalkyl and heterocycloalkyl-alkyl; wherein the cycloalkyl, cycloalkyl-alkyl, aryl, aralkyl, heteroaryl, heteroaryl-alkyl, heterocycloalkyl or heterocycloalkyl-alkyl group is optionally substituted with one or more substituents independently selected from halogen, hydroxy, alkyl, alkoxy, —SH, —S(alkyl), $NO_2$, CN, $CO_2H$, $SO_2$—$NR^DR^E$, $NR^DR^E$, $NR^DSO_2$—$R^F$, -(alkyl)$_{0-4}$-C(O)—NR$^D$R$^E$, -(alkyl)$_{0-4}$-NR$^D$—C(O)—R$^F$, -(alkyl)$_{0-4}$-(Q)$_{0-1}$-(alkyl)$_{0-4}$-NR$^D$R$^E$, -(alkyl)$_{0-4}$-(Q)$_{0-1}$-(alkyl)$_{0-4}$-C(O)—OR$^F$, -(alkyl)$_{0-4}$-(Q)$_{0-1}$-(alkyl)$_{0-4}$-C(O)—NR$^D$R$^E$ or -(alkyl)$_{0-4}$-C(O)-(alkyl)$_{0-4}$-C(O)—OR$^F$;
wherein Q is selected from the group consisting of O, S, NH, N(alkyl) and —CH=CH—;

wherein $R^D$ and $R^E$ are each independently selected from the group consisting of hydrogen and alkyl; alternatively $R^D$ and $R^E$ are taken together with the nitrogen atom to which they are bound to form a 4 to 8 membered ring selected from the group consisting of heteroaryl or heterocycloalkyl; wherein the heteroaryl or heterocycloalkyl group is optionally substituted with one or more substituents independently selected from halogen, hydroxy, alkyl, alkoxy, carboxy, amino, alkylamino, dialkylamino, nitro or cyano;
wherein $R^F$ is selected from the group consisting of hydrogen, alkyl, cycloalkyl, cycloalkyl-alkyl, aryl, aralkyl, heteroaryl, heteroaryl-alkyl, heterocycloalkyl and heterocycloalkyl-alkyl; wherein the cycloalkyl, aryl, heteroaryl, heteroaryl-alkyl, heterocycloalkyl or heterocycloalkyl-alkyl group is optionally substituted with one or more substituents independently selected from halogen, hydroxy, alkyl, alkoxy, carboxy, amino, alkylamino, dialkylamino, nitro or cyano;
$R^2$ is selected from the group consisting of hydroxy, alkyl, cycloalkyl, aryl, aralkyl, heteroaryl and heteroaryl-alkyl; wherein the cycloalkyl, aryl, aralkyl, heteroaryl or heteroaryl-alkyl group is optionally substituted with one or more substituents independently selected from halogen, hydroxy, alkyl, alkoxy, —SH, —S(alkyl), —$NO_2$, CN, $CO_2H$, $R^C$, —$OR^C$, —$SO_2$—$NR^DR^E$, $NR^DR^E$, $NR^D$—$SO_2$—$R^F$, -(alkyl)$_{0-4}$-C(O)NR$^D$R$^E$, (alkyl)$_{0-4}$-NR$^D$—C(O)—R$^F$, -(alkyl)$_{0-4}$-(Q)$_{0-1}$-(alkyl)$_{0-4}$-NR$^D$R$^E$, -(alkyl)$_{0-4}$-(Q)$_{0-1}$-(alkyl)$_{0-4}$-C(O)—OR$^F$, -(alkyl)$^{0-4}$-(Q)$_{0-1}$-(alkyl)$_{0-4}$-C(O)—NR$^D$R$^E$ or -(alkyl)$_{0-4}$-C(O)-(alkyl)$_{0-4}$-C(O)—OR$^F$;
alternatively, $R^1$ and $R^2$ are taken together with the carbon atom to which they are bound to form C(O);
provided that when $R^1$ and $R^2$ are taken together with the carbon atom to which they are bound to form C(O) and X is selected from the group consisting of O and S, then Y is selected from the group consisting of $CR^AR^B$ and $CR^AR^B(CH_2)_{1-2}$;
provided that when $R^1$ and $R^2$ are taken together with the carbon atom to which they are bound to form C(O) and Y is selected from the group consisting of O and S, then X is selected from the group consisting of $CR^AR^B$;
n is an integer selected from 0 to 4;
each $R^3$ is independently selected from the group consisting of halogen, hydroxy, $R^C$, amino, alkylamino, dialkylamino, nitro, cyano, —C(O)R$^G$, —C(O)OR$^G$, —OC(O)R$^G$, —OC(O)OR$^G$, —OC(O)N(R$^G$)$_2$, —N(R$^G$)C(O)R$^G$, —OSi(R$^G$)$_3$, —OR$^G$, —SO$_2$N(R$^G$)$_2$, —O-(alkyl)$_{1-4}$-C(O)R$^G$ and —O-(alkyl)$_{1-4}$-C(O)OR$^G$;
wherein each $R^G$ is independently selected from hydrogen, alkyl, aryl, aralkyl and 1,7,7-trimethyl-2-oxabicyclo[2.2.1]heptan-3-one; wherein the alkyl, aryl or aralkyl group is optionally substituted with one or more substituents independently selected from alkyl, halogenated alkyl, alkoxy, halogen, hydroxy, nitro, cyano, —OC(O)-alkyl or —C(O)O-alkyl;
alternatively two $R^G$ groups are taken together with the nitrogen atom to which they are bound to form a heterocycloalkyl group; wherein the heterocycloalkyl group is optionally substituted with one or more substituents independently selected from halogen, hydroxy, alkyl, alkoxy, carboxy, amino, alkylamino, dialkylamino, nitro or cyano;
m is an integer selected from 0 to 4;
each $R^4$ is independently selected from the group consisting of halogen, hydroxy, $R^C$, amino, alkylamino, dialkylamino, nitro, cyano, —C(O)R$^G$, —C(O)OR$^G$, —OC(O)R$^G$, —OC(O)OR$^G$, —OC(O)N(R$^G$)$_2$, —N(R$^G$)C(O)R$^G$, —OSi(R$^G$)$_3$, —OR$^G$, —SO$_2$N(alkyl)$_2$, —O-(alkyl)$_{1-4}$-C(O)R$^G$ and —O-(alkyl)$_{1-4}$-C(O)OR$^G$;

provided that when ---- is a double bond, X is CH$_2$, Y is O, Z is O and R$^1$ and R$^2$ are taken together with the carbon atom to which they are bound to form C(O), then at least one of n or m is an integer selected from 1 to 4;

provided further that when ---- is a single bond, X is O, Y is CH(alkyl), Z is O, R$^1$ is hydrogen and R$^2$ is alkyl, then at least one of n or m is an integer selected from 1 to 4;

provided further that when ---- is a single bond, X is O, Y is CH(alkyl), Z is O, R$^1$ is hydrogen, R$^2$ is alkyl, n is 1 and m is 1, then R$^3$ and R$^4$ are other than methoxy or ethoxy;

provided further that when ---- is a double bond, X is O, Y is CH$_2$, Z is O, R$^1$ and R$^2$ are taken together with the carbon atom to which they are bound to form C(O), n is 0 and m is 2, then each R$^4$ is not hydroxy or alkoxy;

provided further that when ---- is a double bond, X is CH$_2$; Y is O; Z is O; R$^1$ and R$^2$ are taken together with the carbon atom to which they are bound to form C(O); and m is 2 then R$^4$ is other than methoxy;

provided further that when ---- is a double bond, X is O; Y is CH$_2$; Z is O; R$^1$ and R$^2$ are taken together with the carbon atom to which they are bound to form C(O); n is 0 or 2; R$^3$ is methoxy and m is 1 or 2; then R$^4$ is other than hydroxy or methoxy;

or a pharmaceutically acceptable salt thereof.

11. A pharmaceutical composition comprising a pharmaceutically acceptable carrier and a compound of claim 1.

12. A pharmaceutical composition made by mixing a compound of claim 1 and a pharmaceutically acceptable carrier.

13. A process for making a pharmaceutical composition comprising mixing a compound of claim 1 and a pharmaceutically acceptable carrier.

14. A method of treating a disorder mediated by an estrogen receptor, in a subject in need thereof comprising administering to the subject a therapeutically effective amount of the compound of claim 1, wherein the disorder mediated by an estrogen receptor is selected from the group consisting of osteoporosis, hot flashes, vaginal dryness, breast cancer and endometriosis.

15. A method of treating a disorder mediated by an estrogen receptor in a subject in need thereof comprising administering to the subject a therapeutically effective amount of the composition of claim 11, wherein the disorder mediated by an estrogen receptor is selected from the group consisting of osteoporosis, hot flashes, vaginal dryness, breast cancer and endometriosis.

16. A process for the preparation of a compound of formula (DX)

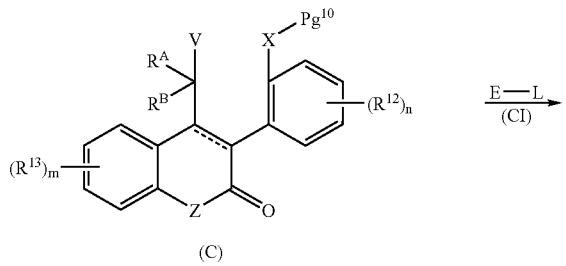

(DX)

wherein

---- represents a single or double bond,

X is selected from the group consisting of O and S;

p is an integer from 0 to 2;

R$^A$ and R$^B$ are each independently selected from hydrogen, hydroxy, alkyl or alkoxy; provided that R$^A$ and R$^B$ are not each hydroxy;

Z is selected from the group consisting of O and S;

n is an integer from 0 to 4;

each R$^{12}$ is independently selected from the group consisting of halogen, hydroxy, alkyl, alkoxy, trialkylsilyl, acyloxy, benzoyloxy, aryloxy, aralkyloxy, SEMoxy, MOMoxy and pivaloyloxy;

m is an integer selected from 0 to 4;

each R$^{13}$ is independently selected from the group consisting of halogen, hydroxy, alkyl, alkoxy, trialkylsilyl, acyloxy, benzoyloxy, aryloxy, aralkyloxy, SEMoxy, MOMoxy and pivaloyloxy;

or a pharmaceutically acceptable salt thereof;

comprising

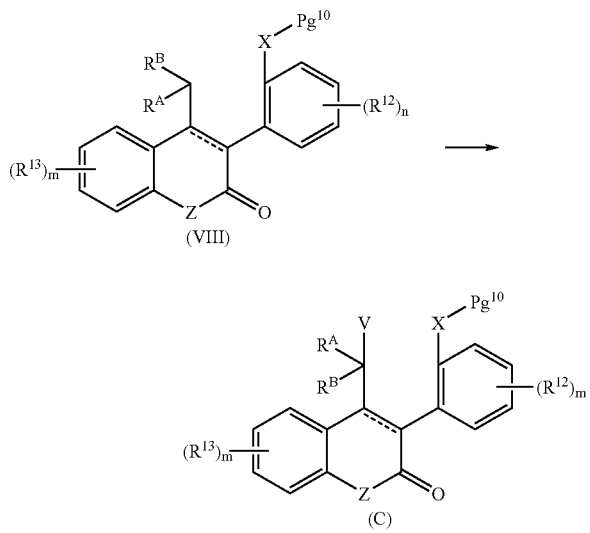

reacting a suitable substituted compound of formula (VIII), a known compound or compound prepared by known methods, wherein Pg$^{10}$ is a protecting group, with an organic base selected from the group consisting of NaHMDS, LiHMDS, KHMDS, LDA and di(lower alkyl)amino lithium, to yield the corresponding compound of formula (C), wherein y is the corresponding base cation;

-continued

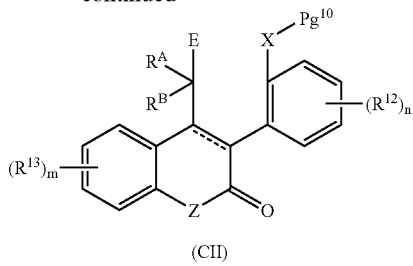

(CII)

reacting the compound of formula (C) with a suitably substituted compound of formula (CI), wherein E is an electrophile and L is a leaving group, to yield the corresponding compound of formula (CII);

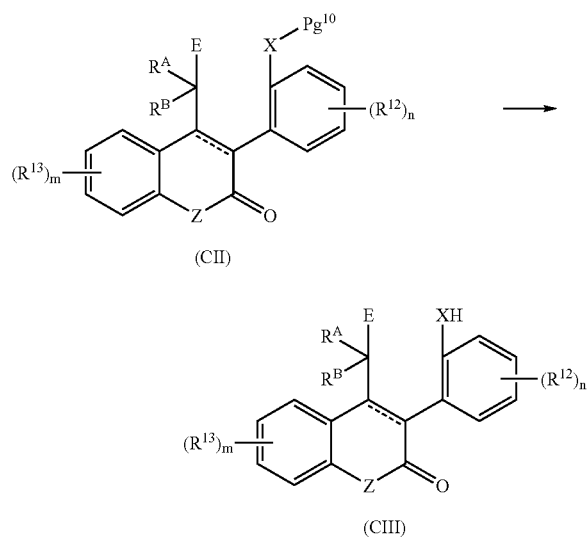

de-protecting the compound of formula (CII), to yield the corresponding compound of formula (CIII);

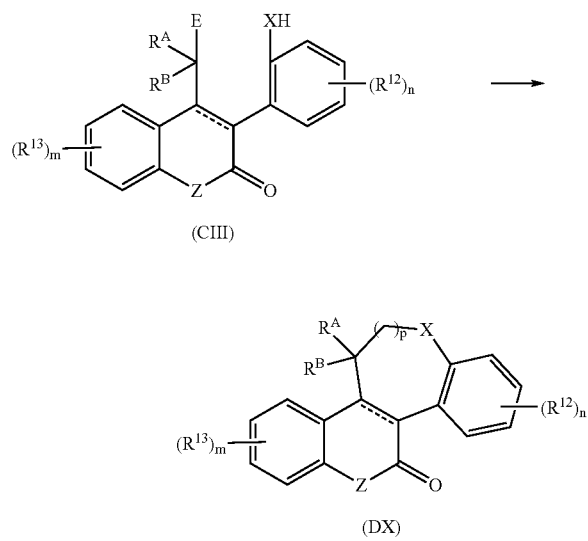

cyclizing the compound of formula (CIII), to yield the corresponding compound of formula (DX).

17. A process for the preparation of a compound of formula (DXI)

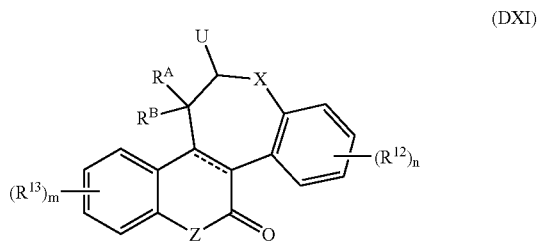

wherein

---- represents a single or double bond,

X is selected from the group consisting of O and S;

U is selected from the group consisting of hydrogen and alkyl;

$R^A$ and $R^B$ are each independently selected from hydrogen, hydroxy, alkyl or alkoxy; provided that $R^A$ and $R^B$ are not each hydroxy;

Z is selected from the group consisting of O and S;

n is an integer from 0 to 4;

each $R^{12}$ is independently selected from the group consisting of halogen, hydroxy, alkyl, alkoxy, trialkylsilyl, acyloxy, benzoyloxy, aryloxy, aralkyloxy, SEMoxy, MOMoxy and pivaloyloxy;

m is an integer selected from 0 to 4;

each $R^{13}$ is independently selected from the group consisting of halogen, hydroxy, alkyl, alkoxy, trialkylsilyl, acyloxy, benzoyloxy, aryloxy, aralkyloxy, SEMoxy, MOMoxy and pivaloyloxy;

or a pharmaceutically acceptable salt thereof;

comprising

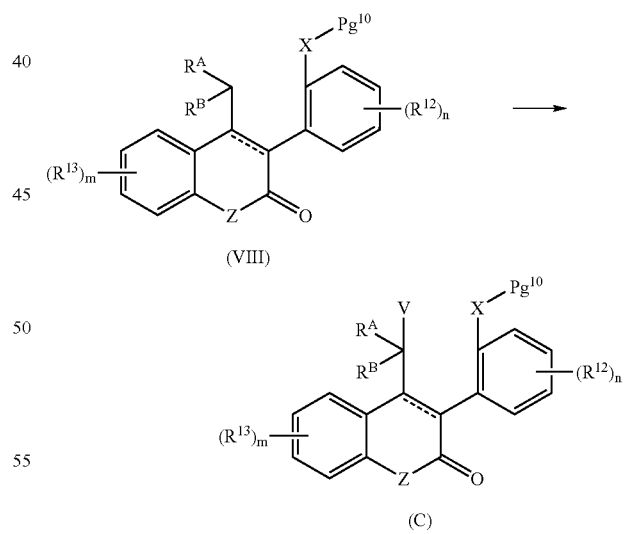

reacting a suitable substituted compound of formula (VIII), a known compound or compound prepared by known methods, wherein $Pg^{10}$ is a protecting group, with an organic base selected from the group consisting of NaHMDS, LiHMDS, KHMDS, LDA and di(lower alkyl)amino lithium, to yield the corresponding compound of formula (C), wherein V is the corresponding base cation;

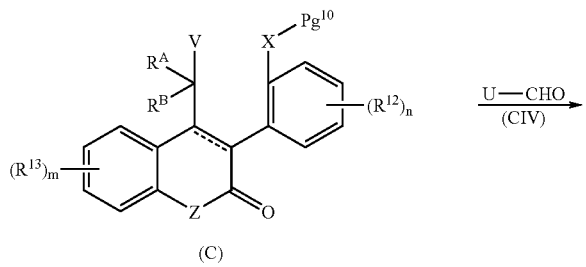

(C)

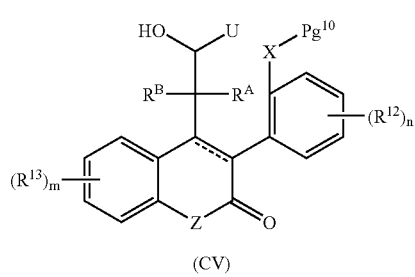

(CV)

reacting the compound of formula (C) with a suitably substituted aldehyde, a compound of formula (CIV), to yield the corresponding compound of formula (CV);

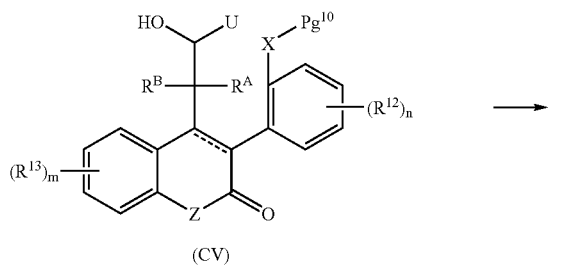

(CV)

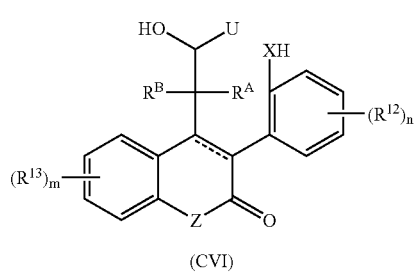

(CVI)

de-protecting the compound of formula (CV), to yield the corresponding compound of formula (CVI);

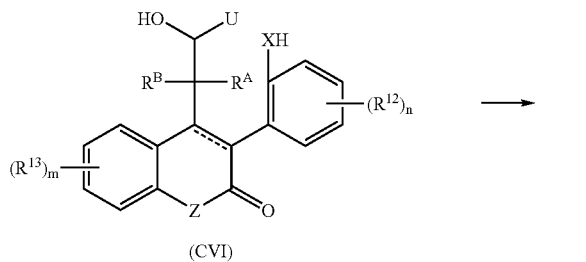

(CVI)

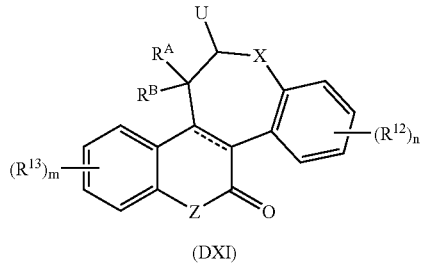

(DXI)

cyclizing the compound of formula (CIVI), to yield the corresponding compound of formula (DXI).

18. A compound prepared according to the process of claim 16.

19. A compound prepared according to the process of claim 17.

20. A compound having the formula:

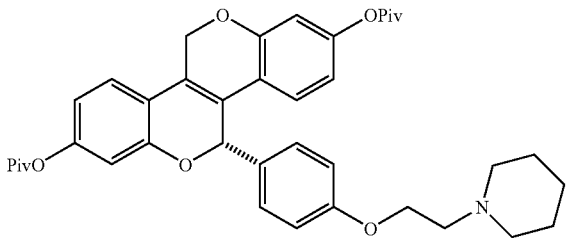

2,2-Dimethyl propionic acid 8-(2,2-dimethyl-propionyloxy)-5S*-[4-(2-piperidin-1-yl-ethoxy)-phenyl]-5,11-dihydro-chromeno[4,3-c]chromen-2-yl ester.

21. A compound having the formula:

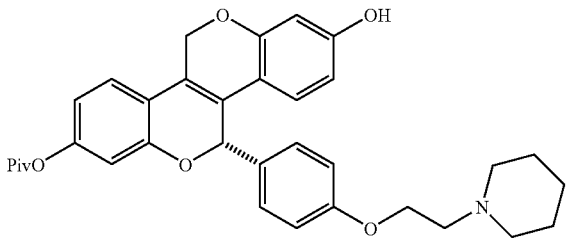

2,2-Dimethyl-propionic acid 8-hydroxy-11S*-[4-(2-piperidin-1-yl-ethoxy)-phenyl]-5,11-dihydro-chromeno[4,3-c]chromen-2-yl ester.

22. A compound having the formula:

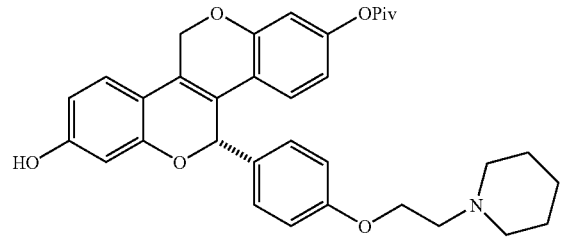

2,2-Dimethyl-propionic acid 8-hydroxy-5S*-[4-(2-piperidin-1-yl-ethoxy)-phenyl]-5,11-dihydro-chromeno[4,3-c]chromen-2-yl ester.

23. A compound having the formula:

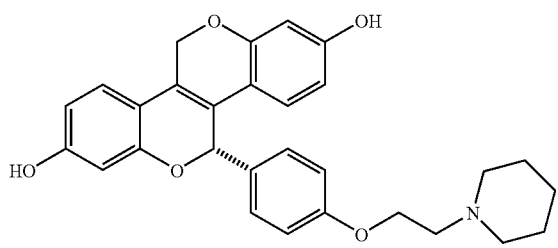

5S*-[4-(2-Piperidin-1-yl-ethoxy)-phenyl]-5,11-d ihydro-chromeno[4,3-c]chromene-2,8-diol.

24. A compound having the formula:

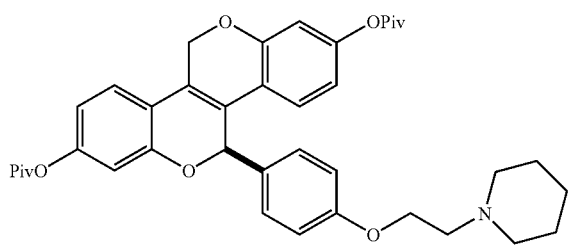

2,2-Dimethyl-propionic acid 8-(2,2-dimethyl-propionyloxy)-5R*-[4-(2-piperidin-1-yl-ethoxy)-phenyl]-5,11-dihydro-chromeno[4,3-c]chromen-2-yl ester.

25. A compound having the formula:

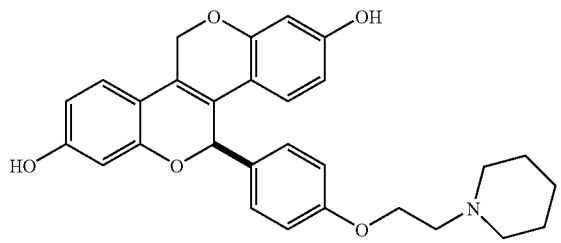

5R*-[4-(2-Piperidin-1-yl-ethoxy)-phenyl]-5,11-dihydro-chromeno[4,3-c]chromene-2,8-diol.

26. A compound having the formula:

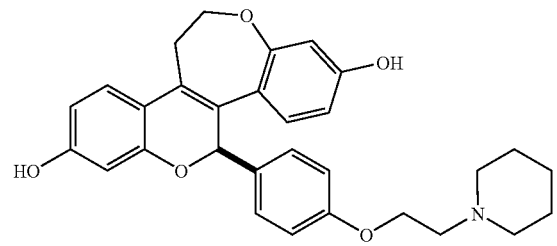

5R*-[4-(2-Piperidin-1-yl-ethoxy)-phenyl]-11,12-dihydro-5H-6,13-dioxa-benzo[3,4]cyclohepta[1,2-a]naphthalene-2,8-diol.

* * * * *